United States Patent
Suh et al.

(10) Patent No.: US 11,066,351 B2
(45) Date of Patent: Jul. 20, 2021

(54) ORGANIC COMPOUND, THREE-DIMENSIONAL ORGANIC FRAMEWORK FORMED BY USING ORGANIC COMPOUND, SEPARATION SIEVE AND OPTICAL LAYER, WHICH COMPRISE ORGANIC FRAMEWORK, AND OPTICAL DEVICE COMPRISING OPTICAL LAYER AS OPTICAL AMPLIFICATION LAYER

(71) Applicant: INDUSTRY-UNIVERSITY COOPERATION FOUNDATION HANYANG UNIVERSITY, Seoul (KR)

(72) Inventors: Donghack Suh, Seongnam-si (KR); Kyounghwan Choi, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 16/072,986

(22) PCT Filed: Jan. 24, 2017

(86) PCT No.: PCT/KR2017/000803
§ 371 (c)(1),
(2) Date: Jul. 26, 2018

(87) PCT Pub. No.: WO2017/131406
PCT Pub. Date: Aug. 3, 2017

(65) Prior Publication Data
US 2019/0031586 A1 Jan. 31, 2019

(30) Foreign Application Priority Data

Jan. 28, 2016 (KR) .................. 10-2016-0011018
May 10, 2016 (KR) .................. 10-2016-0056767
May 19, 2016 (KR) .................. 10-2016-0061682

(51) Int. Cl.
*C07C 43/257* (2006.01)
*B01J 20/22* (2006.01)
(Continued)

(52) U.S. Cl.
CPC ............. *C07C 43/257* (2013.01); *B01J 20/22* (2013.01); *C07C 43/20* (2013.01); *C07C 43/215* (2013.01); *C07C 43/23* (2013.01); *C07C 43/295* (2013.01); *C07C 47/198* (2013.01); *C07C 47/277* (2013.01); *C07C 49/753* (2013.01); *C07C 49/755* (2013.01); *C07C 49/84* (2013.01); *C07C 59/66* (2013.01); *C07C 69/33* (2013.01); *C07C 69/34* (2013.01); *C07C 69/96* (2013.01); *C07C 217/16* (2013.01); *C07C 217/24* (2013.01); *C07C 217/64* (2013.01); *C07C 245/02* (2013.01); *C07C 259/06* (2013.01); *C07C 309/65* (2013.01); *C07C 311/51* (2013.01); *C07C 313/04* (2013.01); *C07C 313/12* (2013.01); *C07C 317/14* (2013.01); *C07C 323/12* (2013.01); *C07C 409/38* (2013.01); *C07D 303/48* (2013.01); *G02B 1/00* (2013.01); *G02B 5/008* (2013.01); *G02B 5/28* (2013.01); *H01L 51/0052* (2013.01); *H01L 51/0054* (2013.01); *H01L 51/0056* (2013.01); *H01L 51/0058* (2013.01); *H01L 51/52* (2013.01);
(Continued)

(58) Field of Classification Search
None
See application file for complete search history.

(56) References Cited

U.S. PATENT DOCUMENTS

| | | | |
|---|---|---|---|
| 7,570,432 B1 | 8/2009 | Yonak | |
| 8,841,411 B2 * | 9/2014 | Kawano | ............... C08G 61/02 313/504 |
| 2011/0186785 A1 | 8/2011 | Kato et al. | |

FOREIGN PATENT DOCUMENTS

JP 2009-190940 A 8/2009

OTHER PUBLICATIONS

Andrey K. Sarychev et al., "Magnetic plasmonic metamaterials in actively pumped host medium and plasmonic nanolaser", Physical Review B 75, 085436 (2007), (received Nov. 15, 2006; published Feb. 27, 2007); 2007 The American Physical Society; pp. 085436-1-085436-9.

Chung-Hao Tsai et al., "A Broadband and Miniaturized Common-Mode Filter for Gigahertz Differential Signals Based on Negative-Permittivity Metamaterials", IEEE Transactions on Microwave Theory and Techniques, vol. 58, No. 1, Jan. 2010, pp. 195-202.

(Continued)

*Primary Examiner* — Samantha L Shterengarts
(74) *Attorney, Agent, or Firm* — Sughrue Mion, PLLC

(57) ABSTRACT

An organic compound, a three-dimensional organic structure formed by using the organic compound, a separation sieve and an optical layer having the organic structure, and an optical device having the optical layer as an optical amplification layer are provided. The organic structure includes a plurality of organic molecules self-assembled by non-covalent bonding. Each of the unit organic molecules has an aromatic ring, a first pair of substituents being connected to immediately adjacent positions of substitutable positions of the aromatic ring, and a second pair of substituents being connected to immediately adjacent positions of remaining substitutable positions of the aromatic ring. The unit organic molecules are self-assembled by van der Waals interaction, London dispersion interaction or hydrogen bonding between the first and the second pairs of the substituents and by pi-pi interactions between the aromatic rings.

12 Claims, 29 Drawing Sheets

(51) Int. Cl.

| | | |
|---|---|---|
| H01L 51/52 | (2006.01) | |
| G02B 1/00 | (2006.01) | |
| G02B 5/28 | (2006.01) | |
| C07C 43/20 | (2006.01) | |
| C07C 409/38 | (2006.01) | |
| C07C 43/23 | (2006.01) | |
| C07C 217/24 | (2006.01) | |
| C07C 47/277 | (2006.01) | |
| C07C 311/51 | (2006.01) | |
| C07C 217/16 | (2006.01) | |
| C07C 313/12 | (2006.01) | |
| C07C 49/755 | (2006.01) | |
| C07C 49/753 | (2006.01) | |
| C07C 43/215 | (2006.01) | |
| C07C 69/33 | (2006.01) | |
| C07C 43/295 | (2006.01) | |
| C07C 47/198 | (2006.01) | |
| C07C 49/84 | (2006.01) | |
| C07C 59/66 | (2006.01) | |
| C07C 69/34 | (2006.01) | |
| C07C 69/96 | (2006.01) | |
| C07C 217/64 | (2006.01) | |
| C07C 245/02 | (2006.01) | |
| C07C 259/06 | (2006.01) | |
| C07C 309/65 | (2006.01) | |
| C07C 313/04 | (2006.01) | |
| C07C 317/14 | (2006.01) | |
| C07C 323/12 | (2006.01) | |
| C07D 303/48 | (2006.01) | |
| G02B 5/00 | (2006.01) | |
| H01L 51/00 | (2006.01) | |
| G02F 1/1333 | (2006.01) | |
| G02F 1/1335 | (2006.01) | |
| H01L 31/054 | (2014.01) | |
| F21V 8/00 | (2006.01) | |
| G02F 1/1337 | (2006.01) | |
| G02F 1/1343 | (2006.01) | |
| G02F 1/1362 | (2006.01) | |
| H01G 9/20 | (2006.01) | |
| H01L 33/58 | (2010.01) | |
| H01L 51/44 | (2006.01) | |

(52) U.S. Cl.
CPC ...... C07C 2603/24 (2017.05); C07C 2603/40 (2017.05); C07C 2603/42 (2017.05); C07C 2603/50 (2017.05); C07C 2603/54 (2017.05); G02B 6/0051 (2013.01); G02B 6/0055 (2013.01); G02F 1/13439 (2013.01); G02F 1/133302 (2021.01); G02F 1/133345 (2013.01); G02F 1/133528 (2013.01); G02F 1/133531 (2021.01); G02F 1/133711 (2013.01); G02F 1/136227 (2013.01); H01G 9/209 (2013.01); H01L 31/054 (2014.12); H01L 33/58 (2013.01); H01L 51/447 (2013.01); H01L 51/5262 (2013.01)

(56) References Cited

OTHER PUBLICATIONS

Fabio Alves et al., "Strong terahertz absorption using $SiO_2$/Al based metamaterial structures", Citation: Appl. Phys. Lett. 100, 111104 (2012); doi: 10.1063/1.3693407; published by the American Institute of Physics.

Jiang Zhu et al., "A Compact Transmission-Line Metamaterial Antenna With Extended Bandwidth", IEEE Antennas and Wireless Propagation Letters, vol. 8, 2009, pp. 295-298.

M. Gorkunov et al., "Tuning of a nonlinear metamaterial band gap by an external magnetic field", Physical Review B 70, 235109 (2004), (received Jun. 30, 2004; published Dec. 7, 2004); 2004 The American Physical Society, pp. 235109-1-235109-9.

Wenshan Cai et al., "Optical cloaking with metamaterials", (published online: Apr. 2, 2007; doi: 10.1038/nphoton.2007.28); Nature Publishing Group, nature photonics, vol. 1, Apr. 2007, pp. 224-227.

Norihiro Murayama, et al., "Mechanism of zeolite synthesis from coal fly ash by alkali hydrothermal reaction", Int. J. Miner. Process. 64 (2002), pp. 1-17.

Hailian Li, et al, "Design and synthesis of an exceptionally stable and highly porous metal-organic framework", Nature | vol. 402 | Nov. 18, 1999 | www.nature.com; pp. 276-279.

Xiang Zhang et al., "Superlenses to overcome the diffraction limit", nature materials 51 vol. 7 | Jun. 2008 | www.nature.com/naturematerials; pp. 435-441.

First Office Action issued in the Korean Patent Office in Korean Application No. KR 10-2016-0011018.

T. Driscoll et al., "Memory Metamaterials", downloaded from http://science.sciencemag.org/ on Jul. 24, 2018; Sep. 18, 2009, vol. 325 Science, www.sciencemag.org; pp. 1518-1521.

Yoshihiro Kikkawa et al., "Two-Dimensional Structures of Anthracene Derivatives: Photodimerization and Host—Guest Chemistry", J. Phys. Chem. B 2010, 114, pp. 16718-16722.

Ning Wang et al., "Synthesis and Photovoltaic Properties of Conjugated D-A Copolymers Based on Thienyl Substituted Pyrene and Diketopyrrolopyrrole for Polymer Solar Cells", www.polymerchemistry.org; Journal of Polymer Science, Part A: Polymer Chemistry 2014, 52, pp. 3198-3204.

Liana M. Klivansky et al, "A complementary disk-shaped π electron donor-acceptor pair with high binding affinity", Chemical Science, 2012, 3, pp. 2009-2014.

Alexandre G. L. Olive et al, Striking Correlation between the Unusual Trigonal Crystal Packing and the Ability to Self-Assemble into Nanofibers of 2,3-Di-n-alkyloxyanthracenes, Langmuir Article, pubs.acs.org/Langmuir; 2009 American Chemical Society, 25(15), 8606-8614.

Ching-En Chou et al., "Synthesis, self-assembly and photovoltaic applications of tribenzopentaphene derivatives", RSC Advances, 2013, 3, 20666-20672.

* cited by examiner

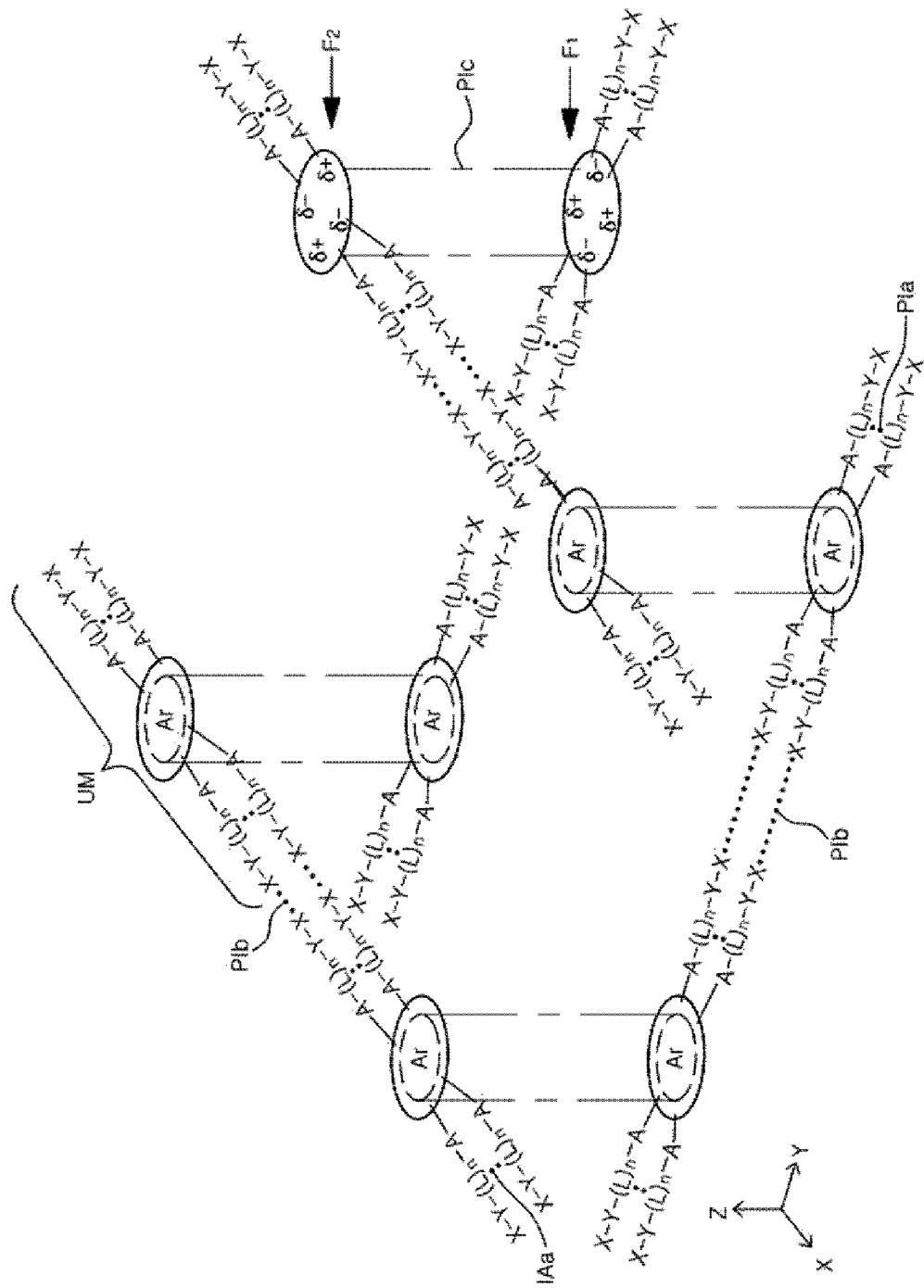
[FIG. 1]

[FIG. 2]
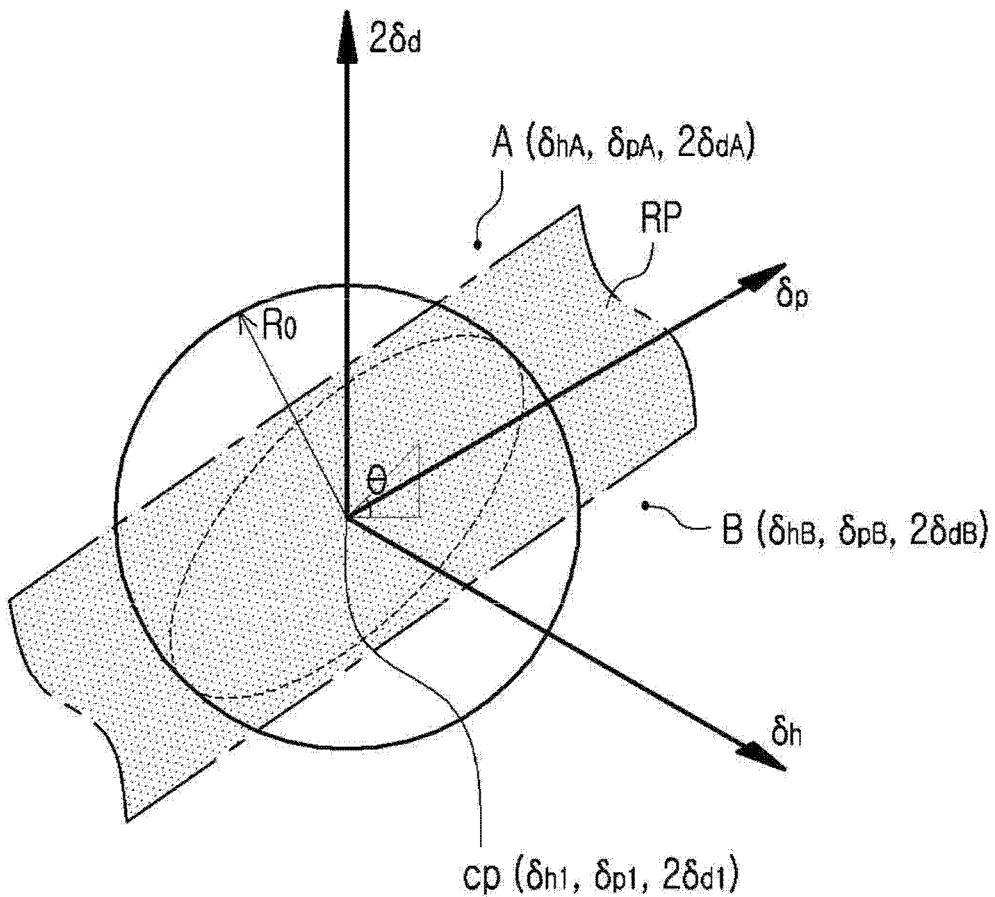
[FIG. 3]
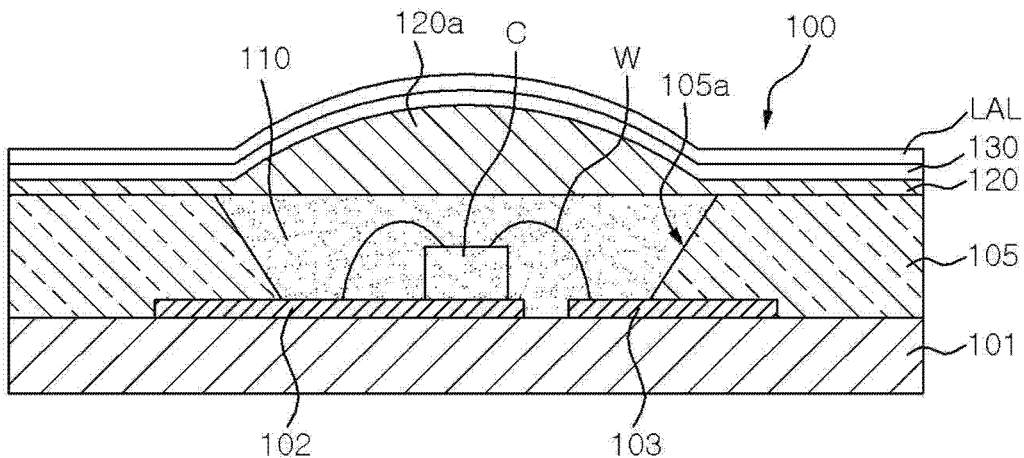

[FIG. 4]
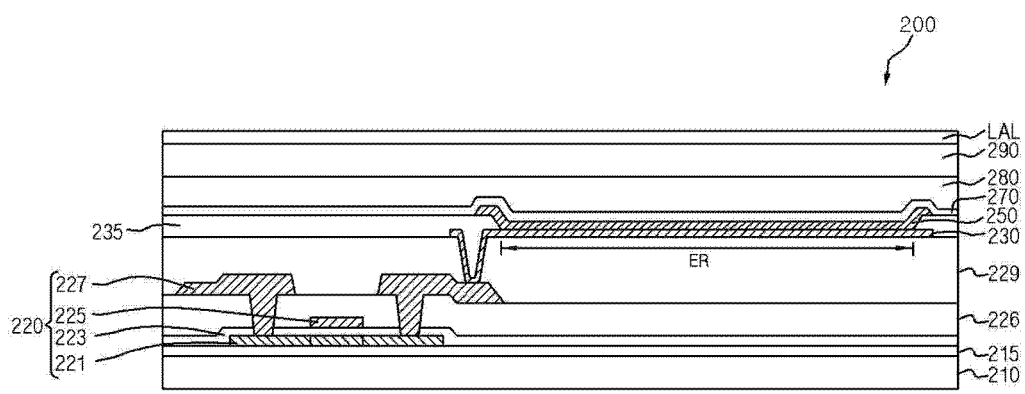
[FIG. 5]
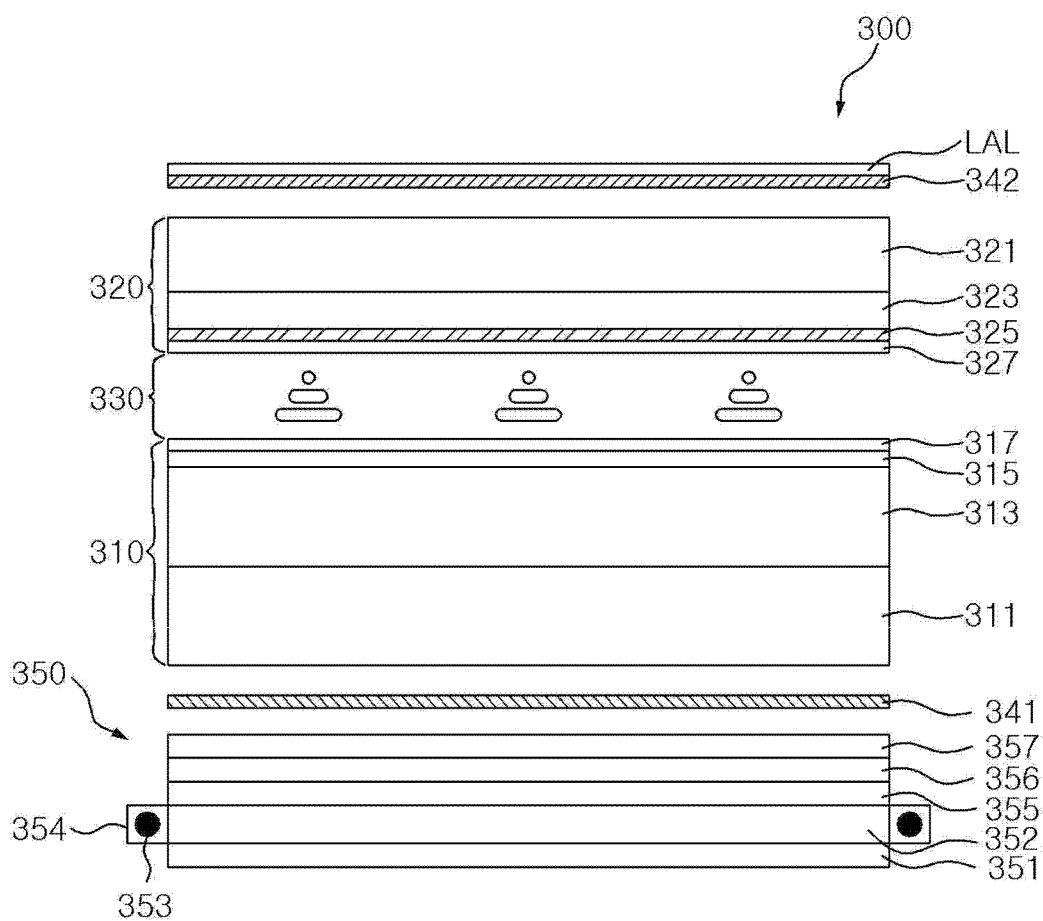

[FIG. 6]
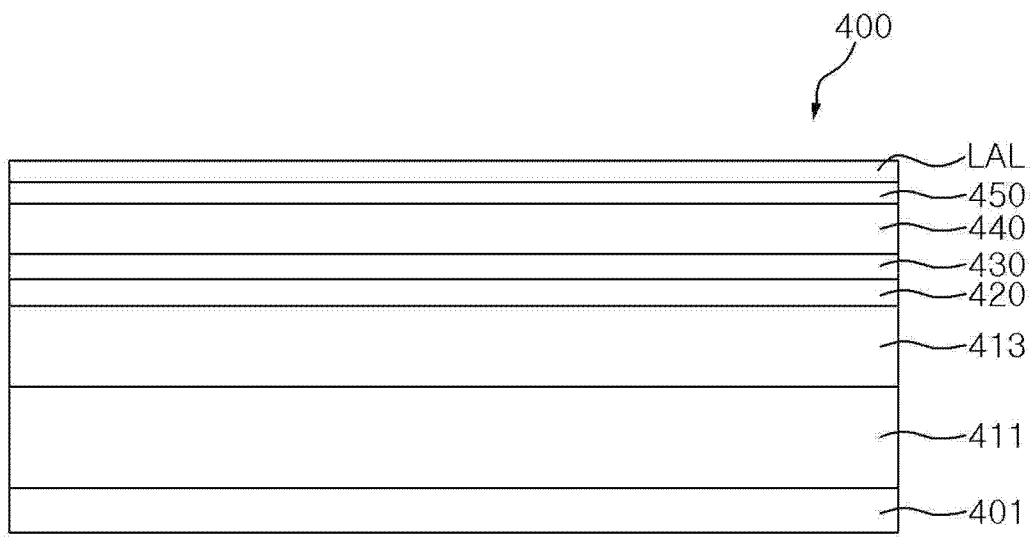
[FIG. 7]
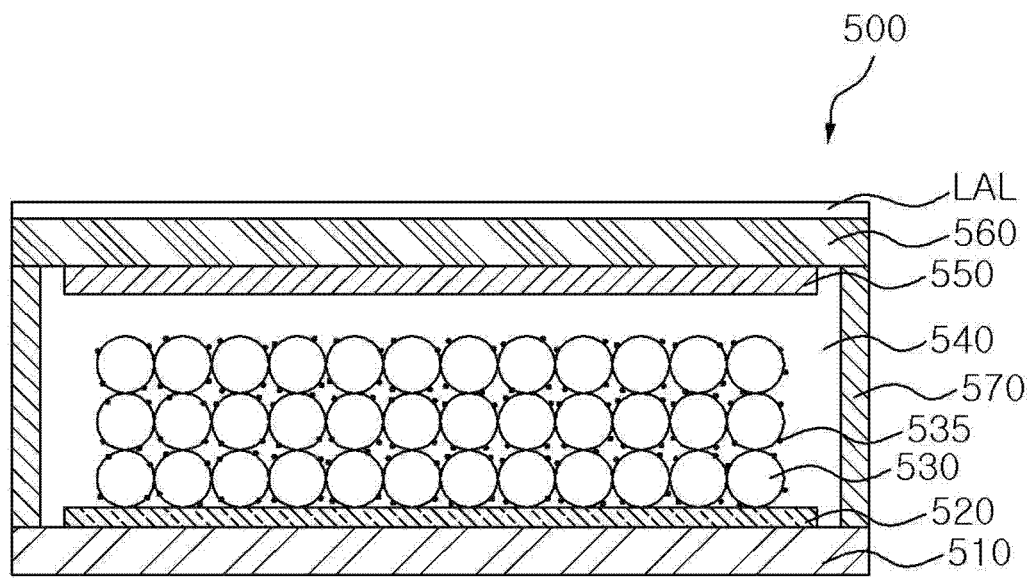

[FIG. 8]
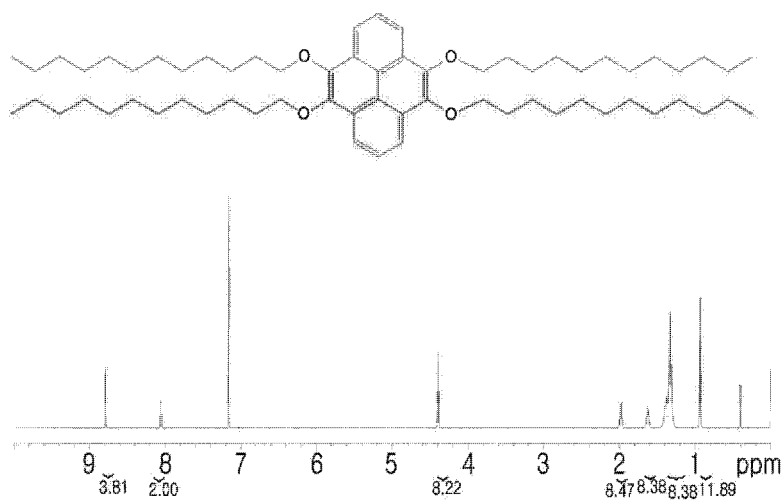
[FIG. 9]
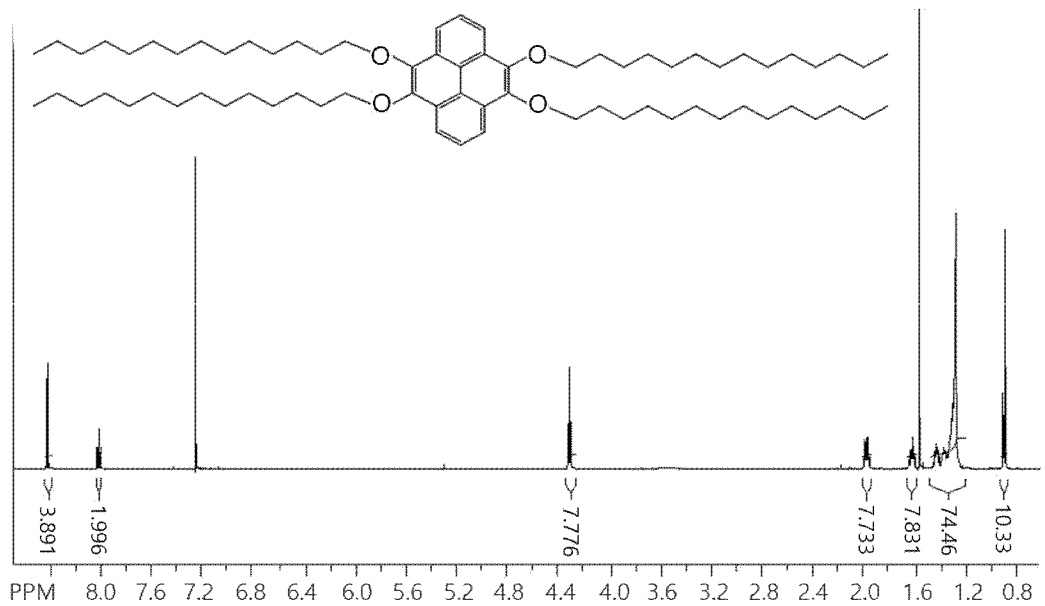

[FIG. 10]
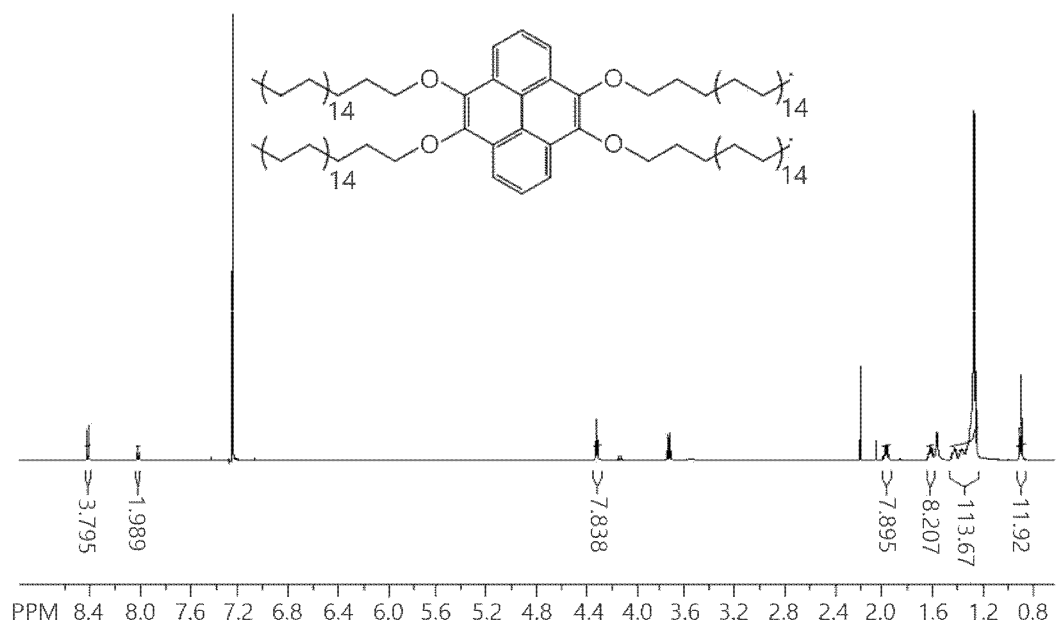
[FIG. 11]
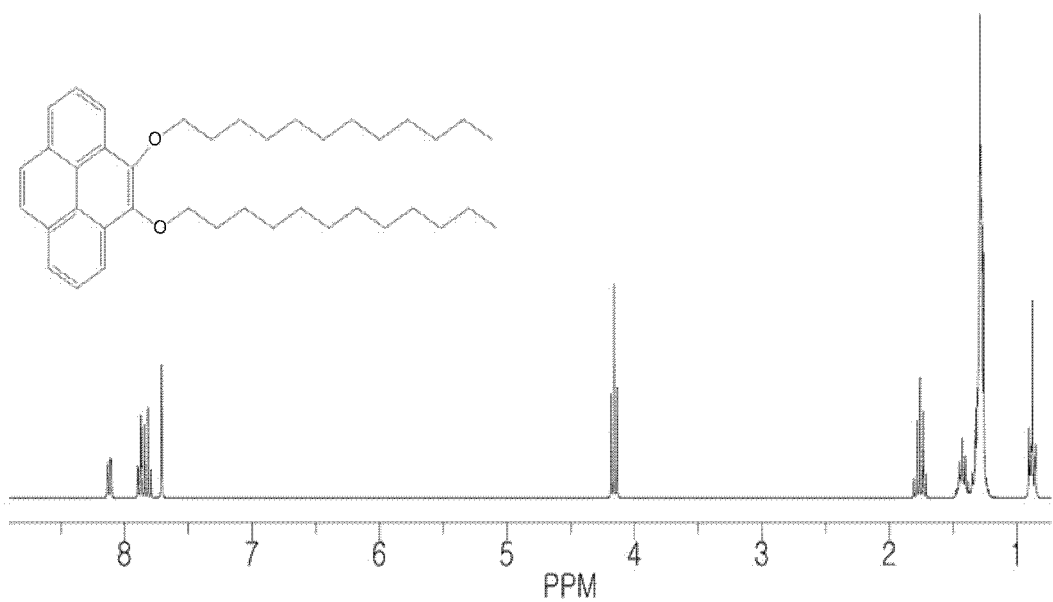

[FIG. 12]
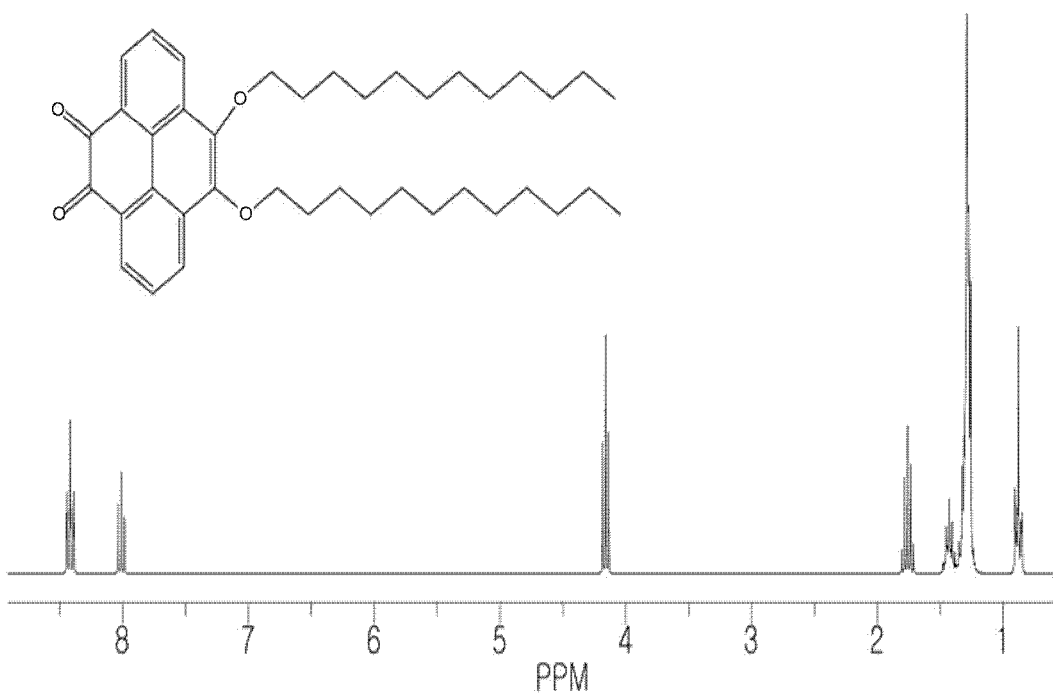
[FIG. 13]
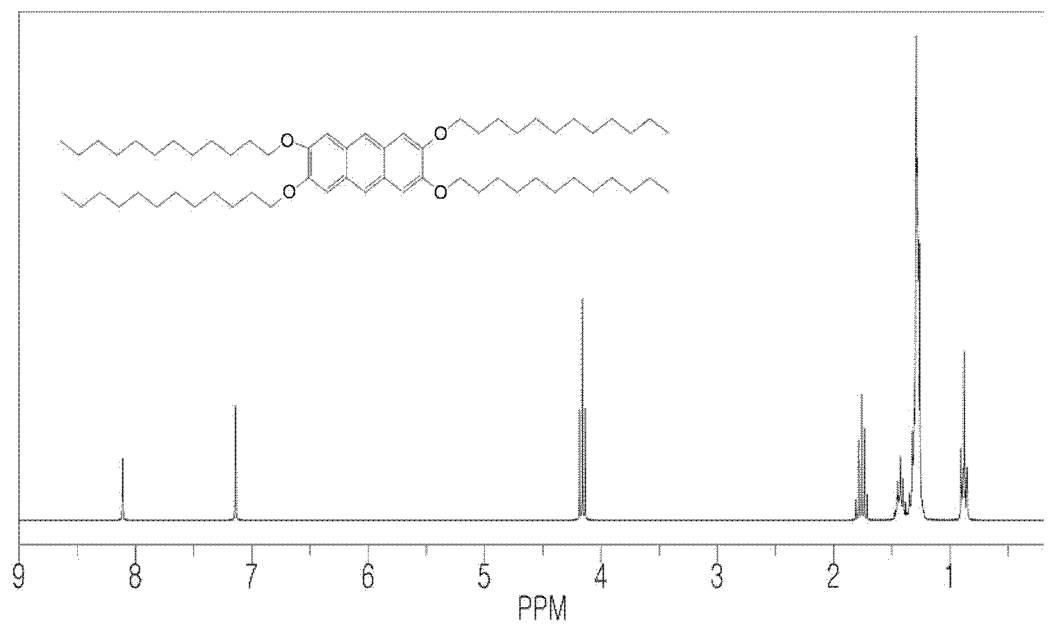

[FIG. 14]
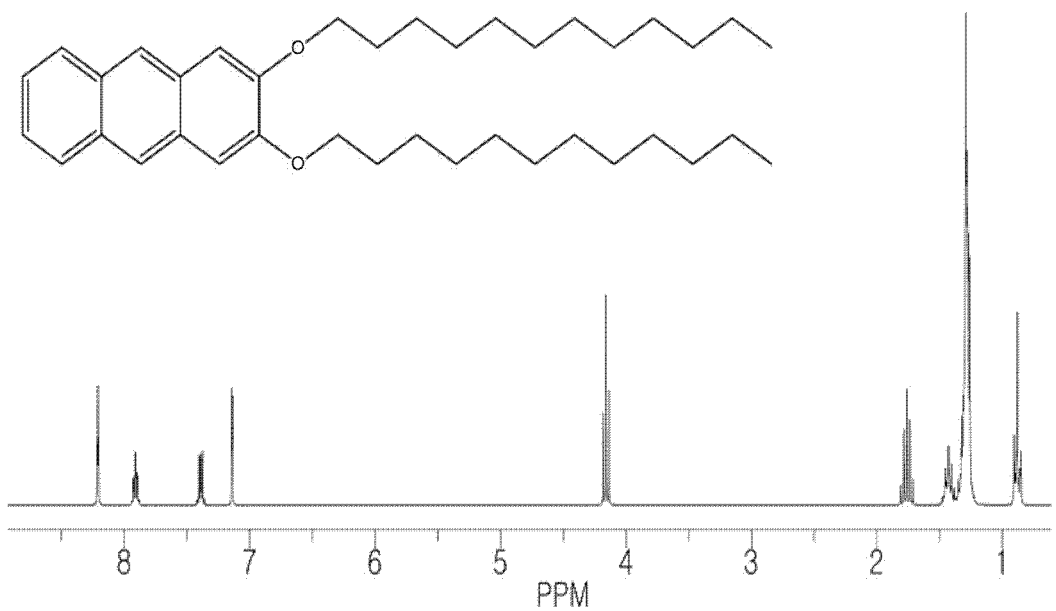
[FIG. 15]
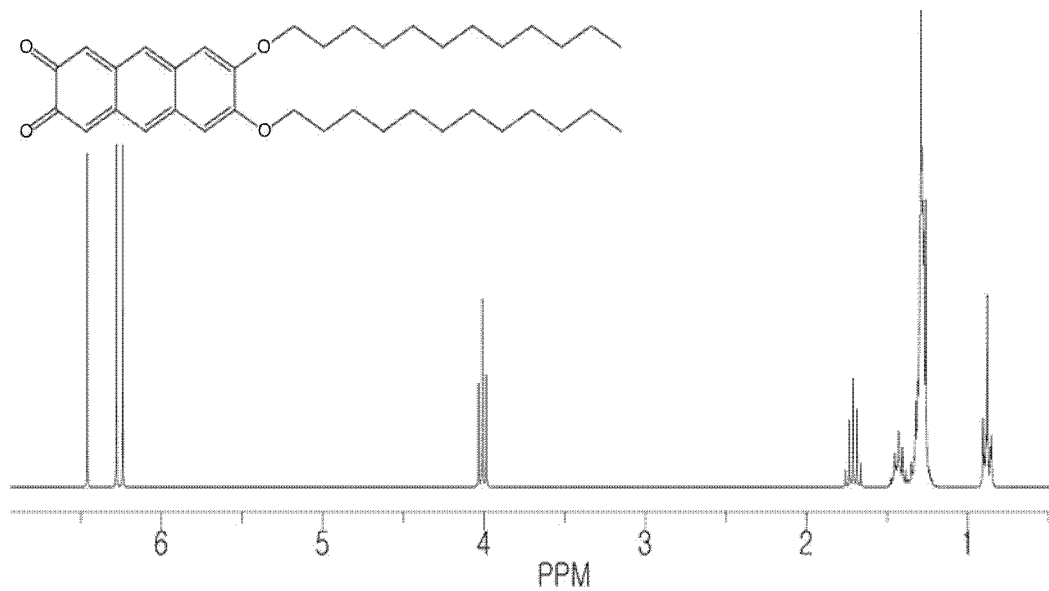

【FIG. 16】
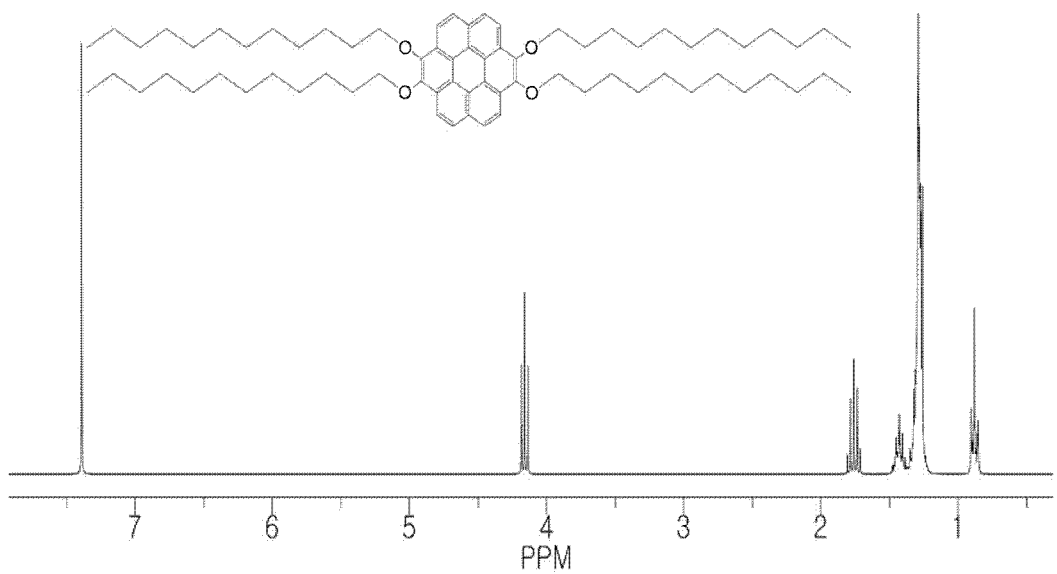
【FIG. 17】
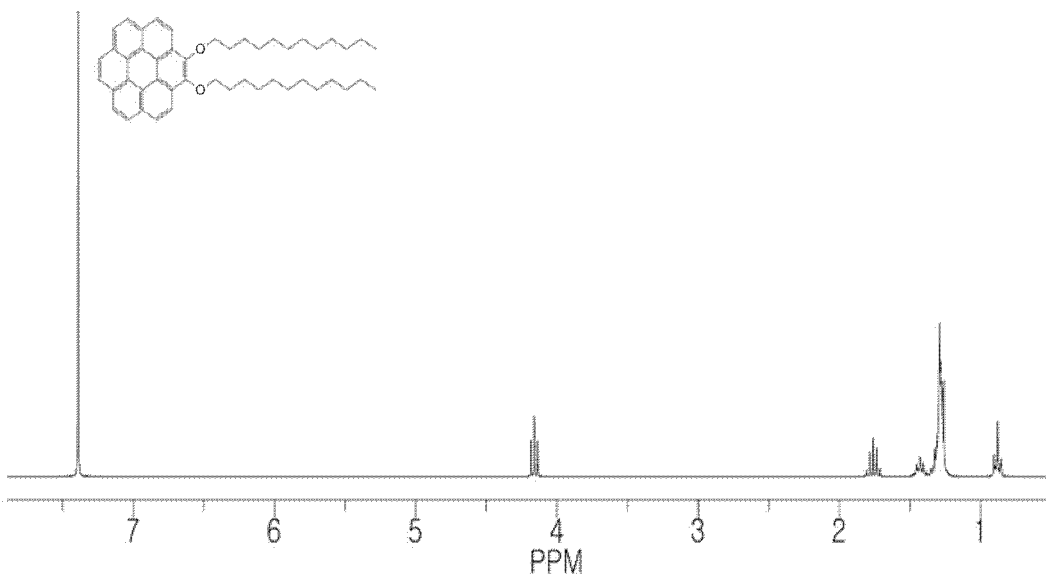

【FIG. 18】
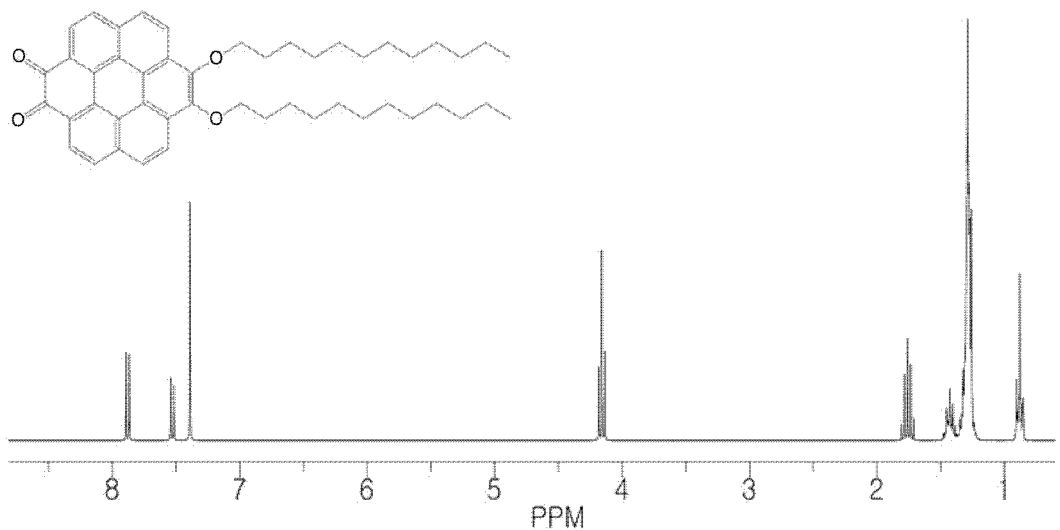
【FIG. 19】
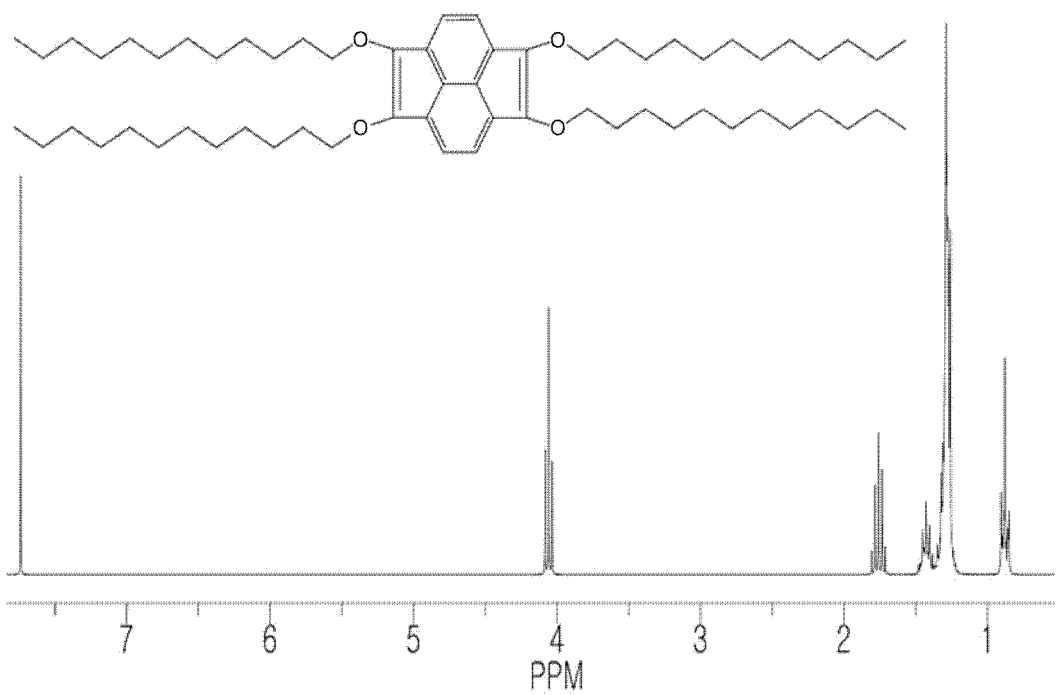

【FIG. 20】
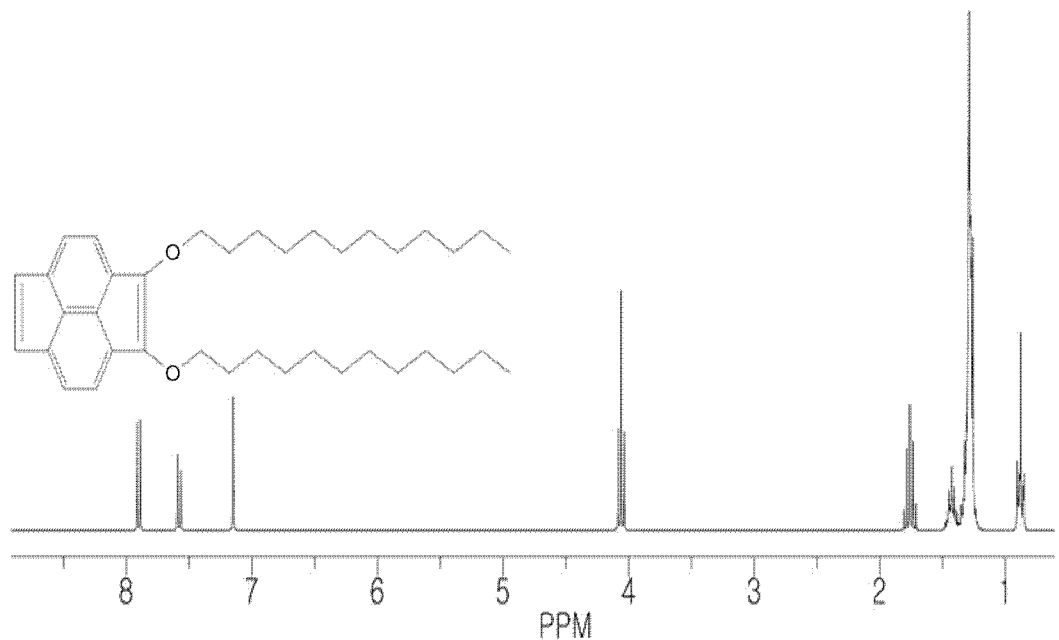
【FIG. 21】
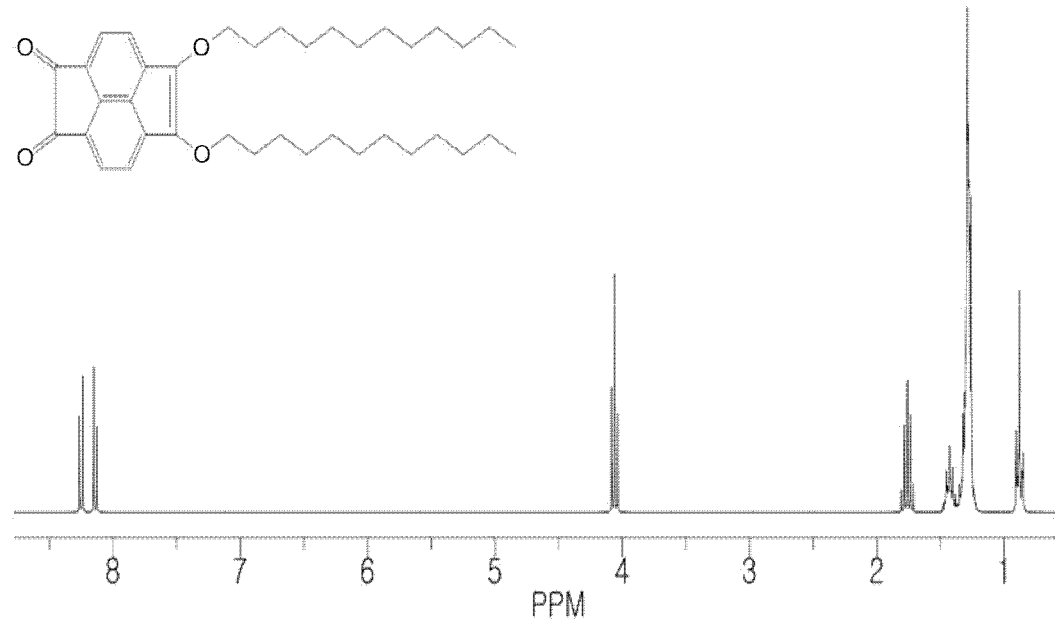

[FIG. 22]
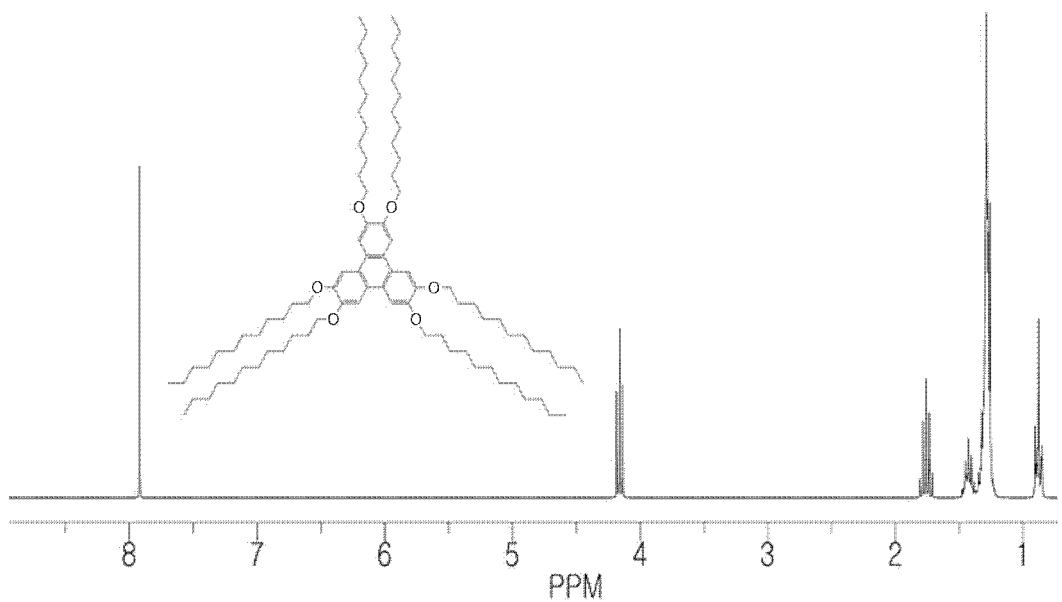
[FIG. 23]
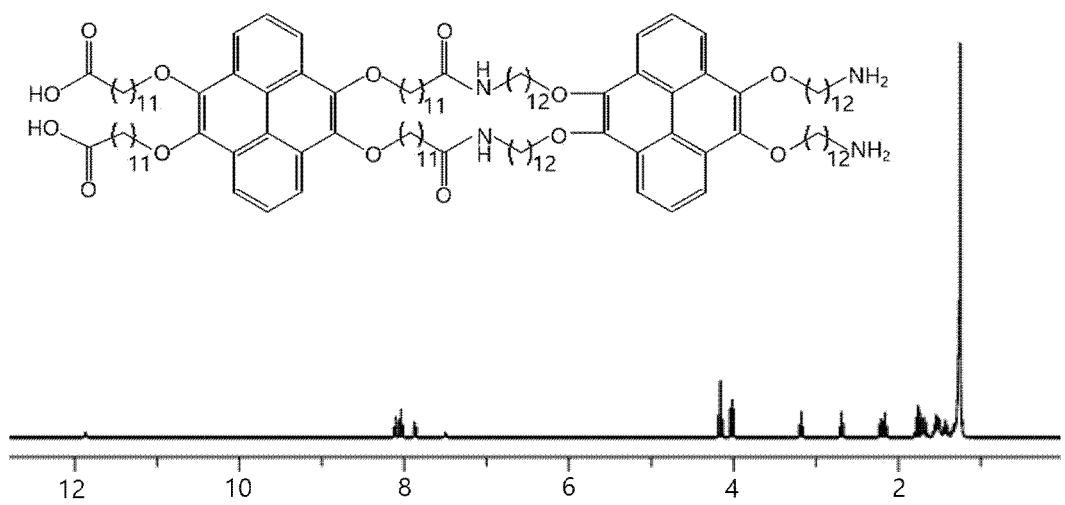

[FIG. 24]
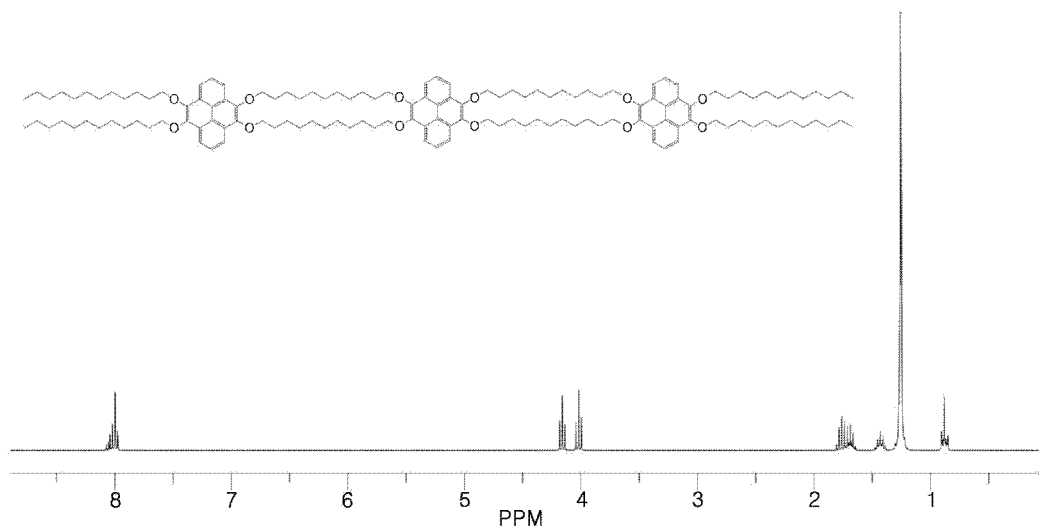
[FIG. 25]
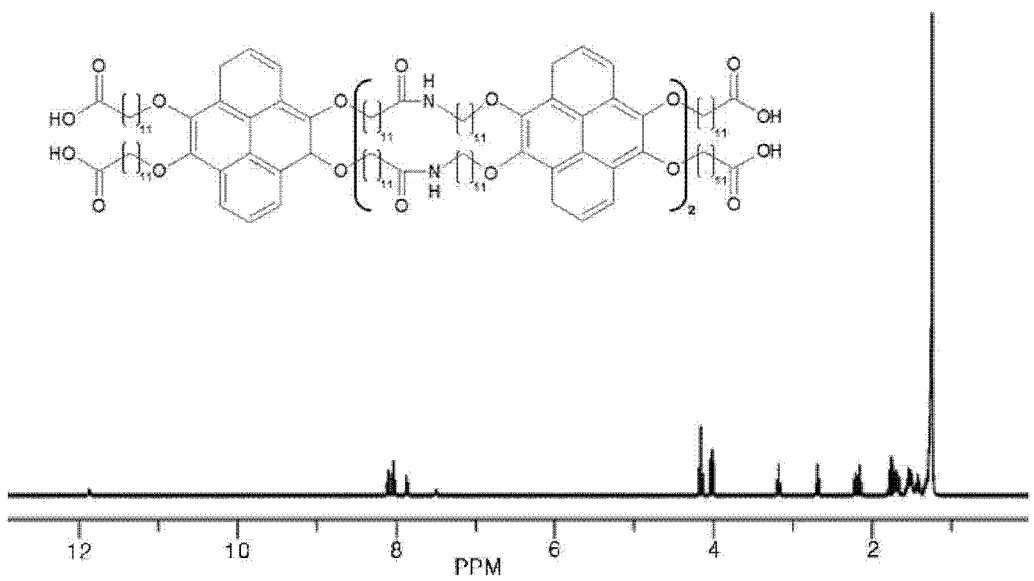

【FIG. 26a】
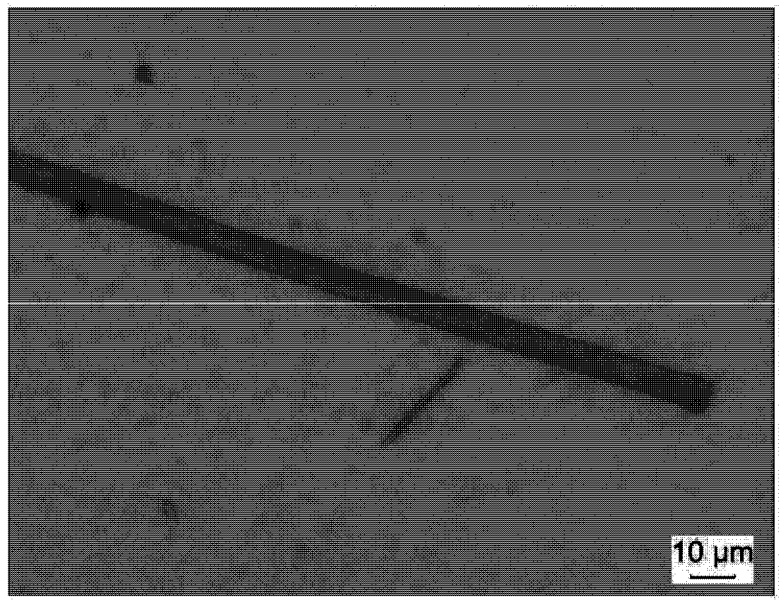
【FIG. 26b】
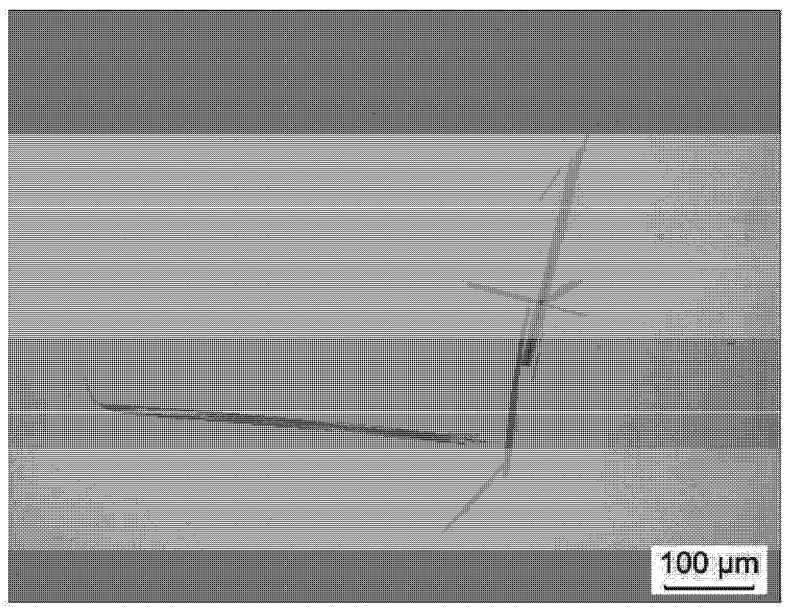

[FIG. 27]
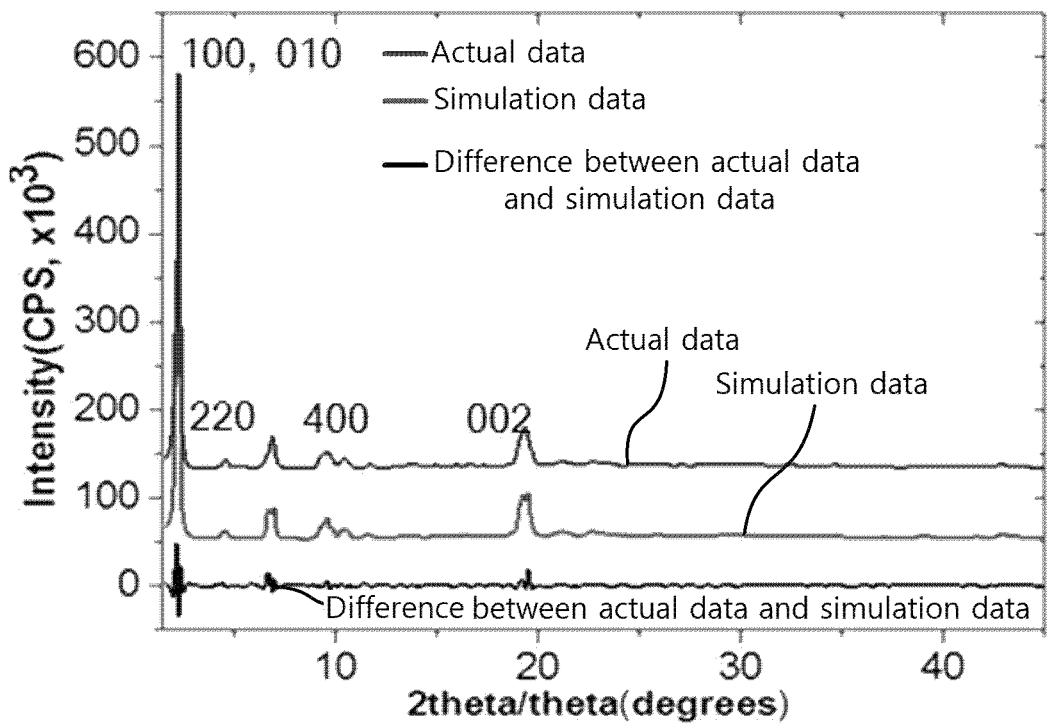
[FIG. 28]
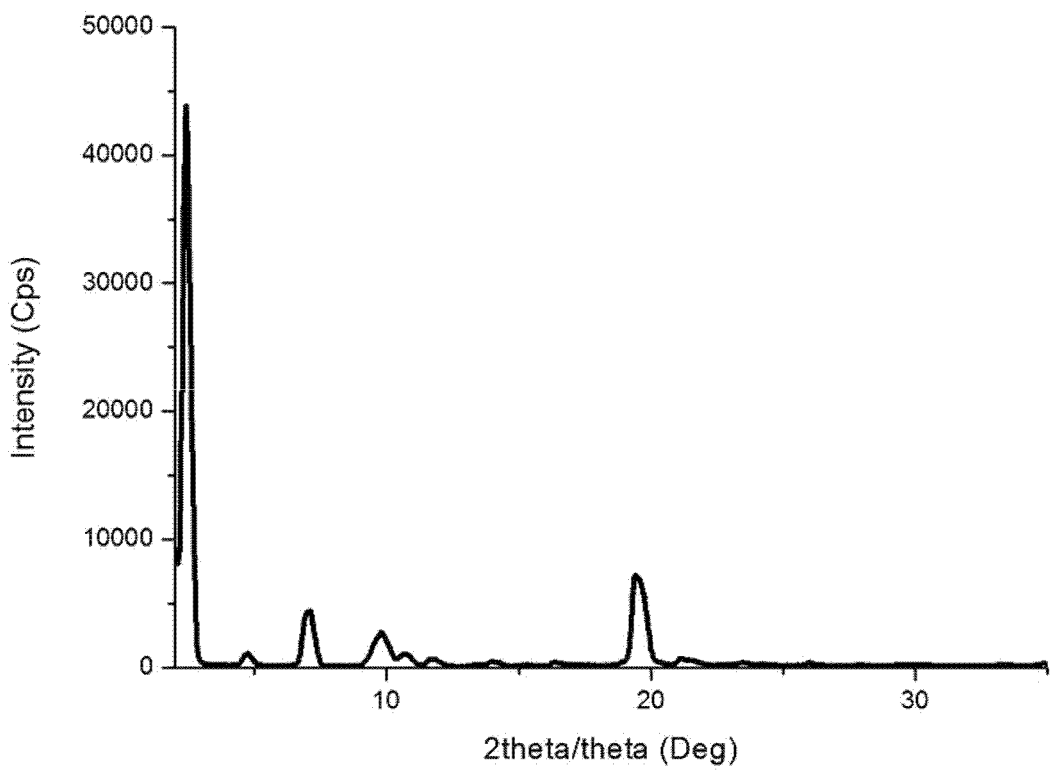

【FIG. 29】
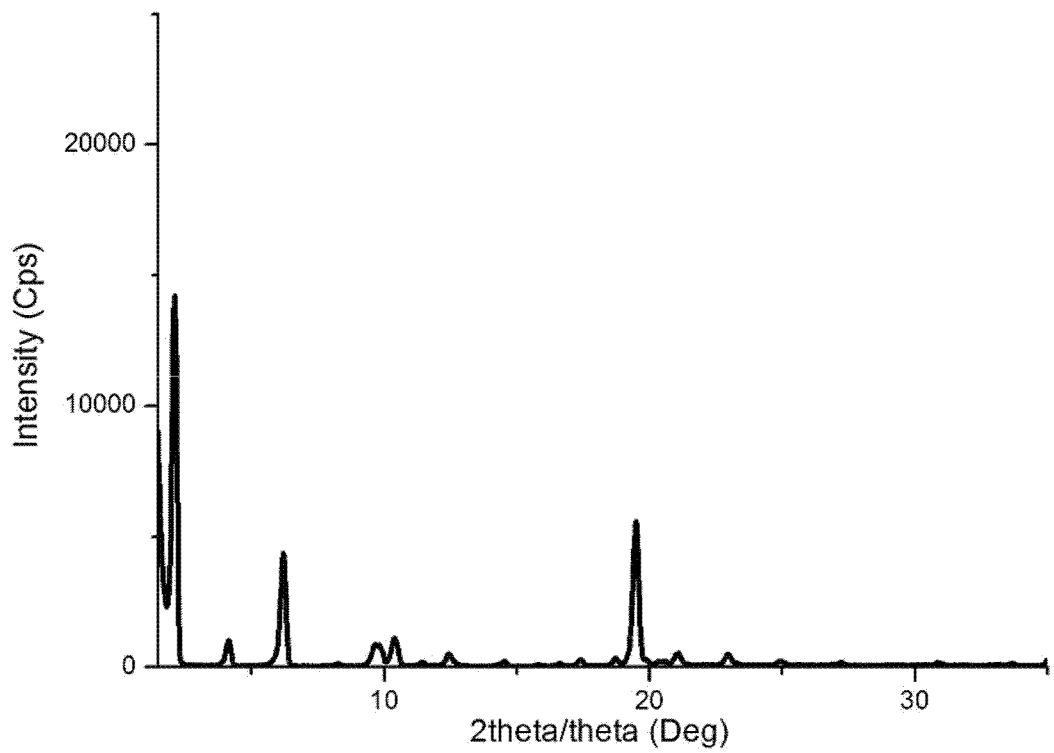
【FIG. 30】
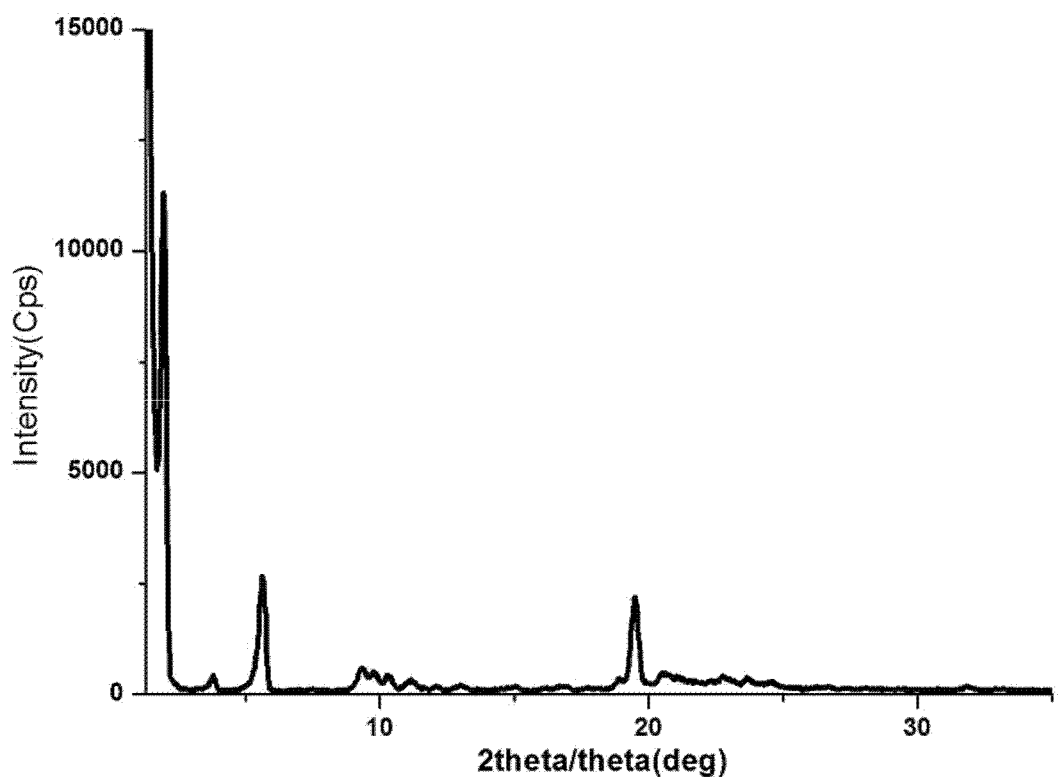

[FIG. 31]
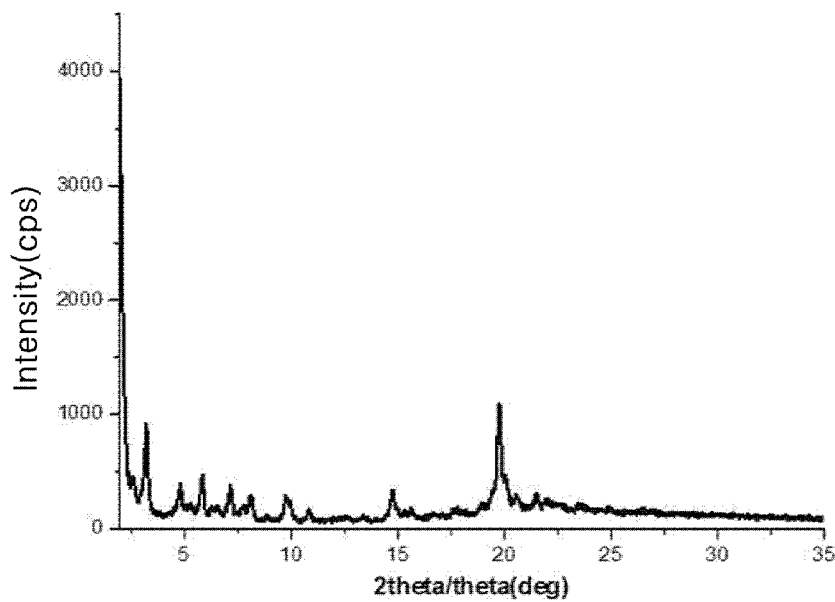
[FIG. 32A]
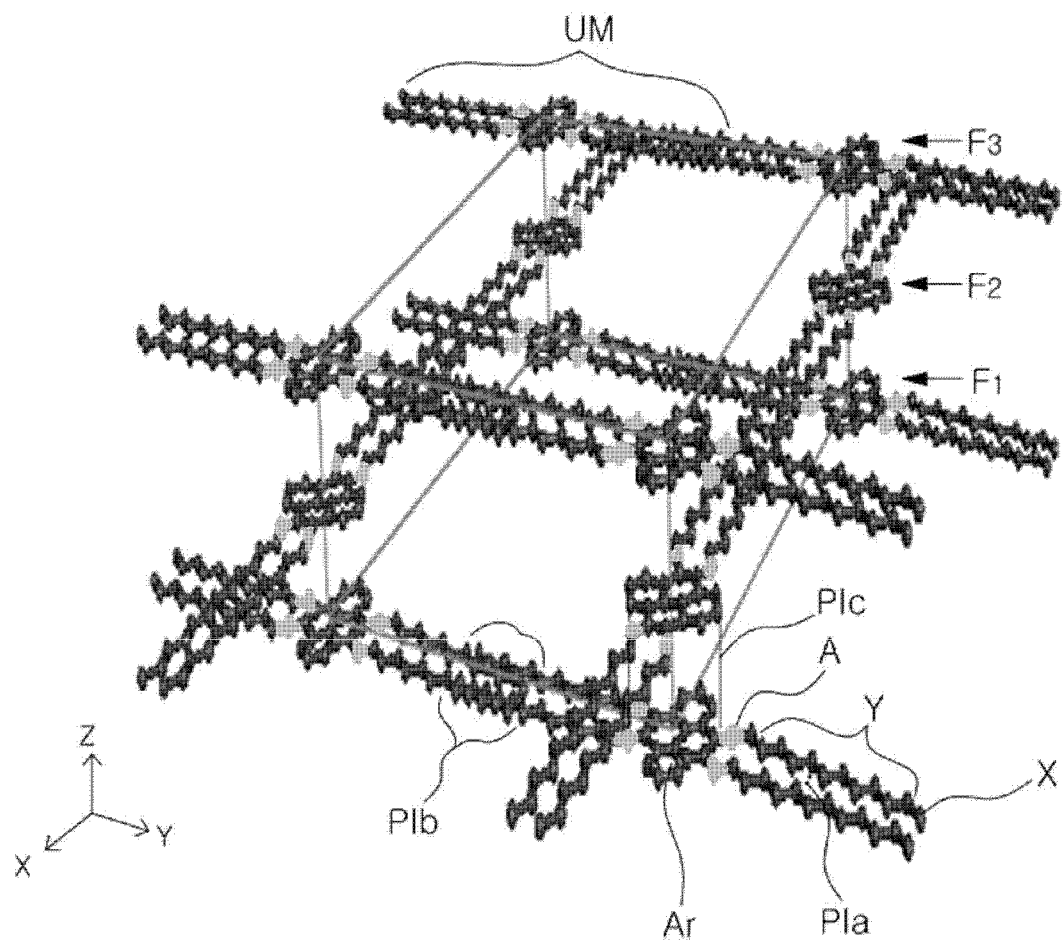

【FIG. 32B】
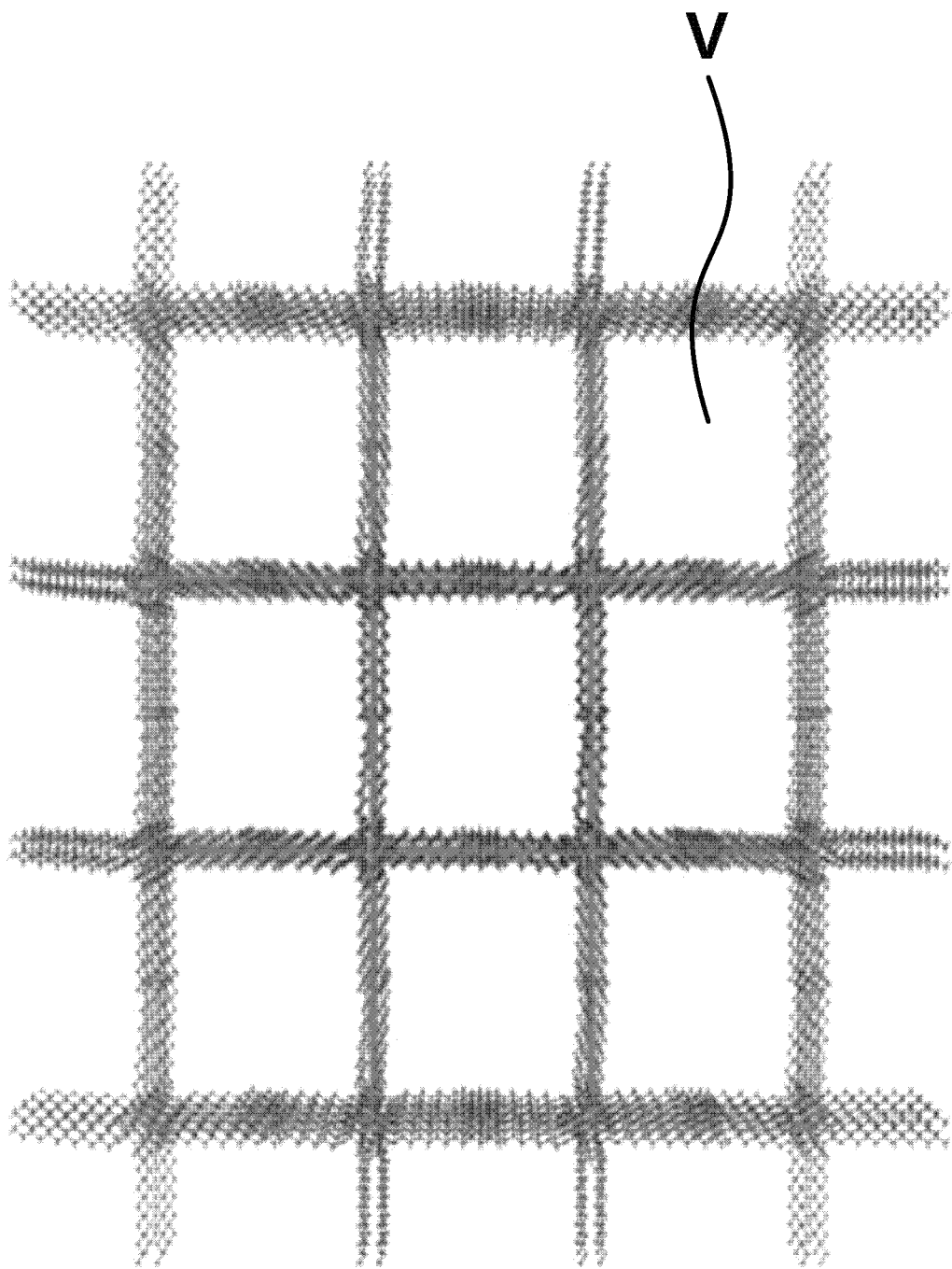

[FIG. 33]
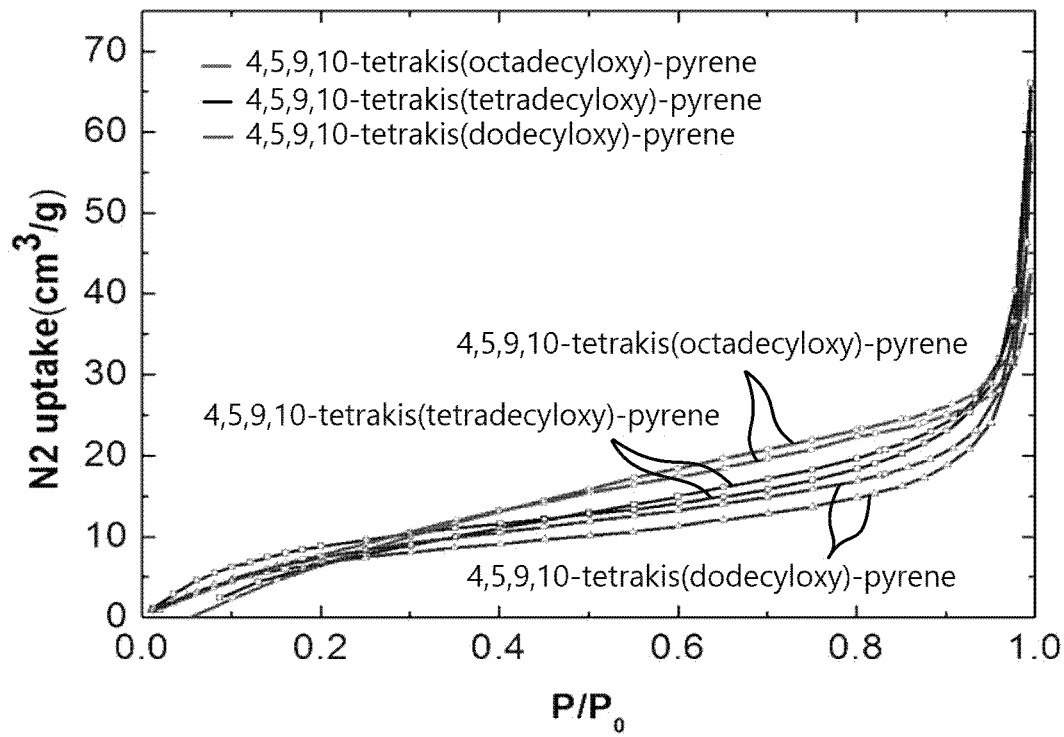
[FIG. 34]
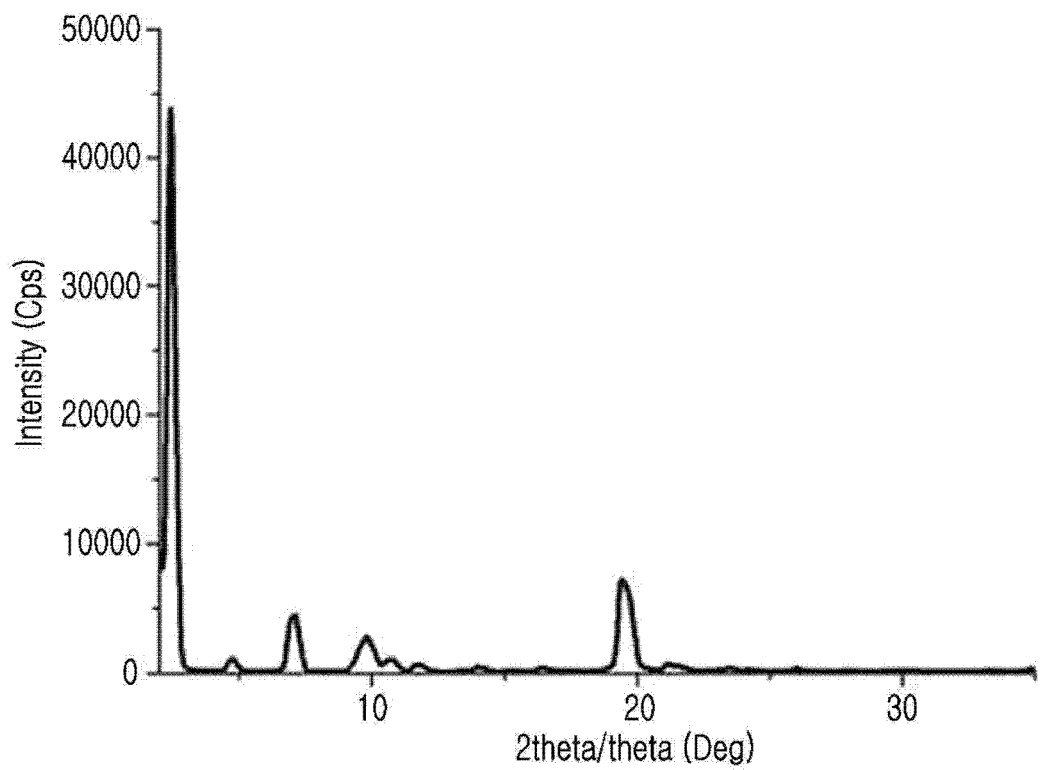

[FIG. 35]
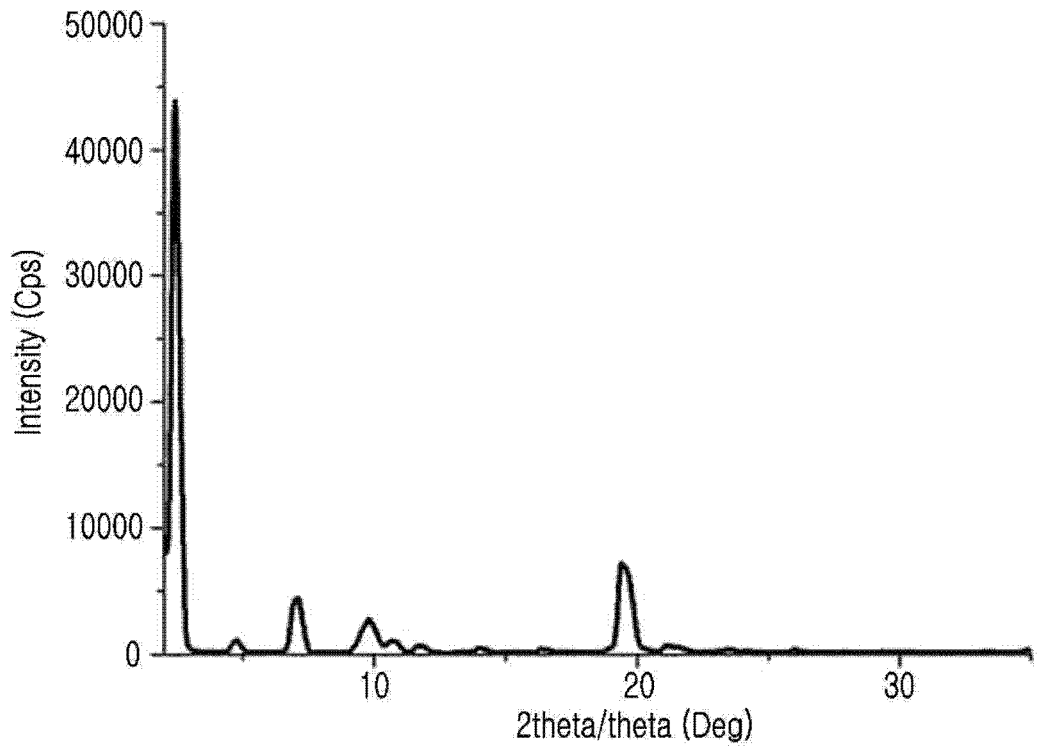
[FIG. 36]
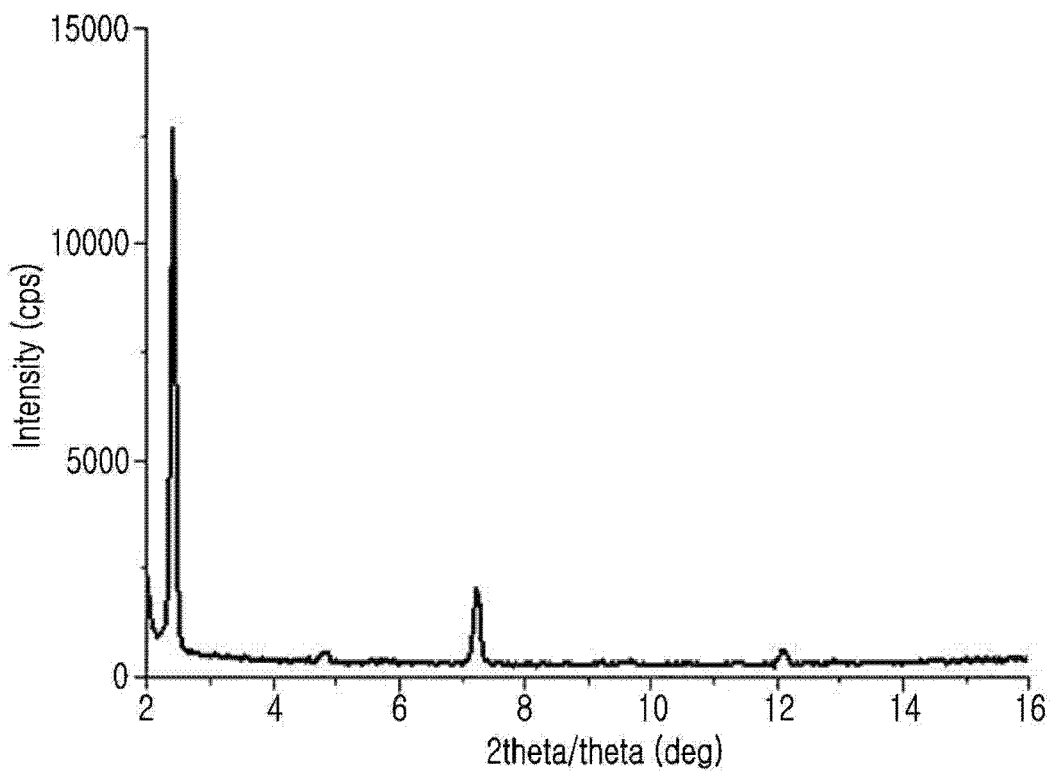

[FIG. 37]
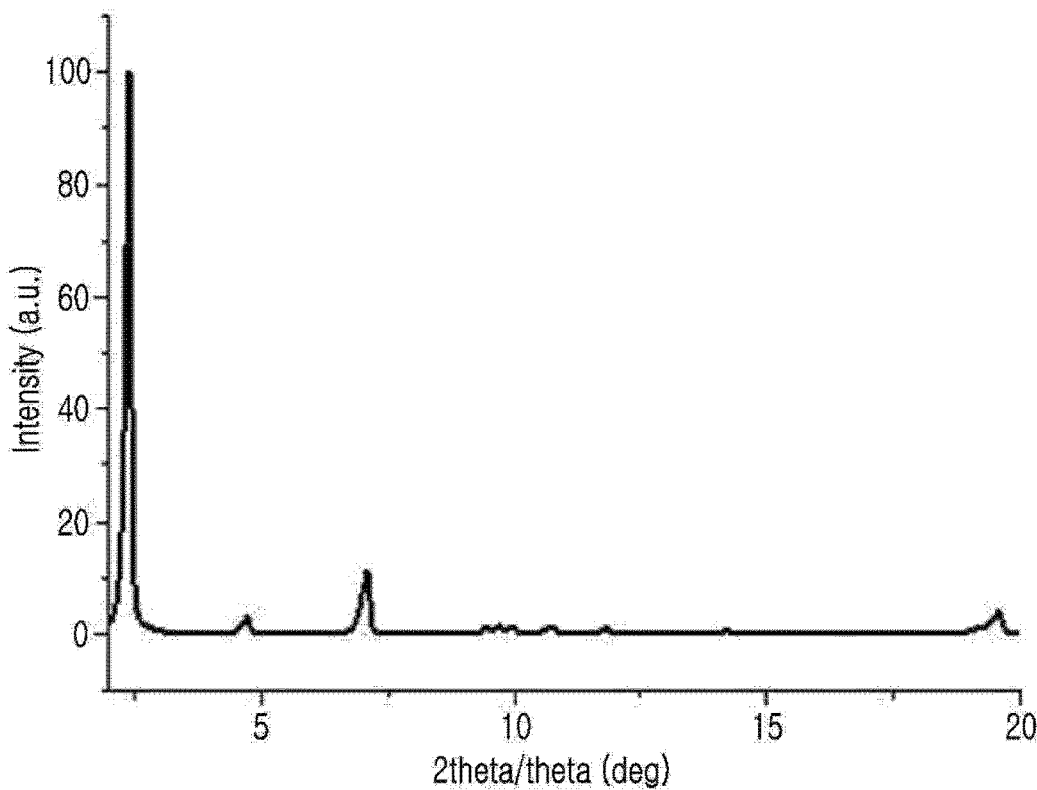
[FIG. 38]
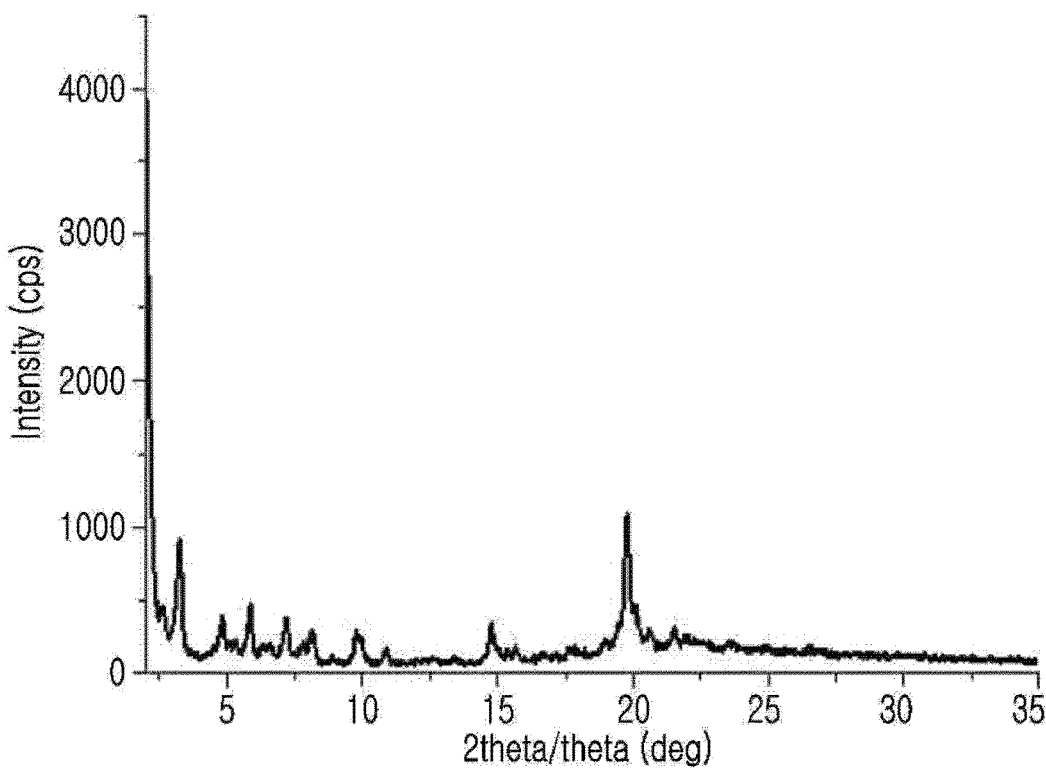

[FIG. 39]
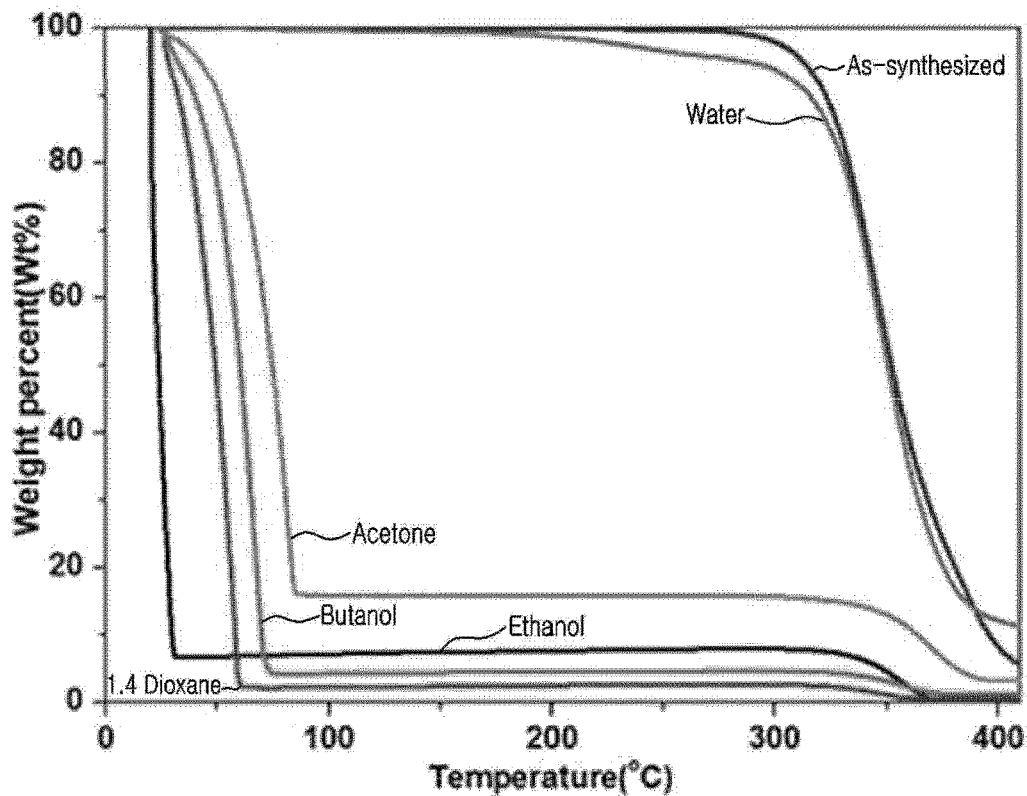
[FIG. 40]
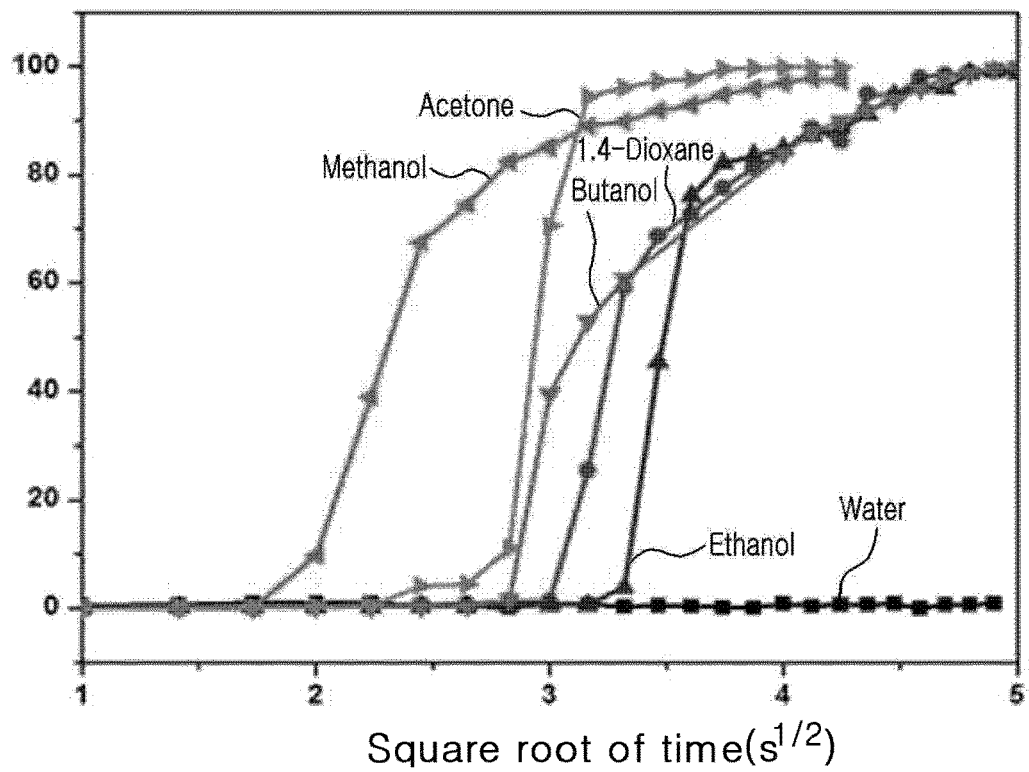

【FIG. 41】
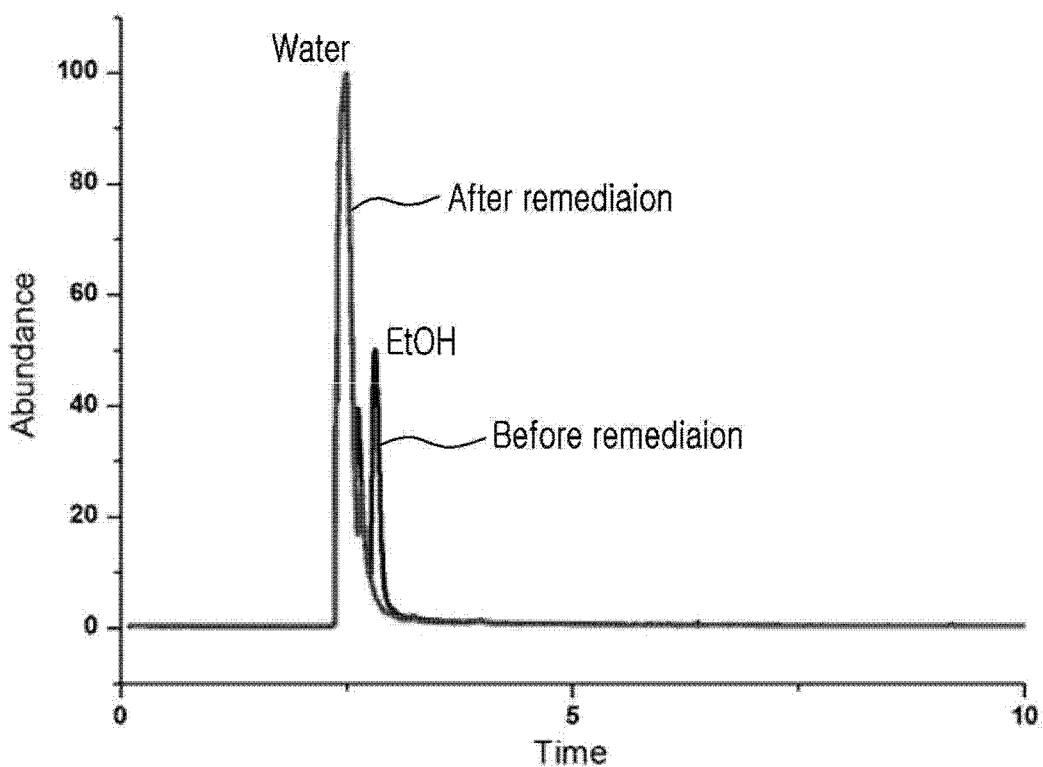
【FIG. 42】
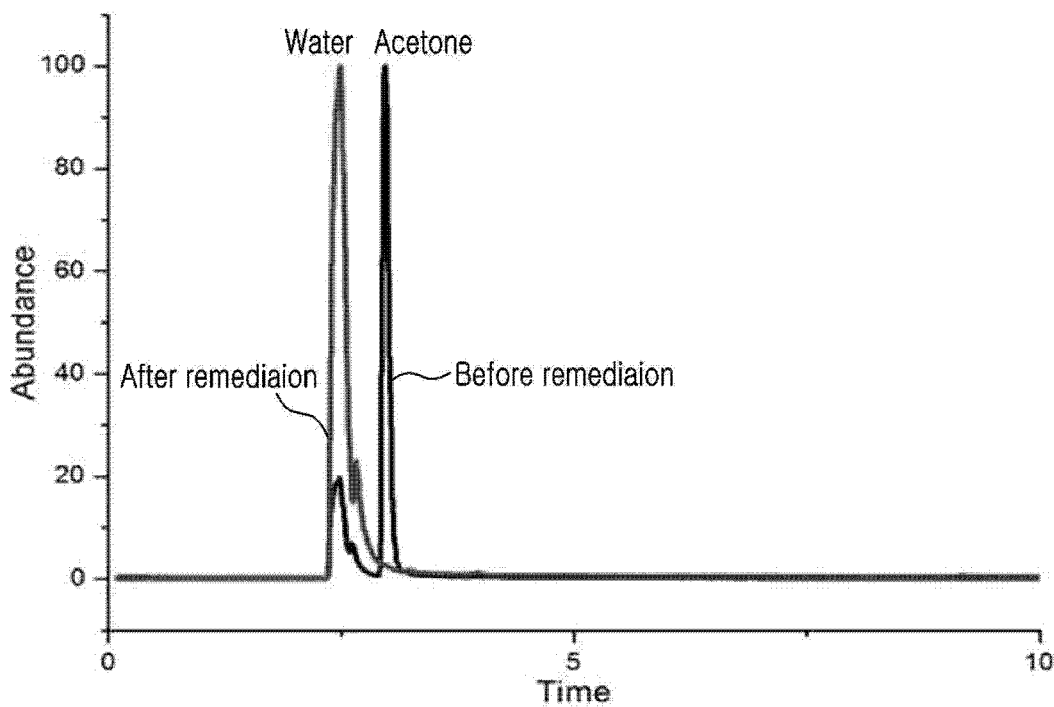

[FIG. 43]
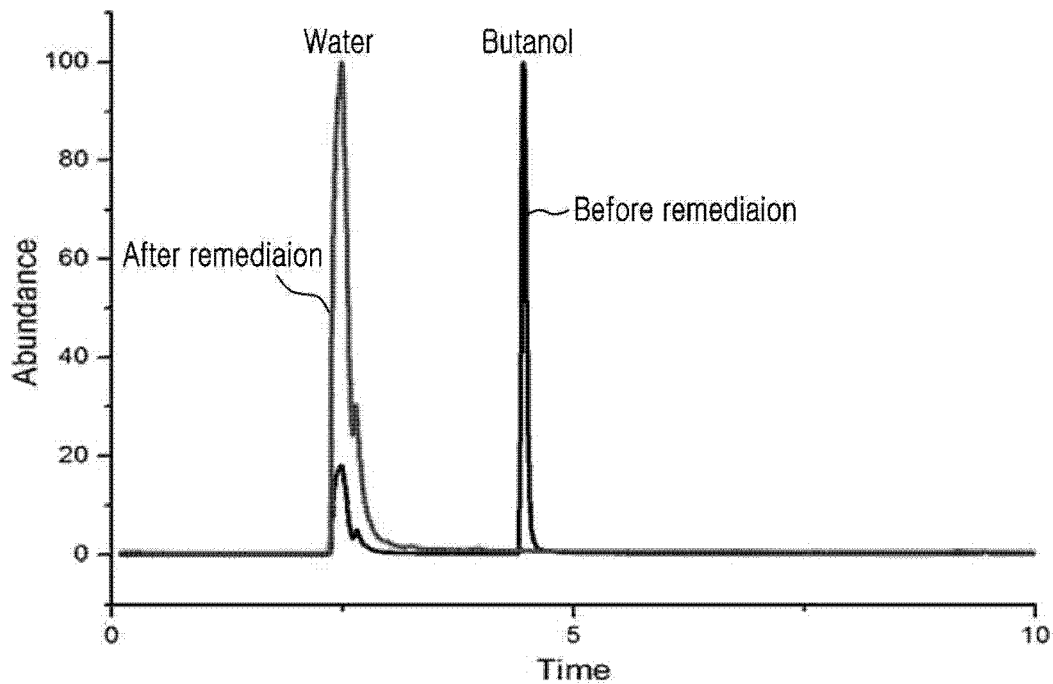
[FIG. 44]
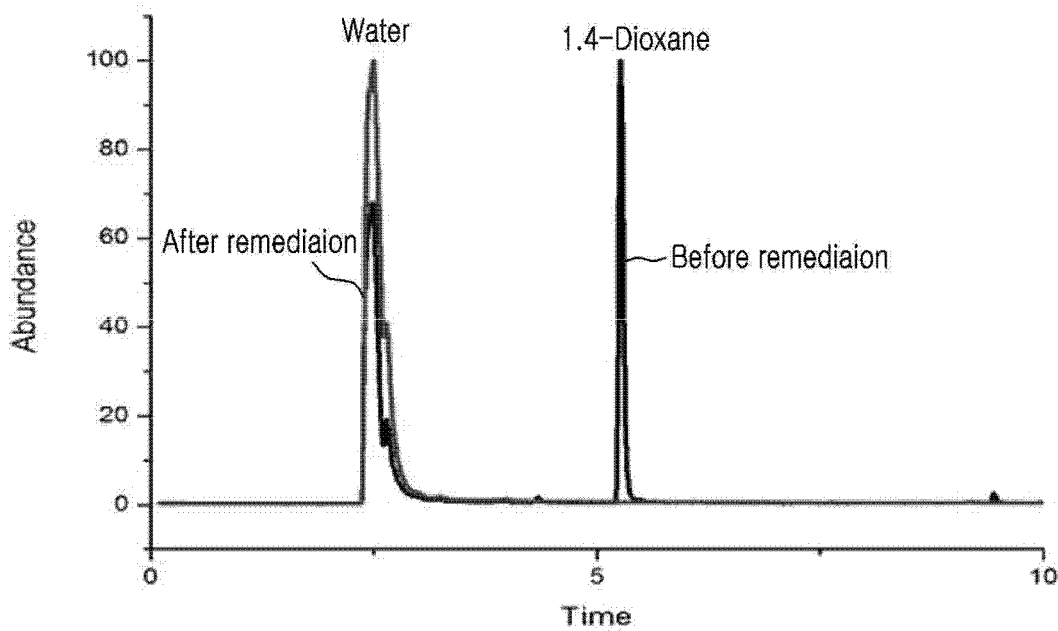

【FIG. 45】
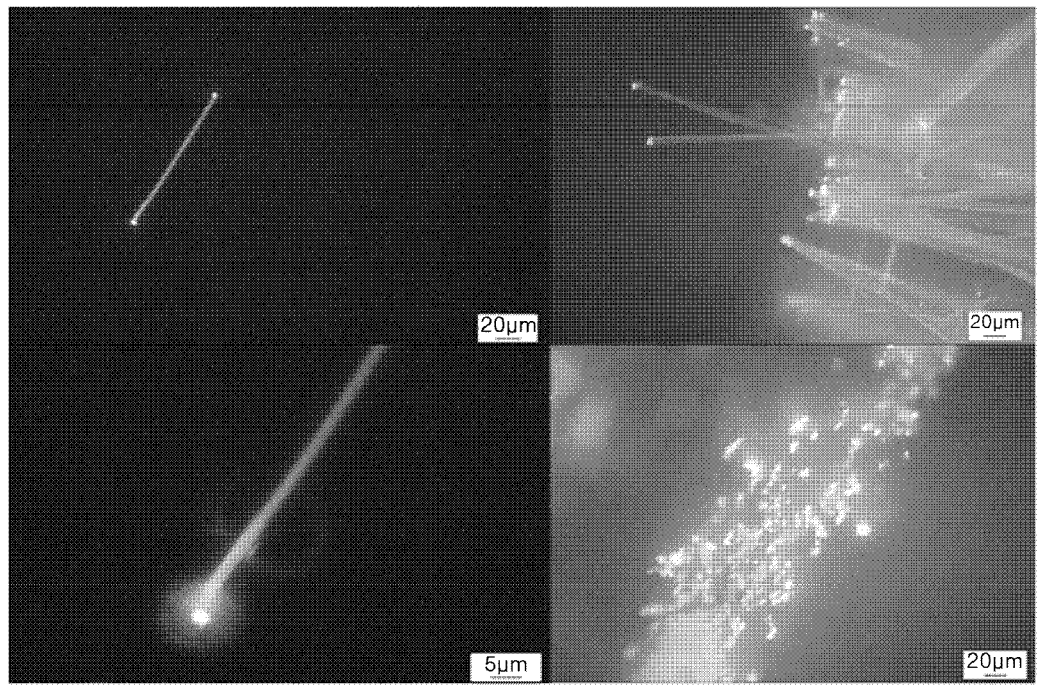
【FIG. 46】
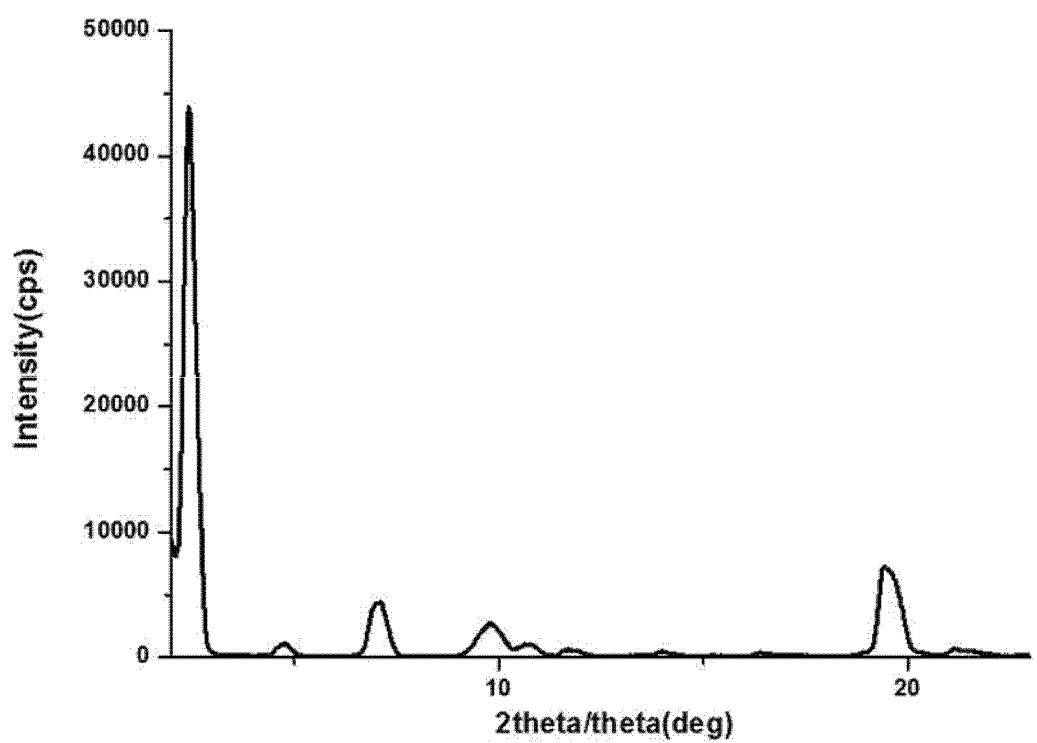

[FIG. 47A]
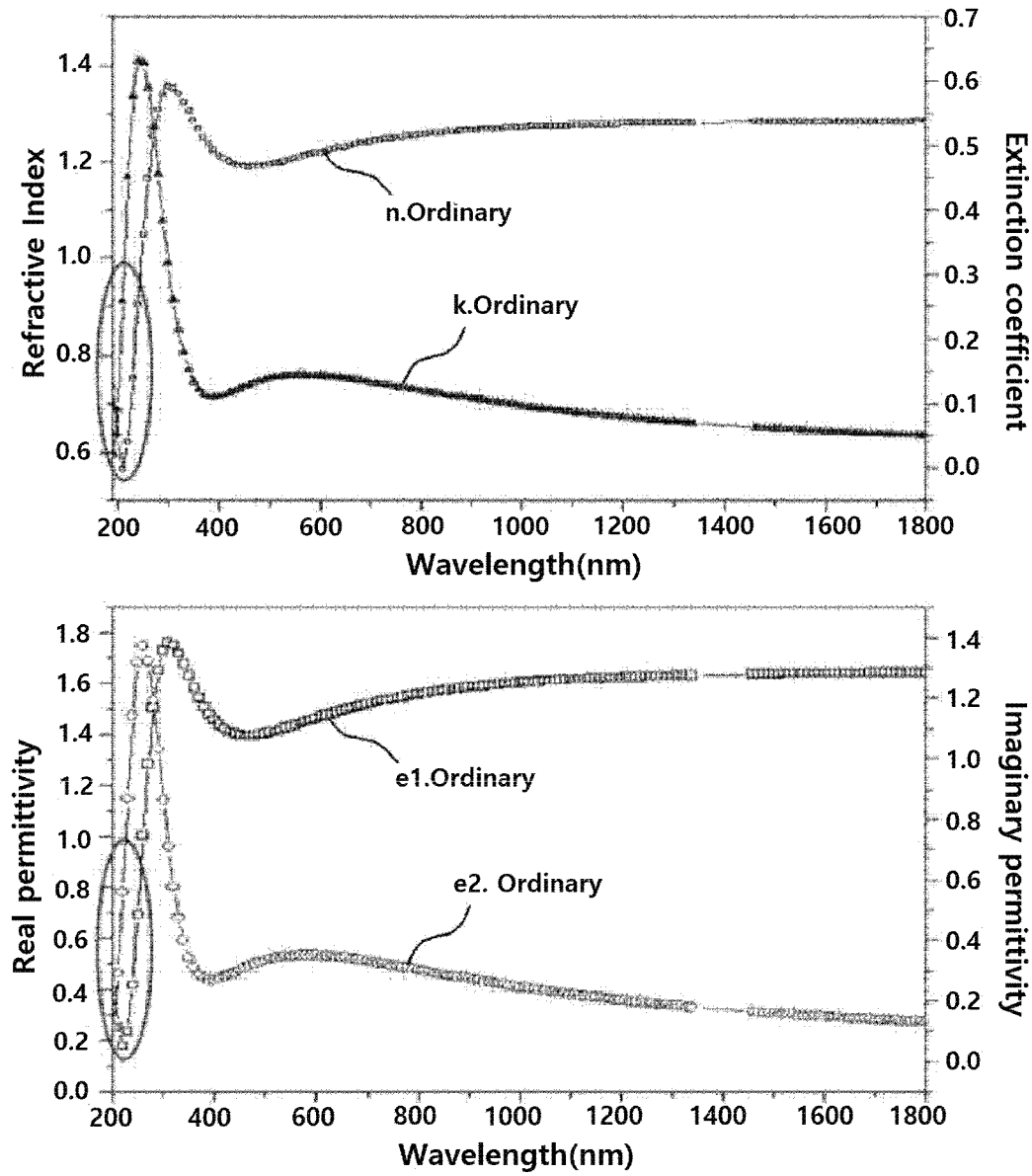

[FIG. 47B]
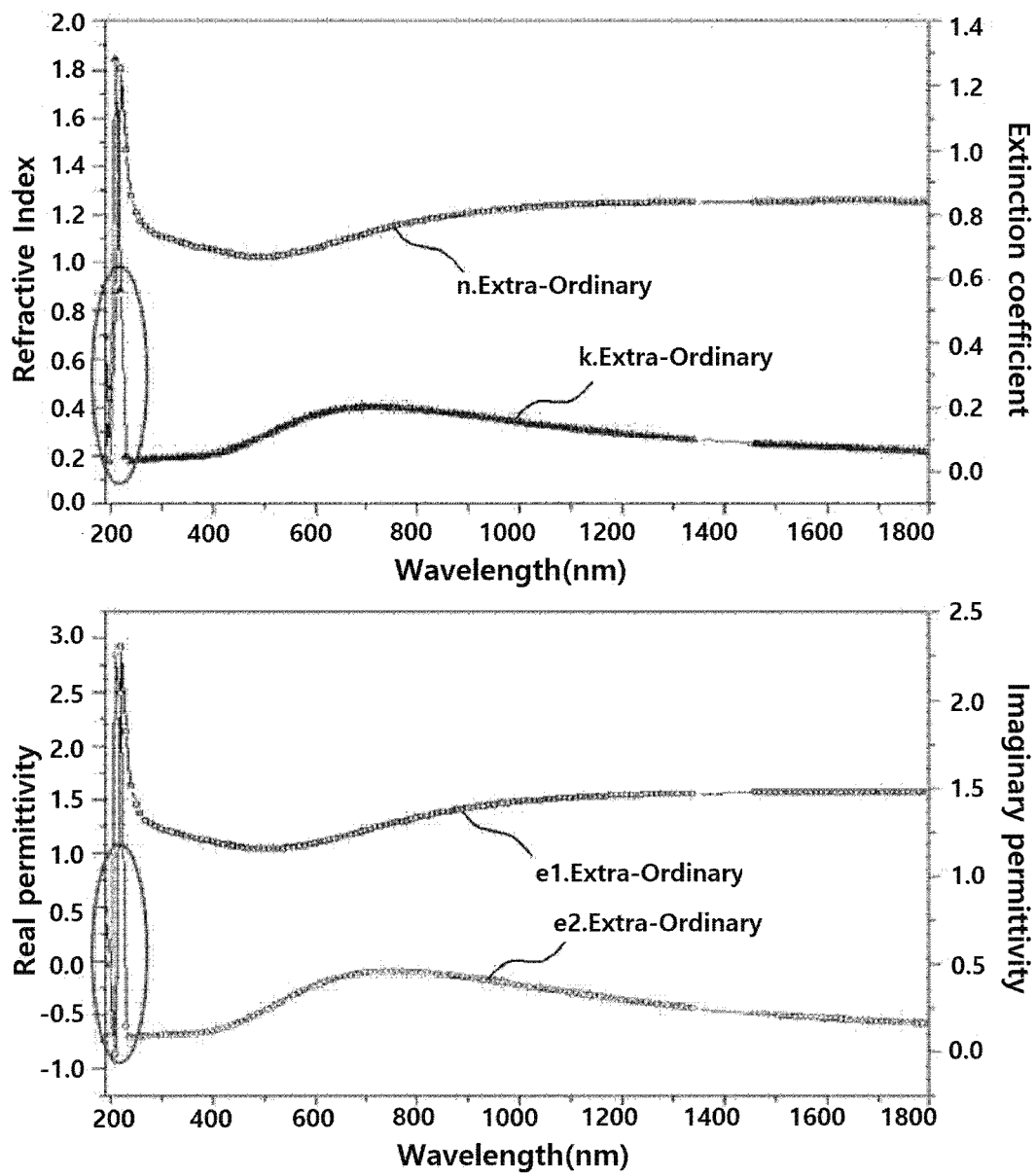

[FIG. 48]
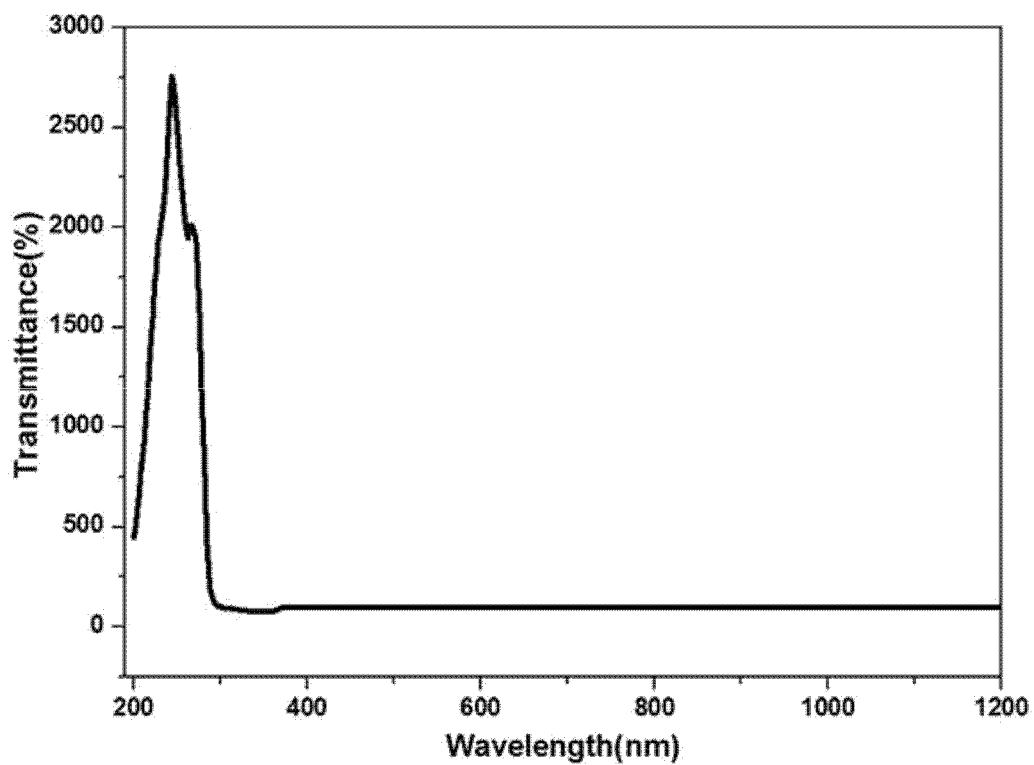
[FIG. 49]
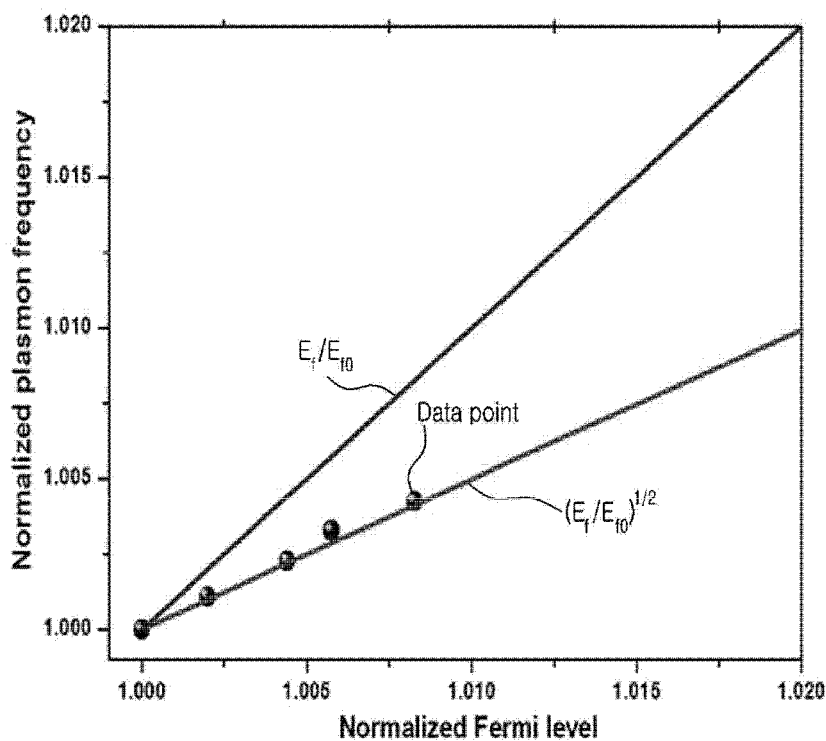

[FIG. 50]
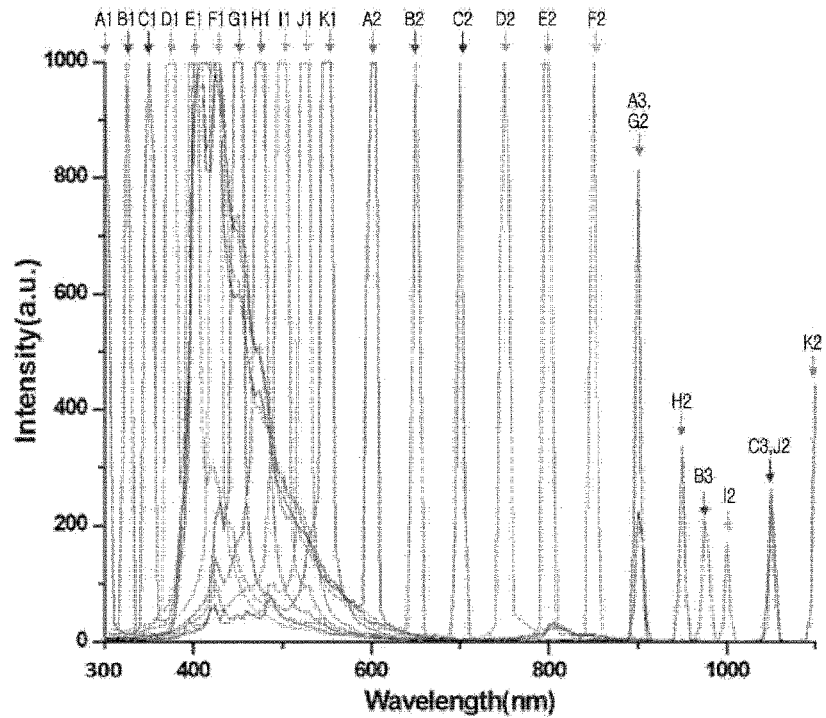
[FIG. 51]
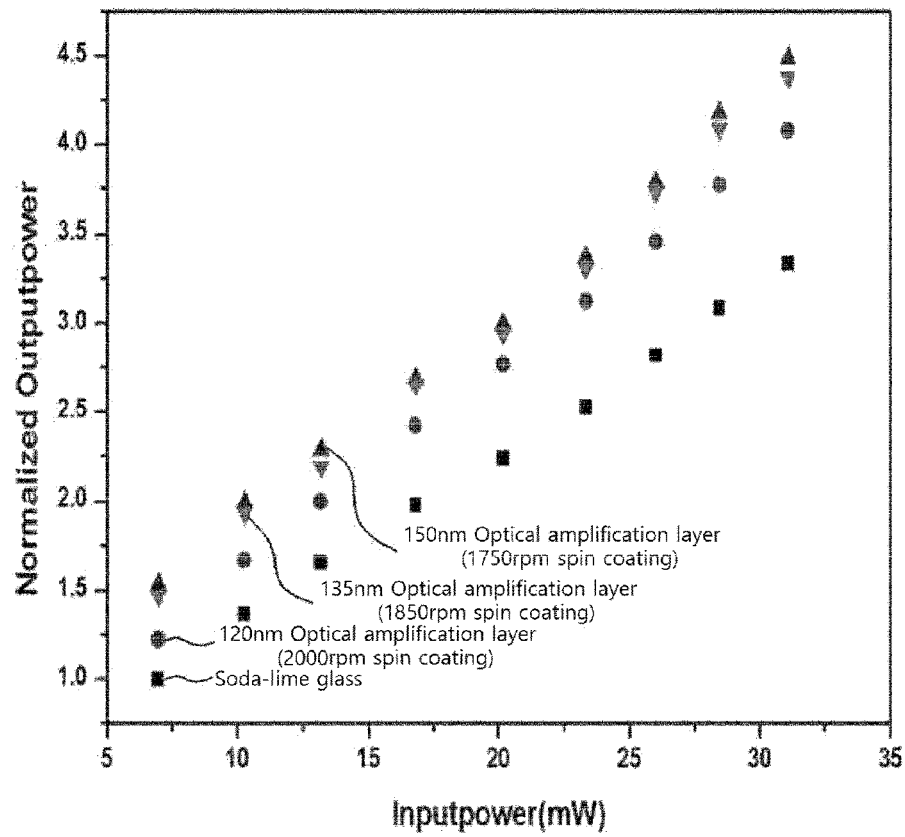

ORGANIC COMPOUND, THREE-DIMENSIONAL ORGANIC FRAMEWORK FORMED BY USING ORGANIC COMPOUND, SEPARATION SIEVE AND OPTICAL LAYER, WHICH COMPRISE ORGANIC FRAMEWORK, AND OPTICAL DEVICE COMPRISING OPTICAL LAYER AS OPTICAL AMPLIFICATION LAYER

CROSS REFERENCE TO RELATED APPLICATIONS

This application is a National Stage of International Application No. PCT/KR2017/000803, filed Jan. 24, 2017, claim priorities based on Korean Patent Application Nos. 10-2016-0011018, filed Jan. 28, 2016, 10-2016-0056767, filed May 10, 2016 and 10-2016-0061682, filed May 19, 2016.

TECHNICAL FIELD

The present invention relates to a three-dimensional porous structure, and more particularly, to a three-dimensional porous organic structure formed using an organic compound.

BACKGROUND ART

Zeolite is a generic term for crystalline aluminosilicates, and Zeolites, which have been obtained from nature and used as water softeners for a long time. However, in the 1950s, a zeolite having a structure different from that of a natural product was formed from an alkaline reactant through a hydrothermal reaction, and research on its industrial use has become active. Furthermore, as the crystal structure of the zeolite has been revealed and it has been found that molecules of different sizes can be selectively adsorbed according to the pore size of the zeolite, much research on the zeolite has been made in the field of adsorbents and catalysts.

Due to the various advantages of the microporous material, various studies on zeolite synthesis (International Journal of Mineral Processing 64.1 (2002): 1-17) and control of micropore size (Occelli, Mario L., and Harry E. Robson. "Zeolite synthesis." (1989)) have been carried out, and studies on organic structures with similar properties have progressed rapidly, the most representative of which is a Metal Organic Framework (MOF) (Nature 402.6759 (1999): 276-279).

The MOF is a structure that connects a variety of organic ligands through coordination by setting transition metal ions or metal clusters as the center of three-dimensional structure formation. However, such MOF is vulnerable to moisture due to the presence of a metal, and thus has a disadvantage that the three-dimensional structure collapses rapidly when exposed to air.

Further, such MOF cannot be used as a separation sieve in an aqueous environment.

DISCLOSURE

Technical Problem

The present invention is directed to providing an organic compound which is stable in water and air and which can be dissolved or melted if necessary and which can form a porous structure again after dissolution or melting, and a three-dimensional organic framework formed using the organic compound.

Another object of the present invention is to provide a separation sieve which is sufficiently stable in a water-based environment and can exhibit high resolution.

Another object of the present invention is to provide a layer which is transparent and has a dielectric constant close to zero using an organic material other than a metal or an inorganic semiconductor and enables optical amplification through a plasmon by a Dirac electron as a topological insulator.

Technical Solution

According to an aspect of the present invention, an embodiment of an organic compound is provided. The organic compound is represented by the following Chemical Formula 1:

[Chemical Formula 1]

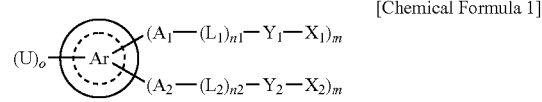

In Chemical Formula 1,

Ar is a 6- to 46-membered homocyclic aromatic ring or heterocyclic aromatic ring, $-A_1-(L_1)_{n1}-Y_1-X_1$ and $-A_2-(L_2)_{n2}-Y_2-X_2$ are bonded to immediately adjacent positions among the substitution positions of Ar, m is an integer of 1 to 8, $A_1$ and $A_2$ are, independently of each other, —O— or —S—, $L_1$ and $L_2$ are, independently of each other,

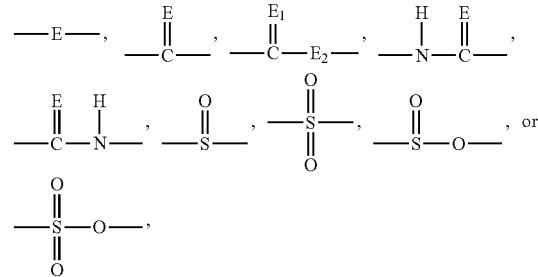

E, $E_1$, and $E_2$ are, independently of each other, O or S, $n_1$ and $n_2$ are, independently of each other, 0 or 1, $Y_1$ and $Y_2$ are, independently of each other,

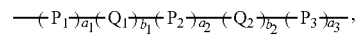

$a_1$, $a_2$, $a_3$, $b_1$, and $b_2$ are, independently of each other, integers of 0 to 30, and $a_1+a_2+a_3+b_1+b_2$ is an integer of 3 to 30, $P_1$, $P_2$, and $P_3$ are, independently of each other, $-CR_aR_b-$ or $-(CR_aR_b)_rO-$, r is an integer of 1 to 3, $Q_1$ and $Q_2$ are, independently of each other, $q_1-(p_1)_{c1}-q_2-(p_2)_{c2}-q_3$, $q_1$ and $q_3$ are, independently of each other, —O— or —S—, $q_2$ is —CH=CH—, —C≡C—, —N=N—,

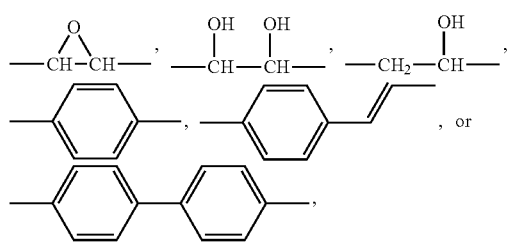

in which the hydrogen group bonded to the carbon is substituted with F, Cl, Br, or I, or unsubstituted, $p_1$ and $p_2$ are, independently of each other, $-CR_aR_b-$, $c_1$ and $c_2$ are, independently of each other, an integer of 0 to 2, $X_1$ and $X_2$ are, independently of each other, $-CR_cR_dR_e$, $-OH$, $-COOH$, $-CHO$, $-SH$, $-COCR_cR_dR_e$, $-COOCR_cR_dR_e$, $-CR_c=CR_dR_e$, $-CN$, $-N=C=O$, $-C=N=N-CR_cR_dR_e$, $-C\equiv CR_a$, $-NHCR_cR_dR_e$, or $-NH_2$, $R_a$ and $R_b$ are, independently of each other, H, F, Cl, Br, or I $R_c$, $R_d$, and $R_e$ are, independently of each other, H, F, Cl, Br, or I, U is one selected from the group consisting of a cyano group, a hydroxyl group, fluorine, chlorine, iodine, a substituted or unsubstituted alkyl group having 1 to 15 carbon atoms, a substituted or unsubstituted alkoxy group having 1 to 15 carbon atoms, a substituted or unsubstituted cycloalkyl group having 3 to 15 carbon atoms, a substituted or unsubstituted alkenyl group having 2 to 15 carbon atoms, a substituted or unsubstituted alkynyl group having 2 to 15 carbon atoms, a substituted or unsubstituted aryl group having 5 to 15 carbon atoms, a substituted or unsubstituted heteroaryl group having 2 to 15 carbon atoms, a substituted or unsubstituted arylalkyl group having 1 to 15 carbon atoms, a substituted or unsubstituted alkylsulfone group having 1 to 15 carbon atoms, a substituted or unsubstituted alkylmercapto group having 1 to 15 carbon atoms, a substituted or unsubstituted alkylthiocyanate group having 1 to 15 carbon atoms, a substituted or unsubstituted alkylphosphate group having 1 or 15 carbon atoms, a substituted or unsubstituted alkylnitro group having 1 or 15 carbon atoms, a substituted or unsubstituted alkylnitroso group having 1 or 15 carbon atoms, a substituted or unsubstituted alkylnitrile group having 1 or 15 carbon atoms, a substituted or unsubstituted alkylisothiocyanate group having 1 to 15 carbon atoms, a substituted or unsubstituted alkylisocyanate group having 1 to 15 carbon atoms, a substituted or unsubstituted alkylcyanate group having 1 to 15 carbon atoms, a substituted or unsubstituted alkylazo group having 1 to 15 carbon atoms, a substituted or unsubstituted alkylazide group having 1 to 15 carbon atoms, a substituted or unsubstituted ketimine group having 1 to 15 carbon atoms, a substituted or unsubstituted aldimine group having 1 to 15 carbon atoms, a substituted or unsubstituted amide group having 1 to 15 carbon atoms, an arylalkyl group having 6 to 24 carbon atoms, an heteroaryl group having 2 to 24 carbon atoms, an arylamino group having 3 to 24 carbon atoms, an arylsilyl group having 3 to 24 carbon atoms, an aryloxy group having 3 to 24 carbon atoms, an alkylsilyl group having 1 to 24 carbon atoms, and an alkylamino group having 1 to 24 carbon atoms, o is an integer between 0 and 16.

According to an another aspect of the present invention, an embodiment of a three-dimensional organic structure is provided. The three-dimensional organic structure has a plurality of unit organic molecules forming the three-dimensional structure. Each of the unit organic molecules has an aromatic ring, a first pair of substituents being connected to immediately adjacent positions of substitutable positions of the aromatic ring, and a second pair of substituents being connected to immediately adjacent positions of remaining substitutable positions of the aromatic ring. Terminal groups of the substituents independently include a group selected from the group consisting of $-CR_cR_dR_e$, $-OH$, $-COOH$, $-CHO$, $-SH$, $-COCR_cR_dR_e$, $-COOCR_cR_dR_e$, $-CR_c=CR_dR_e$, $-CN$, $-N=C=O$, $-C=N=N-CR_cR_dR_e$, $-C\equiv CR_a$, $-NHCR_cR_dR_e$, or $-NH_2$. The unit organic molecules contained in one layer of the three-dimensional structure are self-assembled by van der Waals interaction, London dispersion interaction or hydrogen bonding between the terminal groups of the first pair of the substituents included in one unit organic molecule and the terminal groups the second pair of the substituent groups included in another unit organic molecule among the unit organic molecules. The unit organic molecules contained in one layer and the unit organic molecules contained in another adjacent layer of the three-dimensional structure are self-assembled by pi-pi interactions between the aromatic rings.

According to another aspect of the present invention, there is provided a separation sieve. The separation sieve includes the three-dimensional organic structure. The separation sieve may be in the form of a pellet or a film. The separation sieve may further include a polymer. The mixed liquid may be an azeotropic mixture. The first liquid may be water.

According to another aspect of the present invention, an optical layer is provided. The optical layer includes the three-dimensional organic structure.

The optical layer may be provided in an optical device as an optical amplification layer, and may be disposed on an optical path of the optical device. The optical device may be a light emitting element having a light emitting layer, and the optical amplification layer may be disposed between the light emitting layer and the outside. The optical device may be a solar cell having a light absorbing layer, and the optical amplification layer may be disposed between the light absorbing layer and the outside. The optical device may be a display having a light emitting layer or a light emitting device, and the optical amplification layer may be disposed between the light emitting layer or the light emitting device and the outside. The optical device is an illuminating device having a light emitting layer or a light emitting device, and the optical amplification layer may be disposed between the light emitting layer or the light emitting device and the outside. The optical layer may be included on the optical path of the super lens or the variable wavelength optical amplifier.

Advantageous Effects

Such a porous three-dimensional organic structure, that is, a porous organic crystal is formed by self-assembling based on non-covalent bonding between unit organic molecules, so that a structure having a large void volume and a completely regular and periodic structure can be easily and simply formed.

In addition, since it is formed only by physical interaction or physical bonding between compounds without chemical cross-linking, melting and dissolving are possible at any time and coating is possible in a melted or dissolved state, and after melting and dissolution, three-dimensional structure can be reformed.

In addition, unlike metal organic frameworks (MOF), metal is not used, so structural characteristics can be maintained even in moisture and atmospheric environment.

Unlike a metal organic framework (MOF), a separation sieve containing a porous three-dimensional organic structure, i.e., a porous organic crystal, can be used in a water-based environment because it does not use a metal. Due to the large void volume and the perfectly regular and periodic structure thereof, it is possible to effectively separate even the azeotropic mixture which has been difficult to separate.

Meanwhile, an optical layer containing a porous three-dimensional organic structure, that is, a porous organic crystal uses an organic material that does not have a metal or is not an inorganic semiconductor; is transparent; exhibits a dielectric constant close to 0; and exhibits optical amplification through a plasmon by a Dirac electron as a topological insulator.

However, effects of the present invention are not limited to the above-described effects and other unmentioned effects may be clearly understood by those skilled in the art from the following descriptions.

DESCRIPTION OF DRAWINGS

Example embodiments of the present invention will become more apparent by describing in detail example embodiments of the present invention with reference to the accompanying drawings, in which:

FIG. 1 is a schematic view of a self-assembled three-dimensional organic structure according to an embodiment of the present invention;

FIG. 2 is a schematic diagram illustrating a correlation between a separation sieve according to an embodiment of the present invention and an absorbable or adsorbable fluid using Hansen space;

FIG. 3 is a cross-sectional view illustrating a light emitting diode having an optical amplification layer according to an embodiment of the present invention;

FIG. 4 is a cross-sectional view illustrating an organic light emitting diode having an optical amplification layer according to an embodiment of the present invention;

FIG. 5 is a cross-sectional view illustrating a liquid crystal display having an optical amplification layer according to an embodiment of the present invention;

FIG. 6 is a cross-sectional view of a solar cell having an optical amplification layer according to an embodiment of the present invention;

FIG. 7 is a cross-sectional view of a dye-sensitized solar cell having an optical amplification layer according to an embodiment of the present invention;

FIG. 8 is a $^1$H-NMR spectrum of 4,5,9,10-tetrakis(dodecyloxy)-pyrene according to Preparation Example 1A measured in a CDCl$_3$ solvent;

FIG. 9 is a $^1$H-NMR spectrum of 4,5,9,10-tetrakis(tetradecyloxy)-pyrene according to Preparation Example 1B measured in a CDCl$_3$ solvent;

FIG. 10 is a $^1$H-NMR spectrum of 4,5,9,10-tetrakis(octadecyloxy)-pyrene according to Preparation Example 1C measured in a CDCl$_3$ solvent;

FIG. 11 is a $^1$H-NMR spectrum of 4,5-bis(dodecyloxy)-pyrene according to Preparation Example 1D measured in a CDCl$_3$ solvent;

FIG. 12 is a $^1$H-NMR spectrum of 4,5-bis(dodecyloxy)-pyrene-9,10-dione according to Preparation Example 1E measured in a DMSO-d6 solvent;

FIG. 13 is a $^1$H-NMR spectrum of 2,3,6,7-tetrakis(dodecyloxy)anthracene according to Preparation Example 2A measured in a CDCl$_3$ solvent;

FIG. 14 is a $^1$H-NMR spectrum of 2,3-bis(dodecyloxy) anthracene according to Preparation Example 2B measured in a CDCl$_3$ solvent;

FIG. 15 is a $^1$H-NMR spectrum of 2,3-bis(dodecyloxy) anthracene-6,7-dione according to Preparation Example 2B measured in a CDCl$_3$ solvent;

FIG. 16 is a $^1$H-NMR spectrum of 1,2,7,8-tetrakis(dodecyloxy)coronene according to Preparation Example 3A measured in a CDCl$_3$ solvent;

FIG. 17 is a $^1$H-NMR spectrum of 1,2-bis(dodecyloxy) coronene according to Preparation Example 3B measured in a CDCl$_3$ solvent;

FIG. 18 is a $^1$H-NMR spectrum of 7,8-bis(dodecyloxy) coronene-1,2-dione according to Preparation Example 3C measured in a CDCl$_3$ solvent;

FIG. 19 is a $^1$H-NMR spectrum of 1,2,5,6-tetrakis(dodecyloxy) cyclopenta[fg]acenaphthylene according to Preparation Example 4A measured in a CDCl$_3$ solvent;

FIG. 20 is a $^1$H-NMR spectrum of 1,2-bis(dodecyloxy) cyclopenta[fg] acenaphthalene according to Preparation Example 4B measured in a CDCl$_3$ solvent;

FIG. 21 is a $^1$H-NMR spectrum of 5,6-bis (dodecyloxy) cyclopenta [fg] acenaphthylene-1,2-dione according to Preparation Example 4C measured in a CDCl$_3$ solvent;

FIG. 22 is a $^1$H-NMR spectrum of 2,3,6,7,10,11-hexakis (dodecyloxy) triphenylene according to Preparation Example 5A measured in a CDCl$_3$ solvent;

FIG. 23 is a $^1$H-NMR spectrum of Compound 151 according to Preparation Example 15A measured in a CDCl$_3$ solvent;

FIG. 24 is a $^1$H-NMR spectrum of Compound 152 according to Preparation Example 15B measured in a CDCl$_3$ solvent;

FIG. 25 is a $^1$H-NMR spectrum of Compound 153 according to Preparation Example 15C measured in a CDCl$_3$ solvent;

FIGS. 26A and 26B are optical photographs of 4,5,9,10-tetrakis(dodecyloxy)-pyrene (compound 11) crystals according to a preparation example of the compound;

FIG. 27 shows the X-ray spectrum of the three-dimensional structure crystal by 4,5,9,10-tetrakis(dodecyloxy)-pyrene (compound 11) according to the preparation example of the compound;

FIG. 28 shows the X-ray spectrum of a three-dimensional structure crystal formed by 2,3,6,7-tetrakis(dodecyloxy)anthracene (Compound 21) according to the preparation example of the compound;

FIG. 29 shows the X-ray spectrum of a three-dimensional structure crystal by 1,2,7,8-tetrakis(dodecyloxy)coronene (Compound 31) according to the preparation example of the compound;

FIG. 30 shows the X-ray spectrum of a three-dimensional structure crystal by 1,2,5,6-tetrakis(dodecyloxy)cyclopenta [f,g]acenaphthalene (Compound 41) according to the preparation example of the compound;

FIG. 31 shows the X-ray spectrum of a three-dimensional structure crystal by 2,3,6,7,10,11-hexakis(dodecyloxy)triphenylene (Compound 51) according to the preparation example of the compound;

FIGS. 32A and 32B are a perspective view and a top view, respectively, of the crystal structure of 4,5,9,10-tetrakis (dodecyloxy)-pyrene deduced from the X-ray spectrum of FIG. 27;

FIG. 33 is a nitrogen isotherm adsorption-desorption graph of 4,5,9,10-tetrakis(dodecyloxy)-pyrene crystal, 4,5, 9,10-tetrakis(tetradecyloxy)-pyrene crystal, and 4,5,9,10-tetrakis(octadecyloxy)-pyrene crystal;

FIG. 34 shows an X-ray spectrum of a separation sieve obtained by pelletizing 4,5,9,10-tetrakis(dodecyloxy)-pyrene (compound 11) according to Separation sieve Preparation Example 1;

FIG. 35 shows an X-ray spectrum of a separation sieve obtained by packaging 4,5,9,10-tetrakis(dodecyloxy)-pyrene (compound 11) according to Separation sieve Preparation Example 4;

FIG. 36 shows an X-ray spectrum of a film type separation sieve formed by spin coating a homogeneous solution of 4,5,9,10-tetrakis(dodecyloxy)-pyrene (compound 11) according to Separation sieve Preparation Example 6;

FIG. 37 shows an X-ray spectrum of the film type separation sieve formed by spin-coating a homogeneous solution of 4,5,9,10-tetrakis(dodecyloxy)-pyrene (compound 11) and PMMA according to Separation sieve Preparation Example 10;

FIG. 38 shows an X-ray spectrum of a separation sieve obtained by packaging 2,3,6,7,10,11-hexakis(dodecyloxy) triphenylene (compound 51) according to Separation sieve Preparation Example 11;

FIG. 39 is a graph showing a change in weight of a separation sieve formed according to Separation sieve Preparation Example 1 carrying different solvents according to temperature;

FIG. 40 is a graph showing edge wettability of the separation sieve formed according to Separation sieve Preparation Example 1 for different solvents;

FIG. 41 is a graph showing the resolving power of the separation sieve formed according to Separation sieve Preparation Example 1 for a mixed solution of water and ethanol using gas chromatography;

FIG. 42 is a graph showing the resolving power of the separation sieve formed according to Separation sieve Preparation Example 1 for a mixed solution of water and acetone using gas chromatography;

FIG. 43 is a graph showing the resolving power of the separation sieve formed according to Separation sieve Preparation Example 1 for a mixed solution of water and butanol using gas chromatography;

FIG. 44 is a graph showing the resolving power of the separation sieve formed according to Separation sieve Preparation Example 1 for a mixed solution of water and 1,4-dioxane using gas chromatography;

FIG. 45 is a photograph of the 4,5,9,10-tetrakis(dodecyloxy)-pyrene (compound 11) crystal according to Compound Preparation Example irradiated with light;

FIG. 46 shows the X-ray spectrum of the optical amplification layer obtained in the light-emitting device preparation example 1 having the optical amplification layer;

FIG. 47A is a graph showing a refractive index and permittivity at an ordinary axis of an optical amplification layer according to an embodiment of the present invention, and FIG. 47B is a graph showing a refractive index and permittivity at an extra-ordinary axis of an optical amplification layer according to an embodiment of the present invention;

FIG. 48 is a graph showing light transmittance of an optical amplification layer according to an embodiment of the present invention;

FIG. 49 is a graph showing the relationship between the normalized Fermi level and the normalized plasmon frequency of the optical amplification layer according to the optical amplification layer preparation example;

FIG. 50 is a graph showing the photoluminescence intensity of the optical amplification layer according to an embodiment of the present invention; and FIG. 51 is a graph showing the degree of amplification according to the incident energy of the laser.

MODES OF THE INVENTION

Hereinafter, exemplary embodiments according to the present invention will be described in further detail with reference to the accompanying drawings. However, the present invention can be embodied in various forms without being limited to the embodiments. Like elements are designated by like reference numerals throughout the specification.

In the specification, when the expression "an integer from N to N+X" is used, it should be understood that all integers between N and N+X, that is, N, N+1, N+2 . . . N+X−1, and N+X are should be interpreted as described, where N and X are arbitrary integers.

In the present specification, "alkyl" may refer to an aliphatic hydrocarbon group, unless specified otherwise. The alkyl group may refer to a "saturated alkyl" having no double bonds or triple bonds, or may refer to a "unsaturated alkyl" having at least one double bond or triple bond. The alkyl group, whether saturated or unsaturated, may be branched, straight chain or cyclic.

Hereinafter, exemplary embodiments according to the present invention will be described in further detail.

Organic Compound Forming Three-Dimensional Organic Structure

[Chemical Formula 1]

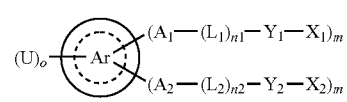

In Chemical Formula 1, Ar may be a 6- to 46-membered aromatic ring, for example a homocyclic aromatic ring in which all members are carbon, or a heterocyclic aromatic ring having at least one of N, P, B or Si. Ar may be a monocyclic aromatic ring consisting of one ring of 6 members, or an aromatic ring having two or more aromatic rings, for example, two to fourteen rings joined together to form a condensed ring, for example, 10 to 46 membered polycyclic aromatic ring.

Specifically, Ar may be any one of the following aromatic rings, but is not limited thereto. Ar may be a benzene-based functional group of Ar1 to Ar16, which comprises a benzene or an aromatic analogues of benzene containing at least one heteroatom as a monocyclic aromatic group; a naphthalene-based functional group of Ar17 to Ar30 comprising a naphthalene or an aromatic analogue of naphthalene containing at least one heteroatom, and having two rings; an anthracene-based functional group of Ar 31 to Ar 45 comprising an anthracene or an aromatic analogue of anthracene containing at least one heteroatom, a phenalene-based functional group of Ar46 to Ar 51 comprising a phenalene or an aromatic analogue of phenalene containing at least one heteroatom, and a phenanthrene-based functional group of Ar 52 to Ar 69 comprising a phenanthrene or an aromatic analogue of phenanthrene containing at least one heteroatom, having three rings; cyclopenta[fg] acenaphthylene-based functional group of Ar70 to Ar71 comprising a cyclopenta[fg] acenaphthylene or an aromatic analogue of cyclopenta[fg] acenaphthylene containing at least one heteroatom, a tetracene-based functional group of Ar 72 to Ar 86 comprising a tetracene or an aromatic analogue of tetracene containing at least one heteroatom, a pyrene-based functional group of Ar 87 to Ar 100 comprising a pyrene or an aromatic analogue of pyrene containing at least one hetero atom, benz[de]anthracene-based functional group of Ar101 to Ar115 comprising a benz[de]anthracene or an aromatic analogue of a benz[de]anthracene containing at least one heteroatom, and a triphenylene-based functional group of Ar116 to Ar130 comprising a triphenylene or an aromatic analogue of triphenylene containing at least one heteroatom, having four rings; a pentacene-based functional group of Ar131 to Ar140 comprising a pentacene or an aromatic analogue of pentacene containing at least one heteroatom, having five rings; a coronene-based functional group of Ar141 to Ar148 comprising a coronene or an aromatic analogue of coronene containing at least one heteroatom, having 6 peri-fused rings; or Ar149 to Ar152 having 7 or more rings.

Ar1

Ar2

Ar3

Ar4

Ar5

Ar6

Ar7

Ar8

Ar9
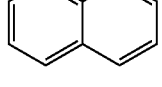

Ar10
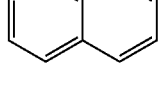

Ar11
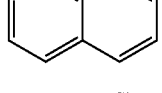

Ar12
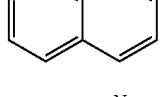

Ar13
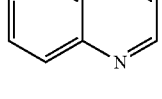

Ar14

Ar15

Ar16

Ar17
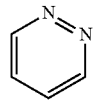

Ar18

Ar19

Ar20
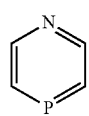

Ar21

Ar22

-continued
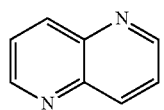  Ar23
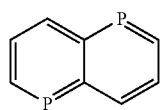  Ar24
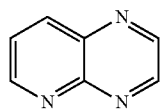  Ar25
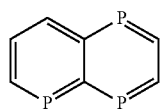  Ar26
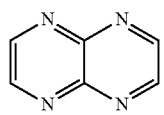  Ar27
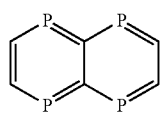  Ar28
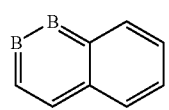  Ar29
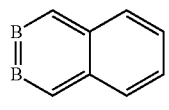  Ar30
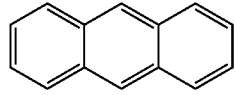  Ar31
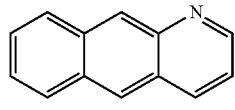  Ar32
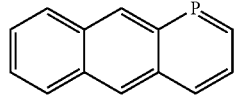  Ar33
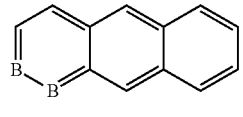  Ar34
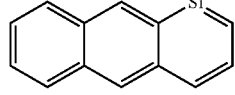  Ar35
-continued
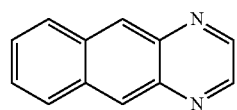  Ar36
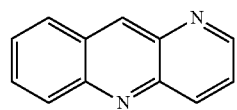  Ar37
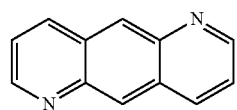  Ar38
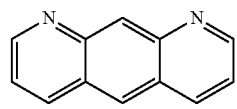  Ar39
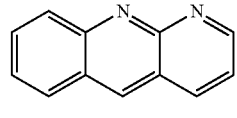  Ar40
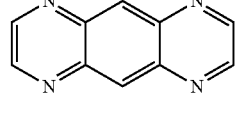  Ar41
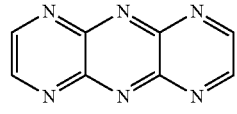  Ar42
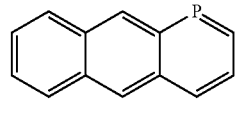  Ar43
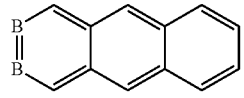  Ar44
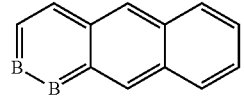  Ar45
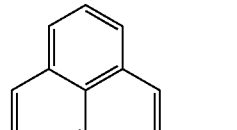  Ar46
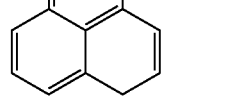  Ar47

Ar48
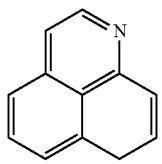
Ar49
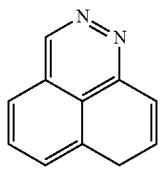
Ar50
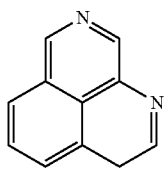
Ar51
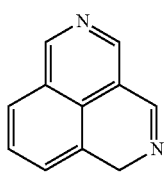
Ar52
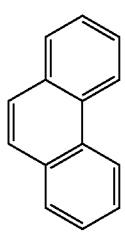
Ar53
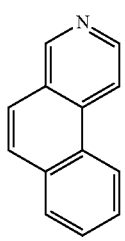
Ar54
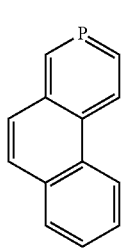
Ar55
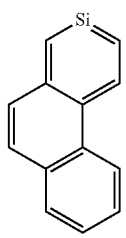
Ar56
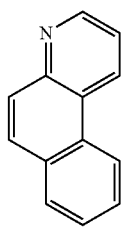
Ar57
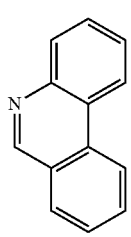
Ar58
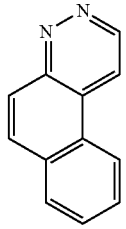
Ar59
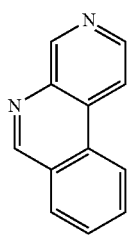
Ar60
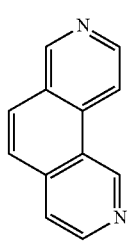

-continued
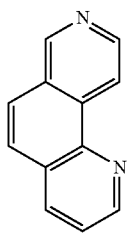
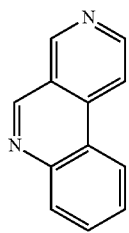
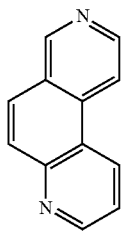
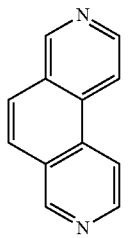
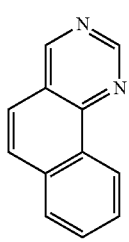
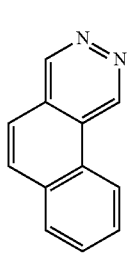
-continued
Ar61
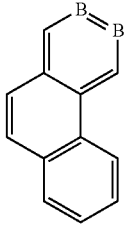
Ar62
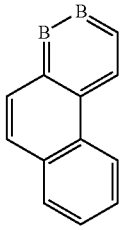
Ar63
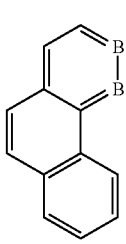
Ar64
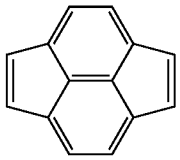
Ar65
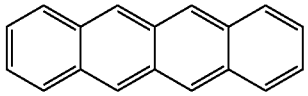
Ar66
Ar67
Ar68
Ar69
Ar70
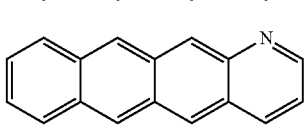
Ar71
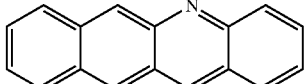
Ar72
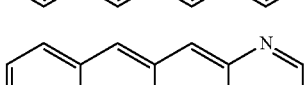
Ar73
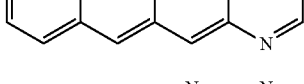
Ar74
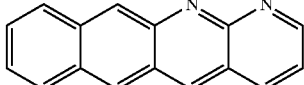
Ar75
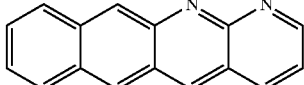
Ar76
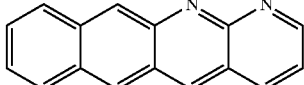

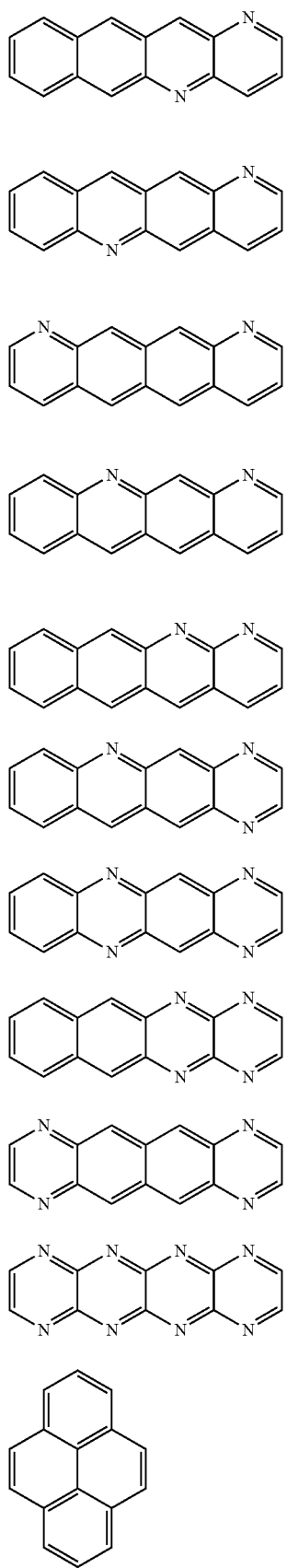
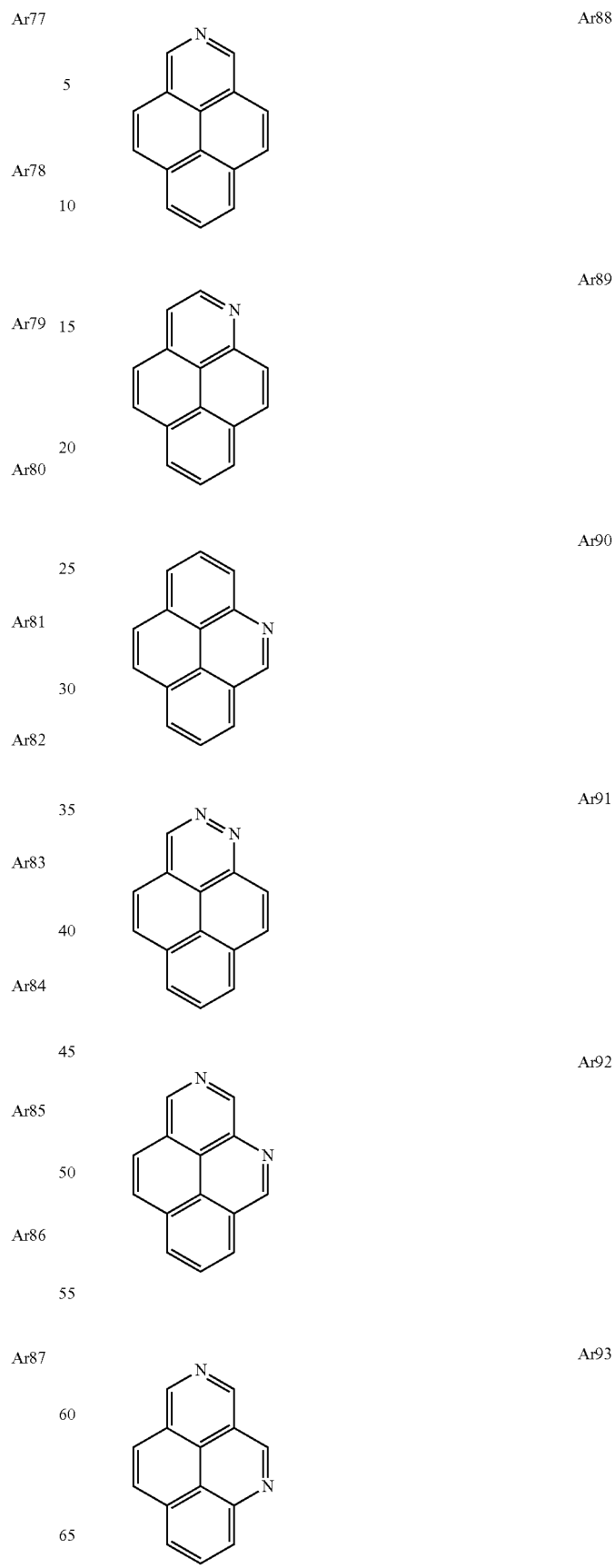

-continued
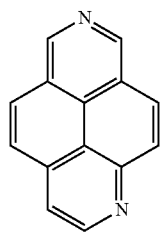
Ar94
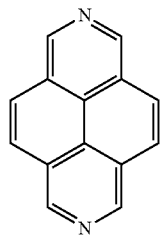
Ar95
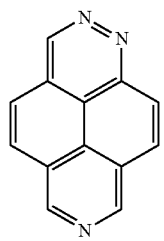
Ar96
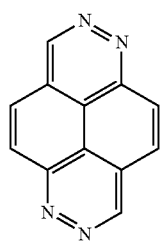
Ar97
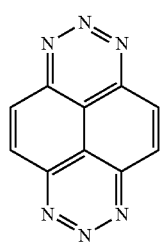
Ar98
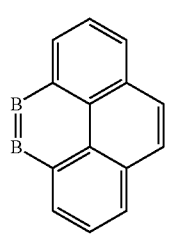
Ar99
-continued
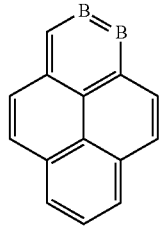
Ar100
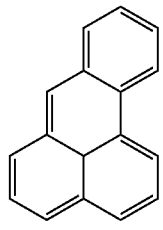
Ar101
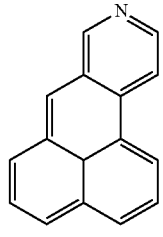
Ar102
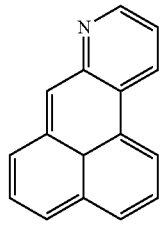
Ar103
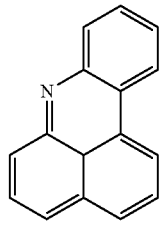
Ar104
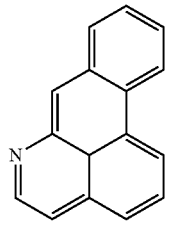
Ar105
Ar106

-continued
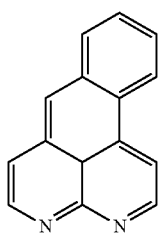
Ar107
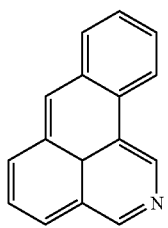
Ar108
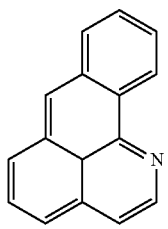
Ar109
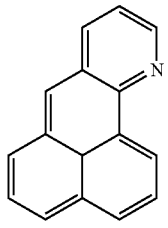
Ar110
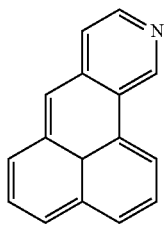
Ar111
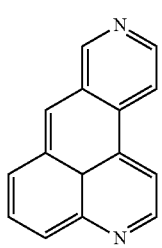
Ar112
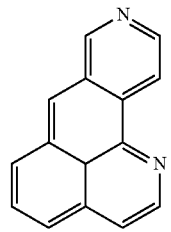
Ar113
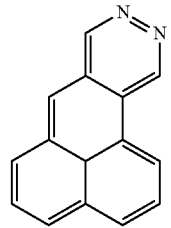
Ar114
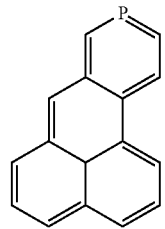
Ar115
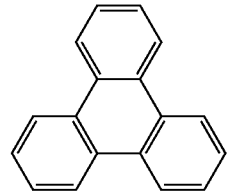
Ar116
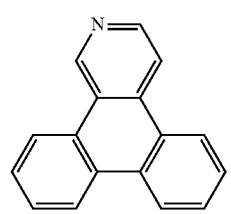
Ar117
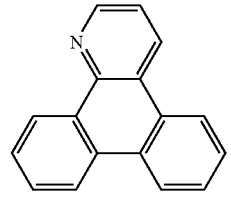
Ar118
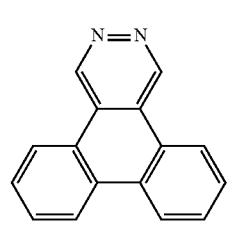
Ar119

Ar120 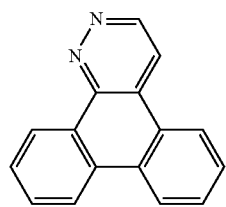
Ar121 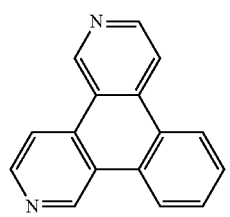
Ar122 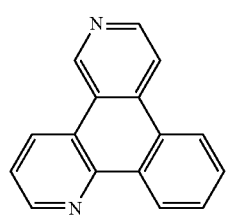
Ar123 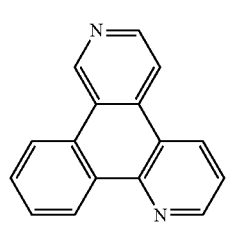
Ar124 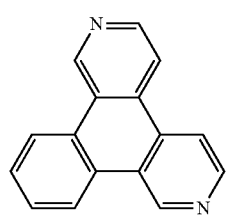
Ar125 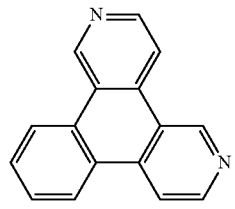
Ar126 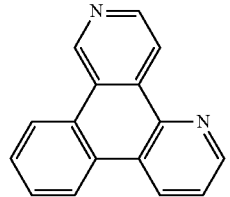
Ar127 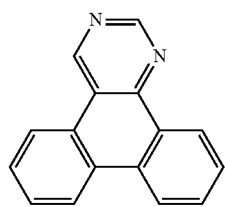
Ar128 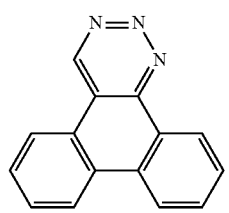
Ar129 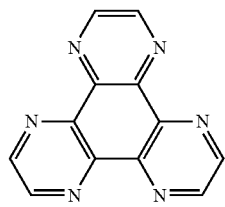
Ar130 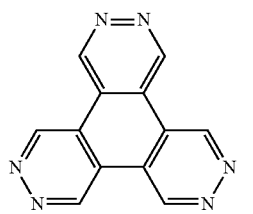
Ar131 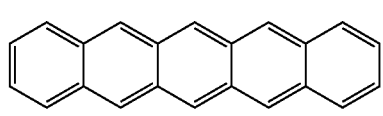
Ar132 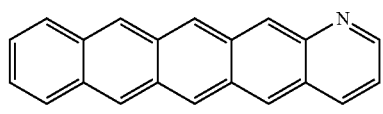
Ar133 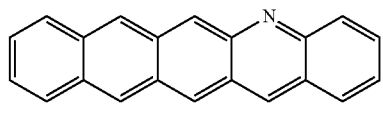
Ar134 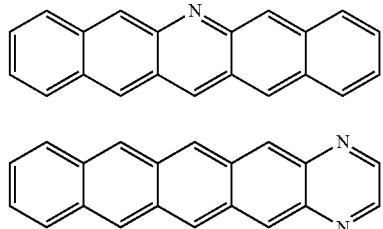
Ar135 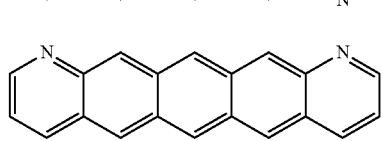

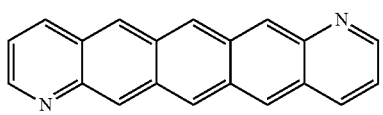 Ar137
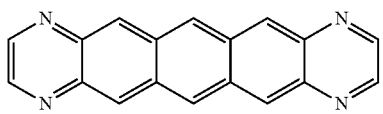 Ar138
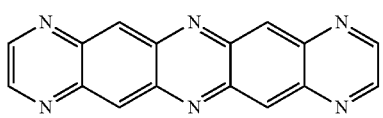 Ar139
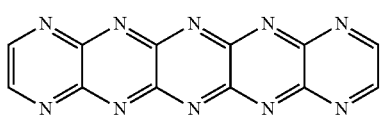 Ar140
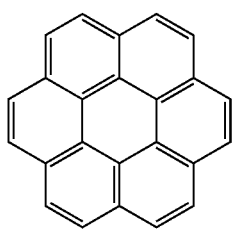 Ar141
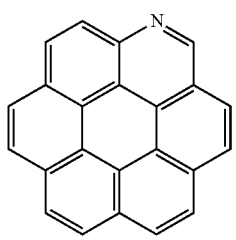 Ar142
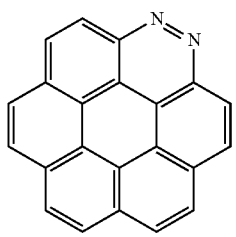 Ar143
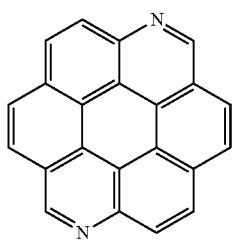 Ar144
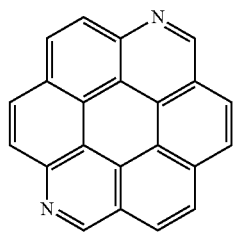 Ar145
Ar146
Ar147
Ar148
Ar149

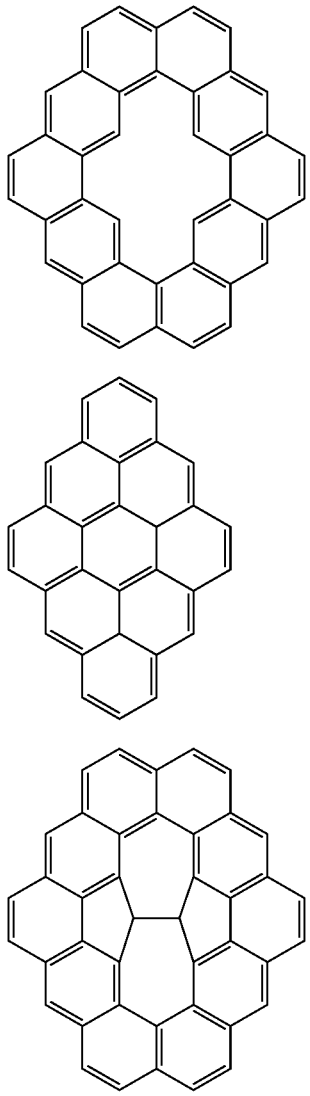

Ar150

Ar151

Ar152

As an example, the Ar may be an aromatic ring having a molecular symmetry axis of $C_n$ (where n is an integer from 2 to 6), such as $C_2$ (180° symmetry), $C_3$ (120° symmetry), $C_4$ (90° symmetry), or $C_6$ (60° symmetry). Here, it is assumed that all members of the Ar are carbon.

Specifically, the benzene-based group of Ar1 to Ar16, the naphthalene-based group of Ar17 to Ar30, the anthracene-based group of Ar31 to Ar45, the cyclopenta[fg] acenaphthylene group of Ar70 to Ar71, the tetracene-based group of Ar72 to Ar86, the pyrene-based group of Ar87 to Ar100, the pentacene-based group of Ar131 to Ar140, the coronene-based group of Ar141 to Ar148, and Ar149 to Ar159 have a $C_2$ (180°) symmetry; the benzene-based group of Ar1 to Ar16, the phenalene-based group of A46 to A51, the triphenylene-based group of Ar116 to Ar130, and the coronene-based group of Ar141 to Ar148 have a $C_3$ (120°) symmetry; the benzene-based group of Ar1 to Ar16 and the coronene-based group of Ar141 to Ar148 have $C_6$ (60°) symmetry.

In the above Chemical Formula 1, $A_1$ and A2 may be chalcogen elements such as —O— or —S—, and may be the same as or different from each other. $A_1$ and $A_2$ have non-covalent electron pairs and can donate electrons to the aromatic ring (Ar) to which they are bonded. This can lead to the localization of the electron density in the pi-electron structure of the aromatic ring (Ar). Specifically, the electron density of the region adjacent to the positions where $A_1$ and $A_2$ are bonded may be relatively higher than that of the other regions, and the electron density of the other regions may be relatively low.

$L_1$ and $L_2$ may be linking groups, may be the same or different from each other, and may be -E-,

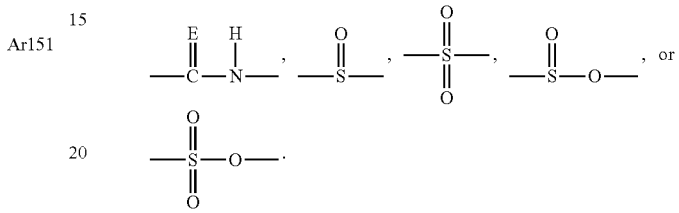

Here, E, $E_1$, and $E_2$ may be 0 or S independently of each other, and $E_1$ and $E_2$ may be the same or different from each other. $n_1$ and $n_2$ may be the same or different from each other and may be 0 or 1.

$Y_1$ and $Y_2$ may be organic groups, for example, linear organic groups, and may be

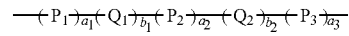

independently of one another. $Y_1$ and $Y_2$ may be the same or different from each other. $a_1$, $a_2$, $a_3$, $b_1$, and $b_2$ are integers of 0 to 30 irrespective of each other, and $a_1+a_2+a_3+b_1+b_2$ may be an integer of 3 to 30. Each of $a_1$, $a_2$, $a_3$, $b_1$, and $b_2$, and $a_1+a_2+a_3+b_1+b_2$ may vary depending on the kind of the functional group constituting $P_1$, $P_2$, $P_3$, $Q_1$ and $Q_2$. However, the number of elements constituting the main chain of each of $Y_1$ and $Y_2$ may be from 6 to 30 so that sufficient physical interaction may occur between $Y_1$ and $Y_2$.

The $P_1$, $P_2$, and $P_3$ may independently be —$CR_aR_b$— or —$(CR_aR_b)_rO$—. In this case, $R_a$ and $R_b$ may be H, F, Cl, Br, or I, independently of each other, and r may be an integer of 1 to 3. Specifically, $P_1$, $P_2$, and $P_3$ may independently represent —($CH_2$)—, —($CF_2$)—, —($CH_2O$)—, —($CH_2CH_2O$)—, or —($CH_2CH_2CH_2O$)—.

$Q_1$ and $Q_2$ may be $q_1$-$(p_1)_{c1}$-$q_2$-$(p_2)_{c2}$-$q_3$, and may be the same or different from each other. $q_1$ and $q_3$ may be —O— or —S— independently of each other, and may be the same or different from each other. $q_2$ may be —CH=CH—, —C≡C—, —N=N—,

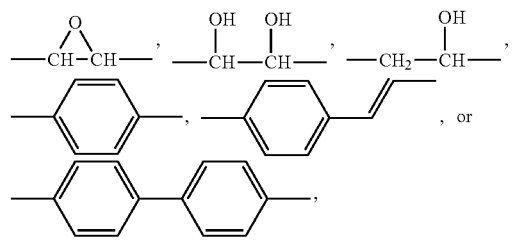

in which the hydrogen group bonded to the carbon may be substituted with another functional group such as F, Cl, Br, or I, or unsubstituted. $p_1$ and $p_2$ may independently be —$CR_aR_b$—, $R_a$ and $R_b$ may independently be H, F, Cl, Br, or I, and $c_1$ and $c_2$ may independently be an integer of 0 to 2. As an example, $Q_1$ and $Q_2$ may be, regardless of each other, —O—CH=CH—O—, —O—C≡C—O—, —O—N=N—O—,

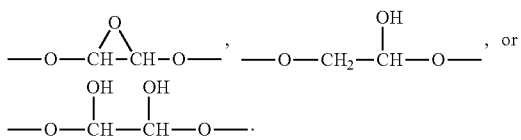

In one embodiment, $Y_1$ and $Y_2$ may be, independently from each other,

(i.e. $a_2$, $a_3$, $b_1$, and $b_2$ are all 0), more specifically —(CH$_2$)$_{a1}$— ($a_1$ is an integer from 6 to 30) or —(CH$_2$CH$_2$O)$_{a1}$— ($a_1$ is an integer of 3 to 10).

In yet another embodiment, $Y_1$ and $Y_2$ may be, independently from one another,

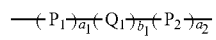

(i.e., $a_3$ and $b_2$ are all 0), more specifically $P_1$ is —(CH$_2$)—, $a_1$ may be an integer from 3 to 15, $Q_1$ may be —O—CH=CH—O—, —O—C≡C—O—, —O—N=N—O—,

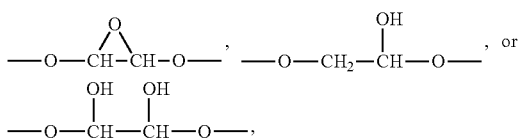

$b_1$ may be 1, $P_2$ may be —(CH$_2$)—, and $a_2$ may be an integer of 1 to 3.

$X_1$ and $X_2$ may be terminal groups and may be, independently of each other, —H, —F, —Cl, —Br, —I, —$CR_cR_dR_e$, —OH, —COOH, —CHO, —SH, —$COCR_cR_dR_e$, —$COOCR_cR_dR_e$, —$CR_c$=$CR_dR_e$, —CN, —N=C=O, —C=N=N—$CR_cR_dR_e$, —C≡$CR_a$, —$NHCR_cR_dR_e$, or —$NH_2$. Here, $R_c$, $R_d$, and $R_e$ may be H, F, Cl, Br, or I, independently of each other. In one example, —$CR_cR_dR_e$ may be —$CH_3$ or —$CF_3$; —$COCR_cR_dR_e$ may be —$COCH_3$; —$COOCR_cR_dR_e$ may be —$COOCH_3$; —$CR_c$=$CR_dR_e$ may be —CH=$CH_2$, —CH=$CF_2$, —CF=$CH_2$, —CF=$CF_2$, —CH=CFH, —CF=CFH or —CF=$CF_2$; and —C=N=N—$CR_cR_dR_e$ may be —C=N=N—$CH_3$; —C≡$CR_a$ may be —C≡CH; and —$NHCR_cR_dR_e$ may be —$NHCH_3$.

In this specification, each of -$A_1$-(L$_1$)$_{n1}$-$Y_1$—$X_1$ and -$A_2$-(L$_2$)$_{n2}$-$Y_2$—$X_2$ may be referred to as a strain. The pair of -$A_1$-(L$_1$)$_{n1}$-$Y_1$—$X_1$ and -$A_2$-(L$_2$)$_{n2}$-$Y_2$—$X_2$ may be located immediately adjacent positions, i.e., ortho positions (e.g., positions $G_4$ and $G_5$ of structure 2 below) or peri positions (e.g., positions $G_1$ and $G_3$ of structure 2 below), among the substitution positions of the aromatic ring (Ar). More specifically, the pair of -$A_1$-(L$_1$)$_{n1}$-$Y_1$—$X_1$ and -$A_2$-(L$_2$)$_{n2}$-$Y_2$—$X_2$ are bonded to the ortho positions of the aromatic ring (Ar). In this case, physical interactions, for example Van Der Waals interactions, between -$A_1$-(L$_1$)$_{n1}$-$Y_1$—$X_1$ and -$A_2$-(L$_2$)$_{n2}$-$Y_2$—$X_2$, specifically between $Y_1$ and $Y_2$ contained therein may be present; and therefore strains can be stabilized and the rigidity of the strains can increase.

The number of pairs of strains, that is, the number of pairs of -$A_1$-(L$_1$)$_{n1}$-$Y_1$—$X_1$ and -$A_2$-(L$_2$)$_{n2}$-$Y_2$—$X_2$ may be one (m=1) or two to eight (m=2~8). That is, in Formula 1, m may be an integer of 1 to 8. The maximum number of pairs of -$A_1$-(L$_1$)$_{n1}$-$Y_1$—$X_1$ and -$A_2$-(L$_2$)$_{n2}$-$Y_2$—$X_2$ which can bond to the aromatic ring (Ar) may vary depending on the number of members and the type of Ar.

When two or more pairs of -$A_1$-(L$_1$)$_{n1}$-$Y_1$—$X_1$ and -$A_2$-(L$_2$)$_{n2}$-$Y_2$—$X_2$ are present, that is, when m is 2 or more, the positions at which the pairs of -$A_1$-(L$_1$)$_{n1}$-$Y_1$—$X_1$ and -$A_2$-(L$_2$)$_{n2}$-$Y_2$—$X_2$ are connected may be positions that maintain $C_n$ (n is an integer of 2 to 6) symmetry of Ar. That is, the positions to which the pairs of -$A_1$-(L$_1$)$_{n1}$-$Y_1$—$X_1$ and -$A_2$-(L$_2$)$_{n2}$-$Y_2$—$X_2$ are bonded may be symmetry-equivalent positions among the substitution positions of Ar. The number of pairs of -$A_1$-(L$_1$)$_{n1}$-$Y_1$—$X_1$ and -$A_2$-(L$_2$)$_{n2}$-$Y_2$—$X_2$, which is m, may be equal to n when Ar has $C_n$ (n is an integer of 2 to 6) symmetry. Specifically, when Ar has $C_2$ (180°) symmetry, m which is the number of pairs of -$A_1$-(L$_1$)$_{n1}$-$Y_1$—$X_1$ and -$A_2$-(L$_2$)$_{n2}$-$Y_2$—$X_2$ is 2, and the positions at which the two pairs of -$A_1$-(L$_1$)$_{n1}$-$Y_1$—$X_1$ and -$A_2$-(L$_2$)$_{n2}$-$Y_2$—$X_2$ are connected are positions that maintain $C_2$ (180°) symmetry of Ar. In another embodiment, when Ar has $C_3$ (120°) symmetry, m which is the number of pairs of -$A_1$-(L$_1$)$_{n1}$-$Y_1$—$X_1$ and -$A_2$-(L$_2$)$_{n2}$-$Y_2$—$X_2$ is 3, and the positions at which the three pairs of -$A_1$-(L$_1$)$_{n1}$-$Y_1$—$X_1$ and -$A_2$-(L$_2$)$_{n2}$-$Y_2$—$X_2$ are connected are positions that maintain $C_3$ (120°) symmetry of Ar. In still another embodiment, when Ar has $C_4$ (90°) symmetry, m which is the number of pairs of -$A_1$-(L$_1$)$_{n1}$-$Y_1$—$X_1$ and -$A_2$-(L$_2$)$_{n2}$-$Y_2$—$X_2$ is 4, and the positions at which the four pairs of -$A_1$-(L$_1$)$_{n1}$-$Y_1$—$X_1$ and -$A_2$-(L$_2$)$_{n2}$-$Y_2$—$X_2$ are connected are positions that maintain $C_4$ (90°) symmetry of Ar. In other words, when the number of pairs of -$A_1$-(L$_1$)$_{n1}$-$Y_1$—$X_1$ and -$A_2$-(L$_2$)$_{n2}$-$Y_2$—$X_2$ is two or more, the interval between these pairs, that is, the angle formed by these pairs with respect to the center of Ar, may be the same.

In addition, a substitution site at which -$A_1$-(L$_1$)$_{n1}$-$Y_1$—$X_1$ and -$A_2$-(L$_2$)$_{n2}$-$Y_2$—$X_2$ are not bonded is located between the pairs of -$A_1$-(L$_2$)$_{n1}$-$Y_1$—$X_1$ and -$A_2$-(L$_2$)$_{n2}$-$Y_2$—$X_2$, so that the localization of electron density in the aromatic ring can be enhanced. Furthermore, U can be attached to at least some of the substitutable positions where -$A_1$-(L$_1$)$_{n1}$-$Y_1$—$X_1$ and -$A_2$-(L$_2$)$_{n2}$-$Y_2$—$X_2$ are not bonded.

U may be one selected from the group consisting of a cyano group, a hydroxyl group, fluorine, chlorine, iodine, a substituted or unsubstituted alkyl group having 1 to 15 carbon atoms, a substituted or unsubstituted alkoxy group having 1 to 15 carbon atoms, a substituted or unsubstituted cycloalkyl group having 3 to 15 carbon atoms, a substituted or unsubstituted alkenyl group having 2 to 15 carbon atoms, a substituted or unsubstituted alkynyl group having 2 to 15 carbon atoms, a substituted or unsubstituted aryl group having 5 to 15 carbon atoms, a substituted or unsubstituted heteroaryl group having 2 to 15 carbon atoms, a substituted or unsubstituted arylalkyl group having 1 to 15 carbon atoms, a substituted or unsubstituted alkylsulfone group having 1 to 15 carbon atoms, a substituted or unsubstituted alkylmercapto group having 1 to 15 carbon atoms, a substituted or unsubstituted alkylthiocyanate group having 1 to 15 carbon atoms, a substituted or unsubstituted alkylphosphate group having 1 or 15 carbon atoms, a substituted or unsubstituted alkylnitro group having 1 or 15 carbon atoms, a substituted or unsubstituted alkylnitroso group having 1 or 15 carbon atoms, a substituted or unsubstituted alkylnitrile group having 1 or 15 carbon atoms, a substituted or unsubstituted alkylisothiocyanate group having 1 to 15 carbon atoms, a substituted or unsubstituted alkylisocyanate group having 1 to 15 carbon atoms, a substituted or unsubstituted alkykyanate group having 1 to 15 carbon atoms, a substituted or unsubstituted alkylazo group having 1 to 15 carbon atoms, a substituted or unsubstituted alkylazide group having 1 to 15 carbon atoms, a substituted or unsubstituted ketimine group having 1 to 15 carbon atoms, a substituted or unsubstituted aldimine group having 1 to 15 carbon atoms, a substituted or unsubstituted amide group having 1 to 15 carbon atoms, an arylalkyl group having 6 to 24 carbon atoms, an heteroaryl group having 2 to 24 carbon atoms, an arylamino group having 3 to 24 carbon atoms, an arylsilyl group having 3 to 24 carbon atoms, an aryloxy group having 3 to 24 carbon atoms, an alkylsilyl group having 1 to 24 carbon atoms, and an alkylamino group having 1 to 24 carbon atoms. o may be an integer between 0 and x, where x is an integer less than 2 m from the number of substitutional positions of Ar. As an example, x may be a maximum of 16.

The compound represented by Formula 1 may be any one selected from the following Structural Formulas 1 to 15, but is not limited to the following structural formulas.

[Structural Formula 1]

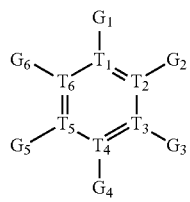

[Structural Formula 2]

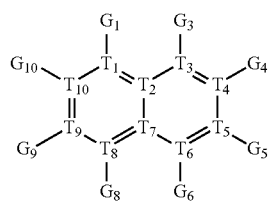

[Structural Formula 3]

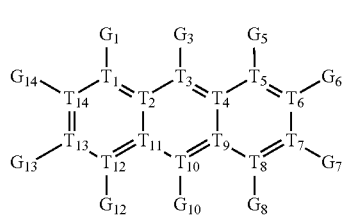

[Structural Formula 4]

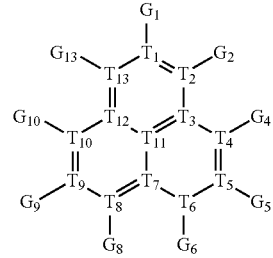

[Structural Formula 5]

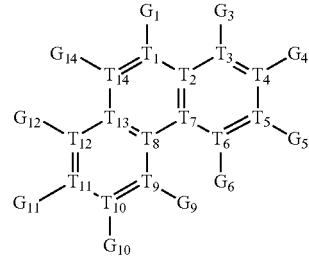

[Structural Formula 6]

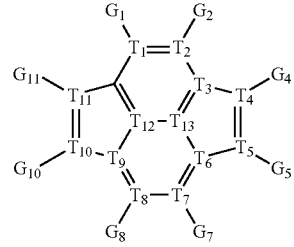

[Structural Formula 7]

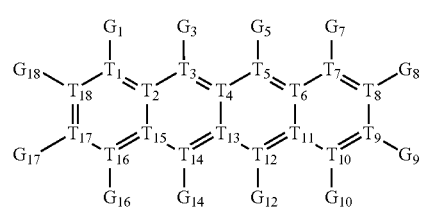

[Structural Formula 8]

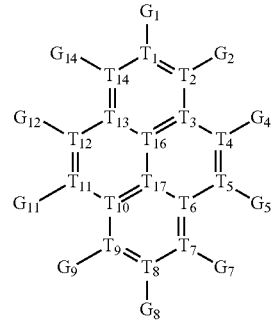

[Structural Formula 9]

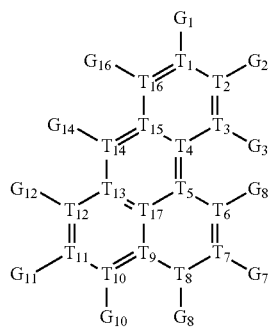

[Structural Formula 10]

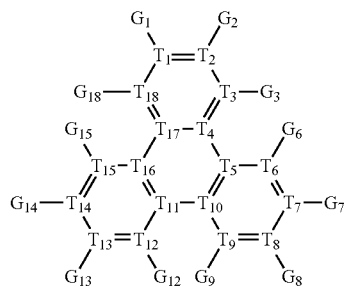

[Structural Formula 11]

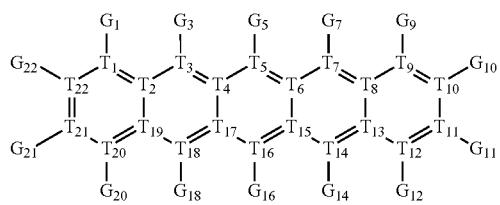

[Structural Formula 12]

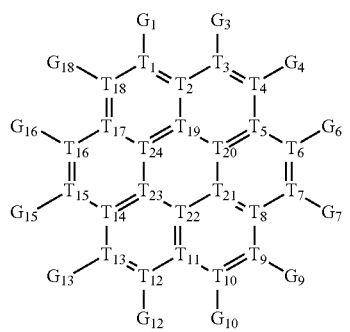

[Structural Formula 13]

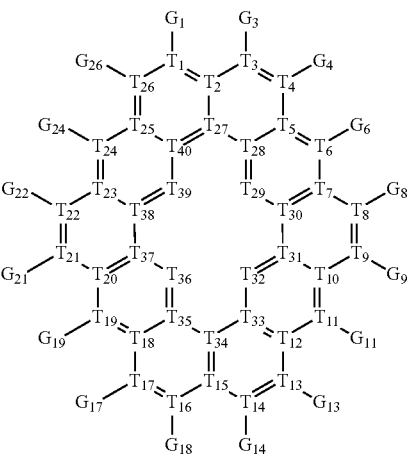

In the above Structural Formulas 1 to 13, $T_1$ to $T_{40}$ may be all C; Some of $T_1$ to $T_{40}$ may be N, P, B or Si independently of each other, and the remainder may be C. In addition, $G_n$ represents the substitution positions of the aromatic ring (Ar of Formula 1).

The compound represented by the Chemical Formula 1 may be a compound represented by any of the following Chemical Formulas 1a to 1e.

[Chemical Formula 1a]

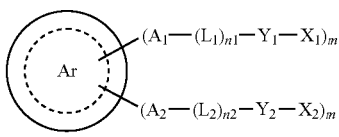

[Chemical Formula 1b]

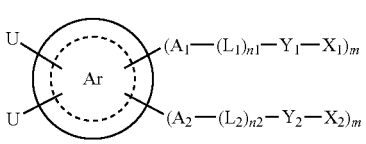

[Chemical Formula 1c]

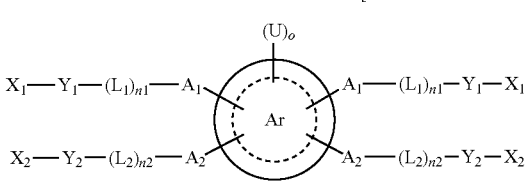

[Chemical Formula 1d]

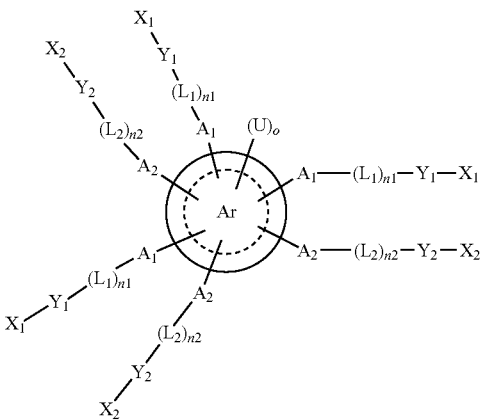

[Chemical Formula 1e]

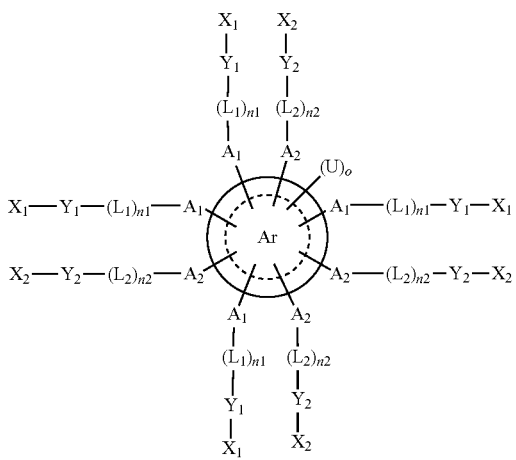

Ar, $A_1$, $A_2$, $L_1$, $L_2$, $n_1$, $n_2$, $Y_1$, $Y_2$, $X_1$, $X_2$, m, U and o in the above Chemical Formulas 1a to 1e may be the same as Ar, $A_1$, $A_2$, $L_1$, $L_2$, $n_1$, $n_2$, $Y_1$, $Y_2$, $X_1$, $X_2$, m, U and o in the above Chemical Formula 1, respectively. In each of Chemical Formulas 1a to 1e, the plurality of $A_1$ may be the same or different from each other, the plurality of $A_2$ may be the same or different from each other, the plurality of $L_1$ may be the same or different from each other, the plurality of $L_2$ may be the same or different from each other, the plurality of $n_1$ may be the same or different from each other, the plurality of $n_2$ may be the same or different from each other, the plurality of $Y_1$ may be the same or different from each other, the plurality of $Y_2$ may be the same or different from each other, the plurality of $X_1$ may be the same or different from each other, the plurality of $X_2$ may be the same or different from each other, and a plurality of U may be the same or different from each other.

In particular, the compound represented by Chemical Formula 1 may be any one of the compounds represented by Chemical Formulas is to 1e.

Specifically, the compound of Chemical Formula 1c has two pairs of $-A_1$-$(L_1)_{n1}$-$Y_1$—$X_1$ and $-A_2$-$(L_2)_{n2}$-$Y_2$—$X_2$, that is, two pairs of strains (m=2 in Chemical Formula 1). In Chemical Formula 1c, Ar may have a $C_2$ (180°) symmetry. Specifically, Ar in Chemical Formula 1c may be any one selected from the group consisting of the benzene group of Ar1 to Ar16, the naphthalene group of Ar17 to Ar30, the anthracene group of Ar31 to Ar45, the cyclopenta[fg]acenaphthylene group of Ar70 to Ar71, the tetracene group of Ar72 to Ar86, the pyrene group of Ar87 to Ar100, the pentacene group of Ar131 to Ar140, the coronene group of Ar141 to Ar148, and Ar149 to Ar159. In addition, the positions at which the strains are connected to the Ar may be positions at which $C_2$ (180°) symmetry is maintained, that is, positions having equivalent symmetry among the substitution positions of Ar. Further, the positions to which each pair of strains are connected to the Ar may be orthogonal to each other. Also, a substitution position where the strain is not connected may be located between the pairs.

Specifically, when Ar is the benzene group of Structural Formula 1, a pair of $-A_1$-$(L_1)_{n1}$-$Y_1$—$X_1$ and $-A_2$-$(L_2)_{n2}$-$Y_2$—$X_2$ may be bonded to $G_1$ and $G_2$ positions, the other pair of $-A_1$-$(L_1)_{n1}$-$Y_1$—$X_1$ and $-A_2$-$(L_2)_{n2}$-$Y_2$—$X_2$ may be bonded to $G_4$ and $G_5$ positions, and U may be bonded to the remaining $G_3$ or $G_6$ positions or not. In this case, o may be an integer of 0 to 2.

When Ar is the naphthalene group of Structural Formula 2, a pair of $-A_1$-$(L_1)_{n1}$-$Y_1$—$X_1$ and $-A_2$-$(L_2)_{n2}$-$Y_2$—$X_2$ may be bonded to $G_4$ and $G_5$ positions, the other pair of $-A_1$-$(L_1)_{n1}$-$Y_1$—$X_1$ and $-A_2$-$(L_2)_{n2}$-$Y_2$—$X_2$ may be bonded to $G_9$ and $G_{10}$ positions, and U may be bonded to the remaining $G_1$, $G_3$, $G_6$, or $G_8$ positions or not. In this case, o may be an integer of 0 to 4.

When Ar is the anthracene group of Structural Formula 3, a pair of $-A_1$-$(L_1)_{n1}$-$Y_1$—$X_1$ and $-A_2$-$(L_2)_{n2}$-$Y_2$—$X_2$ may be bonded to $G_6$ and $G_7$ positions, the other pair of $-A_1$-$(L_1)_{n1}$-$Y_1$—$X_1$ and $-A_2$-$(L_2)_{n2}$-$Y_2$—$X_2$ may be bonded to $G_{13}$ and $G_{14}$ positions, and U may be bonded to the remaining $G_1$, $G_3$, $G_5$, $G_8$, $G_{10}$, or $G_{12}$ positions or not. In this case, o may be an integer of 0 to 6.

When Ar is the cyclopenta[fg]acenaphthylene group of Structural Formula 6, a pair of $-A_1$-$(L_1)_{n1}$-$Y_1$—$X_1$ and $-A_2$-$(L_2)_{n2}$-$Y_2$—$X_2$ may be bonded to $G_1$ and $G_2$ positions, the other pair of $-A_1$-$(L_1)_{n1}$-$Y_1$—$X_1$ and $-A_2$-$(L_2)_{n2}$-$Y_2$—$X_2$ may be bonded to $G_7$ and $G_8$ positions, and U may be bonded to the remaining $G_4$, $G_5$, $G_{10}$, or $G_{11}$ positions or not. In this case, o may be an integer of 0 to 4. In another example in which Ar is the cyclopenta[fg]acenaphthylene group of Structural Formula 6, a pair of $-A_1$-$(L_1)_{n1}$-$Y_1$—$X_1$ and $-A_2$-$(L_2)_{n2}$-$Y_2$—$X_2$ may be bonded to $G_4$ and $G_5$ positions, the other pair of $-A_1$-$(L_1)_{n1}$-$Y_1$—$X_1$ and $-A_2$-$(L_2)_{n2}$-$Y_2$—$X_2$ may be bonded to $G_{10}$ and $G_{11}$ positions, and U may be bonded to the remaining $G_1$, $G_2$, $G_7$, or $G_8$ positions or not. In this case, o may be an integer of 0 to 4.

When Ar is the tetracene group of Structural Formula 7, a pair of $-A_1$-$(L_1)_{n1}$-$Y_1$—$X_1$ and $-A_2$-$(L_2)_{n2}$-$Y_2$—$X_2$ may be bonded to $G_8$ and $G_9$ positions, the other pair of $-A_1$-$(L_1)_{n1}$-$Y_1$—$X_1$ and $-A_2$-$(L_2)_{n2}$-$Y_2$—$X_2$ may be bonded to $G_{17}$ and $G_{18}$ positions, and U may be bonded to the remaining $G_1$, $G_3$, $G_5$, $G_7$, $G_{10}$, $G_{12}$, $G_{14}$, or $G_{16}$ positions or not. In this case, o may be an integer of 0 to 8.

When Ar is the pyrene group of Structural Formula 8, a pair of $-A_1$-$(L_1)_{n1}$-$Y_1$—$X_1$ and $-A_2$-$(L_2)_{n2}$-$Y_2$—$X_2$ may be bonded to $G_4$ and $G_5$ positions, the other pair of $-A_1$-$(L_1)_{n1}$-$Y_1$—$X_1$ and $-A_2$-$(L_2)_{n2}$-$Y_2$—$X_2$ may be bonded to $G_{11}$ and $G_{12}$ positions, and U may be bonded to the remaining $G_1$, $G_2$, $G_7$, $G_8$, $G_9$, or $G_{14}$ positions or not. In this case, o may be an integer of 0 to 6.

When Ar is the pentacene group of Structural Formula 11, a pair of $-A_1$-$(L_1)_{n1}$-$Y_1$—$X_1$ and $-A_2$-$(L_2)_{n2}$-$Y_2$—$X_2$ may be bonded to $G_{10}$ and $G_{11}$ positions, the other pair of $-A_1$-$(L_1)_{n1}$-$Y_1$—$X_1$ and $-A_2$-$(L_2)_{n2}$-$Y_2$—$X_2$ may be bonded to $G_{21}$ and $G_{22}$ positions, and U may be bonded to the remaining $G_1$, $G_3$, $G_5$, $G_7$, $G_9$, $G_{12}$, $G_{14}$, $G_{16}$, $G_{18}$, or $G_{20}$ positions or not. In this case, o may be an integer of 0 to 10.

When Ar is the coronene group of Structural Formula 12, a pair of -$A_1$-$(L_1)_{n1}$-$Y_1$—$X_1$ and -$A_2$-$(L_2)_{n2}$-$Y_2$—$X_2$ may be bonded to $G_6$ and $G_7$ positions, the other pair of -$A_1$-$(L_1)_{n1}$-$Y_1$—$X_1$ and -$A_2$-$(L_2)_{n2}$-$Y_2$—$X_2$ may be bonded to $G_{15}$ and $G_{16}$ positions, and U may be bonded to the remaining $G_1$, $G_3$, $G_4$, $G_9$, $G_{10}$, $G_{12}$, $G_{13}$, or $G_{18}$ positions or not. In this case, o may be an integer of 0 to 8.

When Ar is the aromatic group of Structural Formula 13, a pair of -$A_1$-$(L_1)_{n1}$-$Y_1$—$X_1$ and -$A_2$-$(L_2)_{n2}$-$Y_2$—$X_2$ may be bonded to $G_8$ and $G_9$ positions, the other pair of -$A_1$-$(L_1)_{n1}$-$Y_1$—$X_1$ and -$A_2$-$(L_2)_{n2}$-$Y_2$—$X_2$ may be bonded to $G_{21}$ and $G_{22}$ positions, and U may be bonded to the remaining $G_1$, $G_3$, $G_4$, $G_6$, $G_{11}$, $G_{13}$, $G_{14}$, $G_{16}$, $G_{17}$, $G_{19}$, $G_{24}$, or $G_{26}$ positions or not. In this case, o may be an integer of 0 to 12.

In other embodiment, the compound of Chemical Formula 1d has three pairs of -$A_1$-$(L_1)_{n1}$-$Y_1$—$X_1$ and -$A_2$-$(L_2)_{n2}$-$Y_2$—$X_2$, that is, three pairs of strains (m=3 in Chemical Formula 1). In Chemical Formula 1d, Ar may have a $C_3$ (120°) symmetry. Specifically, Ar in Chemical Formula 1d may be any one selected from the group consisting of the phenalene group of Ar46 to Ar51, the triphenylene group of Ar116 to Ar130, and the coronene group of Ar141 to Ar148. In addition, the positions at which the strains are connected to the Ar may be positions at which $C_3$ (120°) symmetry is maintained, that is, positions having equivalent symmetry among the substitution positions of Ar. Further, the positions to which each pair of strains are connected to the Ar may be orthogonal to each other. Also, a substitution position where the strain is not connected may be located between the pairs.

Specifically, when Ar is the phenalene group of Structural Formula 4, the first pair of -$A_1$-$(L_1)_{n1}$-$Y_1$—$X_1$ and -$A_2$-$(L_2)_{n2}$-$Y_2$—$X_2$ may be bonded to $G_1$ and $G_2$ positions, the second pair of -$A_1$-$(L_1)_{n1}$-$Y_1$—$X_1$ and -$A_2$-$(L_2)_{n2}$-$Y_2$—$X_2$ may be bonded to $G_5$ and $G_6$ positions, the third pair of -$A_1$-$(L_1)_{n1}$-$Y_1$—$X_1$ and -$A_2$-$(L_2)_{n2}$-$Y_2$—$X_2$ may be bonded to $G_9$ and $G_{10}$ positions, and U may be bonded to the remaining $G_4$, $G_8$, or $G_{13}$ positions or not. In this case, o may be an integer of 0 to 3.

When Ar is the triphenylene group of Structural Formula 10, a pair of -$A_1$-$(L_1)_{n1}$-$Y_1$—$X_1$ and -$A_2$-$(L_2)_{n2}$-$Y_2$—$X_2$ may be bonded to $G_1$ and $G_2$ positions, another pair of -$A_1$-$(L_1)_{n1}$-$Y_1$—$X_1$ and -$A_2$-$(L_2)_{n2}$-$Y_2$—$X_2$ may be bonded to $G_7$ and $G_8$ positions, the other pair of -$A_1$-$(L_1)_{n1}$-$Y_1$—$X_1$ and -$A_2$-$(L_2)_{n2}$-$Y_2$—$X_2$ may be bonded to $G_{13}$ and $G_{14}$ positions, and U may be bonded to the remaining $G_3$, $G_6$, $G_9$, $G_{12}$, $G_{15}$, or $G_{18}$ positions or not. In this case, o may be an integer of 0 to 6.

When Ar is the coronene group of Structural Formula 12, a pair of -$A_1$-$(L_1)_{n1}$-$Y_1$—$X_1$ and -$A_2$-$(L_2)_{n2}$-$Y_2$—$X_2$ may be bonded to $G_6$ and $G_7$ positions, another pair of -$A_1$-$(L_1)_{n1}$-$Y_1$—$X_1$ and -$A_2$-$(L_2)_{n2}$-$Y_2$—$X_2$ may be bonded to $G_{12}$ and $G_{13}$ positions, the other pair of -$A_1$-$(L_1)_{n1}$-$Y_1$—$X_1$ and -$A_2$-$(L_2)_{n2}$-$Y_2$—$X_2$ may be bonded to $G_{18}$ and $G_1$ positions, and U may be bonded to the remaining $G_3$, $G_4$, $G_9$, $G_{10}$, $G_{15}$, or $G_{16}$ positions or not. In this case, o may be an integer of 0 to 6.

In other embodiment, the compound of Chemical Formula 1e has four pairs of -$A_1$-$(L_1)_{n1}$-$Y_1$—$X_1$ and -$A_2$-$(L_2)_{n2}$-$Y_2$—$X_2$, that is, four pairs of strains (m=4 in Chemical Formula 1). In addition, the positions at which the strains are connected to the Ar may be positions at which $C_4$ (90°) symmetry is maintained, that is, positions having equivalent symmetry among the substitution positions of Ar. Further, the positions to which each pair of strains are connected to the Ar may be orthogonal to each other. Also, a substitution position where the strain is not connected may be located between the pairs.

In another embodiment, an organic compound forming three-dimensional organic structure may be a compound represented by the following Chemical Formula 2.

[Chemical Formula 2]

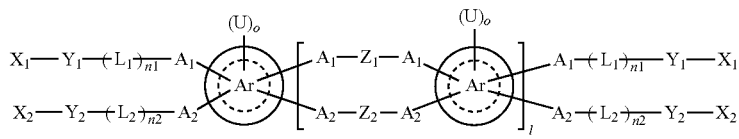

Ar, $A_1$, $A_2$, $L_1$, $L_2$, $n_1$, $n_2$, $Y_1$, $Y_2$, $X_1$, $X_2$, U and o in the above Chemical Formula 2 may be the same as Ar, $A_1$, $A_2$, $L_1$, $L_2$, $n_1$, $n_2$, $Y_1$, $Y_2$, $X_1$, $X_2$, U and o in the above Chemical Formula 1, respectively. In each Chemical Formula, the plurality of $A_1$ may be the same or different from each other, the plurality of $A_2$ may be the same or different from each other, the plurality of $L_1$ may be the same or different from each other, the plurality of $L_2$ may be the same or different from each other, the plurality of $n_1$ may be the same or different from each other, the plurality of $n_2$ may be the same or different from each other, the plurality of $Y_1$ may be the same or different from each other, the plurality of $Y_2$ may be the same or different from each other, the plurality of $X_1$ may be the same or different from each other, the plurality of $X_2$ may be the same or different from each other, a plurality of U may be the same or different from each other, and a plurality of o may be the same or different from each other.

$Z_1$ and $Z_2$ in the above Chemical Formula 2 may, irrespectively to each other, be one selected from the group consisting of a substituted or unsubstituted alkyl group having 1 to 15 carbon atoms, a substituted or unsubstituted alkoxy group having 1 to 15 carbon atoms, a substituted or unsubstituted cycloalkyl group having 3 to 15 carbon atoms, a substituted or unsubstituted alkenyl group having 2 to 15 carbon atoms, a substituted or unsubstituted alkynyl group having 2 to 15 carbon atoms, a substituted or unsubstituted aryl group having 5 to 15 carbon atoms, a substituted or unsubstituted heteroaryl group having 2 to 15 carbon atoms, a substituted or unsubstituted arylalkyl group having 1 to 15 carbon atoms, a substituted or unsubstituted alkylsulfone group having 1 to 15 carbon atoms, a substituted or unsubstituted alkylmercapto group having 1 to 15 carbon atoms, a substituted or unsubstituted allylthiocyanate group having 1 to 15 carbon atoms, a substituted or unsubstituted alkylphosphate group having 1 or 15 carbon atoms, a substituted or unsubstituted alkylnitro group having 1 or 15 carbon atoms, a substituted or unsubstituted alkylnitroso group having 1 or 15 carbon atoms, a substituted or unsubstituted alkylnitrile group having 1 or 15 carbon atoms, a substituted or unsubstituted alkylisothiocyanate group having 1 to 15 carbon atoms, a substituted or unsubstituted alkylisocyanate group having 1 to 15 carbon atoms, a substituted or unsubstituted alkylcyanate group having 1 to 15 carbon atoms, a substituted or unsubstituted alkylazo group having 1 to 15 carbon atoms, a substituted or unsubstituted alkylazide group having 1 to 15 carbon atoms, a substituted or unsubstituted ketimine group having 1 to 15 carbon atoms, a substituted or unsubstituted aldimine group having 1 to 15 carbon atoms, a substituted or unsubstituted amide group having 1 to 15 carbon atoms, an arylalkyl group having 6 to 24 carbon atoms, an heteroaryl group having 2 to 24 carbon atoms, an arylamino group having 3 to 24 carbon atoms, an arylsilyl group having 3 to 24 carbon atoms, an aryloxy group having 3 to 24 carbon atoms, an alkylsilyl group having 1 to 24 carbon atoms, and an alkylamino group having 1 to 24 carbon atoms.

In the above Chemical Formula 2, l may be an integer between 1 and 4.

In another embodiment, an organic compound forming three-dimensional organic structure may be a compound represented by the following Chemical Formula 3.

[Chemical Formula 3]

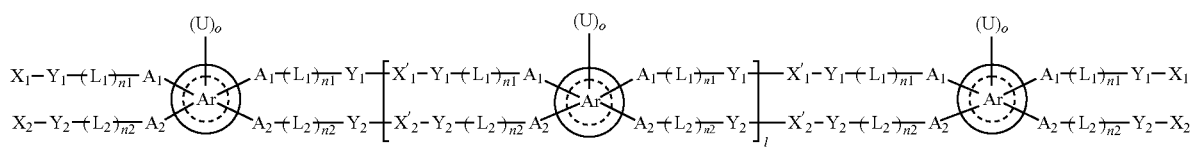

Ar, $A_1$, $A_2$, $L_1$, $L_2$, $n_1$, $n_2$, $Y_1$, $Y_2$, $X_1$, $X_2$, U and o in the above Chemical Formula 3 may be the same as Ar, $A_1$, $A_2$, $L_1$, $L_2$, n, $n_2$, $Y_1$, $Y_2$, $X_1$, $X_2$, U and o in the above Chemical Formula 1, respectively. In each Chemical Formula, the plurality of $A_1$ may be the same or different from each other, the plurality of $A_2$ may be the same or different from each other, the plurality of $L_1$ may be the same or different from each other, the plurality of $L_2$ may be the same or different from each other, the plurality of $n_1$ may be the same or different from each other, the plurality of $n_2$ may be the same or different from each other, the plurality of $Y_1$ may be the same or different from each other, the plurality of $Y_2$ may be the same or different from each other, the plurality of $X_1$ may be the same or different from each other, the plurality of $X_2$ may be the same or different from each other, a plurality of U may be the same or different from each other, and a plurality of o may be the same or different from each other.

In the above Chemical Formula 3, $X_1'$ and $X_2'$ may be, independently from one another, -A'-,

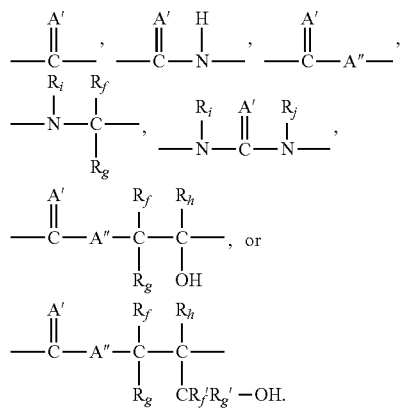

Here, A' and A'' may be, independently from one another, O or S, and $R_f$, $R_g$, $R_h$, $R_i$, $R_j$, $R_f'$, and $R_g'$ may be, independently from one another, H or an alkyl group of C1 to C3.

In the above Chemical Formula 3, l may be an integer between 1 and 4.

Three-Dimensional Organic Structure

FIG. 1 is a schematic view of a self-assembled three-dimensional organic structure according to an embodiment of the present invention.

Referring to FIG. 1, the compounds represented by Chemical Formulas 1 to 3, that is, the unit organic molecules (UM) can be self-assembled to form a three-dimensional organic structure, that is, an organic crystal. FIG. 1 shows an organic structure using the unit organic molecules shown in Chemical Formula 1c, but is not limited thereto.

In one unit organic molecule (UM), a pair of substituents -A-$(L)_n$-Y—X, which are connected to an aromatic ring are immediately adjacent positions of substitutable positions of the aromatic ring, for example ortho positions or peri positions relative to each other. In this case, a pair of substituents -A-$(L)_n$-Y—X, specifically Y groups contained in each of them are stabilized by a physical interaction (PIa) specifically by Van Der Waals interaction. As a result, a pair of -A-$(L)_n$-Y—X, i.e., a pair of strains, may be more rigid due to reduced flexibility compared to one strain of -A-$(L)_n$-Y—X.

Meanwhile, A has non-covalent electron pairs and can donate electrons to the aromatic ring (Ar) to which it is bonded. As a result, the electron density of the pi (π)-electronic structure in the aromatic ring (Ar) is localized, so that a region having a relatively high electron density and a region having a relatively low electron density can be positioned. In other words, A bonded to the aromatic ring (Ar) can induce the localization of electron density in the aromatic ring (Ar).

Specifically, the electric multipole corresponding to twice the number (m in Chemical Formula 1) of the pair of -A-$(L)_n$-Y—X (strains) can be intensified. For example, in the case of 1-coordinate type organic molecules represented by Chemical Formulas 1a and 1b, a quadrupole can be intensified in the aromatic ring (Ar); and, in the case of 2-coordinate type organic molecule represented by Chemical Formula 1c, the quadrupole in the aromatic ring (Ar) can be further strengthened. In the case of the 3-coordinate type organic molecule represented by Chemical Formula 1d, hexapole can be strengthened in the aromatic ring (Ar); and, in the case of the 4-coordinate type organic molecule represented by Chemical Formula 1e, octapole can be strengthened.

When a plurality of such unit organic molecules (UM) are located, the X groups between the unit organic molecules (UM) adjacent in one direction (e.g., the X direction) can be non-covalently connected (PIb) by physical interactions, specifically, Van Der Waals interaction, London dispersion interaction, or hydrogen bonding. For example, when each of Xs is —$CF_3$, —SH, —F, —Cl, —Br, —I, —CH=$CF_2$, —CF═CH$_2$, —CF═CF$_2$, —CF═CH$_2$, —CF═CFH, —CF═CF$_2$, —COCH$_3$, —COOCH$_3$, —CHO, —CN, —N═C═O, or —C≡N═N—CH$_3$, they can bonded by Van Der Waals interaction; when each of Xs is —H, —CH$_3$, —CH═CH$_2$, or —C≡CH, they can bonded by London dispersion interaction; and when each of Xs is —OH, —COOH, —NH$_2$, or —NHCH$_3$, they can bonded by hydrogen bonding.

In addition, the aromatic rings contained in each of the unit organic molecules (UM) adjacent in the other direction (for example, the Z direction) or contained in one layer (F$_1$) and the other layer (F$_2$) can be self-assembled or laminated by π-π interactions (PIc). Specifically, as described above, an electron-rich region (δ−) and an electron-deficient region (δ+) can be induced in the aromatic ring group (Ar) by the functional group of A; and, due to attraction between the electron-rich region (δ−) and the electron-deficient region (δ+) between the adjacent aromatic rings in the Z direction, the direction in which the unit organic molecule (UM) of the second layer (F$_2$) extends may be shifted by a predetermined angle relative to the direction X in which the unit organic molecule (UM) of the first layer (F$_1$) extends. As an example, the direction in which the unit organic molecule (UM) of the second layer (F$_2$) extends relative to the direction X in which the unit organic molecule (UM) of the first layer (F$_1$) extends can be shifted by 90 degrees; therefore, the extending direction of the unit organic molecule (UM) of the second layer (F$_2$) may be the Y direction.

Also, the X groups between the unit organic molecules (UM) in the second layer (F$_2$) can be non-covalently connected (PIb) by Van Der Waals interaction, London dispersion interaction, or hydrogen bonding.

As described above, the porous three-dimensional organic structure according to the present embodiment, that is, the porous organic crystal, can be formed by the unit organic molecules self-assembled through physical interactions, specifically, pi-pi interactions, dipole-dipole interactions, induced dipole-dipole interactions, and induced dipole-induced dipole interactions.

In addition, these organic crystals may have regularity and periodicity, and thus may have a basic lattice of triclinic, monoclinic, orthorhombic, tetragonal, hexagonal, or cubic structure. Specifically, the 1-coordinate type organic molecules represented by Chemical Formulas 1a and 1b and the 2-coordinate type organic molecules represented by Chemical Formula 1c, that is, the linear organic molecules, can form triclinic, orthorhombic, tetragonal, or cubic structure. The 3-coordinate type organic molecules represented by Chemical Formula 1d can form hexagonal or monoclinic structure.

Specifically, FIG. 1 shows a lattice structure of a orthorhombic system.

Such a porous three-dimensional organic structure, that is, a porous organic crystal may be formed easily and simply as it is formed by self-assembly based on non-covalent bonding, specifically weak organic-organic interaction between unit organic molecules. In addition, since the porous three-dimensional organic structure is formed by using pure physical bonding between compounds without chemical cross-linking, melting and dissolution are possible at all times, and a large pore volume and a completely regular and periodic structure can be secured. Also, unlike metal organic framework (MOF), the porous three-dimensional organic structure does not contain a metal, so that structural characteristics can be maintained even in a moisture and atmospheric environment. In addition, the compounds according to this embodiment can be self-assembled fairly quickly to form structures, and have the advantage of producing sophisticated and orderly complex and hierarchical structures despite the rapid rate.

Manufacturing Method for Organic Compound Forming Self-Assembled Three-Dimensional Organic Structure Method for Preparing a Compound According to Chemical Formula 1

In one embodiment, the compound according to Chemical Formula 1 can be prepared by the following Reaction Schemes 1 to 2. However, it is not limited thereto.

[Reaction Scheme 1]

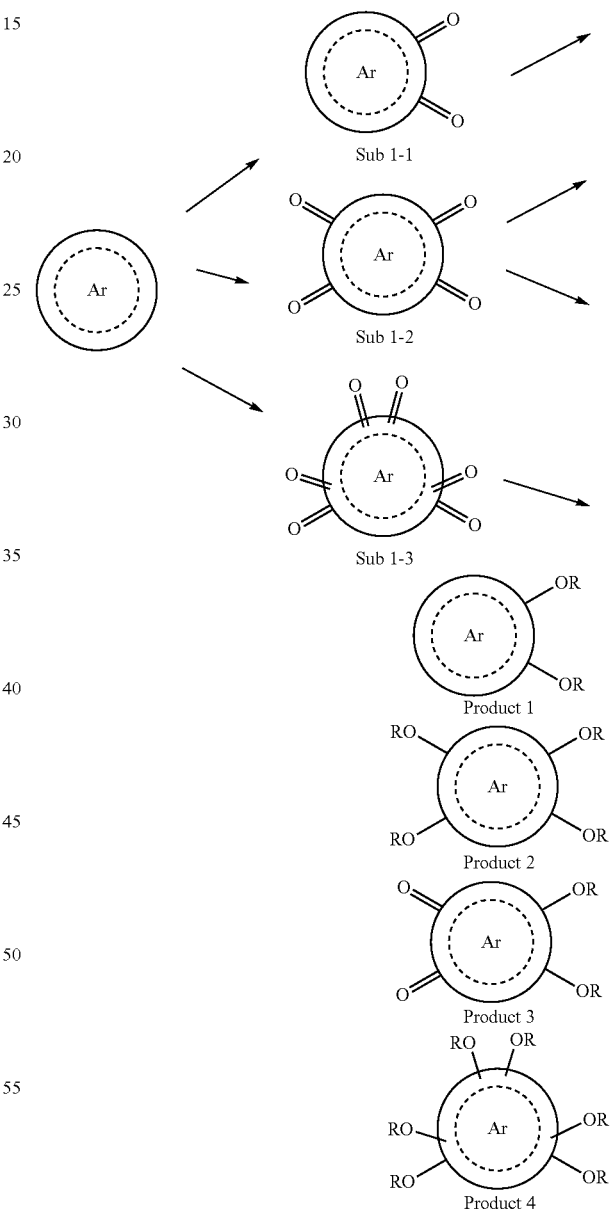

(1) Synthesis of Sub 1-1, Sub 1-2, and Sub 1-3

Aromatic ring (Ar) dissolved in dichloromethane and acetonitrile solution can be reacted with ruthenium (III) chloride hydrate and sodium metaperiodate (NaIO$_4$) in distilled water at a predetermined temperature and for a predetermined time by refluxing to obtain Sub1-1, Sub1-2, and Sub1-3. Here, Sub1-1, Sub1-2, and Sub1-3 can be obtained at different the reflux temperatures.

(2) Synthesis of Products 1 to 4

One of Sub1-1, Sub1-2, and Sub1-3 can be dissolved in distilled water and tetrahydrofuran (THF) together with bromotetrabutylammonium ($Bu_4NBr$) and sodium hydrosulfite ($Na_2S_2O_4$) and refluxed at a predetermined temperature for a predetermined time, and then an aqueous solution prepared by dissolving X'—R and KOH in distilled water can be added hereto, and then the resultant can be refluxed at a predetermined temperature for a predetermined time to obtain any one of the final products, Products 1 to 4. X' may be Br as an example of a halide and —R may be -$(L_1)_{n1}$-$Y_1$—$X_1$. $L_1$, $n_1$, $Y_1$, and $X_1$ may be as defined in the description of Chemical Formula 1. Specifically, $X_1$ may be $CR_cR_dR_e$ or —OH, wherein $R_c$, $R_d$ and $R_e$ are independently selected from the group consisting of H, F, Cl, Br, or I. Here, any one of Products 1 to 4 can be obtained by adjusting the molar ratio of X'—R to each of Sub1-1, Sub1-2, and Sub1-3.

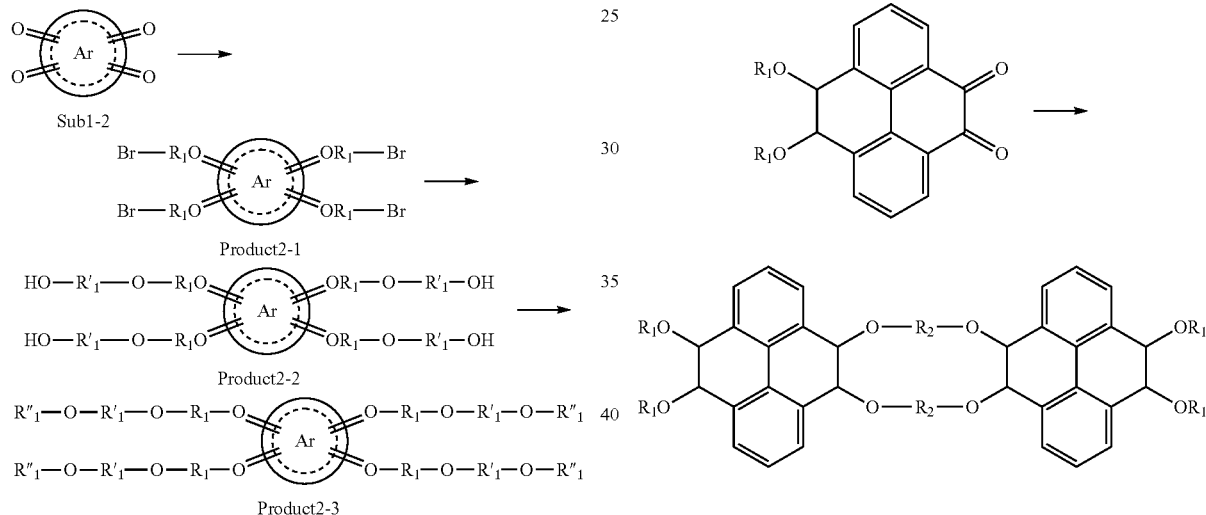

(1) Synthesis of Product 2-1

Product 2-1 can be obtained by performing the same method as that of product 2 in the above Reaction Scheme 1, except that X'—$R_1$—X" is used instead of X'—R. In this case, X' and X" may be Br as an example of a halide and —$R_1$— may be -$L_1$-$(P_1)_{a1}$—. Here, $L_1$, $P_1$, and $a_1$ may be as defined in the description of Chemical Formula 1.

(2) Synthesis of Product 2-2

Product 2-1 and HO—$R_1'$—OH may be dissolved in dimethylformamide, refluxed and reacted for a predetermined time at a predetermined temperature, extracted with chloroform, the water may be removed with magnesium sulfite, and purified by column chromatography to obtain product 2-2. Here, —$R_1'$— may be -$q_2$-described in the above Chemical Formula 1.

(3) Synthesis of Product 2-3

Product 2-2 and X'—$R_1"$ may be placed in tetrahydrofuran, refluxed and reacted for a predetermined time at a predetermined temperature, and column chromatography using chloroform as a developing solution may give product 2-3. Here, X' is Br as an example of a halide and —$R_1"$ may be —$(P_2)_{a2}$—$CH_3$. $P_2$ and $a_2$ may be as defined in the description of Chemical Formula 1.

Method for Preparing a Compound According to Chemical Formula 2

In one embodiment, the compound according to Chemical Formula 2 can be prepared by the following Reaction Scheme 3. However, it is not limited thereto.

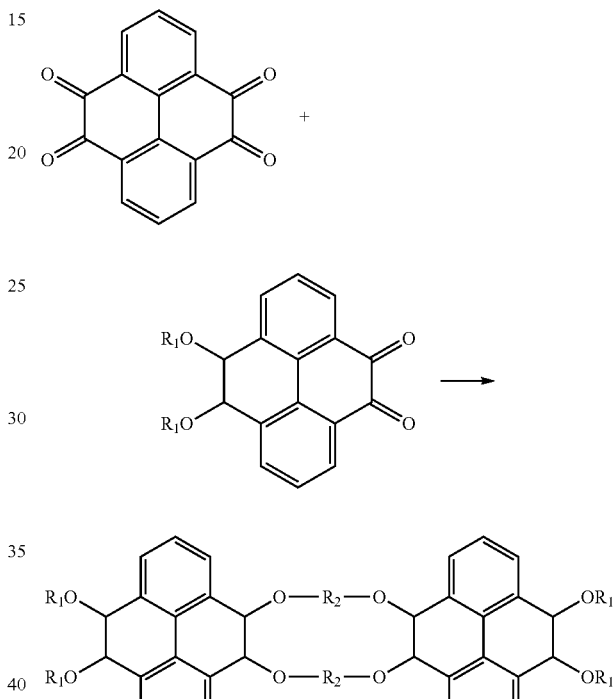

Sub 1-2 and Product 3 (Molar ratio of Sub 1-2 and Product 3=1:2) may be mixed together with bromotetrabutylammonium ($Bu_4NBr$) and sodium hydrosulfite ($Na_2S_2O_4$) in distilled water and tetrahydrofuran (THF), refluxed at a predetermined temperature for a predetermined time, an aqueous solution prepared by dissolving X'—R and KOH in distilled water can be added hereto, and refluxed at a predetermined temperature for a predetermined time to obtain a final product, product 5. X' may be Br as an example of a halide and —R may be -$(L_1)_{n1}$-$Y_1$—$X_1$. $L_1$, $n_1$, $Y_1$, and $X_1$ may be as defined in the description of Chemical Formula 1. Specifically, $X_1$ may be $CR_cR_dR_e$ or —OH, wherein $R_c$, $R_d$ and $R_e$ are independently selected from the group consisting of H, F, Cl, Br, or I.

Method for Preparing a Compound According to Chemical Formula 3

In one embodiment, the compound according to Chemical Formula 3 can be prepared by the following Reaction Scheme 4. However, it is not limited thereto.

[Reaction Scheme 4]

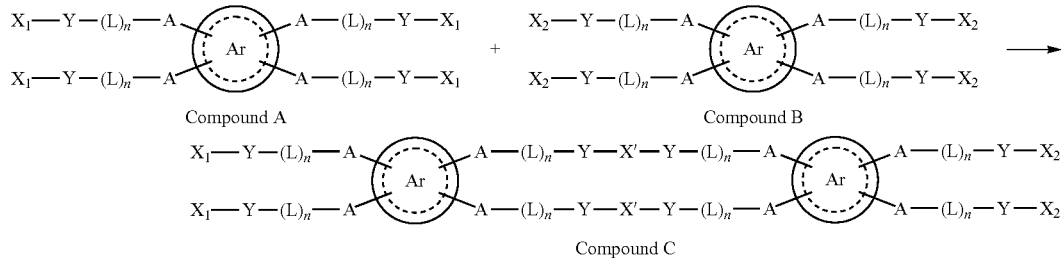

Among the compounds represented by Chemical Formula 1c, two or more compounds (compounds A and B) in which the terminal groups ($X_1$, $X_2$) can react with each other may be selected, and a solution may be obtained by dissolving them in distilled water and chlorobenzene, To this solution, an aqueous solution prepared by dissolving KOH in distilled water may be added, and the mixture may be refluxed at a predetermined temperature for a predetermined time to obtain Compound 3 as a final product.

In the above Reaction Scheme 4, Ar, A, L, n, Y, l and X' may be the same as Ar, $A_1$, $L_1$, $n_1$, $Y_1$, 1 and $X_1$' in the description of Chemical Formula 3. Meanwhile, $X_1$ and $X_2$ can be appropriately selected from examples of $X_1$ in Chemical Formula 1 so as to form X' by a reaction therebetween.

Method for Preparing Self-Assembled Three-Dimensional Organic Structure

The above-described organic compound or organic molecule may be dissolved in an appropriate organic solvent, followed by recrystallization and drying to obtain a three-dimensional structure by self-assembly of the organic molecules. The drying may be vacuum drying. Specifically, the powder containing self-assembled three-dimensional structure particles can be obtained through the 1st to 4th methods described below. The self-assembled three-dimensional structure particles may have a nano-rod shape.

In addition, through the following 5th and 6th methods, a self-assembled three-dimensional structure having a specific shape can be obtained, specifically, a fiber containing a self-assembled three-dimensional structure can be obtained through the following 5th method, and a thin film containing a self-assembled three-dimensional structure can be obtained by the following 6th method.

1st Method: Method for Preparing Powder Containing a Three-Dimensional Structure Using an Organic Solvent Evaporation Method Powder containing the three-dimensional structure can be obtained by performing:

1) dissolving the organic molecules in an organic solvent having a medium solubility to form a homogeneous solution;

2) gradually evaporating the solvent in the solution to gradually change the solution to a homogeneous solution with a thick concentration;

3) forming a three-dimensional structure by self-assembly of the organic molecules at a critical concentration; and 4) filtering the structure and removing residual organic solvent in vacuum.

2nd Method: Method for Preparing Powder Containing a Three-Dimensional Structure Using a Cooling Method Powder containing the three-dimensional structure can be obtained by performing:

1) dissolving the organic molecules in a heated insoluble organic solvent to prepare a homogeneous solution at a low concentration;

2) cooling the homogeneous solution in a state of blocking the movement of a substance from outside;

3) forming a three-dimensional structure by self-assembly of the organic molecules at a critical temperature; and 4) filtering the structure and removing residual organic solvent in vacuum.

3rd Method: Method for Preparing Powder Containing a Three-Dimensional Structure Using Multi-Solvent with Different Solubility Powder containing the three-dimensional structure can be obtained by performing:

1) providing two different systems in a closed space, disposing a homogeneous solution in which the organic molecules are dissolved in a first organic solvent having a high solubility for the organic molecules in one system, and disposing a second organic solvent which can be evaporated well, have very low solubility to the organic molecules but has good mixing property with respect to the first organic solvent in the other system;

2) allowing the second organic solvent to be evaporated and allowing the evaporated second organic solvent to be mixed into the homogeneous solution to lower the solubility of the organic molecules;

3) forming a three-dimensional structure by self-assembly of the organic molecules at a critical solubility; and 4) filtering the structure and removing residual organic solvents in vacuum.

4th Method: Method for Preparing Powder Containing a Three-Dimensional Structure Using Multi-Solvent with Different Solubility Powder containing the three-dimensional structure can be obtained by performing:

1) obtaining a homogeneous solution by dissolving the organic molecules in a first organic solvent having a high solubility with saturation solubility;

2) dropping the homogeneous solution into a second organic solvent in which the organic molecules exhibit a very low solubility to lower the solubility of the organic molecules in the solution;

3) forming a three-dimensional structure by self-assembly of the organic molecules at a critical solubility; and 4) filtering the structure and removing residual organic solvents in vacuum.

5th Method: Method for Preparing Fiber Containing a Three-Dimensional Structure

Fibers containing the three-dimensional structure can be obtained by performing:

1) dissolving organic molecules in an organic solvent having a high solubility to obtain a spinning solution;

2) electrospinning the spinning solution to form a fiber; and 3) filtering the formed fiber, and removing the residual organic solvent in vacuum.

6th Method: Method for Preparing Thin Film Containing a Three-Dimensional Structure A thin film containing the three-dimensional structure can be obtained by performing:

1) obtaining a homogeneous solution by dissolving organic molecules in an organic solvent having high solubility and high volatility; and 2) spin-coating the solution to obtain a thin film.

In addition, when the nuclei for self-assembly of the organic molecules are generated and then the nuclei are grown, specifically, at step 3) in the 1st to 4th methods, a compound represented by the above Chemical Formula 1 different from the organic molecules may be added. As a result, a structure having different kinds of organic molecules in one structure can be formed.

Use of Self-Assembled Three-Dimensional Organic Structure

Such a self-assembled three-dimensional organic structure may be able to absorb and adsorb materials using micropores between organic molecules.

Specifically, the three-dimensional organic structure can also be used as an organic gelator containing an organic solvent in the micropores.

In another embodiment, the three-dimensional organic structure may be used as an organic or inorganic complex containing inorganic particles in the micropores. The inorganic particles may be introduced into the micropores through an organic solvent capable of being adsorbed or absorbed in the organic structure. The inorganic particles may have a size of 1 to 4 nm and include ceramic nanoparticles such as titanium oxide ($TiO_2$), silicon oxide ($SiO_2$), aluminum oxide ($Al_2O_3$), and zirconium oxide ($ZrO_2$); metal nanoparticles such as gold (Au), silver (Ag), platinum (Pt), and lead (Pd); semiconductor nanoparticles such as cadmium sulfide (CdS), cadmium selenide (CdSe), lead sulfide (PbS), and zinc sulfide (ZnS); magnetic nanoparticles such as iron oxide (II) ($Fe_3O_4$), iron oxide (III) ($Fe_2O_3$), and the like. These inorganic particles may be introduced using a sol-gel method.

In yet another embodiment, the three-dimensional organic structure may be capable of selective separation between affinity and non-affinity materials. As an example, it can be used for selective separation of harmful substances from the aqueous environment.

Separation Sieve Containing Self-Assembled Three-Dimensional Organic Structure

A separation sieve or separator according to the present embodiment may contain a three-dimensional organic structure formed by self-assembly of the organic compounds represented by Chemical Formulas 1 to 3, that is, an organic crystal, for example, the three-dimensional organic structure described with reference to FIG. 1.

Method for Preparing Separation Sieve Containing Self-Assembled Three-Dimensional Organic Structure A separation sieve can be manufactured using the three-dimensional organic structure obtained by the above-described three-dimensional organic structure manufacturing method.

A specific method for producing the separation sieve may be as follows.

In one example, a powder containing a three-dimensional structure may be pressed to produce a pellet or a film-like separation sieve. The pressurization can be performed within a pressure range of 1,000 to 15,000 $kgf/cm^2$, and the crystal can become large as the three-dimensional structure is further self-assembled during the pressing process. Specifically, the pellet form can be produced by pressing the powder in a pellet die in which the powder is filled, and the form of the film can be produced by pressing the powder uniformly on a support.

In another example, a powder containing a three-dimensional structure may be filled in a support to prepare a separation sieve package including a separation sieve and the support. The support can have, for example, a tubular shape, a basket shape with a porous bottom, or a porous pouch shape.

In another example, powder containing the three-dimensional structure may be put into a mixed solvent of a first solvent capable of dissolving the powder containing the three-dimensional structure and a second solvent capable of mixing with the first solvent to form a solution, and then the solution can be coated on a support to form a thin film-like separation sieve. In this case, the first solvent and the second solvent may be mixed in a volume ratio of 1:1 to 7:1, specifically 1:1 to 4:1, for example, 1.5:1 to 2.5:1. The solution may have a concentration of 5 mM to 40 mM. The coating may be spin coating, bar coating, slot die coating, spray coating, roll to roll coating, or inverse roll coating.

In another example, a selected polymer having miscibility with the three-dimensional structure may be placed in a mixed solvent of a first solvent capable of dissolving a powder containing the three-dimensional structure and a second solvent capable of mixing with the first solvent to form a first solution. After forming the first solution, a powder containing the three-dimensional structure may be placed in the first solution to form a second solution, and the second solution may be coated on a support to form a thin film-like separation sieve. The separation sieve may be micro-phase-separated to have a region containing the three-dimensional structure and a region containing the polymer therein. In this case, the first solvent and the second solvent may be mixed in a volume ratio of 1:1 to 7:1, specifically 1:1 to 4:1, for example, 1.5:1 to 2.5:1. The first solution may have a concentration of 1 mM to 20 mM, and the second solution may have a concentration of 5 mM to 40 mM. The coating may be spin coating, bar coating, slot die coating, spray coating, roll to roll coating, or inverse roll coating. The polymer may be selected from the group consisting of polyvinyl chloride (PVC), polyamide (PA), polyethylene (PE), polyethersulfone (PES), polytetrafluoroethylene (PTFE), polymethylmethacrylate (PMMA), high-density polyethylene (HDPE), low-density polyethylene (LDPE), polypropylene (PP), polystyrene (PS), polyvinyl acetate (PVAC), polyethylene oxide (PEO), NYLON, polyethylene terephthalate (PET), polyimide (PI) and combinations of two or more thereof.

The separation sieve may have a thickness of 50 to 500 nm, and more specifically, a thickness of 100 to 200 nm.

Fluid Separation Method Using a Separation Sieve Having a Three-Dimensional Organic Structure The separation sieve according to this embodiment may be capable of absorbing or adsorbing substances, particularly fluids, such as gases or liquids, using micropores between organic molecules in the three-dimensional organic structure. The pore size of the separation sieve that enables the absorption or the absorption of gas or liquid may be as small as 2 nm to as large as 9 nm, and may be, for example, 3 to 6 nm.

The mixed fluid that can be separated using the separation sieve having the three-dimensional organic structure may be a mixed liquid in which two or more liquids are mixed, and the mixed two or more liquids may be separated from each other due to selective absorption or adsorption to the separation sieve, or may be separated from each other due to the difference in the transmission time through the separation sieve due to the difference in the degree of absorption or the degree of adsorption. In this case, a first liquid having a large degree of absorption or adsorption to the separation sieve may be a liquid having a larger interaction with the separation sieve in comparison with a second liquid having a relatively low degree of absorption or adsorption. The interaction may be wettability, surface tension, or stereoisomeric interaction. To this end, the polarity and/or stereoisomeric properties of $Y_1$ and $Y_2$, specifically,

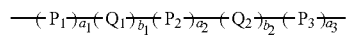

of the compound represented by Chemical Formula 1 may be controlled depending on the kind of the mixed liquid. As an example, when $Y_1$ and $Y_2$ are $CH_2$ chains, the lowest polarity may be exhibited, and when $Y_1$ and $Y_2$ are $CF_2O$ chains, the highest polarity may be exhibited.

Further, when the lengths of $Y_1$ and $Y_2$ are adjusted, the porosity of the separation sieve can be controlled.

Specifically, a first liquid absorbed or adsorbed in the separation sieve may be wettable to the separation sieve in contrast to a second liquid not absorbed or adsorbed in the separation sieve. More specifically, the first liquid may have a surface tension equal to or less than the critical surface tension of the separation sieve, and the second liquid may have a surface tension greater than the critical surface tension of the separation sieve.

FIG. 2 is a schematic diagram illustrating a correlation between a separation sieve according to an embodiment of the present invention and an absorbable or adsorbable fluid using Hansen space. The Hansen space is a coordinate system in which the hydrogen bonding parameter ($\delta_h$) is represented by the X axis, the polarity parameter ($\delta_p$) is represented by the Y axis, and the value corresponding to twice the dispersion parameter value ($2\delta_d$) is represented by the Z axis, among the Hansen Solubility Parameters.

Referring to FIG. 2, a Hansen solubility sphere can be defined by a central point (cp ($\delta_{h1}$, $\delta_{p1}$, $2\delta_{d1}$)) and an interaction radius ($R_0$) obtained by a hydrogen bonding parameter ($\delta_{h1}$), a polarity parameter ($\delta_{p1}$), and a dispersion parameter ($\delta_{d1}$) of a separation sieve having a three-dimensional organic structure according to an embodiment.

The Hansen solubility parameters and the interaction radius ($R_0$) of the separation sieve can be affected by various functional groups constituting the organic molecule represented by Chemical Formula 1 forming the three-dimensional organic structure. This can be mainly influenced by $Y_1$ and $Y_2$, specifically

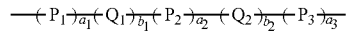

of the compound shown in the above Chemical Formula 1.

As an example, the separation sieve with the three-dimensional organic structure may exhibit a hydrogen bonding interaction ($\delta_{h1}$) of 0 to 11, a polar interaction ($\delta_{p1}$) of 0 to 19, and a dispersion force ($\delta_{d1}$) of 15 to 20, and may exhibit an interaction radius ($R_0$) of from about 2.5 to about 4, specifically from about 3.2 to about 3.6.

The separation sieve having the three-dimensional organic structure may absorb or adsorb a first liquid or a second liquid from the mixed liquid in which two or more liquids, i.e., the first liquid and the second liquid are mixed. Here, the first liquid and the second liquid should not dissolve the separation sieve. In other words, in the Hansen space, points A ($\delta_{hA}$, $\delta_{pA}$, $2\delta_{dA}$) and points B ($\delta_{hB}$, $\delta_{pB}$, $2\delta_{dB}$), respectively, defined by the Hansen dissolution parameters of the first liquid and the second liquid can be disposed outside the Hansen solubility sphere. In other words, the Hansen Relative Energy Difference (RED) between the separation sieve and the liquids may be greater than one. The Hansen relative energy difference can be defined as follows.

$$RED = R_a/R_0$$

$$R_a = \sqrt{(2\delta_{h2}-2\delta_{h1})^2 + (\delta_{p2}-\delta_{p1})^2 + (\delta_{d2}-\delta_{d1})^2}$$

In the above equation, $R_0$ is the interaction radius of the separation sieve, $\delta_{h1}$ is the hydrogen bonding interaction of the separation sieve, $\delta_{p1}$ is the polar interaction of the separation sieve, $\delta_{d1}$ is the dispersion force of the separation sieve, $\delta_{h2}$ is the hydrogen bond interaction of the liquid, $\delta_{p2}$ is the polar interaction of the liquid, and $\delta_{d2}$ is the dispersion force of the liquid.

Meanwhile, point A ($\delta_{hA}$, $\delta_{pA}$, $2\delta_{dA}$) and point B ($\delta_{hB}$, $\delta_{pB}$, $2\delta_{dB}$), which respectively defined by the Hansen dissolution parameters of the first liquid and the second liquid in the Hansen space, can be respectively disposed in two regions separated by a reference plane (RP) passing a center point (cp) of the sphere. The reference plane (RP) may have a dihedral angle ($\theta$) of 0.05 to $0.5\pi$, specifically 0.1 to $0.45\pi$ with respect to the XY plane consisting of the X-axis and the Y-axis. Specifically, point A ($\delta_{hA}$, $\delta_{pA}$, $2\delta_{dA}$) defined by the Hansen dissolution parameters of the first liquid may be disposed on one side of the reference plane (RP), that is, on the left side, point B ($\delta_{hB}$, $\delta_{pB}$, $2\delta_{dB}$) defined by the Hansen dissolution parameters of the second liquid can be disposed on the other side of the reference plane (RP), that is, on the right side.

For example, if $Y_1$ and $Y_2$, specifically

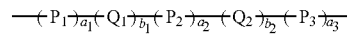

of the compound represented by Chemical Formula 1 forming the separation sieve have a dielectric constant value of 1 to less than 15 and the polarity is relatively low, the separation sieve may more absorb or adsorb the first liquid located on the left side of the reference plane than the second liquid located on the right side of the reference plane. Furthermore, the separation sieve may not adsorb or absorb the second liquid at all.

In another example, if $Y_1$ and $Y_2$, specifically

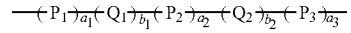

of the compound represented by Chemical Formula 1 forming the separation sieve have a dielectric constant value of 15 or more and the polarity is relatively high, the separation sieve may more absorb or adsorb the second liquid located on the right side of the reference plane than the first liquid located on the left side of the reference plane. Furthermore, the separation sieve may not adsorb or absorb the first liquid at all.

Wherein the mixed liquid may have at least two liquids which are selected from the group consisting of water, acetaldehyde, acetaldioxime, acetamines, acetalylide, acetic acid, acetic anhydride, acetone, acetone methyl oxime, acetonitrile, acetophenone, acetoxime, 1-acetoxy-1,3-butadiene, N-acetylcaprolactam, N-acetylmorpholine, N-acetylpiperidine, N-acetylpyrrolidone, 2-acetylthiophene, acetylacetone, acetyl bromide, acetylene, acetylacetyl fluoride, acrolein, acrylamide, acrylic acid, acrylonitrile, acryl chloride, aryl acetate, aryl acetic acid, aryl acetoacetate, aryl acetonitrile, aryl alcohol, aryl amine, aryl bromide, aryl chloride, arylcyanide, aryl ethyl ether, aryl fluoride, aryl formate, aryl iodide, aryl isocyanates, aryl mercaptanes, aryl methyl ethers, ammonia, amyl acetates, anethiol, anilyl p-anisidines, anisole, acidoethane, 3-azidopropene, benzaldehyde, 1,3-benzenediol, benzoic acid, benzonitrile, benzophenone, benzoyl chloride, benzyl alcohol, benzyl butyl phthalate, benzyl chloride, benzyl methacrylate, N-benzylpyrrolidone, biphenyl, borine carbonyl, 2-bromoaryl alcohol, 2-bromopropene, 1-bromopropene, 4-bromo-1-butane, 4-bromo-1,2-butadiene, 5-bromo-2-nitrobenzotrifluoride, 1-bromo-4-ethoxybenzene, bromoacetylene, o-bromoanisole, bromobenzene, p-bromobenzenonitrile, p-bromobenzoyl chloride, 2-bromobutane, o-bromochlorobenzene, bromochloromethane, bromochloromethane, bromoethylene, bromoform, bromomethyl methyl ether, 1-bromonaphthalene, p-nitrobenzene, bromoprene, 3-bromopropine, o-bromostyrene, 2-bromothiophene, o-bromotoluene, p-bromotoluene, 1,2-butadiene, 1,3-butadiene-1-chloro, 2,3-butadiene-1-ol, 1,3-butadiene-1,2-dichloro, butadiene-4-cyano, butadione, 1,4-butanediol diacrylate, 1,3-butanediol, 1,4-butanediol, 1-butanol, 2-butanol, 1-butene, 2-butene, butoxyethoxypropanol, n-butyl acetoacetate, n-butyl acrylate, t-butyl alcohol, n-butyl cyclopentane, 2-butyloctanol, n-butylbenzene, butylene oxide, butylaldehyde, butyric acid, butyric acid hydride, butyronitrile, butyryl chloride, chlorine, chloroacetaldehyde, chloroacetic acid, 3-chloroaryl alcohol, 1-chloromethyl acrylate, 1-chloro-1-nitroethane, 3-chloro-1-propanol, 1-chloro-2-butene, 1-chloro-2-methylpropene, 4-chloro-2-nitrotoluene, chloroacetone, chloroacetonitrile, chloroacetyl chloride, 1,2-chlorobromoethylene, 1-chlorobutane, 2-chlorobutane, 2-chlorocyclohexanone, chlorocyclopropene, chlorodifluoromethane, bis (chloromethyl)ether, chloromethylsulfide, p-chloronitrobenzene, chloronitromethane, 2-chloropropenal, chloropropene, p-chlorostyrene, o-chlorostyrene, 4-chlorothiophenol, o-chlorothiophenol, m-cresol crotonaldehyde, crotonic acid, croton lactone, cyanogen, cyanogen bromide, 1-decanol, 2-decanol, 1-decane, dibutyl ester, dibutyl fumarate, di-isobutyl sulfoxide, di-isopropyl sulfoxide, di-n-butyl ether, di-n-butyl sulfoxide, di-n-propyl sulfoxide, di-p-tolyl sulfoxide, di-2-methoxyethyl ether, di-(2-chloro-isopropyl)ether, diarylamine, diazomethane, dibenzyl ether, 1,1-dibromoethylene, dibromomethane, dibutyl phthalide, dibutyl sebacate, 1,3-dichloro-2-propanol, N,N-dichloroethylamine, 2,5-dichlorophenol, 2,6-dichlorophenol, 2,3-dichloropropanol, diethanolamine, N,N-diethylacetamide, N,N-diethylformamide, diethylketone, diethyl phthalate, diethylsulfate, 2-(diethylamino) ethanol, diethylene glycol, diethylene glycol hexyl ether, diethylene glycol monobutyl ether, diethylene glycol monopropyl ether, dihexyl phthalate, di-isobutyl carbinol, diketene, dimethylamine, dimethyldiketone, dimethylethanolamine, dimethylformamide, 1,1-dimethylhydrazine, 2,6-dimethylphenol, 3,4-dimethylphenol, dimethylsulfide, dipropylene glycol, ethanol, ethanolamine, 1-ethoxyethoxy-2-propanol, 3-ethoxypropionaldehyde, ethoxyethyl propionate, ethyl acetate, ethylamine, ethyl carbamate, ethyl lactate, 2-ethyl-1-butanol, 2-ethyl-hexanol, ethylene chlorohydrin, ethylene cyanohydrin, ethylene glycol, ethylene diamine, ethylene oxide, 1-fluoroacrylic acid, formamide, formic acid, furfuryl alcohol, glycerol, glyoxal-ethane dial, hexafluoro isopropanol, hexafluorohexanol, hexamethylphosphoramide, hexyleneglycol, hydroxyethyl acrylate, isobutyl alcohol, isocyanic acid, isooctyl alcohol, isoxazole, lactic acid, methacrylamide, methacrylic acid, methanol, o-methoxyphenol, 3-methoxypropionitrile, 2-methyl-acrylic acid, methyl acetate, 3-methylaryl alcohol, methylamine, methyl formate, methylhydrazine, methyl hydroperoxide, methyl isobutylcarbinol, methyl isothiocyanate, 3-methyl isoxazole, methyl salicylate, 2-methyl-1-butanol, 2-methyl-1-propanol, N, N, N, N-tetramethyl methyl thiourea, nonylphenol, 1-pentanol, pentachlorophenol, 2-propanol, beta-propiolactone, propionaldehyde-2,3-epoxy, propionamide, propionic acid, propylamine, pyridazine, 2-pyrrolidone, pyrrole, quinoline, salicylaldehyde, succinaldehyde, succinic anhydride, sulfur dioxide, tetramethylenesulfone, tetrahydrofuran, tetramethylurea, thiazole, thioacetamide, thiocyanic acid, thiophenol, thiourea, 1,2,3-triazole, tricloroacetic acid, 2,4,6-trichlorophenol, triethanolamine, triethylene glycol, triethylene glycol monomethyl ether, tetramethyl phosphate, urea, vinylacetic acid, vinylacetylene, and vinylamine.

The mixed liquid may be an aqueous azeotropic mixture which is difficult to separate by fractional distillation. The aqueous azeotropic mixture may contain water and at least one of the following liquids at a composition ratio that can exhibit an azeotropic point: formic acid (bp 100.8° C.), nitromethane (bp 100° C.), carbon disulfide (bp 46.24° C.), acetonitrile (bp 81° C.), nitroethane (bp 112° C.), ethyl acetate (bp 77.1° C.), 1-butanol (bp 117.7° C.), 2-butanol (bp 98° C.), t-butanol (bp 82° C.), 1-butenyl ethyl ether (bp 55° C.), 1-butoxy-2-propanol (bp 171° C.), butyl acetate (bp 126° C.), butyl acetoacetate (bp 71° C.), butyl acrylate (bp 126° C.), butylamine (bp 77° C.), n-butyl aniline (bp 236° C.), butyl benzoate (bp 249° C.), Butyl butyrate (bp 164° C.), butyl 2-ethoxyethanol (bp 124° C.), butyl chloride (bp 78° C.), butyl ether (bp 142° C.), butyl isopropylene ether, 2-butyloctanol (bp 145° C.), butyl salicylate (bp 268° C.), butyraldehyde (bp 74° C.), butyric acid (bp 163° C.), butyronitrile (bp 117° C.), carbon tetrachloride (bp 76.72° C.), chloral (bp 100.8° C.), chlorobenzene (bp 131° C.), 2-chloroethyl ether (bp 178° C.), chloroisopropyl ether (bp 187° C.), 1-chloro-2-propanol (bp 126° C.), crotonaldehyde, cyclohexanol (bp 161° C.), cyclohexanone (bp 155° C.), cyclohexylamine (bp 134° C.), cyclopentanol (bp 139° C.), cyclopentanone (bp 130° C.), diaryl acetal, diarylamine, dibutyl acetal, dibutylamine (bp 159° C.), dibutylethanolamine (bp 134° C.), dibutyl formal, dibutyl fumarate (bp 285° C.), dibutylmalate (bp 281° C.), di(2-chloroethal) formal, 2,3-dichloropropanol (bp 183° C.), dicyclopentadiene (bp 170° C.), diethyl ethyl acetal, diethyl aminodecyl amine (bp 54° C.), diethyl butyral, diethyleneglycol dibutyl ether, diethylethanolamine (bp 161° C.), diethyl fumarate (bp 192° C.), di(2-ethylhexyl) acetate (bp 199° C.), diethylisopropanolamine (bp 66° C.), diethyl phthalate (bp 295° C.), diethyl fumarate (bp 192° C.), diethyl succinate (bp 218° C.), dihexylamine (bp 192° C.), diisobutylene (bp 101° C.), iisobutyl ketone (bp 163° C.), diisopropyl amine (bp 83° C.), diisopropylethanolamine, diisopropyl maleate (bp 195° C.), 1,2-dimethylbutylamine (bp 94° C.), dimethylbutyral, dimethyl ethanolamine (bp 134° C.), 2,5-dimethylfuran (bp 92°

C.), 2,6-dimethyl-4-heptanol (bp 176° C.), dimethyl isobutyral, 2,6-dimethylmorpholine (bp 147° C.), dimethyl phthalate (bp 282° C.), dimethyl pimerate (bp 192° C.), 1,4-dioxane (bp 101° C.), 1,3-dioxolane (bp 75° C.), dipropyl acetal, dipropyl ketone (bp 144° C.), epichlorohydrin (bp 117° C.), 2-ethoxyethanol (bp 135° C.), 1-ethoxy-2-propanol (bp 132° C.), ethylbenzene (bp 34° C.), 2-ethylbutanol (bp 146° C.), 2-ethylbutyl acetate (bp 160° C.), 2-ethylbutyl butyrate, ethyl butyl ether, ethyl butyl ketone (bp 146° C.), 2-ethyl butyl aldehyde (bp 117° C.), 2-ethylbutyric acid (bp 100° C.), ethyl crotonate, n-ethyl cyclohexylamine (bp 165° C.), ethylene chlorohydrin, ethylenediamine (bp 118° C.), ethylene dichloride (bp 83° C.), ethyl-3-ethoxypropionate (bp 166° C.), ethyl formate (bp 52° C.), 2-ethylhexanoic acid, 2-ethylhexanol (bp 183° C.), 2-ethylhexyl acetate (Bp 199° C.), 2-ethylhexylamine (bp 169° C.), n-ethylhexyl aniline, 2-ethylhexyl chloride, 2-ethylhexyl ether, 2-ethylhexyl hexanoate, ethylidine acetone, N-ethylmorpholine (bp 139° C.), 4-ethyl octanol, ethyl propionate, glycol diacetate (bp 193° C.), hexanoic acid, 2-hexenal (bp 47° C.), hexyl acetate (bp 168° C.), hexylamine (bp 131° C.), hexyl chloride (bp 135° C.), hexyl-2-ethyl butyrate, hexylhexanoate, 10 vol. % hydrochloric acid (bp 103° C.), bromic acid (bp 101° C.), hydrofluoric acid, iodic acid, nitric acid, isoamyl alcohol (bp 131° C.), isobutyl alcohol (bp 107° C.), isophorone (bp 215° C.), isopropyl acetate (bp 88° C.), isopropyl alcohol (bp 82° C.), isopropylbenzene (bp 152° C.), isopropyl chloride (bp 35° C.), isopropyl ether (bp 68° C.), methacrylic aldehyde (bp 69° C.), 1-ethoxy-1,3-butadiene (bp 110° C.), 3-methoxybutylacetate, 2-methoxyethanol (bp 124° C.), 1-methoxy-2-propanol (bp 118° C.), methyl acetate (bp 57° C.), methyl alcohol (bp 41° C.), methyl amyl ketone (bp 149° C.), α-methylbenzylamine (bp 185° C.), α-methylbenzyl ether (bp 174° C.), n-methylbutylamine (bp 90° C.), n-methyl dibutylamine (bp 49° C.), methylene chloride, methyl ethyl ketone (bp 80° C.), 2-methyl-5-ethylpyridine (bp 178° C.), 5-methyl-2-hexanone, methyl isobutyl ketone (bp 117° C.), methyl isopropenyl ketone, N-methylmorpholine (bp 115° C.), 2-methylpentanal (bp 119° C.), 2-methylpentanoic acid, 2-methylpentanol (148° C.), 4-methyl-2-pentanol (bp 134° C.), 4-methyl-2-pentanone, 4-methyl-2-pentene (bp 58° C.), 4-methyl-2-pentyl acetate (bp 144° C.), 4-methyl-2-pentylbutyrate, methylphenylcarbinol (bp 204° C.), methylphenyl ketone (bp 202° C.), 2-methylpropyl acetate (bp 116° C.), methyl propyl ketone (bp 101° C.), methyl vinyl chloride, methyl vinyl ketone (bp 80° C.), nonane (bp 151° C.), 1-octanol (bp 196° C.), paraldehyde, pentaene, 2,4-pentanedione (bp 140° C.), 3-pentanol (bp 141° C.), pentanol (bp 137° C.), 3-pentanol (bp 115° C.), 2-pentanol (bp 119° C.), 4-pentanol, phenol (bp 182° C.), phenyl ether (bp 259° C.), v-picoline (bp 145° C.), propanol (bp 97° C.), propionaldehyde, propionic acid (bp 141° C.), propionitrile (bp 97° C.), propyl acetate (bp 102° C.), propyl chloride (bp 46° C.), propylene chlorohydrin (bp 126° C.), propylene dichloride (bp 95° C.), propylene oxide (bp 34° C.), styrene (bp 145° C.), tetrachlorethylene (bp 121° C.), 1,2,3,6-tetrahydrobenzene aldehyde, tetrahydrobenzonitrile, toluene (bp 111° C.), triarylamine, tributylamine (bp 214° C.), 1,1,2-trichloroethane, 1,1,2-trichlorethylene (bp 87° C.), 1,1,2-trichlorotrifluoroethane (bp 47° C.), tridecanol (bp 155° C.), tridecyl acrylate (bp 150° C.), 1,1,3-trichlorotrifluoroethane (bp 47° C.), tridecanol (bp 155° C.), tridecyl acrylate (bp 150° C.), 1,1,3-triethoxyethane, 1,1,3-triethoxypropane, triethylamine (bp 88° C.), triglycol dichloride (bp 265° C.), valeraldehyde, valeric acid (bp 110° C.), vinyl acetate (bp 72° C.), vinyl aryl ether, vinyl benzoate (bp 95° C.), vinyl butyl ether (bp 94° C.), vinyl 2-chloroethyl (bp 109° C.), ether (bp 34° C.), vinyl crotonate (bp 133° C.), vinyl ethyl ether (bp 33° C.), vinyl-2-ethyl hexanoate (bp 128° C.), vinyl-2-ethylhexyl ether (bp 177° C.), 2-vinyl-5-ethylpyridine, vinyl isobutyl ether (bp 83° C.), vinyl isobutyrate, vinyl isopropyl ether, vinyl-2-methylpentanoate (bp 193° C.), vinyl propyl ether (bp 65° C.), pyridine (bp 115° C.), piperidine (bp 106° C.), 1,3-dimethylbenzene (bp 139° C.), dibutyl ether (bp 142° C.), tributylamine (bp 214° C.), ethanol (bp 78° C.), methanol (bp 64° C.), n-propanol (bp 97° C.), isopropanol (bp 82° C.), n-butanol (bp 117° C.), isobutanol (bp 107° C.), tetrabutanol (bp 82° C.), benzyl alcohol (bp 205° C.), benzene (bp 80° C.), acetone cyanohydrin (bp 95° C.), Acrolein (bp 53° C.), and acrylonitrile (bp 77° C.).

Further, the mixed liquid may be a three-component aqueous azeotropic mixture as exemplified below: water/acetone/X1 (X1: any one of carbon disulfide, isoprene, isopropyl ether), water/ethanol/X2 (X2: any one of acetal, acrylonitrile, benzene, bromodichloromethane, 1-bromopropane, butenyl methyl ether, butenyl methyl ether, butyl amine, butyl aldehyde, carbon disulfide, carbon tetrachloride, chloroform, chloro-2-methylpropene, crotonaldehyde, cyclohexane, cyclohexane, 1,2-dichloroethane, cis-1,2-dichloroethylene, trans-1,2-dichloroethylene, diethoxymethane, diethyl formate, ethyl acrylate, ethyl butyl ether, ethyl chloroacetate, ethylene dichloride, ethyl isobutyl ether, heptane, hexane, isobutyl chloride, isopropyl acetate, isopropyl ether, methyl butyl ether, methyl ethyl ketone, propyl isopropyl ether, toluene, triethylamine, vinylisobutyl ether, vinyl propyl ether, and acetonitrile), water/acetonitrile/X3 (X3: any one of benzene, trichloroethane, and triethylamine), water/aryl alcohol/X4 (X4: any one of aryl ether, benzene, carbon tetrachloride, cyclohexene, hexene, toluene and trichlorethylene), water/benzene/X5 (X5: any one of isopropanol, isopropanol, 2-butanol, 2-methyl-2-propanol, propanol, propyl alcohol), water/1-butanol/X6 (X6: any one of butyl acetate, butyl acrylate, butyl ether, vinyl butyl ether), water/2-butanol/X7 (X7: any one of butyl ether, cyclohexene, diisobutylene, hexene, carbon tetrachloride, hexene, carbon tetrachloride, cyclohexane), water/t-butyl alcohol/carbon tetrachloride, water/methanol/X8 (X8: any one of carbon disulfide, chloroform, methyl chloroacetate), water/propanol/X9 (X9: any one of carbon tetrachloride, 1,3-cyclohexadiene, diethylketone, dipropyl acetal, propyl ether, propyl acetate, trichlorethylene, Isopropyne ether, cyclohexane), water/isopropanol/X10 (X10: any one of diisobutylene, ethylbutyl ether, ethylene dichloride, isopropyl ether, methyl ethyl ketone, isopropyl ether, methyl ethyl ketone, toluene, cyclohexane), water/cyclohexane/2-methyl-2-propanol, water/vinyl-2-ethylhexyl ether/X11 (X11:2-methoxyethanol, 2-ethoxyethanol), water/fluorosilicic acid/hydrofluoric acid, water/formic acid/m-xylene, water/isoamyl acetate/isopropyl acetate, water/3-pentanone/n-propyl alcohol.

In addition, the mixed liquid may be a mixture of water and an environmental hormone. The environmental hormones may be selected from the group consisting of 1,4-dioxane, 17β-estradiol, estrone, estriol, β-sitosterol, genistein, daidzein or zeraleon, 17α-ethinylestradiol (EE2), mestranol (ME), diethylstilbestrol (DES), 4-nonylphenol (NP), 4-tert-octylphenol (OP), bisphenol A (BPA), tributyltin (TBT), methyl mercury, phthalate, PAK and PCB.

In another example, the mixed liquid may be a mixture of water and a volatile organic compound. The volatile organic compound may be acetaldehyde, acetylene, acetylene dichloride, acrolein, acrylonitrile, 1,3-butadiene, carbon tetrachloride, 1,2-dichloroethane, formaldehyde, methyl ethyl ketone, or propylene oxide.

In another example, the mixing liquid may be a racemic mixture.

The separation sieve having the three-dimensional organic structure can effectively separate a multicomponent mixed liquid containing a plurality of liquids having miscibility with each other to a resolution of less than a ppb (part per billion) level. Furthermore, even water-based azeotropes, which are known to be very difficult to separate, can be separated to a resolution of less than a ppb (part per billion) level. Particularly, separating butanol, methanol and acetone from the aqueous environment is one of the key technologies in recent petroleum industry and biomass processing. When the separation sieve having the three-dimensional organic structure is used, such a material can be effectively separated in a very short time with a resolution of less than ppb (part per billion).

An Optical Layer Containing a Self-Assembled Three-Dimensional Organic Structure The optical layer according to the present embodiment may contain a three-dimensional organic structure formed by self-assembly of the organic compounds represented by Chemical Formulas 1 to 3, that is, an organic crystal, for example, the three-dimensional organic structure described with reference to FIG. 1.

An Optical Layer Manufacturing Method Comprising a Three-Dimensional Organic Structure The optical layer can be manufactured using the three-dimensional organic structure obtained by the above-described three-dimensional organic structure manufacturing method. A specific method of manufacturing the optical layer may be as follows.

The Optical Layer Manufacturing Method According to the First Embodiment

The powder containing the three-dimensional structure may be put into a mixed solvent of a first solvent capable of dissolving the powder containing the three-dimensional structure and a second solvent capable of mixing with the first solvent to form a solution. The solution may be coated on a support to form an optical layer. In this case, the first solvent and the second solvent may be mixed in a volume ratio of 1:1 to 7:1, specifically 1:1 to 4:1, for example, 1.5:1 to 2.5:1. The solution may have a concentration of 5 mM to 50 mM, as an example, 5 mM to 40 mM, as another example, 1 mM to 30 mM. The coating may also be spin coating, dip coating, bar coating, slot die coating, spray coating, roll to roll coating, or inverse roll coating. The first solvent may be, for example, chloroform, and the second solvent may be, for example, ethyl acetate.

The Optical Layer Manufacturing Method According to the Second Embodiment

In another example, a selected polymer having miscibility with the three-dimensional structure may be placed in a mixed solvent of a first solvent capable of dissolving a powder containing the three-dimensional structure and a second solvent capable of mixing with the first solvent to form a first solution. After forming the first solution, a powder containing the three-dimensional structure may be placed in the first solution to form a second solution, and the second solution may be coated on a support to form an optical layer. The first solvent may be, for example, chloroform, and the second solvent may be, for example, ethyl acetate. Such an optical layer may be micro-phase-separated into a region containing the three-dimensional structure and a region containing the polymer. In this case, the first solvent and the second solvent may be mixed in a volume ratio of 1:1 to 7:1, specifically 1:1 to 4:1, for example, 1.5:1 to 2.5:1. The first solution may have a concentration of 1 mM to 20 mM, and the second solution may have a concentration of 5 mM to 50 mM, for example, 5 mM to 40 mM. The coating may also be spin coating, dip coating, bar coating, slot die coating, spray coating, roll to roll coating, or inverse roll coating. The polymer may be polyvinyl chloride (PVC), polyamide (PA), polyethylene (PE), polyethersulfone (PES), Polytetrafluoroethylene (PTFE), polydimethylsiloxane (PDMS), polymethylmethacrylate (PMMA), high-density polyethylene (HDPE), low-density polyethylene (LDPE), Polypropylene (PP), polystyrene (PS), Polyvinyl acetate (PVAC), polyethylene oxide (PEO), NYLON, polyethylene terephthalate (PET), polyimide (PI), or a combination of two or more of them.

The Optical Layer Manufacturing Method According to the Third Embodiment

In the first and second embodiments, instead of using a mixed solvent of the first solvent and the second solvent, a single solvent capable of dissolving or dispersing the powder containing the three-dimensional structure may be used.

The Optical Layer Manufacturing Method According to the Fourth Embodiment

The solutions or dispersions of the first, second, and third embodiments may further contain an antioxidant. The antioxidant may be contained in the solution in an amount of 0.5 to 3% by weight, for example, 1 to 2% by weight. The antioxidant may be a primary antioxidant and a secondary antioxidant. Here, the primary antioxidant may be a radical scavenger, and the secondary antioxidant may be a hydroperoxide decomposer. The primary antioxidant and the secondary antioxidant may be contained in a weight ratio of 1:1 to 1:3.

The primary antioxidant may be selected from the group consisting of phenolics, monophenolics, bisphenolics, polyphenol antioxidants, amine-based antioxidants, or a combination thereof. The secondary antioxidant may also be sulfur-based antioxidants, phosphorus-based antioxidants, or a combination thereof.

The phenolic antioxidants may be phenolic, monophenolic, biphenolic, polyphenolic and thiobisphenolic or hindered phenolics. The polyphenolic antioxidant may be tetrakis[methylene(3,5-di-t-butyl-4-hydroxy-hydrocinnamate)]methane or octadecyl 3-(3,5-di-tert-butyl-4-hydroxyphenyl)-propionate. The amine-based antioxidant may play a role of hydrogen donation similar to the phenol-based antioxidant, and also act as a peroxide decomposer at a high temperature. Examples of the amine-based antioxidant may include an N-substituent of an amine of p-phenylene such as an alkyl-substituted phenylamine, a diaryl-p-phenylene amine or a substituent thereof, a substituted quinoline such as 6-ethoxy-2,2',4-trimethyl-1,2-dihydroxyquinoline, a substituted piperazine such as 2,2',6,6'-tetralkylpiperazine, and the like.

The sulfur-based antioxidant is useful as a peroxide decomposer which is effective for long-term exposure to heat, such as dilauryl 3,3'-thiodipropionate or dimyristyl 3,3-thiodipropionate (DMTP). The phosphorus-based antioxidant may be converted into phosphates after the hydrogen peroxide is changed to alcohol. Examples of such phosphorus-based antioxidants include trialkylphosphite (alkyl: isodecyl-, tridecyl-), phenyldialkylphosphite (alkyl: isodecyl, isooctyl), diphenylalkylphosphite (alkyl: isodecyl, isooctyl), triphenylphosphite, Phosphorus acid (1,1-biphenyl-4, 4'-diyl), bistetra(2,4-bis(1,1'-dimethylethyl)phenyl) ester, 3,5-di-t-butyl-4-hydroxy-benzylphosphate-diethyl ester, 9,10-dihydro-9-oxa-10-phosphaphenanthrene-10-oxide, sodium bis(4-t-butylphenyl)phosphite, sodium 2,2'-methylene-bis-(4,6-di-tert-butylphenyl)phosphate, 1,3-bis(diphenoxy-phosphonyloxy)benzene, bis(2,6-di-tert-butyl-4-methylphenyl)pentaerythritoldiphosphite, tris(2,4-di-t-butylphenyl) phosphite, or 2,2-methylene bis[4,6-di-tert-butylphenyl]octylphosphite.

In addition, the solution may include at least one biostable antioxidant selected from the group of biostability-proven antioxidants consisting of butylhydroxyanisole, dibutylhydroxytoluene, vitamin c, tocopherol, lecithin, propyl gallate, tertiary butyl hydroquinone, erythorbinic acid, ascorbyl palmitate, L-ascorbyl stearate.

The Optical Layer Manufacturing Method According to the Fifth Embodiment

In another example, 20 to 75% by weight of the powder containing the three-dimensional structure, 5 to 75% by weight of the miscible polymer with the three-dimensional structure, and the remaining amount of the antioxidant may be mixed to form a mixture, and the mixture may be coated on a substrate to form an optical layer. The coating may also be spin coating, dip coating, bar coating, slot die coating, spray coating, roll to roll coating, or inverse roll coating. The polymer may be as described in the optical layer manufacturing method according to the second embodiment, and the antioxidant may be as described in the optical layer manufacturing method according to the fourth embodiment.

The optical layer may have a thickness of 50 to 500 nm, and more specifically, may have a thickness of 100 to 200 nm.

Such an optical layer may be a three-dimensional organic structure layer having a periodic and regular structure. The optical layer is a layer in which the characteristics as a meta material having a dielectric constant close to zero and the characteristics as a topological insulator are mixed, thereby exhibiting excellent properties as an optical amplifying material.

Specifically, the characteristic of the optical layer as a meta-material is due to a periodic and regular structure of the three-dimensional organic structure. Within the wavelength range defined by the lattice spacing of the three-dimensional structure, the optical layer exhibits a dielectric constant of less than 1, specifically close to zero, thereby showing space distortion and resulting elliptic dispersion; and therefore optical amplification or light-amplifying characteristic can be shown. The lattice spacing can be controlled by the length of $-A-(L)_n-Y-X$ shown in FIG. 1, that is, $-A_1-(L_1)_{n1}-Y_1-X_1$ or $-A_2-(L_2)_{n2}-Y_2-X_2$ of the compound shown in the above Chemical Formula 1. More specifically, the lattice spacing can be adjusted by the setting of the respective components of $Y_1$ and $Y_2$, specifically

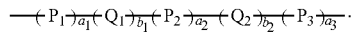

As an example, if the compound forming the periodic and regularly ordered three-dimensional structure is 4,5,9,10-tetrakis(dodecyloxy)-pyran (compound 11), the lattice spacing can be about 3.4 nm. As a result, it is possible to exhibit the characteristic as a meta material having a dielectric constant of less than 1, specifically, close to 0, in a range of about 300 nm or less.

In addition to the optical amplification characteristics, the optical layer can exceed the resolution limit of a general medium because, in the optical layer, there is no generation of evanescent waves unlike in the general medium. Further, as there is no loss of electromagnetic wave in the optical layer, the electromagnetic wave can be guided or amplified with respect to the region where the dielectric constant is lower than 1. Using these properties, the optical layer can be used as a novel magnetic resonance image, a novel optical circuit for a near-infrared, visible, or ultraviolet region, a super-lens beyond the diffraction limit, a tunable metamaterials for switching and modulating electromagnetic waves, and the like. In addition, the optical layer may be used in more practical areas such as invisible cloaks, illusion optics, optical black holes, bean shifters, field rotators, light concentrators, lossless waveguide bends, and the like.

On the other hand, topological insulators can be realized by 1) lattice symmetry and 2) spin-orbital coupling. The periodic and regularly ordered three-dimensional structure according to this embodiment can exhibit lattice symmetry. In addition, spin-orbit coupling may occur due to periodic and regularly arranged aromatic rings in the structure. Accordingly, the optical layer having a periodic and regularly ordered three-dimensional structure can have characteristics as a topological insulator. Therefore, the optical layer according to the present embodiment can have a Dirac band structure, and Dirac plasmons generated by the periodic and regular arrangement of the aromatic ring groups cause local surface plasmon resonance, thereby exhibiting an amplifying effect on light coming from the outside. The optical layer exhibiting characteristics of such a topological insulator can be extended to a topological insulator having a magnetic property and a topological insulator having an electrical property, and can be used as a quantum computer, a detector of a terahertz band, a device of a spintronic device, or tunable amplifier.

In addition, the optical layer may exhibit various linear or nonlinear optical properties caused by the anisotropic properties of the electrical multipoles of the quadrupole or more of the aromatic rings in the regular, periodic three-dimensional organic structure. Using this, the optical layer can be used in a wide range of materials, such as an n-harmonic generation material by the n-order polarization, an optical parametric amplifying material by sum frequency and difference frequency, an optical parametric generating material, an optical parametric vibrating material, and an electromagnetic wave binding material by self-binding effect, electromagnetic wave magnetic focusing material. When such anisotropic properties cause synergy with the meta-material properties, the optical layer functions as a linear or non-linear metamaterial. In this case, the optical layer may be used as a giant local field amplifier, a hysteretic transition material, an unusual wave mixer, a solitary wave propagator, a backward phase matching material with the second harmonic, or the optical parametric amplifier.

As described above, the optical layer may secure both the properties originating from the meta-material and the properties originating from the topological insulator. Due to the property as a meta-material, the optical layer can be used as a super lenses exceeding the diffraction limit [Nature materials, 7.6, 435-441 (2008)], a transparent material through distortion of light [Nature photonics, 1.4, 224-227 (2007)], Antenna using superior characteristics [Antennas and Wireless Propagation Letter, IEEE, 8, 295-298 (2008)], and the like. In addition to the recent structural features of meta-materials, as well as the viewpoints of the basic unit material constituting the meta-material, the optical layer can be used as a variable bandgap material[physical review B 70.23 235109 (2004)], a nano-laser [Physical Review B 75.8 085436 (2007)], and an electromagnetic wave shielding material capable of blocking electromagnetic waves having a specific band gap [Microwave Theory and Techniques, IEEE Transactions 58.1, 195-202 (2010)]. Further, it can be used as an absorber for terahertz band [Applied Physics Letter, 100.11, 111104 (2012)], a gradient refractive index lens material (GRIN) [U.S. Pat. No. 7,570,432, 4 Aug. (2009)], and a terahertz active element which can be optically and electrically controlled, and can be used as a memory [Science 325, 5947, 1518-1521 (2009)].

An optical device including an optical amplification layer Examples of optical devices including the optical layer having the above-described three-dimensional organic structure as an optical amplification layer or light-amplifying layer will be described below.

FIG. 3 is a cross-sectional view illustrating a light emitting diode having an optical amplification layer according to an embodiment of the present invention.

Referring to FIG. 3, there may be provided a base substrate 101 having an device region and a peripheral region surrounding the device region. The base substrate 101 may be a silicon substrate, a metal substrate, or a ceramic substrate. The device region may be a region where a light emitting diode semiconductor chip to be described later is mounted, and the peripheral region may be an region other than the device region. The base substrate 101 may have bonding pads 102 and 103 on its device region. A housing 105 having a cavity 105a may be disposed on a peripheral region of the base substrate 101. Portions of the bonding pads 102 and 103 may be exposed in the cavity 105a. The housing 105 may be formed of silicon, metal, ceramics, or resin. The base substrate 101 and the housing 105 may be integrally formed without being separated from each other.

The light emitting diode chip C may be disposed on one of the bonding pads exposed in the cavity 105a. The light emitting diode chip (C) includes an n-type semiconductor layer, a p-type semiconductor layer, and a photoactive layer interposed therebetween. The photoactive layer may be a depletion region between the n-type semiconductor layer and the p-type semiconductor layer or may be a separately introduced layer. When the electric field is applied between the n-type semiconductor layer and the p-type semiconductor layer, the light emitting diode chip C emits light while recombining electrons and holes in the photoactive layer. The light emitting diode chip C may be any one of GaAlAs type, AlGaIn type, AlGaInP type, AlGaInPAs type, and GaN type. The light emitting diode chip C may be an element that emits visible light, ultraviolet light, or infrared light. The n-electrode and the p-electrode of the light emitting diode chip C may be electrically connected to the bonding pads 102 and 103 via the wires W, respectively.

An organic sealing layer 110 filling the cavity 105a may be disposed in the cavity 105a. The organic sealing layer 110 may contain a light-transmitting resin and a light converter. The light converter converts light generated from the light emitting diode chip C into light having a lower wavelength, and may be a phosphor or a quantum dot, thereby implementing white light.

The glass sealing layer 120 may be formed on the organic encapsulation layer 110. The glass sealing layer 120 may have a lens portion 120a corresponding to the position of the light emitting diode chip (C). The anti-reflection layer 130 may be disposed on the organic sealing layer 120.

An optical amplification layer LAL may be disposed on the path of light generated from the photoactive layer of the light emitting diode, that is, between the photoactive layer and the exterior. Specifically, an optical amplification layer LAL may be disposed on the anti-reflection layer 130. However, the present invention is not limited to this, and the optical amplification layer LAL may be formed between the glass sealing layer 120 and the anti-reflective layer 130, between the glass sealing layer 120 and the organic encapsulation layer 110, and may be disposed between the organic encapsulation layer 110 and the light emitting diode chip C.

The light emitting diode shown in FIG. 3 may be a light emitting diode module. However, the present invention is not limited to this, a light emitting diode array having a plurality of the light emitting diode modules or the light emitting diode chips C may be implemented.

FIG. 4 is a cross-sectional view illustrating an organic light emitting diode or a quantum dot light emitting diode panel having an optical amplification layer according to an embodiment of the present invention. The organic light emitting diode or the quantum dot light emitting diode panel may be a display panel or an illumination panel. In the case of the display panel, the unit pixels shown in FIG. 4 may be arranged in a matrix form. In the case of an illumination panel, it may be the unit module shown in FIG. 4, or an array in which a plurality of such unit modules are arranged.

Referring to FIG. 4, the organic light emitting diode or quantum dot light emitting diode panel 200 includes a pixel electrode 230 disposed on an device substrate 210, a light emitting functional layer 250 disposed on the pixel electrode 230, a common electrode 270 disposed on the light emitting functional layer 250 and an encapsulation substrate 290 disposed on the common electrode 270. An encapsulant 280 for blocking or absorbing moisture and oxygen may be disposed between the common electrode 270 and the encapsulation substrate 290.

In the case of the display panel, a thin film transistor 220 electrically connected to the pixel electrode 230 and supplying or blocking an electric signal to the pixel electrode 230 may be disposed on the device substrate 210. In detail, the buffer layer 215 may be disposed on the device substrate 210. A semiconductor layer 221 having source and drain regions and a channel region disposed therebetween may be disposed on the buffer layer 215 and a gate insulating layer 223 may be disposed on the semiconductor layer 221, and a gate electrode 225 crossing over the semiconductor layer 221 may be disposed on the gate insulating layer 223. A first interlayer insulating film 226 covering the gate electrode 225 may be disposed on the gate electrode 225. Source and drain electrodes 227 are formed on the first interlayer insulating film 226. The source and drain electrodes 227 penetrate the first interlayer insulating film 226 and the gate insulating layer 223 and connect to the source and drain regions, respectively. A second interlayer insulating film 229 covering the source and drain electrodes 227 may be disposed on the source and drain electrodes 227. The pixel electrode 230 may be formed on the second interlayer insulating film 229. The pixel electrode 230 may be a transparent conductive film such as indium tin oxide (ITO) or indium zinc oxide (IZO).

A pixel defining layer 235 having an opening for exposing the pixel electrode 230 may be disposed on the pixel electrode 230. The opening may define the light emitting region ER. The light emitting functional layer 250 may be disposed on the pixel electrode 230 exposed in the opening. The light emitting function layer 250 may include a photoactive layer that is a light emitting layer. The light emitting layer may be an organic light emitting layer or a quantum dot light emitting layer. The light-emitting functional layer 250 may further include at least one of a hole injection layer, a hole transport layer, an electron transport layer, and an electron injection layer. The common electrode 270 may be a light transmitting or transparent electrode, and may be formed by using a metal such as aluminum, magnesium, calcium, sodium, potassium, indium, yttrium, lithium, silver, lead and cesium or a combination of two or more thereof.

Holes injected from the pixel electrode 230 and electrons injected from the common electrode 270 are recombined in the light emitting layer of the light emitting functional layer 250 to emit light when an electric field is applied between the pixel electrode 230 and the common electrode 270. At least one of the device substrate 210 and the encapsulation substrate 290 may be a light transmitting substrate, and may be a glass substrate or a resin substrate. For example, the device substrate 210 may be a light transmitting substrate, and the encapsulation substrate 290 may be a light reflecting substrate. In this case, the light emitted from the light emitting layer may be emitted to the outside through the device substrate 210. This case is referred to as a back-emission type panel. As another example, the device substrate 210 may be a light reflecting substrate and the encapsulation substrate 290 may be a light transmitting substrate. In this case, the light emitted from the light emitting layer may be emitted to the outside through the encapsulation substrate 290. This case is referred to as a top-emission type panel. As another example, both the device substrate 210 and the encapsulation substrate 290 may be a light transmitting substrate. In this case, the light emitted from the light emitting layer may be emitted to the outside through both the device substrate 210 and the encapsulation substrate 290. This case is referred to as a double-sided emission type panel. Further, when both the device substrate 210 and the encapsulation substrate 290 are resin substrates, a flexible element can be realized.

An optical amplification layer (LAL) may be disposed in a path along which light generated from the light emitting layer of the organic light emitting diode panel travels. Specifically, in the case of a bottom-emission type panel, an optical amplification layer (LAL) may be disposed on the lower surface of the device substrate 210. However, the present invention is not limited to this, the optical amplification layer (LAL) may be disposed between the device substrate 210 and the buffer layer 215, between the buffer layer 215 and the thin film transistor 220, between the thin film transistor 220 and the first interlayer insulating film 226, or between the first interlayer insulating film 226 and the pixel electrode 230. On the other hand, in the case of a top-emission type panel, the optical amplification layer (LAL) may be disposed on the encapsulation substrate 290. However, the present invention is not limited thereto, the optical amplification layer LAL may be disposed between the encapsulation substrate 290 and the encapsulant 280, or between the encapsulant 280 and the common electrode 270. On the other hand, in the case of a double-sided emission type panel, the position of the optical amplification layer (LAL) in the case of the top-emission type panel can be combined with the case of the back-emission type panel.

Meanwhile, the optical amplification layer according to an embodiment of the present invention can be used for various illumination devices. Specifically, the optical amplification layer can be disposed in the path along which light propagates in each illumination device. The illumination device may be a light emitting diode module, a light emitting diode array, an organic light emitting diode lighting module, a quantum dot light emitting diode lighting module, an organic light emitting diode array, a quantum dot light emitting diode array, a fluorescent lamp, an incandescent lamp, or the like.

FIG. 5 is a cross-sectional view illustrating a liquid crystal display having an optical amplification layer according to an embodiment of the present invention.

Referring to FIG. 5, a liquid crystal display includes a lower substrate 310, an upper substrate 320, and a liquid crystal layer 330 positioned between the upper and lower substrates 310 and 320.

The lower substrate 100 includes a lower base substrate 311. The lower base substrate 311 may be a glass substrate as a light-transmitting substrate. A thin film transistor (not shown) may be formed on the upper surface of the lower base substrate 311. An interlayer insulating film 313 covering the thin film transistor may be formed on the lower base substrate 311. The interlayer insulating film 313 may be an inorganic insulating film such as a silicon nitride film or a silicon oxide film, an organic insulating film such as a resin, or a multilayer thereof. A pixel electrode 315 can be formed on the interlayer insulating film 313. The pixel electrode 315 may be electrically connected to the thin film transistor through the interlayer insulating layer 313. The pixel electrode 315 may be a transparent conductive film such as indium tin oxide (ITO) or indium zinc oxide (IZO). A lower alignment layer 317 may be formed on the pixel electrode 315.

The upper substrate 320 includes an upper base substrate 321. The upper base substrate 321 may be a glass substrate as a light-transmitting substrate. Shading patterns (not shown) and color filters (not shown) may be formed on the lower surface of the upper base substrate 321. A protective film 323 may be formed on the color filters. The protective film 323 may be an inorganic insulating film such as a silicon nitride film or a silicon oxide film, an organic insulating film such as a resin, or a multilayer thereof. And the counter electrode 325 may be formed on the protective film 323. The counter electrode 325 may also be a transparent conductive film such as ITO (Indium Tin Oxide) or IZO (Indium Zinc Oxide). An upper alignment layer 327 may be formed on the counter electrode 325. The upper alignment layer 327 and the lower alignment layer 317 may be formed of poly-amic acid, polyimide, lecithin, nylon, or PVA (polyvinylalcohol). The liquid crystal in the liquid crystal layer 330 is initially oriented by the alignment layers and can perform light blocking or light transmission operation by an electric field applied between the first and second electrodes 315 and 325.

A lower polarizing film 341 may be disposed adjacent to a lower surface of the lower base substrate 311 and an upper polarizing film 342 may be disposed adjacent to an upper surface of the upper base substrate 321. The lower polarizing film 341 and the upper polarizing film 342 may be arranged such that the transmission axes thereof are orthogonal to each other.

A backlight unit 350 may be disposed below the lower polarizing film 341. The backlight unit 350 may include a reflective sheet 351, a light guide plate 352, a diffusion sheet 355, a prism sheet 356, and a protective sheet 357 which are sequentially stacked. Further, the light emitting device 353 and the light emitting device mounting portion 354 for mounting the light emitting device 353 may be disposed at the edge portions of the light guide plate 352. The light emitting device 353 may be a cold cathode fluorescent lamp or the light emitting diode described with reference to FIG. 3. The illustrated backlight unit 350 may be of the edge type in which the light emitting device is located at the edge. But it may not be limited thereto, the light emitting device 353 may be positioned between the reflective sheet 351 and the diffusion sheet 355, and the light guide plate 352 may be omitted.

An optical amplification layer (LAL) may be disposed in a path along which light generated from the light emitting device 353 of the liquid crystal display panel proceeds. Specifically, the optical amplification layer (LAL) may be disposed on the upper polarizing film 342. However, the present invention is not limited thereto, the optical amplification layer LAL may be formed between the upper polarizer film 342 and the upper base substrate 321, between the upper base substrate 321 and the color filters (not shown), between the color filters and the protective film 323, between the protective film 323 and the counter electrode 325, between the counter electrode 325 and the upper alignment film 327, between the lower alignment film 317 and the pixel electrode 315, between the pixel electrode 315 and the interlayer insulating film 313, between the interlayer insulating film 313 and the thin film transistor (not shown), between the thin film transistor and the lower base plate 311, between the lower base plate 311 and the lower polarizing film 341, between the lower polarizing film 341 and the backlight unit 350, or in the backlight unit 350. When the optical amplification layer LAL is disposed in the backlight unit 350, the optical amplification layer LAL may be disposed between the protective sheet 357 and the prism sheet 356, between the prism sheet 356 and the diffusion sheet 355, between the diffusion sheet 355 and the light guide plates 352, or between the light guide plate 352 and the light emitting device 353.

FIG. 6 is a cross-sectional view of a solar cell having an optical amplification layer according to an embodiment of the present invention.

Referring to FIG. 6, a second conductivity type semiconductor layer 413 may be disposed on the first conductivity type semiconductor layer 411. The first and second conductivity type semiconductor layers 411 and 413 may be inorganic semiconductor layers that are silicon semiconductor layers, germanium semiconductor layers, silicon germanium semiconductor layers, or compound semiconductor layers. In this case, a PN junction where excitons are generated by light absorption may be formed between the first and second conductivity type semiconductor layers 411 and 413. The compound semiconductor layer may be a III-v semiconductor layer, and may be a GaAs-based, an AlAs-based, a GaP-based, or an InP-layer, specifically an $AlxGa_{1-x}As$ ($0 \leq X \leq 1$) or $Ga_xIn_{1-x}P$ ($0<X<1$).

Meanwhile, the first conductivity type semiconductor layer 411 may be a chalcogenide-based material layer such as an I-III-$VI_2$ compound semiconductor layer or an II-VI compound semiconductor layer. The I-III-$VI_2$ compound semiconductor layer may be $CuInS_2$ (CIS), $CuGaS_2$ (CGS), $CuInSe_2$ (CISe), $CuGaSe_2$ (CGSe), $CuAlSe_2$ (CASe), $CuInTe_2$ (CITe), $CuGaTe_2$ (CGTe), $Cu(In, Ga)S_2$ (CIGS), $Cu(In, Ga)Se_2$ (CIGSe), $Cu_2ZnSn\delta_4$ (CZTS), or $Cu(In,Ga)Se_2$ (CIGS) layer. The II-VI compound semiconductor layer may be a CdTe layer. In this case, the second conductive semiconductor layer 413 may be a CdS, $Zn(O, S, OH)_x$, $In(OH)_xSy$, $ZnIn_xSe_y$, or ZnSe layer and may be referred to as a buffer layer.

These semiconductor layers 411 and 413 may be crystalline semiconductor layers, polycrystalline semiconductor layers or amorphous semiconductor layers. Further, these semiconductor layers 411 and 413 may be polycrystalline semiconductor layers or amorphous semiconductor layers which can realize a thin film solar cell.

Alternatively, the first and second conductive semiconductor layers 411 and 413 may be organic semiconductor layers. In this case, a photoactive layer (not shown) in which excitons are generated by light irradiation may be additionally formed between the first and second conductivity type semiconductor layers 411 and 413. The photoactive layer may be a bulk heterojunction (BHJ) layer in which an electron donor material and an electron acceptor material are mixed with each other. Or the photoactive layer has the formula $RMX_3$ wherein R may be a monovalent cation selected from the group consisting of $C_nH_{2n+1}NH_3^+$ (where n is an integer of 1 to 0), $NH_4^+$, $HC(NH_2)_2^+$, $CS^+$, $NF_4^+$, $NCl_4^+$, $PF_4^+$, $PCl_4^+$, $CH_3PH_3^+$, $CH_3AsH_3^+$. $PH_4^+$, $ASH_4^+$, $SbH_4^+$, and combinations thereof, wherein M may be a divalent metal cation selected from the group consisting of $Pb_2^+$, $Sn_2^+$, $Ge_2^+$, and combinations thereof, wherein X may be a halogen anion. Here, the first conductive semiconductor layer 411 may be a dense $TiO_2$ layer and may be referred to as a recombination preventing layer.

A reflective layer may be formed under the first conductive semiconductor layer 411. The reflective layer may serve as the first electrode 401. The second electrode 420 may be formed on the second conductive semiconductor layer 413. The second electrode 420 may be a light-transmitting electrode. The light-transmitting electrode may be a carbon nanotube layer, a graphene layer, a transparent conductive oxide layer, or a metal layer, and may be formed by coating, thermal evaporation, electron beam evaporation, or sputtering.

An anti-reflection layer 430 may be additionally disposed on the second electrode 420. The anti-reflection layer 430 may be a silicon nitride film ($SiN_x$ layer). A glass substrate 440 may be formed on the second electrode 420 or the anti-reflection film 430 when the anti-reflection film 430 is formed. The glass substrate 440 may be a silica ($SiO_2$) layer or a silicate layer having a refractive index of about 1.4 to about 1.6, for example, borosilicate glass, soda-lime glass, aluminum silicate glass, or spin on glass (SOG). However, it is not limited thereto.

A protective film 450 may be disposed on the glass substrate 440. The protective film 450 may be PDMS (Polydimethylsiloxane), PMMA (polymethyl methacrylate), or EVA (Ethylene Vinyl Acetate) having a refractive index of about 1.4 to about 1.5.

When the solar cell is irradiated with light, for example, sunlight, the PN junction or the photoactive layer between the first and second conductive type semiconductor layers 411 and 413 absorbs the photon to produce electron-hole pairs, and the electron-hole pairs are separated so that the electrons are transferred to the second electrode 420 and the holes are transferred to the first electrode 401 to produce electricity.

An optical amplification layer (LAL) may be disposed in the path of light, for example, sunlight, into the solar cell. Specifically, an optical amplification layer (LAL) may be disposed on the protective film 450. However, the present invention is not limited to this, and the optical amplification layer LAL may be formed between the protective film 450 and the glass substrate 440, between the glass substrate 440 and the antireflection film 430, or between the antireflection film 430 and the second electrode (420).

FIG. 7 is a cross-sectional view of a dye-sensitized solar cell having an optical amplification layer according to an embodiment of the present invention.

Referring to FIG. 7, a lower substrate 510 may be provided. The lower substrate 510 may be a light-transmitting substrate, and the material thereof may be glass or a light-transmitting polymer. A first electrode 520 may be formed on the lower substrate 510. The first electrode 520 is a light-transmitting electrode. The first electrode 520 may be a conductive polymer film such as polyaniline or a conductive oxide thin film such as ITO (indium tin oxide), FTO (F-doped $SnO_2$), or ATO (antimony tin oxide) or FTO coated ITO. A semiconductor layer may be formed on the first electrode 520.

The semiconductor layer may have stacked metal oxide particles 530. Although the metal oxide particles 530 are illustrated as being spherical, the metal oxide particles 530 may be tubular, wire, or rod-shaped, and may be nanomaterials having a length in at least one direction of less than 1000 nm. The metal oxide may be selected from the group consisting of titanium oxide (e.g., $TiO_2$), tin oxide (e.g., $SnO_2$), tungsten oxide (e.g., $WO_3$), zinc oxide (e.g., ZnO), zirconium oxide (e.g., $ZrO_2$), strontium oxide (e.g., SrO), or niobium oxide (e.g., $Nb_2O_5$). Dye particles 535 can be adsorbed on the surface of the metal oxide particles 530. The dye 535 may be a material capable of absorbing sunlight to generate an electron-hole pair, for example, an organic dye or a quantum dot inorganic dye. The organic dye may be a ruthenium-based organometallic compound or an organic compound, and the quantum dot inorganic dye may be InP or CdSe. Among those, the ruthenium-based organometallic compound may be a dye in which pyridine-based ligands, or pyridine-based ligands and SCN ligands are coordinated around the central metal ruthenium.

After the dye 535 is adsorbed on the surface of the metal oxide particles 530, an encapsulating material 570 may be formed on the edge of the substrate 510 at a height greater than a height of the semiconductor layer. An upper substrate 560 having a second electrode 550 formed on one surface thereof may be prepared and an upper substrate 560 may be disposed such that the second electrode 550 faces the metal oxide particles 530. The rim of the upper substrate 560 is closely contacted with the encapsulating material 570, so that the second electrode 550 and the semiconductor layer are spaced apart from each other by a predetermined distance. Here, the upper substrate 560 may be a light-transmitting substrate like the lower substrate 510, and the material thereof may be glass or a light-transmitting polymer.

The space between the upper substrate 560 and the lower substrate 510 may be filled with an electrolyte 540 through an electrolyte injection port (not shown in the figure) formed in advance on one side of the encapsulating material 570, and then the electrolyte injection hole may be sealed to fabricate the dye-sensitized solar cell 500 according to an embodiment of the present invention.

Here, the electrolyte 540 may be introduced into the porous semiconductor layer, and may be a liquid electrolyte to facilitate diffusion in the porous semiconductor layer. The liquid electrolyte may contain a liquid such as acetonitrile as a medium and may contain $I^-/I_3^-$ as an oxidation-reduction species. As the source of $I^-$, LiI, NaI, or imidazolium iodine can be used, and $I_3^-$ can be generated by dissolving $I_2$ in the medium.

A specific wavelength band of the entire wavelength band of the solar light incident through the lower substrate 510 may be absorbed by the dye 535 and the dye 535 absorbing the light energy may generate electron-hole pairs by an MLCT (Metal to Ligand Charge Transfer) when the dye 535 is organic dye. The generated electrons may be transmitted to the first electrode 520 through the metal oxide particles 530. $I^-$ in the electrolyte may be oxidized to $I_3^-$ to transfer electrons to the oxidized dye 535, and the dye 535 may be reduced again. $I_3^-$ may receive electrons from the second electrode 550 and be reduced back to $I^-$.

The optical amplification layer (LAL) may be disposed in the path of the light for example, sunlight traveling into the dye-sensitized solar cell in the dye-sensitized solar cell. Specifically, the optical amplification layer (LAL) may be disposed on the upper substrate 560. However, the present invention is not limited to this, and the optical amplification layer LAL may be disposed between the upper substrate 560 and the second electrode 550.

As described with reference to FIGS. 3 to 7, the optical amplification layer (LAL) can be disposed on the optical path of the optical element. Specifically, in the case of the light emitting device described with reference to FIGS. 3 and 4, an optical amplification layer (LAL) may be disposed on an optical path where light generated from the light emitting layer is extracted to the outside, that is, between the light emitting layer and the outside of the device. In addition, in the case of the liquid crystal display device described with reference to FIG. 5, the optical amplification layer (LAL) may be disposed on the optical path in which light emitted from the light emitting device is extracted to the outside of the device. On the other hand, in the case of the light receiving device, i.e., the solar cell described with reference to FIGS. 6 and 7, an optical amplification layer (LAL) may be disposed on an optical path in which external light is introduced into the light absorption layer, in other words, between the outside of the device and the light absorption layer.

Such an optical amplification layer (LAL) is a periodic and regular three-dimensional organic structure as described above. Particularly, by forming a regular periodic three-dimensional structure having a nanometer periodicity, a meta material having a dielectric constant close to zero in a specific wavelength region can be realized. Thus, it can exhibit an optical amplification effect. The particular wavelength region may be near-infrared, visible or ultraviolet region, which can be controlled by adjusting the lattice spacing of the three-dimensional structure. In addition, the optical amplification layer (LAL) may exhibit characteristics as a topological insulator. Particularly, the optical amplification layer (LAL) having the periodic and regular structure can amplify light by local surface plasmon resonance of Dirac plasmon generated by the characteristic as a topological insulator.

The periodic and regular three-dimensional organic structure described above can exhibit excellent characteristics as an optical amplifying material by mixing the characteristic of a meta material having a dielectric constant close to zero and the characteristic of a topological insulator. The three-dimensional organic structure can realize an optical element having higher efficiency by using these characteristics.

Hereinafter, exemplary experimental examples will be described for promoting understanding of the present invention. However, the following experimental examples are only examples to help understanding of the present invention, and the present invention is not limited thereto.

Compound Preparation Examples 1A to 3A:
Preparation of tetrakis (alkyloxy)-pyrene

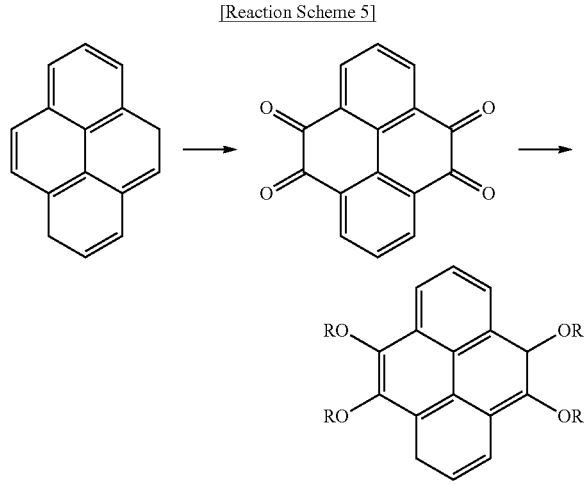

[Reaction Scheme 5]

Compound Preparation Example 1A: Preparation of 4,5,9,10-tetrakis (dodecyloxy)-pyrene 1A-1. Preparation of pyrene-4,5,9,10-tetraone Pyrene (10 mmol) was dissolved in a solution of dichloromethane (40.0 ml) and acetonitrile (40 ml), and then the solution was refluxed at 40° C. for 16 hours with ruthenium (III) chloride hydrate (0.25 g, 1.2 mmol) and sodium metaperiodate ($NaIO_4$) (17.5 g, 81.8 mmol) in distilled water (50.0 mL) to produce pyrene-4,5,9,10-tetraone.

Pyrene-4,5,9,10-tetraone: $^1$H NMR (600 MHz, DMSO-d6) δ 8.32 (d, 4H), 7.71 (t, 2H)

1A-2. Preparation of 4,5,9,10-tetrakis(dodecyloxy)-pyrene

The pyrene-4,5,9,10-tetraone (10 mmol) obtained in 1A-1 was dissolved in distilled water (50 ml) and tetrahydrofuran (THF) with bromotetrabutylammonium ($Bu_4NBr$) (13 mmol) and sodium hydrosulfite ($Na_2S_2O_4$) (115 mmol) and refluxed at 65° C. for 5 minutes. An aqueous solution prepared by dissolving bromododecyl (60 mmol) and KOH (306 mmol) in distilled water (50 ml) was added to the reaction solution and refluxed at 65° C. for 16 hours to obtain 4,5,9,10-tetrakis(dodecyloxy)-pyrene (R=$C_{12}H_{25}$ in Reaction Scheme 5, compound 11) (yield: 72%).

4,5,9,10-tetrakis(dodecyloxy)-pyrene: $^1$H NMR (600 MHz, $CDCl_3$)δ 8.32 (d, 4H), 7.71 (t, 2H), 4.21 (t, 8H), 1.91 (m, 8H), 1.57 (m, 8H), 1.40-1.27 (m, 64H), 0.88 (t, 12H)

FIG. 8 is a $^1$H-NMR spectrum of 4,5,9,10-tetrakis(dodecyloxy)-pyrene according to Preparation Example 1A measured in a $CDCl_3$ solvent.

Compound Preparation Example 1B: Preparation of 4,5,9,10-tetrakis (tetradecyloxy)-pyrene The same procedure as in Preparation Example 1A was conducted except that bromotetradecyl was used instead of bromododecyl in the above 1A-2 to prepare 4,5,9,10-tetrakis (tetradecyloxy)-pyrene (R=$C_{14}H_{29}$ in Reaction Scheme 5, compound 12) (yield: 70%).

4,5,9,10-tetrakis(tetradecyloxy)-pyrene: $^1$H NMR (600 MHz, $CDCl_3$) δ 8.32 (d, 4H), 7.71 (t, 2H), 4.21 (t, 8H), 1.91 (m, 8H), 1.57 (m, 8H), 1.40-1.27 (m, 64H), 0.88 (t, 12H)

FIG. 9 is a $^1$H-NMR spectrum of 4,5,9,10-tetrakis(tetradecyloxy)-pyrene according to Preparation Example 1B measured in a $CDCl_3$ solvent.

Compound Preparation Example 1C: Preparation of 4,5,9,10-tetrakis (octadecyloxy)-pyrene The same procedure as in Preparation Example 1A was conducted except that bromooctadecyl was used instead of bromododecyl in the above 1A-2 to obtain 4,5,9,10-tetrakis (octadecyloxy)-pyrene (R=$C_{18}H_{37}$ in Reaction Scheme 5, compound 13) (yield: 72%).

4,5,9,10-tetrakis(octadecyloxy)-pyrene: $^1$H NMR (600 MHz, $CDCl_3$)δ 8.32 (d, 4H), 7.71 (t, 2H), 4.21 (t, 8H), 1.91 (m, 8H), 1.57 (m, 8H), 1.40-1.27 (m, 64H), 0.88 (t, 12H)

FIG. 10 is a $^1$H-NMR spectrum of 4,5,9,10-tetrakis(octadecyloxy)-pyrene according to Preparation Example 1C measured in a $CDCl_3$ solvent.

Compound Preparation Example 1D: Preparation of 4,5-bis(dodecyloxy)-pyrene

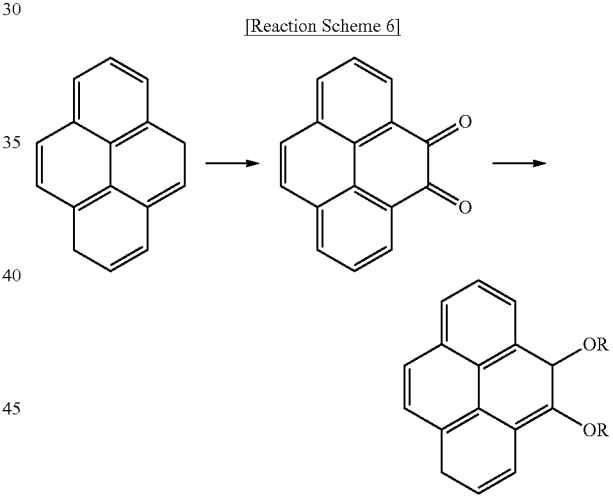

[Reaction Scheme 6]

1D-1. Preparation of pyrene-4,5-dione

The same procedure as in the step 1A-1 of Preparation Example 1A was conducted except that the reaction temperature was changed from 40° C. to 30° C. to obtain pyrene-4,5-dione.

1D-2. Preparation of 4,5-bis(dodecyloxy)-pyrene

The same procedure as in the step 1A-2 of Preparation Example 1A was conducted except that pyrene-4,5-dione obtained in the step 1D-1 was used instead of pyrene-4,5,9,10-tetraone to obtain 4,5-bis(dodecyloxy)-pyrene (R=$C_{12}H_{25}$ in Reaction Scheme 6, compound 14) (yield: 68%).

4,5-bis(dodecyloxy)-pyrene: $^1$H NMR (600 MHz, CDCl$_3$)δ 8.12 (d, 2H), 7.83 (m, 4H), 7.71 (s, 2H), 4.21 (t, 4H), 1.91 (m, 4H), 1.57 (m, 4H), 1.40-1.27 (m, 36H), 0.88 (t, 6H)

FIG. 11 is a $^1$H-NMR spectrum of 4,5-bis(dodecyloxy)-pyrene according to Preparation Example 1D measured in a CDCl$_3$ solvent.

Compound Preparation Example 1E: Preparation of 4,5-bis(dodecyloxy)-pyrene-9,10-dione

[Reaction Scheme 7]

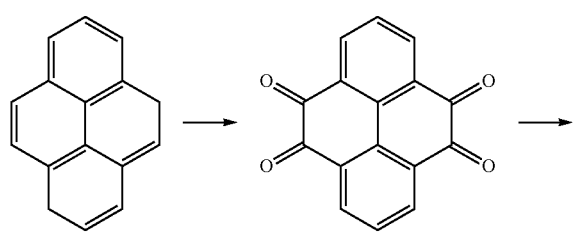

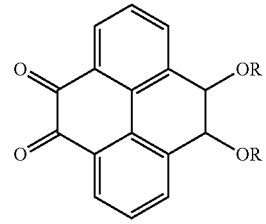

The same procedure as in Preparation Example 1A was conducted except that 20 mmol of bromododecyl in the step 1A-2 was used to obtain 4,5-bis(dodecyloxy)-pyrene-9,10-dione (R=C$_{12}$H$_{25}$ in Reaction Scheme 7, compound 15) (yield: 63%).

4,5-bis(dodecyloxy)-pyrene-9,10-dione: $^1$H NMR (600 MHz, DMSO-d6) δ 8.40 (m, 4H), 8.01 (t, 2H), 4.21 (t, 4H), 1.91 (m, 4H), 1.57 (m, 4H), 1.40-1.27 (m, 36H), 0.88 (t, 6H)

FIG. 12 is a $^1$H-NMR spectrum of 4,5-bis(dodecyloxy)-pyrene-9,10-dione according to Preparation Example 1E measured in a DMSO-d6 solvent.

TABLE 1

| Prep. Ex. # | Comp. # | Compound Chemical Structure | Compound Name | Yield (%) |
|---|---|---|---|---|
| 1A | 11 | | 4,5,9,10-tetrakis(dodecyloxy)-pyrene | 72 |
| 1B | 12 | | 4,5,9,10-tetrakis(tetradecyloxy)-pyrene | 70 |
| 1C | 13 | | 4,5,9,10-tetrakis(octadecyloxy)-pyrene | 72 |
| 1D | 14 | | 4,5-bis(dodecyloxy)-pyrene | 68 |

TABLE 1-continued

| Prep. Ex. # | Comp. # | Compound Chemical Structure | Compound Name | Yield (%) |
|---|---|---|---|---|
| 1E | 15 | 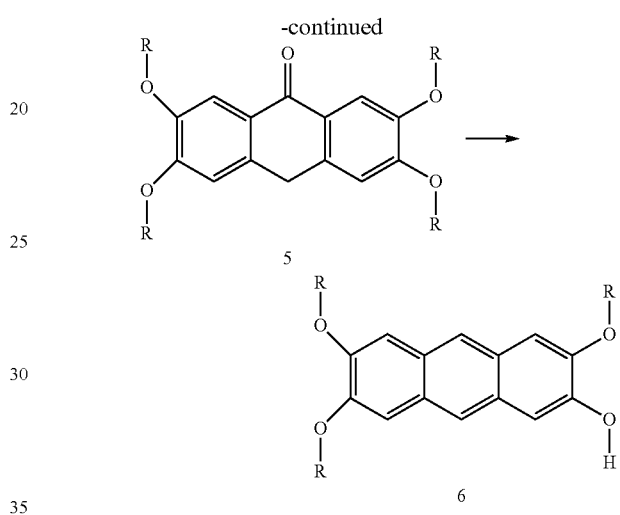 | 4,5-bis(dodecyloxy)-pyrene-9,10-dione | 63 |

Compound Preparation Example 2A: Preparation of 2,3,6,7-tetrakis (dodecyloxy)-anthracene

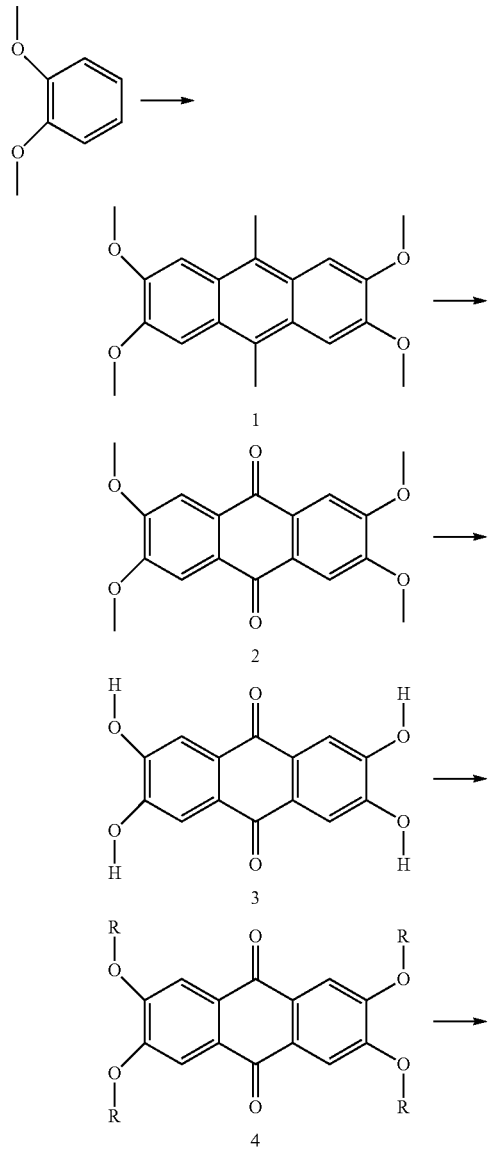

In Reaction Scheme 8, R is $C_{12}H_{25}$.

2A-1. Preparation of 2,3,6,7-tetrakis(methoxy)-9,10-dimethyl anthracene (1)

The cooled solution of veratrol (32 ml) and acetic acid (125 ml) was slowly added to a cooled solution of methanol (20 ml) and acetaldehyde (21 ml). The mixed solution was thoroughly stirred for 1 hour, then concentrated sulfuric acid (95%, 125 ml) was added over 2 hours and reacted with stirring for 20 hours. After the reaction was completed, the reaction mixture was poured into ice water to terminate the reaction. The reaction mixture was filtered, washed with water and subjected to column chromatography using chloroform as a developing solution to obtain isolated 2,3,6,7-tetrakis(methoxy)-9,10-dimethylanthracene (1).

2A-2. Preparation of 2,3,6,7-tetrakis(methoxy) anthracene-9,10-dione (2)

A solution of 2,3,6,7-tetrakis(methoxy)-9,10-dimethylanthracene (10.0 g) obtained from the step 2A-1, sodium dichromate (50 g) and acetic acid (500 ml) was refluxed for 60 minutes to obtain 2,3,6,7-tetrakis(methoxy) anthracene-9,10-dione (2).

2,3,6,7-tetrakis(methoxy) anthracene-9,10-dione: $^1$H NMR (600 MHz, CDCl$_3$) δ 7.32 (s, 4H), 4.06 (t, 8H), 1.76 (m, 8H), 1.57 (m, 8H), 1.43-1.26 (m, 72H), 0.88 (t, 12H)

2A-3. Preparation of 2,3,6,7-tetrakis(dodecyloxy) anthracene-9,10-dione (4)

2,3,6,7-tetrakis(methoxy)anthracene-9,10-dione (2) (470 mg, 1.6 mmol) obtained from the step 2A-2 and tetra-n-butyl-ammonium bromide (6 mg) was added to concentrated hydrobromic acid (30 mg). The resultant was refluxed for 12 hours, was poured into ice water to terminate the reaction, and was filtered to obtain a brown precipitate (3). Dimethylformamide (100 ml) and potassium carbonate (17.64 g) were added to the brown precipitate (5 g, 18.3 mmol). After 5 minutes, 1-bromododecane (183 mmol) was added and the mixture was reacted at room temperature for 90 minutes. Then, the temperature was gradually raised to 60° C. and reacted for 12 hours. Thereafter, distilled water (80 ml) was added to dissolve the unreacted potassium carbonate to dissolve the entangled product, and the reaction product was poured into ice water and filtered to obtain 2,3,6,7-tetrakis (dodecyloxy) anthracene-9,10-dione (4).

2,3,6,7-tetrakis (dodecyloxy) anthracene-9, 10-dione: $^1$H NMR (600 MHz, CDCl$_3$)δ 8.11 (s, 2H), 7.14 (s, 4H), 4.16 (t, 8H), 1.76 (m, 8H), 1.43-1.26 (m, 72H), 0.88 (t, 12H)

2A-4. Preparation of 2,3,6,7-tetrakis(dodecyloxy)anthracene-9-one (5)

The zinc powder (16.9 g) was added to a solution of copper sulfide (0.4 g) in distilled water (250 ml) and activated with stirring for 10 minutes. The activated zinc powder solution was decanted and a solution of 10% sodium hydroxide solution (160 mL) and the resultant product of step 2A-3, which is 2,3,6,7-tetrakis(dodecyloxy) anthracene-9,10-dione (4) (9.82 g, 10.4 mmol) in toluene (150 ml) was added to the activated zinc powder solution. The resultant product was stirred at 120° C. for 15 hours. After completion of the reaction, the product was washed with water to remove unreacted zinc powder, recrystallized at −5° C., filtered, and dried in a vacuum oven to obtain 2,3,6,7-tetrakis (dodecyloxy) anthracene-9-one (5).

2A-5. Preparation of 2,3,6,7-tetrakis(dodecyloxy)anthracene (6)

The resulting 2,3,6,7-tetrakis (dodecyloxy) anthracene-9-one (5) (8.38 g, 8.98 mmol) obtained in step 2A-4 was dissolved in dichloromethane (200 ml), sodium borohydride (5.25 g, 135 mmol) was added, and the mixture was stirred at room temperature while methanol (30 ml) was added. Sodium borohydride (15 g, 385 mmol) was added after 90 minutes with stirring. After 7 hours, acetic acid (10 ml) was slowly added and the reaction was further continued for 12 hours, followed by adding concentrated sulfuric acid (10 ml) and successively adding distilled water (50 ml). After the reaction was completed, the dichloromethane layer was extracted, washed thoroughly with water, recrystallized at −5° C., filtered, and stored in a vacuum oven for one day to obtain 2,3,6,7-tetrakis(dodecyloxy)anthracene (6, compound 21) (yield: 53%).

FIG. 13 is a $^1$H-NMR spectrum of 2,3,6,7-tetrakis(dodecyloxy)anthracene according to Preparation Example 2A measured in a CDCl$_3$ solvent.

Compound Preparation Examples 2B and 2C: Preparation of 2,3-bis (dodecyloxy) anthracene and 6,7-bis (dodecyloxy) anthracene-2,3-dione

[Reaction Scheme 9]

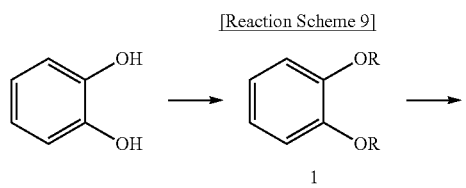

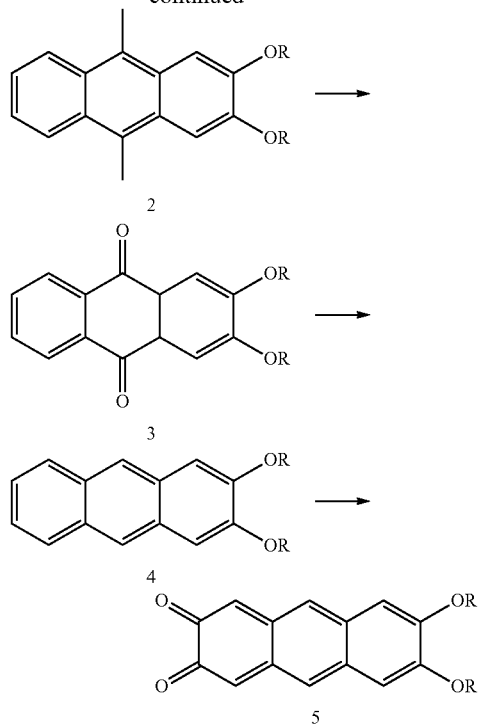

In Reaction Scheme 9, R is $C_{12}H_{25}$.

Compound Preparation Example 2B: Preparation of 2,3-bis (dodecyloxy) anthracene

2B-1. Preparation of 1,2-bis (dodecyloxy) benzene (1)

Catechol (0.1 mol) was added to dimethylformamide (20 ml), and the temperature was raised to 100° C. Then, 1-bromododecyl (0.3 mol) was added and reacted for 18 hours. After completion of the reaction, the reaction mixture was slowly cooled to room temperature, and the reaction was terminated by adding water to the reaction mixture. The reaction mixture was extracted with chloroform, evaporated, and clean 1,2-bis (dodecyloxy) benzene (1) was obtained through a flash column.

1,2-bis (dodecyloxy) benzene: $^1$H NMR (600 MHz, CDCl$_3$)δ 6.88 (s, 4H), 4.06 (t, 2H), 1.76 (m, 4H), 1.43 (m, 4H), 1.43-1.26 (m, 36H), 0.88 (t, 6H)

2B-2. Preparation of 2,3-bis(dodecyloxy)-9,10-dimethylanthracene (2)

1,2-bis (dodecyloxy) benzene (12.8 ml, 0.1 mol) obtained from the step 2B-1, benzene (9 ml, 0.1 mmol), and propionaldehyde (7.4 ml, 0.1 mol) were dissolved in acetonitrile (5.3 ml, 0.1 mol), was reacted for 2 hours with stirring with 50 ml of concentrated sulfuric acid. The reaction product was poured into ice to obtain 2,3-bis (dodecyloxy)-9,10-dimethyl anthracene (2).

2,3-bis (dodecyloxy)-9,10-dimethyl anthracene: 1H NMR (600 MHz, CDCl$_3$) δ 7.98 (d, 2H), 7.35 (d, 2H), 7.14 (s, 2H), 4.16 (t, 4H), 2.64 (s, 6H), 1.76 (m, 4H), 1.57 (m, 4H), 1.43-1.26 (m, 36H), 0.88 (t, 6H)

2B-3. Preparation of 2,3-bis(dodecyloxy) anthracene-9,10-dione (3)

The resultant product of step 2B-2, 2,3-bis(dodecyloxy)-9,10-dimethyl anthracene (10.0 g), sodium dichromate (50 g) and acetic acid (500 ml) was refluxed for 60 minutes to obtain 2,3-bis(dodecyloxy) anthracene-9,10-dione (3).

2,3-bis(dodecyloxy)anthracene-9,10-dione: ¹H NMR (600 MHz, CDCl₃)δ 8.05 (s, 4H), 4.73 (s, 2H), 4.18 (d, 2H), 4.01 (t, 4H), 1.76 (m, 4H), 1.43-1.26 (m, 36H), 0.88 (t, 6H)

2B-4. Preparation of 2,3-bis(dodecyloxy) anthracene (4)

The resultant product of step 2B-3, 2,3-bis(dodecyloxy) anthracene-9,10-dione (10 g, 41.3 mmol), and activated zinc powder (167 g, 2.6 mol) were added in a solution in which sodium hydroxide (50 g, 1.25 mol) was dissolved in distilled water (670 ml), and the mixture was reacted at 100° C. for 48 hours while replacing the atmosphere with nitrogen to obtain 2,3-bis(dodecyloxy) anthracene (4, compound 22) (yield: 63%).

2,3-bis(dodecyloxy) anthracene: ¹H NMR (600 MHz, CDCl₃)δ 8.21 (s, 2H), 7.91 (t, 2H), 7.36 (d, 2H) 7.14 (s, 2H), 4.16 (t, 4H), 1.76 (m, 4H), 1.43-1.26 (m, 36H), 0.88 (t, 6H)

FIG. 14 is a ¹H-NMR spectrum of 2,3-bis(dodecyloxy) anthracene according to Preparation Example 2B measured in a CDCl₃ solvent.

Compound Preparation Example 2C: Preparation of 2,3-bis (dodecyloxy) anthracene-6,7-dione (5)

2,3-bis (dodecyloxy) anthracene (10 mmol) obtained in Production Example 2B was dissolved in a solution of dichloromethane (40.0 ml) and acetonitrile (40 ml), and then was refluxed in distilled water (50.0 ml) at 25° C. for 16 hours together with ruthenium (III) chloride hydrate (0.25 g, 1.2 mmol) and sodium metaperiodate (NaIO₄) (17.5 g, 81.8 mmol) to obtain 2,3-bis(dodecyloxy) anthracene-6,7-dione (5, compound 23) (yield: 58%).

2,3-bis(dodecyloxy) anthracene-6,7-dione: ¹H NMR (600 MHz, DMSO-d6)δ 6.46 (s, 2H), 6.28 (s, 2H), 6.24 (s, 2H), 4.16 (t, 4H), 1.76 (m, 4H), 1.43-1.26 (m, 36H), 0.88 (t, 6H)

FIG. 15 is a ¹H-NMR spectrum of 2,3-bis(dodecyloxy) anthracene-6,7-dione according to Preparation Example 2B measured in a CDCl₃ solvent.

Compound Preparation Example 3A: Preparation of 1,2,7,8-tetrakis (dodecyloxy) coronene

[Reaction Scheme 10]

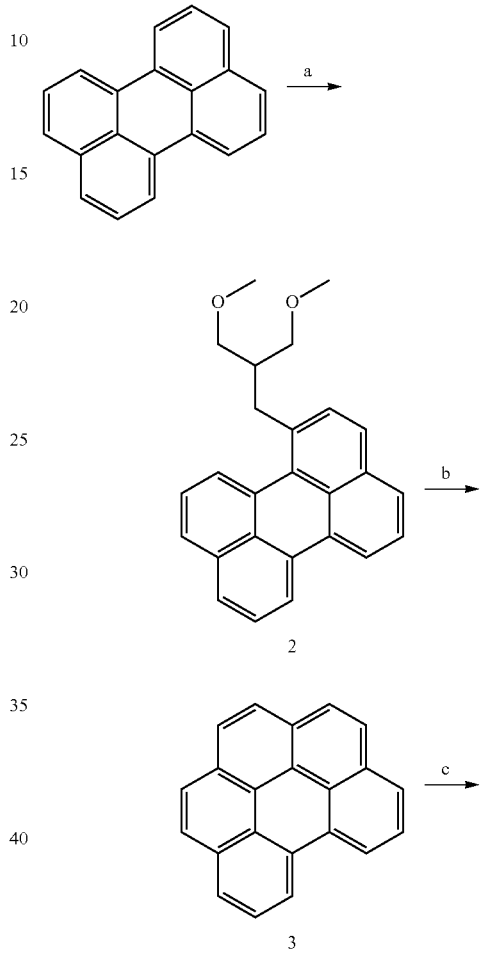

TABLE 2

| Prep. Ex. # | Comp. # | Compound Chemical Structure | Compound Name | Yield (%) |
|---|---|---|---|---|
| 2A | 21 | H₃C-(CH₂)₁₁-O-[anthracene]-O-(CH₂)₁₁-CH₃ / H₃C-(CH₂)₁₁-O-...-O-(CH₂)₁₁-CH₃ | 2,3,6,7-tetrakis (dodecyloxy)-anthracene | 53 |
| 2B | 22 | [anthracene]-O-(CH₂)₁₁-CH₃ / -O-(CH₂)₁₁-CH₃ | 2,3-bis (dodecyloxy) anthracene | 63 |
| 2C | 23 | O=[anthracene-dione]-O-(CH₂)₁₁-CH₃ / -O-(CH₂)₁₁-CH₃ | 2,3-bis (dodecyloxy) anthracene-6,7-dione | 58 |

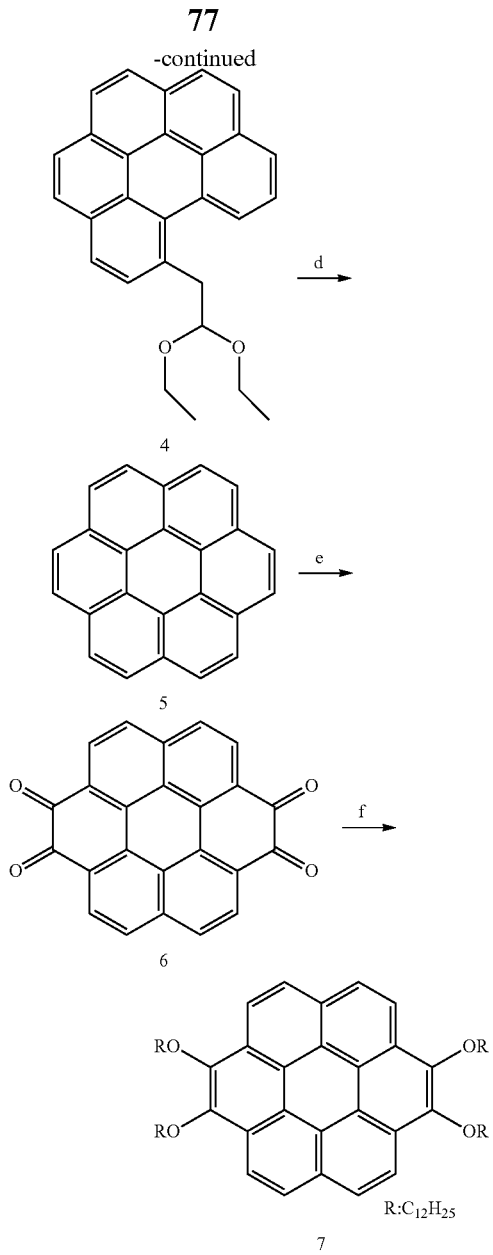

3A-1. Preparation of 1-(2,2-diethoxyethyl)perylene (2)

Perylene (4.00 g, 15.9 mmol), tetrahydrofuran (THF) (250 ml) and sodium (0.80 g) were placed in a reactor substituted with argon and ultrasonicated at 30° C. for 3 hours, cooled to −60° C., and bromoacetaldehyde diethyl acetal (3.13 g, 15.9 mmol) was added with stirring. Then, iodine (6.05 g, 23.8 mmol) was added and sodium thiosulfate (100 ml) was added to obtain 1-(2,2-diethoxyethyl) perylene (2).

1-(2,2-diethoxyethyl) perylene: $^1$H NMR (600 MHz, CDCl$_3$)δ 7.91 (s, 3H), 7.39 (s, 6H), 7.26 (s, 1H), 7.17 (s, 1H), 4.58 (t, 1H), 3.50 (m, 4H), 3.28 (d, 2H), 1.10 (t, 6H)

3A-2. Preparation of benzo [ghi] perylene (3)

Concentrated sulfuric acid (4 ml) was added dropwise while stirring the resultant product of Step 3A-1, 1-(2,2-diethoxyethyl) perylene (4.29 g, 11.6 mmol), with methanol (8 ml) to obtain benzo [ghi] perylene (3).

Benzo [ghi] perylene: $^1$H NMR (600 MHz, CDCl$_3$)δ 7.91 (d, 2H), 7.71 (s, 2H), 7.39 (s, 8H)

3A-3. Preparation of 7-(2,2-diethoxyethyl)benzol[ghi]perylene (4)

The same procedure as in step 3A-1 was conducted except that benzo[ghi]perylene (3), the product of step 3A-2, was used instead of perylene to obtain 7-(2,2-diethoxyethyl) benzo[ghi]perylene (4).

7-(2,2-diethoxyethyl)benzo[ghi]perylene: $^1$H NMR (600 MHz, CDCl$_3$)δ 7.91 (d, 1H), 7.71 (s, 2H), 7.39 (s, 6H), 7.26 (s, 1H), 7.17 (s, 1H), 4.58 (t, 1H), 3.50 (m, 4H), 3.29 (d, 2H), 1.10 (t, 6H)

3A-4. Preparation of Coronene (5)

The same procedure as in step 3A-2 was conducted except that 7-(2,2-diethoxyethyl)benzo[ghi]perylene, the product of step 3A-3, was used instead of 1-(2,2-diethoxyethyl) perylene to obtain coronene (5).

Coronene: $^1$H NMR (600 MHz, CDCl$_3$)δ 7.39 (s, 12H)

3A-5. Preparation of coronene-1,2,7,8-tetraone (6)

The same procedure as in step 1A-1 was conducted except that coronene, the product of step 3A-4, was used instead of perylene to obtain coronene-1,2,7,8-tetraone (6).

Coronene-1,2,7,8-tetraone: $^1$H NMR (600 MHz, DMSO-d6)δ 7.83 (d, 4H), 7.49 (d, 4H)

3A-6. Preparation of 1,2,7,8-tetrakis (dodecyloxy) coronene (7)

The same procedure as in step 1A-2 was conducted except that coronene-1,2,7,8-tetraone, the product of step 3A-5, was used instead of perylene-4,5,9,10-tetraone to obtain 1,2,7,8-tetrakis (dodecyloxy) coronene (7, compound 31) (yield: 61%).

1,2,7,8-tetrakis (dodecyloxy) coronene: $^1$H NMR (600 MHz, CDCl$_3$)δ 7.39 (s, 4H), 4.16 (t, 8H), 1.76 (m, 8H), 1.43-1.26 (m, 72H), 0.88 (t, 12H)

FIG. 16 is a $^1$H-NMR spectrum of 1,2,7,8-tetrakis(dodecyloxy)coronene according to Preparation Example 3A measured in a CDCl$_3$ solvent.

Compound Preparation Examples 3B and 3C: Preparation of 1,2-bis (dodecyloxy) coronene and 7,8-bis (dodecyloxy) coronene-1,2-dione

[Reaction Scheme 11]

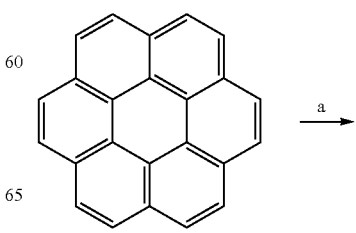

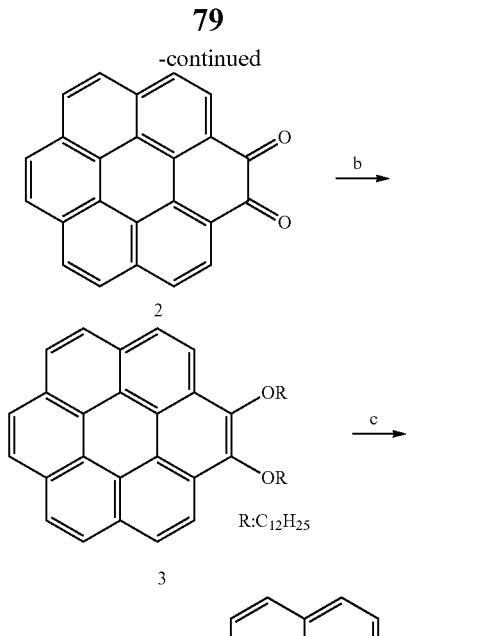

Compound Preparation Example 3B: Preparation of 1,2-bis (dodecyloxy) coronene

The same procedure as in Preparation Example 1A was conducted except that coronene was used instead of pyrene and the reaction temperature was changed from 40° C. to 30° C. in the step 1A-1 of to obtain 1,2-bis (dodecyloxy) coronene (3, compound 32) (yield: 63%).

1,2-bis (dodecyloxy) coronene: $^1$H NMR (600 MHz, CDCl$_3$)δ 7.39 (s, 10H), 4.16 (t, 4H), 1.76 (m, 4H), 1.43-1.26 (m, 36H), 0.88 (t, 6H)

FIG. 17 is a $^1$H-NMR spectrum of 1,2-bis(dodecyloxy) coronene according to Preparation Example 3B measured in a CDCl$_3$ solvent.

Compound Preparation Example 3C: Preparation of 7,8-bis(dodecyloxy)coronene-1,2-dione The same procedure as in Preparation Example 2C was conducted except that 1,2-bis(dodecyloxy)coronene obtained from Production Example 3B was used instead of 2,3-bis(dodecyloxy)anthracene to obtain 7,8-bis(dodecyloxy)coronene-1,2-dione (4, compound 33) (yield: 62%).

7,8-bis(dodecyloxy)coronene-1,2-dione: $^1$H NMR (600 MHz, CDCl$_3$) δ 7.88 (d, 2H), 7.53 (d, 2H), 7.39 (s, 4H), 4.16 (t, 4H), 1.76 (m, 4H), 1.43-1.26 (m, 36H), 0.88 (t, 6H)

FIG. 18 is a $^1$H-NMR spectrum of 7,8-bis(dodecyloxy) coronene-1,2-dione according to Preparation Example 3C measured in a CDCl$_3$ solvent.

TABLE 3

| Prep. Ex. # | Comp. # | Compound Chemical Structure | Compound Name | Yield (%) |
|---|---|---|---|---|
| 3A | 31 | | 1,2,7,8-tetrakis (dodecyloxy) coronene | 61 |
| 3B | 32 | | 1,2-bis(dodecyloxy) coronene | 63 |
| 3C | 33 | | 7,8-bis(dodecyloxy) coronene-1,2-dione | 62 |

Compound Preparation Example 4A: Preparation of 1,2,5,6-tetrakis (dodecyloxy) cyclopenta [fg] acenaphthylene

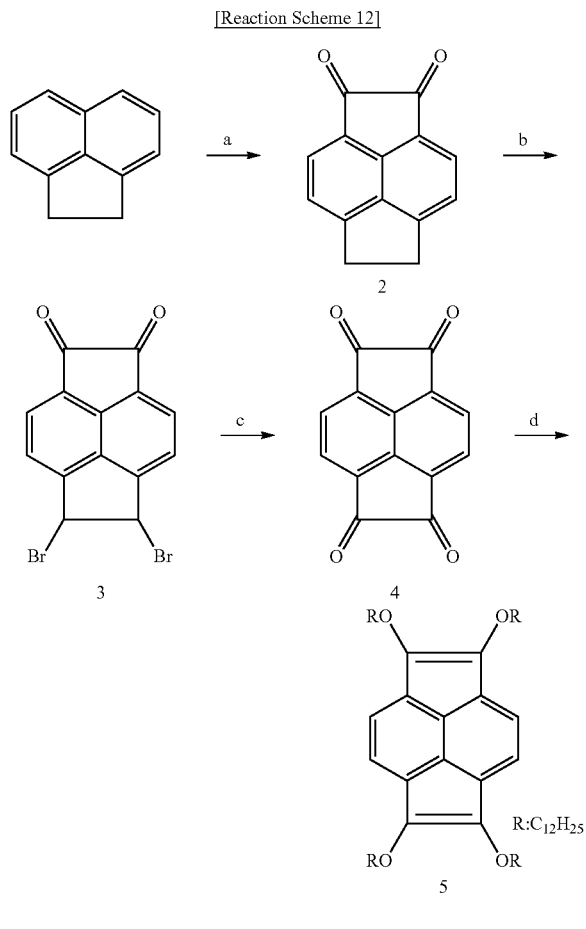

[Reaction Scheme 12]

4A-1. Preparation of the diketopyracene (2)

Acenaphthene (17.60 g, 0.114 mol) was dissolved in carbon disulfide (1500 ml) and then oxalyl bromide (25.00 g, 0.116 mol) was added at −5° C. Aluminum bromide (62.50 g, 0.234 mol) was added to the resultant over 10-15 minutes with vigorous stirring, and was reacted overnight at room temperature to obtain diketopyracene (2).

Diketopyracene: $^1$H NMR (600 MHz, CDCl$_3$) δ 8.36 (d, 2H), 7.64 (d, 2H), 3.52 (s, 4H)

4A-2. Preparation of 5,6-dibromo-1,2-diketopyracene (3)

N-bromosuccinimide (2.60 g, 15.0 mmol) and dibenzoyl peroxide (100 mg) were added to a solution of the diketopyracene (1.00 g, 4.8 mmol) obtained in step 4A-1 in carbon tetrachloride (100 ml), and the mixture was refluxed for 5 hours to obtain 5,6-dibromo-1,2-diketopyracene (3).

5,6-dibromo-1,2-diketopyracene: $^1$H NMR (600 MHz, CDCl$_3$) δ 8.36 (d, 2H), 7.64 (d, 2H), 5.69 (s, 2H)

4A-3. Preparation of cyclopenta[fg]acenaphthylene-1,2,5,6-tetraone (4)

The resultant product of step 4A-2, 5,6-dibromo-1,2-diketopyracene (0.832 g, 4.0 mmol) and benzeneseleninic anhydride (2.88 g, 8.0 mmol) was dissolved in chlorobenzene (70 ml), and the mixture was refluxed at 125° C. for 72 hours to obtain cyclopenta [fg] acenaphthylene-1,2,5,6-tetraone (4).

cyclopenta [fg] acenaphthylene-1,2,5,6-tetraone: $^1$H NMR (600 MHz, CDCl$_3$) δ 8.65 (s, 4H)

4A-4. Preparation of 1,2,5,6-tetrakis(dodecyloxy) cyclopenta[fg] acenaphthylene (5)

The same procedure as in step 1A-2 of Preparation Example 1A was conducted except that cyclopenta[fg]acenaphthylene-1,2,5,6-tetraone, which is the result of step 4A-3, was used instead of pyrene-4,5,9,10-tetraone to obtain 1,2,5,6-tetrakis(dodecyloxy)cyclopenta[fg] acenaphthylene (5, compound 41) (yield: 59%).

1,2,5,6-tetrakis(dodecyloxy)cyclopenta[fg]acenaphthylene: $^1$H NMR (600 MHz, CDCl$_3$) δ 7.34 (s, 4H), 4.16 (t, 8H), 1.76 (m, 8H), 1.43-1.26 (m, 72H), 0.88 (t, 12H)

FIG. 19 is a $^1$H-NMR spectrum of 1,2,5,6-tetrakis(dodecyloxy) cyclopenta[fg]acenaphthylene according to Preparation Example 4A measured in a CDCl$_3$ solvent.

Compound Preparation Examples 4B and 4C: Synthesis of 1,2-bis (dodecyloxy)cyclopenta[fg]acenaphthylene and 5,6-bis(dodecyloxy)cyclopenta [fg]acenaphthylene-1,2-dione

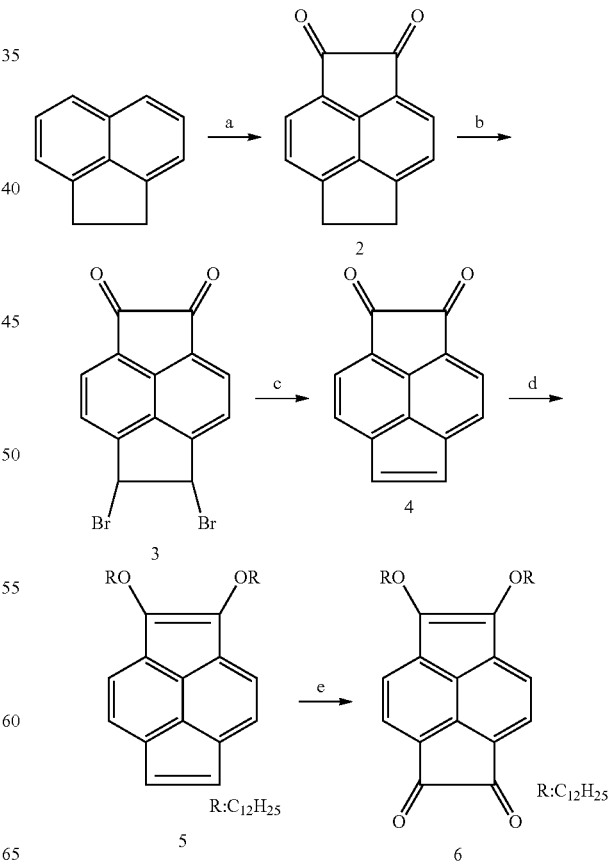

[Reaction Scheme 13]

Compound Preparation Example 4B: Synthesis of 1,2-bis (dodecyloxy)cyclopenta[fg]acenaphthylene

4B-1. Preparation of cyclopenta[fg] acenaphthalene-1,2-dione (4)

5,6-dibromo-1,2-diketopyracene (3, 10 mmol) prepared in Preparation Example 4A-2 was dissolved in acetone together with excess potassium iodide and refluxed overnight to obtain cyclopenta[fg]acenaphthalene-1,2-dione (4).

Cyclopenta[fg]acenaphthalene-1,2-dione: $^1$H NMR (600 MHz, CDCl$_3$)δ 7.90 (d, 2H), 7.58 (d, 2H), 7.15 (s, 2H)

4B-2. Preparation of 1,2-bis(dodecyloxy)cyclopenta [fg] acenaphthalene (5)

The procedure of Production Example 1D was conducted except that cyclopenta[fg]acenaphthalene-1,2-dione, which is the result of Step 4B-1, was used instead of pyrene-4,5-dione to obtain 1,2-bis(dodecyloxy)cyclopenta[fg] acenaphthalene (5, compound 42) (yield: 62%).

1,2-bis(dodecyloxy)cyclopenta[fg] acenaphthalene: $^1$H NMR (600 MHz, CDCl$_3$)δ 7.90 (d, 2H), 7.58 (d, 2H), 7.15 (s, 2H), 4.16 (t, 4H), 1.76 (m, 4H), 1.43-1.26 (m, 36H), 0.88 (t, 6H)

FIG. 20 is a $^1$H-NMR spectrum of 1,2-bis(dodecyloxy) cyclopenta[fg] acenaphthalene according to Preparation Example 4B measured in a CDCl$_3$ solvent.

Compound Preparation Example 4C: Preparation of 5,6-bis(dodecyloxy) cyclopenta [fg] acenaphthylene-1,2-dione (6)

The procedure of Preparation Example 2C was conducted except that 1,2-bis (dodecyloxy) cyclopenta [fg] acenaphthalene (5), which is the product of Production Example 4B, was used instead of 2,3-bis (dodecyloxy) anthracene to obtain 5,6-bis (dodecyloxy) cyclopenta [fg] acenaphthylene-1,2-dione (6, compound 43) (Yield: 60%).

5,6-bis (dodecyloxy) cyclopenta [fg] acenaphthylene-1,2-dione: $^1$H NMR (600 MHz, CDCl$_3$)δ 8.25 (d, 2H), 8.14 (d, 2H), 4.16 (t, 4H), 1.76 (m, 4H), 1.43-1.26 (m, 36H), 0.88 (t, 6H)

FIG. 21 is a $^1$H-NMR spectrum of 5,6-bis (dodecyloxy) cyclopenta [fg]acenaphthylene-1,2-dione according to Preparation Example 4C measured in a CDCl$_3$ solvent.

TABLE 4

| Prep. Ex. # | Comp. # | Compound Chemical Structure | Compound Name | Yield (%) |
|---|---|---|---|---|
| 4A | 41 | | 1,2,5,6-tetras(dodecyloxy) cyclopenta[fg] acenaphthylene | 59 |
| 4B | 42 | | 1,2-bis(dodecyloxy) cyclopenta[fg] acenaphthylene | 62 |
| 4C | 43 | | 5,6-bis (dodecyloxy) cyclopenta [fg] acenaphthylene-1,2-dione | 60 |

Compound Preparation Example 5A: Preparation of 2,3,6,7,10,11-hexakis (dodecyloxy) triphenylene

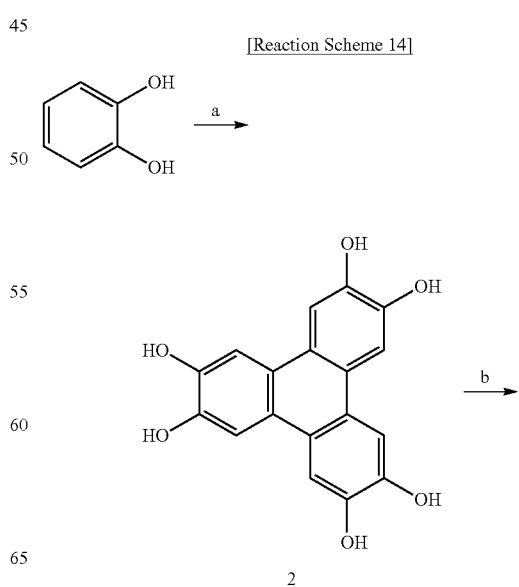

[Reaction Scheme 14]

-continued

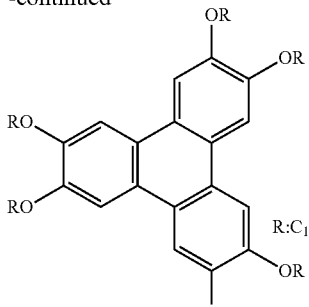

R:C₁₂H₂₅

3

5A-1. Preparation of triphenylene-2,3,6,7,10,11-hexanol (2)

Catechol (20 g, 0.182 mol) and ferric chloride (III) hexahydrate (196.8 g, 0.728 mol) were reacted for 24 hours using ultrasound. The reaction mixture was washed with diluted hydrochloric acid and water, and extracted with heated cyclopentanone to obtain triphenylene-2,3,6,7,10,11-hexanol (2).

Triphenylene-2,3,6,7,10,11-hexanol: $^1$H NMR (600 MHz, CDCl$_3$) δ 7.82 (s, 6H), 5.35 (s, 6H)

5A-2. Preparation of 2,3,6,7,10,11-hexakis (dodecyloxy) triphenylene (3)

Triphenylene-2,3,6,7,10,11-hexanol (10 mmol) obtained from Step 5A-1 was added to a solution in which bromododecyl (60 mmol) and potassium hydroxide (306 mmol) were dissolved in distilled water (50 ml), and the mixture was refluxed at 65° C. for 16 hours to obtain 2,3,6,7,10,11-hexakis (dodecyloxy) triphenylene (3, compound 51) (yield: 74%).

2,3,6,7,10,11-hexakis (dodecyloxy) triphenylene: $^1$H NMR (600 MHz, CDCl$_3$) δ 7.92 (s, 6H), 4.16 (t, 8H), 1.76 (m, 8H), 1.43-1.26 (m, 72H), 0.88 (t, 12H)

FIG. 22 is a $^1$H-NMR spectrum of 2,3,6,7,10,11-hexakis (dodecyloxy) triphenylene according to Preparation Example 5A measured in a CDCl$_3$ solvent.

Compound Preparation Example 6A: Preparation of pyrene-4,5,9,10-tetrayl tetraundecanoate The procedure of Preparation Example 1A was conducted except that undecanoyl bromide was used instead of bromododecyl in Step 1A-2 of Preparation Example 1A to obtain pyrene-4,5,9,10-tetrayl tetraundecanoate (compound 61).

Compound Preparation Example 6B: Preparation of pyrene-4,5-diyldidodecanoate The procedure of Preparation Example 1D was conducted except that dodecanoyl bromide was used instead of bromododecyl in Step 1D-2 of Preparation Example 1D to obtain pyrene-4,5-diyldidodecanoate (compound 62).

Compound Preparation Example 6C: Preparation of 9,10-dioxo-9,10-dihydropyrene-4,5-diyldidodecanoate The procedure of Preparation Example 1E was conducted except that dodecanoyl bromide was used instead of bromododecyl in Preparation Example 1E to obtain 9,10-dioxo-9,10-dihydropyrene-4,5-diyldidodecanoate (compound 63).

TABLE 5

| Prep. Ex. # | Comp. # | Compound Chemical Structure | Compound Name | Yield (%) |
|---|---|---|---|---|
| 5A | 51 | (structure shown) | 2,3,6,7,10,11-hexakis (dodecyloxy) triphenylene | 74 |

TABLE 6

| Prep. Ex. # | Comp. # | Compound Chemical Structure | Compound Name | Reagent | Yield (%) |
|---|---|---|---|---|---|
| 6A | 61 | | pyrene-4,5,9,10-tetrayl tetra undecanoate | undecanoyl bromide | 72 |
| 6A | 61-1 | | pyrene-4,5,9,10-tetrayl tetra dodecanoate | dodecanoyl bromide | 74 |
| 6A | 61-2 | | pyrene-4,5,9,10-tetrayltetrakis (dodecane-1-sulfonate) | dodecyl sulfinyl bromide | 20 |
| 6A | 61-3 | | pyrene-4,5,9,10-tetrayltetra undecyl tetracarbonate | carbonobromic acid, undecyl ester | 45 |
| 6A | 61-4 | | 4,5,9,10-tetrakis ((dodecylthio) oxy) pyrene | dodecyl thio bromide | 78 |
| 6A | 61-5 | | 12,12',12'',12'''-(pyrene-4,5,9,10-tetrayltetrakis (oxy) tetrakis (dodecan-1-ol) | 12-bromo dodecan-1-ol | 73 |

TABLE 6-continued

| Prep. Ex. # | Comp. # | Compound Chemical Structure | Compound Name | Reagent | Yield (%) |
|---|---|---|---|---|---|
| 6A | 61-6 | | 12,12',12'',12'''-(pyrene-4,5,9,10-tetrayltetrakis(oxy))tetra-dodecanoic acid | 12-bromo dodecanoic acid (cas number 73367-80-3) | 56 |
| 6B | 62 | | pyrene-4,5-diyl di dodecanoate | dodecanoyl bromide | 54 |
| 6B | 62-1 | | pyrene-4,5-diyl bis(undecan-1-sulfinate) | Undecyl sulfinyl bromide | 33 |
| 6B | 62-2 | | pyrene-4,5-diylbis(dodecane-1-sulfinate) | Dodecyl sulfinyl bromide | 22 |
| 6B | 62-3 | | pyrene-4,5-diyldi undecylbis(carbonate) | carbonobromic acid, undecyl ester | 85 |
| 6B | 62-4 | | 4,5-bis((undecylthio)oxy) pyrene | undecyl thio bromide | 59 |

TABLE 6-continued

| Prep. Ex. # | Comp. # | Compound Chemical Structure | Compound Name | Reagent | Yield (%) |
|---|---|---|---|---|---|
| 6B | 62-5 | | 12,12'-(pyrene-4,5-diylbis(oxy))bis(dodecane-1-ol) | 12-bromo dodecane-1-ol | 47 |
| 6C | 63 | | 9,10-dioxo-9,10-dihydro pyrene-4,5-diyldi dodecanoate | dodecanoyl bromide | 71 |
| 6C | 63-1 | | 9,10-dioxo-9,10-dihydro pyrene-4,5-diyldiundecyl dicarbonate | carbonobromic acid, undecyl ester | 76 |
| 6C | 63-2 | | 9,10-bis((dodecylthio)oxy)pyrene-4,5-dione | dodecyl thio bromide | 47 |

Compound Preparation Example 7A: Preparation of anthracene-2,3,6,7-tetrayltetradodecanoate The procedure of Preparation Example 2A was conducted except that dodecanoyl bromide was used instead of 1-bromododecane in Step 2A-3 of Preparation Example 2A to obtain anthracene-2,3,6,7-tetrayltetradodecanoate (compound 71).

Compound Preparation Example 7B: Preparation of anthracene-2,3-diyldidodecanoate The procedure of Preparation Example 2B was conducted except that dodecanoyl bromide was used instead of 1-bromododecyl in Step 2B-1 of Preparation Example 2B to obtain anthracene-2,3-diyldidodecanoate (compound 72).

Compound Preparation Example 7C: Preparation of 6,7-dioxo-6,7-dihydroanthracene-2,3-diyldidodecanoate The procedure of Preparation Examples 2B and 2C was conducted except that dodecanoyl bromide was used instead of 1-bromododecyl in Step 2B-1 of Preparation Example 2B to obtain 6,7-dioxo-6,7-dihydroanthracene-2,3-diyldidodecanoate (compound 73).

| Prep. Ex. # | Comp. # | Compound Structure | Compound Name | Reagent | Yield (%) |
|---|---|---|---|---|---|
| 7A | 71 | | anthracene-2,3,6,7-tetrayltetradodecanoate | dodecanoyl bromide | 71 |
| 7A | 71-1 | | anthracene-2,3,6,7-tetrayltetraundecaneperoxoate | 1-(bromooxy)-1-oxoundecane | 64 |
| 7A | 71-2 | | N,N',N'',N'''-(anthracene-2,3,6,7-tetrayltetrakis(oxy))tetraundecaneamide | N-bromoundecaneamide | 67 |
| 7A | 71-3 | | 2,3,6,7-tetrakis((undecylthio)oxy)anthracene | undecyl thio bromide | 38 |
| 7A | 71-4 | | anthracene-2,3,6,7-tetrayltetrakis(dodecane-1-sulfinate) | dodecyl sulfinyl bromide | 59 |
| 7A | 71-5 | | 12,12',12'',12'''-(anthracene-2,3,6,7-tetrayltetrakis(oxy))tetrakis(dodecane-1-ol) | 12-bromododecane-1-ol | 33 |
| 7A | 71-6 | | anthracene-2,3,6,7-tetrayl)tetrakis(oxy))tetradodecanoic acid | 12-bromododecanoic acid (cas number 73367-80-3) | 56 |
| 7B | 72 | | anthracene-2,3-diyldidodecanoate | dodecanoyl bromide | 42 |
| 7B | 72-1 | | anthracene-2,3-diyldiundecyl dicarbonate | carbonobromic acid, undecyl ester | 33 |
| 7B | 72-2 | | N,N'-(anthracene-2,3-diylbis(oxy))diundecaneamide | N-bromoundecaneamide | 58 |

| Prep. Ex. # | Comp. # | Compound Structure | Compound Name | Reagent | Yield (%) |
|---|---|---|---|---|---|
| 7B | 72-3 | 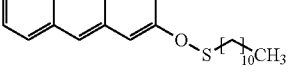 | 2,3-bis((undecylthio)oxy)anthracene | undecyl thio bromide | 37 |
| 7B | 72-4 | 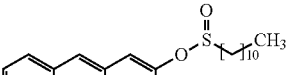 | anthracene-2,3-diylbis(undecane-1-sulfinate) | undecyl sulfinyl bromide | 40 |
| 7B | 72-5 | 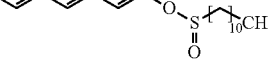 | 12,12'-(anthracene-2,3-diylbis(oxy))bis(dodecane-1-ol) | 12-bromododecane-1-ol | 32 |
| 7C | 73 | 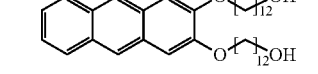 | 6,7-dioxo-6,7-dihydroanthracene-2,3-diyldidodecanoate | dodecanoyl bromide | 49 |
| 7C | 73-1 | 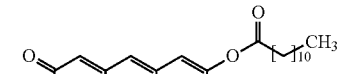 | didecyl(6,7-dioxo-6,7-dihydroanthracene-2,3-diyl) dicarbonate | carbonobromic acid, undecyl ester | 38 |
| 7C | 73-2 | 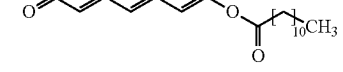 | N,N'-((6,7-dioxo-6,7-dihydroanthracene-2,3-diyl)bis(oxy))diundecane amine | N-bromoundecaneamide | 62 |
| 7C | 73-3 | 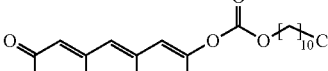 | 7,8-bis((undecylthio)oxy)coronene-1,2-dione | undecyl thio bromide | 59 |
| 7C | 73-4 |  | 7,8-dioxo-7,8-dihydro coronene-1,2-diylbis (undecan-1-sulfonate) | undecyl sulfonyl bromide | 83 |

Compound Preparation Example 8A: Preparation of coronene-2,7,8-tetrayltetradodecanoate The procedure of Preparation Example 3A was conducted except that dodecanoyl bromide was used instead of bromododecyl in Step 3A-6 of Preparation Example 3A to obtain coronene-1,2,7,8-tetrayltetradodecanoate (compound 81).

Compound Preparation Example 8B: Preparation of coronene-1,2-diyldidodecanoate

The procedure of Preparation Example 3B was conducted except that dodecanoyl bromide was used instead of bromododecyl in Preparation Example 3B to obtain coronene-1,2-diyldidodecanoate (compound 82).

Compound Preparation Example 8C: Preparation of 7,8-dioxo-7,8-dihydrocoronene-1,2-diyldidodecanoate The procedure of Preparation Examples 3B and 3C was conducted except that dodecanoyl bromide was used instead of bromododecyl in Preparation Example 3B to obtain 7,8-dioxo-7,8-dihydrocoronene-1,2-diyldidodecanoate (compound 83).

TABLE 8

| Prep. Ex. # | Comp. # | Compound Structure | Compound Name | Reagent | Yield (%) |
|---|---|---|---|---|---|
| 8A | 81 | | coronene-1,2,7,8-tetrayltetradodecanoate | dodecanoyl bromide | 28 |
| 8A | 81-1 | | coronene-1,2,7,8-tetrayltetrakis (undecyl) tetracarbonate | carbon bromic acid, undecyl ester | 66 |
| 8A | 81-2 | | N,N',N'',N'''-(coronene-1,2,7,8-tetrayltetrakis (oxy))tetra undecaneamide | N-bromoundecaneamide | 49 |
| 8A | 81-3 | | 1,2,7,8-tetrakis ((undecylthio)oxy) coronene | undecyl thio bromide | 47 |
| 8A | 81-4 | | coronene-1,2,7,8-tetrayltetrakis (undecane-1-sulfinate) | undecyl sulfinyl bromide | 56 |
| 8A | 81-5 | | 12,12',12'',12'''-(coronene-1,2,7,8-tetrayltetrakis (oxy))tetrakis (dodecane-1-ol) | 12-bromododecane-1-ol | 49 |
| 8A | 81-6 | | (coronene-1,2,7,8-tetrayltetrakis (oxy))tetra dodecanoic acid | 12-bromododecanoic acid (cas number 73367-80-3) | 51 |

TABLE 8-continued

| Prep. Ex. # | Comp. # | Compound Structure | Compound Name | Reagent | Yield (%) |
|---|---|---|---|---|---|
| 8B | 82 | 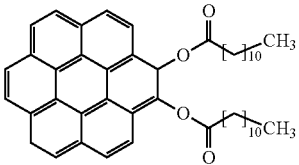 | coronene-1,2-diyldidodecanoate | dodecanoyl bromide | 61 |
| 8B | 82-1 | 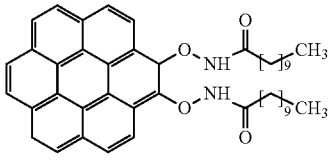 | N,N'-(coronene-1,2-diylbis(oxy)) diundecane amide | N-bromoundecane amide | 79 |
| 8B | 82-2 | 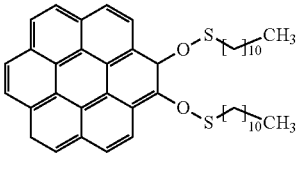 | 1,2-bis((undecylthio) oxy)coronene | undecyl thio bromide | 79 |
| 8B | 82-3 | 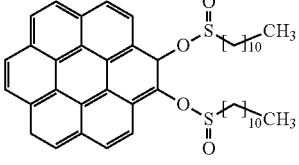 | coronene-1,2-diylbis(undecan-1-sulfinate) | undecyl sulfinyl bromide | 75 |
| 8B | 82-4 | 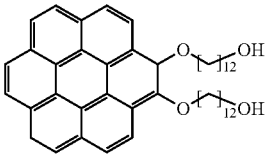 | 12,12'-(coronene-1,2-diylbis(oxy)) bis(dodecane-1-ol) | 12-bromododecane-1-ol | 31 |
| 8B | 82-5 | 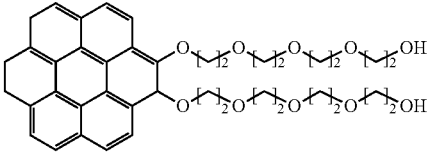 | 2,2'-((((((coronene-1,2-diylbis(oxy)) bis(ethane-3,1-diyl))bis(oxy)) bis(ethane-2,1-diyl))bis(oxy)) bis(ethane-2,1-diyl)bis(oxy)) bis(ethane-1-ol) | 1-bromo-2-(2-(2-(2-hydroxyethoxy) ethoxy)ethoxy)ethane | 59 |
| 8C | 83 | 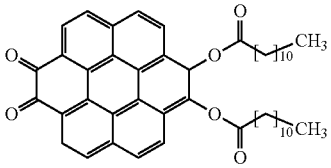 | 7,8-dioxo-7,8-dihydrocoronene-1,2-diyldidodecanoate | dodecanoyl bromide | 35 |
| 8C | 83-1 | 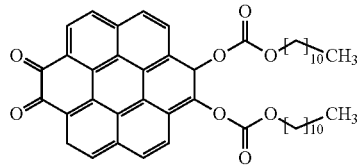 | diundecyl(7,8-dioxo-7,8-dihydrocoronene-1,2-diyl) | carbonobromic acid, undecyl ester | 51 |

TABLE 8-continued

| Prep. Ex. # | Comp. # | Compound Structure | Compound Name | Reagent | Yield (%) |
|---|---|---|---|---|---|
| 8C | 83-2 | 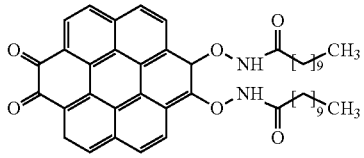 | N,N'-((7,8-dioxo-7,8-dihydrocoronene-1,2-diyl)bis(oxy)) diundecane amide | N-bromoundecane amide | 45 |

Compound Preparation Example 9A: Preparation of cyclopenta[fg]acenaphthylene-1,2,5,6-tetrayltetradodecanoate The procedure of Preparation Example 4A was conducted except that dodecanoyl bromide was used instead of bromododecyl in Step 4A-4 of Preparation Example 4A to obtain cyclopenta[fg]acenaphthylene-1,2,5,6-tetrayltetradodecanoate (compound 91).

Compound Preparation Example 9B: Preparation of cyclopenta[fg]acenaphthylene-1,2-diyldidodecanoate The procedure of Preparation Example 4B was conducted except that dodecanoyl bromide was used instead of bromododecyl in Step 4B-2 of Preparation Example 4B to obtain cyclopenta[fg]acenaphthylene-1,2-diyldidodecanoate (compound 92).

Compound Preparation Example 9C: Preparation of 5,6-bis((1,2-hydroxydodecyl)oxy)cyclopenta[fg]acenaphthylene-1,2-dione The procedure of Preparation Example 4C was conducted except that 1,2-bromododecane-1-ol was used instead of bromododecyl in Preparation Example 4C to obtain 5,6-bis((1,2-hydroxydodecyl)oxy)cyclopenta[fg]acenaphthylene-1,2-dione (compound 93).

TABLE 9

| Prep. Ex. # | Comp. # | Compound Structure | Compound Name | Reagent | Yield (%) |
|---|---|---|---|---|---|
| 9A | 91 | 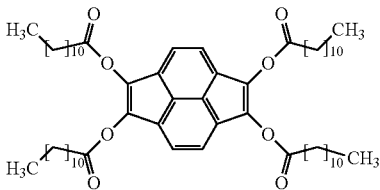 | cyclopenta[fg]acenaphthylene-1,2,5,6-tetrayltetradodecanoate | dodecanoyl bromide | 39 |
| 9A | 91-1 | 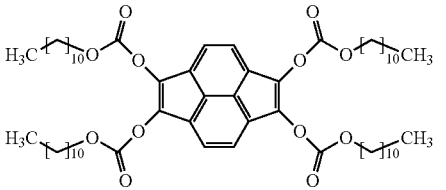 | cyclopenta[fg]acenaphthylene-1,2,5,6-tetrayltetrakis(undecyl) tetracarbonate | carbonobromic acid, undecyl ester | 54 |
| 9A | 91-2 | 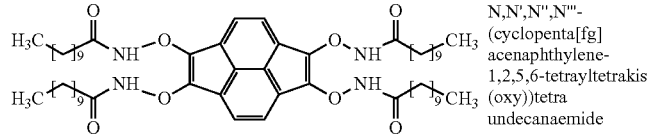 | N,N',N'',N'''-(cyclopenta[fg]acenaphthylene-1,2,5,6-tetrayltetrakis(oxy))tetra undecanaemide | N-bromoundecane amide | 31 |
| 9A | 91-3 | 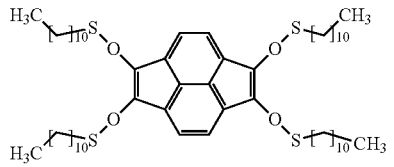 | 1,2,5,6-tetrakis((undecylthio)oxy)cyclopenta[fg]acenaphthylene | undecyl thio bromide | 80 |

TABLE 9-continued

| Prep. Ex. # | Comp. # | Compound Structure | Compound Name | Reagent | Yield (%) |
|---|---|---|---|---|---|
| 9A | 91-4 | | cyclopenta[fg]acenaphthylene-1,2,5,6-tetrayltetrakis(undecan-1-sulfinate) | undecyl sulfinyl bromide | 28 |
| 9A | 91-5 | | 12,12',12'',12'''-(1,2,5,6-cyclopenta[fg]acenaphthylene-1,2,5,6-tetrayltetrakis(oxy)tetrakis(dodecane-1-ol) | 12-bromododecane-1-ol | 76 |
| 9A | 91-6 | | 12,12',12'',12'''-(cyclopenta[fg]acenaphthylene-1,2,5,6-tetrayltetrakis(oxy))tetradodecanoic acid | 12-bromododecanoic acid (cas number 73367-80-3) | 70 |
| 9B | 92 | | cyclopenta[fg]acenaphthylene-1,2-diyldidodecanoate | dodecanoyl bromide | 85 |
| 9B | 92-1 | | cyclopenta[fg]acenaphthylene-1,2-diyldiundecyl dicarbonate | carbon bromic acid, undecyl ester | 80 |
| 9B | 92-2 | | 12,12'-(cyclopenta[fg]acenaphthylene-1,2-diylbis(oxy))bis(dodecane-1-ol) | 12-bromododecane-1-ol | 63 |
| 9C | 93 | 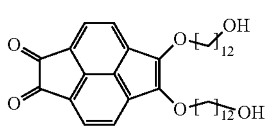 | 5,6-bis((12-hydroxydodecyl)oxy)cyclopenta[fg]acenaphthylene-1,2-dione | 12-bromododecane-1-ol | 37 |

Compound Preparation Example 10A: Preparation of 12,12',12'',12''',12'''',12'''''-(triphenylene-2,3,6,7,10,11-hexaylhexakis(oxy)) hexakis(dodecane-1-ol)

The procedure of Preparation Example 5A was conducted except that 1,2-bromododecane-1-ol was used instead of bromododecyl in Preparation Example 5A-2 to obtain 12,12',12'',12''',12'''',12'''''-(triphenylene-2,3,6,7,10,11-hexaylhexakis(oxy)) hexakis(dodecane-1-ol) (compound 101).

TABLE 10

| Prep. Ex. # | Comp. # | Compound Structure | Compound Name | Reagent | Yield (%) |
|---|---|---|---|---|---|
| 10A | 101 | | 12,12',12'',12''',12'''',12'''''-(triphenylene-2,3,6,7,10,11-hexaylhexakis(oxy))hexakis(dodecane-1-ol) | 12-bromododecane-1-ol | 50 |
| 10A | 101-1 | | 2,2',2'',2''',2'''',2'''''-((((((triphenylene-2,3,6,7,10,11-hexaylhexakis(oxy))hexakis(ethane-2,1-diyl))hexakis(oxy))hexakis(ethane-2,1-diyl))hexakis(oxy))hexakis(ethane-2,1diyl))hexakis(oxy))hexaethaneol | 1-bromo-2-(2-(2-(2-hydroxyethoxy)ethoxy)ethoxy)ethane | 56 |

Compound Preparation Example 11A: Preparation of 4,5,9,10-tetrakis((6-((2-ethoxyvinyl)oxy)hexyl)oxy)pyrene

[Reaction Scheme 15]

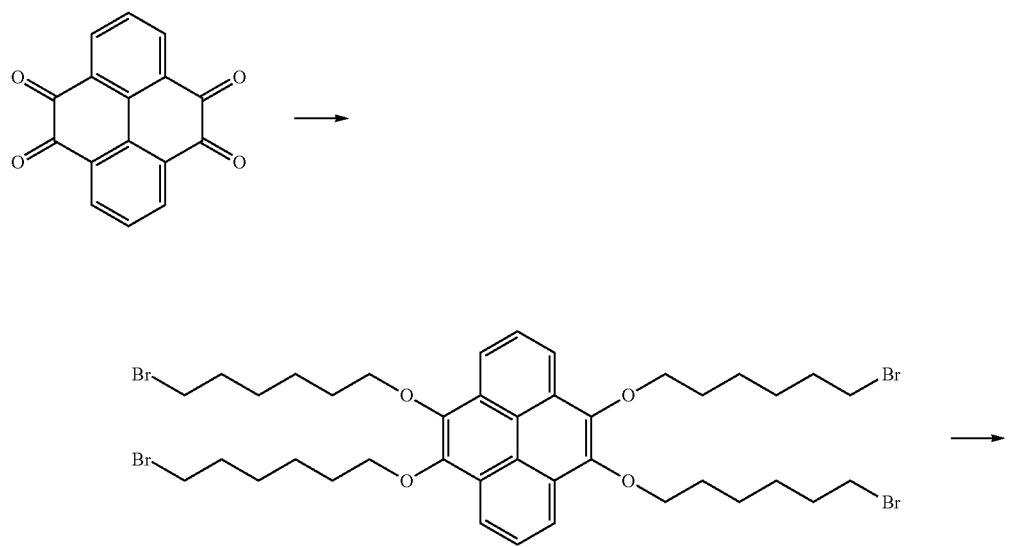

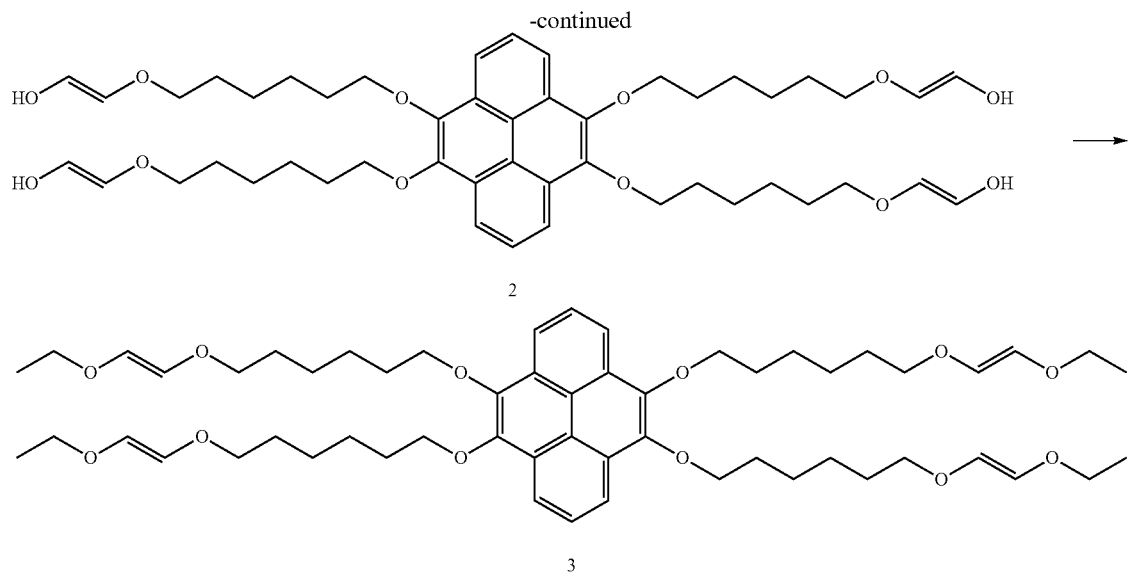

11A-1. Preparation of 4,5,9,10-tetrakis((6-bromohexyl)oxy)pyrene (1)

The procedure of Step 1A-2 of Preparation Example 1A was conducted except that 1,6-dibromohexane was used instead of bromododecyl to obtain 4,5,9,10-tetrakis((6-bromohexyl)oxy)pyrene (1).

4,5,9,10-tetrakis((6-bromohexyl)oxy)pyrene: $^1$H NMR (600 MHz, CDCl$_3$) δ 8.00 (d, 4H), 7.82 (m, 2H), 4.16 (d, 8H), 3.51 (t, 8H), 1.73 (m, 16H), 1.43-1.29 (m, 8H)

11A-2. Preparation of 2,2',2'',2'''-(((pyrene-4,5,9,10-tetrayltetrakis(oxy)) tetrakis(hexane-6,1-diyl))tetrakis (oxy))tetraethanol (2)

4,5,9,10-tetrakis((6-bromohexyl)oxypyrene (1 mmol) obtained from Step 11A-1 and 1,2-ethenediol (5 mmol) were dissolved in dimethylformamide (20 ml), and the mixture was reacted at reflux at 80° C. for 14 hours. Then, the mixture was extracted with chloroform, and water was removed with magnesium sulfite. The residue was purified by column chromatography to obtain 2,2',2'',2'''-(((pyrene-4,5,9,10-tetrayltetrakis(oxy))tetrakis(hexane-6,1-diyl))tetrakis(oxy))tetraethanol (2).

2,2',2'',2'''-(((pyrene-4,5,9,10-tetrayltetrakis(oxy))tetrakis (hexane-6,1-diyl))tetrakis(oxy))tetraethanol: $^1$H NMR (600 MHz, CDCl$_3$) δ 16.7 (s, 4H), 8.00 (d, 4H), 7.82 (m, 2H), 6.44 (d, 4H), 4.15 (m, 12H), 1.71 (m, 16H), 1.43 (m, 16H)

11A-3. Preparation of 4,5,9,10-tetrakis((6-((2-ethoxyvinyl)oxy)hexyl)oxy) pyrene (3)

The result of 11A-2, 2,2',2'',2'''-(((pyrene-4,5,9,10-tetrayltetrakis(oxy)) tetrakis(hexane-6,1-diyl))tetrakis(oxy))tetraethanol (1 mmol) and 1-bromoethane (6 mmol) were added to tetrahydrofuran (30 ml) and refluxed at 70° C. for 12 hours to obtain 4,5,9,10-tetrakis((6-((2-ethoxyvinyl)oxy)hexyl)oxy)pyrene (3, compound 111).

4,5,9,10-tetrakis((6-((2-ethoxyvinyl)oxy)hexyl)oxy)pyrene: $^1$H NMR (600 MHz, CDCl$_3$) δ 8.00 (d, 4H), 7.82 (m, 2H), 5.40 (s, 4H), 4.49 (t, 4H), 4.16 (t, 8H), 4.01 (t, 8H), 1.71 (m, 16H), 1.43 (m, 16H), 1.21 (t, 12H)

Compound Preparation Example 11B: Preparation of 2,3,6,7-tetrakis((7-((2-ethoxyvinyl)oxy)heptyl) oxy)anthracene

11B-1. Preparation of 2,3,6,7-tetrakis((7-bromoheptyl)oxy)anthracene

The procedure of Preparation Example 2A was conducted except that 1,7-dibromoheptane was used instead of 1-bromododecane in Step 2A-3 of Preparation Example 2A to obtain 2,3,6,7-tetrakis((7-bromoheptyl)oxy)anthracene.

11B-2. Preparation of 2,3,6,7-tetrakis((7-((2-ethoxyvinyl)oxy)heptyl)oxy) anthracene The procedure of Steps 11A-2 and 11A-3 of Preparation Example 11A was conducted except that 2,3,6,7-tetrakis((7-bromohexyl)oxy)anthracene was used instead of 4,5,9,10-tetrakis((6-bromohexyl)oxy)pyrene in Step 11A-2 of Preparation Example 11A to obtain 2,3,6,7-tetrakis((7-((2-ethoxyvinyl)oxy)heptyl)oxy) anthracene (compound 112).

Compound Preparation Example 11C: Preparation of 1,2,7,8-tetrakis((7-((2-ethoxyvinyl)oxy)heptyl) oxy)coronene

11C-1. Preparation of 1,2,7,8-tetrakis((7-bromoheptyl)oxy)coronene

The procedure of Preparation Example 3A was conducted except that 1,7-dibromoheptane was used instead of bromododecyl in Step 3A-6 of Preparation Example 3A to obtain 1,2,7,8-tetrakis((7-bromoheptyl)oxy)coronene.

11C-2. Preparation of 1,2,7,8-tetrakis((7-((2-ethoxyvinyl)oxy)heptyl)oxy) coronene The procedure of Steps 11A-2 and 11A-3 of Preparation Example 11A was conducted except that 1,2,7,8-tetrakis((7-bromohexyl)oxy)coronene was used instead of 4,5,9,10-tetrakis((6-bromohexyl)oxy)pyrene in Step 11A-2 of Preparation Example 11A to obtain 1,2,7,8-tetrakis((7-((2-ethoxyvinyl)oxy)heptyl)oxy) coronene (compound 113).

Compound Preparation Example 11D: Preparation of 1,2,5,6-tetrakis((7-((2-ethoxyvinyl)oxy)heptyl)oxy)cyclopenta[fg]acenaphthylene 11D-1. Preparation of 1,2,5,6-tetrakis((7-bromoheptyl)oxy)cyclopenta[fg] acenaphthylene The procedure of Preparation Example 4A was conducted except that 1,6-dibromoheptane was used instead of bromododecyl in Step 4A-4 of Preparation Example 4A to obtain 1,2,5,6-tetrakis((7-bromoheptyl)oxy)cyclopenta[fg] acenaphthylene.

11D-2. Preparation of 1,2,5,6-tetrakis((7-((2-ethoxyvinyl)ox)heptyl)oxy) cyclopenta [fg] acenaphthylene The procedure of Steps 11A-2 and 11A-3 of Preparation Example 11A was conducted except that 1,2,5,6-tetrakis((7-bromoheptyl)oxy)cyclopenta[fg] acenaphthylene was used instead of 4,5,9,10-tetrakis((6-bromohexyl)oxy)pyrene in Step 11A-2 of Preparation Example 11A to obtain 1,2,5,6-tetrakis((7-((2-ethoxyvinyl)oxy)heptyl)oxy) cyclopenta [fg] acenaphthylene (compound 114).

TABLE 11

| Prep. Ex. # | Comp. # | Compound Structure | Compound Name | Reagent | Yield (%) |
|---|---|---|---|---|---|
| 11A | 111 | | 4,5,9,10-tetrakis((6-((2-ethoxyvinyl)oxy)hexyl)oxy)pyrene | 1,2-ethenediol | |
| 11A | 111-1 | | 4,5,9,10-tetrakis((6-((ethoxyethynyl)oxy)hexyl)oxy)pyrene | 1,2-ethynediol | 71 |
| 11A | 111-2 | | 4,5,9,10-tetrakis((6-((ethoxydiazenyl)oxy)hexyl)oxy)pyrene | Hyponitrous acid | 37 |
| 11B | 112 | | 2,3,6,7-tetrakis((7-((2-ethoxyvinyl)oxy)heptyl)oxy)anthracene | 1,2-ethenediol | 44 |
| 11B | 112-1 | | 2,3,6,7-tetrakis((7-((ethoxyethynyl)oxy)heptyl)oxy)anthracene | 1,2-ethynediol | 58 |
| 11B | 112-2 | | 2,3,6,7-tetrakis((7-((ethoxydiazenyl)oxy)heptyl)oxy)anthracene | Hyponitrous acid | 25 |
| 11C | 113 | | 1,2,7,8-tetrakis((7-((2-ethoxyvinyl)oxy)heptyl)oxy)coronene | 1,2-ethenediol | 79 |
| 11C | 113-1 | | 1,2,7,8-tetrakis((7-((ethoxyethynyl)oxy)heptyl)oxy)coronene | 1,2-ethynediol | 42 |

TABLE 11-continued

| Prep. Ex. # | Comp. # | Compound Structure | Compound Name | Reagent | Yield (%) |
|---|---|---|---|---|---|
| 11C | 113-2 | 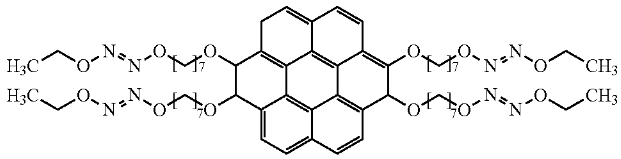 | 1,2,7,8-tetrakis((7-((ethoxydiazenyl)oxy)heptyl)oxy)coronene | Hyponitrous acid | 53 |
| 11D | 114 | | 1,2,5,6-tetrakis((7-((2-ethoxyvinyl)oxy)heptyl)oxy)-1,2,5,6-tetrahydrocyclopenta[fg]acenaphthylene | 1,2-ethenediol | 71 |
| 11D | 114-1 | | 1,2,5,6-tetrakis((7-((ethoxyethynyl)oxy)heptyl)oxy)-1,2,5,6-tetrahydroxycyclopenta[fg]acenaphthylene | 1,2-ethynediol | 32 |
| 11D | 114-2 | | 1,2,5,6-tetrakis((7-((ethoxydiazenyl)oxy)heptyl)oxy)-1,2,5,6-tetrahydrocyclopenta[fg]acenaphthylene | Hyponitrous acid | 34 |

Compound Preparation Example 12A: Preparation of 4,5,9,10-tetrakis ((6-((3-ethoxyoxirane)-2-yl)oxy)hexyl)oxy)pyrene After dissolving iron chloride (0.001 mmol) in toluene (2 ml), sufficiently replacing atmosphere with nitrogen, the 4,5,9,10-tetrakis((6-((2-ethoxyvinyl)oxy)hexyl)oxy)pyrene (compound 111, 1 mmol) was added, and the mixture was refluxed and reacted for 10 hours. Thereafter, the reaction mixture was extracted with chloroform, and subjected to flash column chromatography using chloroform and hexane as eluent to give 4,5,9,10-tetrakis((6-((3-ethoxyoxirane-2-yl)oxy) hexyl) oxy) pyrene (Compound 121) (yield: 68%).

Compound Preparation Example 12B: 2,2',2'',2'''-(((pyrene-4,5,9,10-tetrayltetrakis(oxy))tetrakis(hexane-6,1-diyl))tetrakis(oxy))tetrakis(1-ethoxy-ethan-1,2-diol)

2 mmol of 4,5,9,10-tetrakis((6-((3-ethoxyoxirane-2-yl)oxy)hexyl)oxy) pyrene (Compound 121) was dissolved in 5 ml of a mixed solvent of methanol and dichloromethane (1:1v) to make a solution, and iron (III) porphyrin complex meso-tetrakis (2,3,5,6-tetrafluoro-4-N, N, N-trimethylaniline) propinato was added in the solution. The reaction mixture was stirred at room temperature for 12 hours to obtain a final product, 2,2',2'',2'''-(((pyrene-4,5,9,10-tetrayltetrakis(oxy))tetrakis(hexane-6,1-diyl))tetrakis(oxy))tetrakis(1-ethoxyethan-1,2-diol) (compound 122) (Yield: 37%).

Compound Preparation Example 12C: Synthesis of 1,1',1'',1'''-(((pyrene-4,5,9,10-tetrayltetrakis(oxy))tetrakis(hexane-6,1-diyl)tetrakis(oxy)) tetrakis(2-ethoxyethanol)

1 mmol of 4,5,9,10-tetrakis((6-((3-ethoxyoxirane-2-yl)oxy)hexyl)oxy)pyrene (Compound 121) and 2 mmol of NaBH$_4$ were added in 1 ml of urea/chlorine chloride eutectic salt, and reacted at 60° C. for 30 minutes to obtain 1,1',1'',1'''-(((pyrene-4,5,9,10-tetrayltetrakis(oxy))tetrakis(hexane-6,1-diyl))tetrakis(oxy)) tetrakis(2-ethoxyethanol) (Compound 123) (Yield: 76%).

TABLE 12

| Prep. Ex. # | Comp. # | Compound Structure | Compound Name | Reagent | Yield (%) |
|---|---|---|---|---|---|
| 12A | 121 | 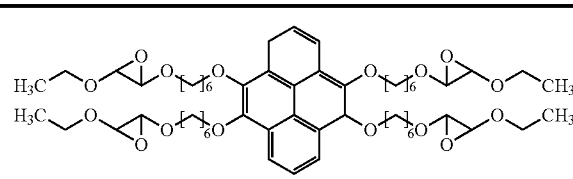 | 4,5,9,10-tetrakis((6-((3-ethoxyoxirane-2-yl)oxy)hexyl)oxy)pyrene | compound 101 | 68 |

TABLE 12-continued

| Prep. Ex. # | Comp. # | Compound Structure | Compound Name | Reagent | Yield (%) |
|---|---|---|---|---|---|
| 12A | 121-1 | | 2,3,6,7-tetrakis((7-((3-ethoxyoxirane-2-yl)oxy)heptyl)oxy)anthracene | compound 102 | 79 |
| 12A | 121-2 | | 1,2,7,8-tetrakis((7-((3-ethoxyoxirane-2-yl)oxy)heptyl)oxy)coronene | compound 103 | 63 |
| 12A | 121-3 | | 1,2,5,6-tetrakis((7-((3-ethoxyoxirane-2-yl)oxy)heptyl)oxy)-1,2,5,6-tetrahydrocyclopenta[fg]acenaphthylene | compound 104 | 65 |
| 12B | 122 | | 2,2',2'',2'''-(((pyrene-4,5,9,10-tetrayltetrakis(oxy))tetrakis(hexane-6,1-diyl))tetrakis(oxy))tetrakis(1-ethoxyethane-1,2-diol) | compound 111 | 37 |
| 12B | 122-1 | | 2,2',2'',2'''-(((anthracene-2,3,6,7-tetrayltetrakis(oxy))tetrakis(heptane-7,1-diyl))tetrakis(oxy))tetrakis(1-ethoxyethane-1,2-diol) | compound 111-1 | 45 |
| 12B | 122-2 | | 2,2',2'',2'''-(((coronene-1,2,7,8-tetrayltetrakis(oxy))tetrakis(heptane-7,1-diyl))tetrakis(oxy))tetrakis(1-ethoxyethane-1,2-diol) | compound 111-2 | 25 |
| 12B | 122-3 | | 2,2',2'',2'''-((((1,2,5,6-tetrahydrocyclopenta[fg]acenaphthylene-1,2,5,6-tetrayl)tetrakis(oxy))tetrakis(heptane-7,1-diyl))tetrakis(oxy))tetrakis(1-ethoxyethane-1,2-diol) | compound 111-3 | 24 |

TABLE 12-continued

| Prep. Ex. # | Comp. # | Compound Structure | Compound Name | Reagent | Yield (%) |
|---|---|---|---|---|---|
| 12C | 123 | | 1,1',1",1"'-(((pyrene-4,5,9,10-tetrayltetrakis(oxy))tetrakis(hexane-6,1-diyl))tetrakis(oxy))tetrakis(2-ethoxyethaneol) | compound 111 | 76 |
| 12C | 123-1 | | 1,1',1",1"'-(((anthracene-2,3,6,7-tetrayltetrakis(oxy))tetrakis(heptane-7,1-diyl))tetrakis(oxy))tetrakis(2-ethoxyethaneol) | compound 111-1 | 57 |
| 12C | 123-2 | | 1,1',1",1"'-(((coronene-1,2,7,8-tetrayltetrakis(oxy))tetrakis(heptane-7,1-diyl))tetrakis(oxy))tetrakis(2-ethoxyethaneol) | compound 111-2 | 52 |
| 12C | 123-3 | | 1,1',1",1"'-((((1,2,5,6-tetrahydrocyclopenta[fg]acenaphthylene-1,2,5,6-tetrayl)tetrayltetrakis(oxy))tetrakis(heptane-7,1-diyl))tetrakis(oxy))tetrakis(2-ethoxyethaneol) | compound 111-3 | 65 |

Compound Preparation Example 13A: 13,13',13",13"'-(pyrene-4,5,9,10-tetrayltetrakis(oxy))tetratridecanal 12,12',12",12"'-(pyrene-4,5,9,10-tetrayltetrakis(oxy)tetrakis(dodecane-1-ol) (Compound 61-5) (0.8 mmol) was added into 1 ml of dichloromethane at 0° C., 0.5 M KBr (0.16 ml) was added, pH 8.6, 0.35 M sodium hypochlorite (2.86 ml) was added, and the mixture was reacted for 3 hours. After completion of the reaction, only the organic layer was extracted, and the water was removed with magnesium sulfate and evaporated. The resulting product was filtered through a column to obtain end products 13,13',13",13"'-(pyrene-4,5,9,10-tetrayltetrakis(oxy))tetratridecanal (Compound 131) (yield: 38%).

TABLE 13

| Prep. Ex. # | Comp. # | Compound Structure | Compound Name | Reagent | Yield (%) |
|---|---|---|---|---|---|
| 13A | 131 | | 13,13',13",13"'-(pyrene-4,5,9,10-tetrayltetrakis(oxy))tetratridecanal | compound 61-5 | 38 |
| 13A | 131-1 | | 13,13',13",13"'-((tetradecahydroanthracene-2,3,6,7-tetrayl)tetrakis(oxy))tetratridecanal | compound 71-5 | 39 |

TABLE 13-continued

| Prep. Ex. # | Comp. # | Compound Structure | Compound Name | Reagent | Yield (%) |
|---|---|---|---|---|---|
| 13A | 131-2 | | 13,13',13'',13'''-(coronene-1,2,7,8-tetrayltetrakis(oxy)) tetratridecanal | compound 81-5 | 38 |
| 13A | 131-3 | | 13,13',13'',13'''-(cyclopenta[fg]acenaphthylene-1,2,5,6-tetrayltetrakis(oxy)) tetratridecanal | compound 91-5 | 30 |

Compound Preparation Example 14A: 12,12',12'',12'''-(pyrene-4,5,9,10-tetrayltetrakis(oxy))tetrakis(dodecane-1-thiol)

15 mmol of hydrogensulfide, 4 mmol of disodium carbonate, and 3 mmol of calcium carbonate hydroxide phosphate were added to 12,12',12'',12'''-(pyrene-4,5,9,10-tetrayltetrakis(oxy)tetrakis(dodecan-1-ol) (compound 61-5), and the mixture was reacted at 250° C. under stirring to obtain 12,12',12'',12'''-(pyrene-4,5,9,10-tetrayltetrakis(oxy))tetrakis(dodecane-1-thiol) (Compound 141) (yield: 47%).

Compound Preparation Example 14B: 12,12',12'',12'''-(pyrene-4,5,9,10-tetrayltetrakis(oxy)tetrakis(dodecane-1-amine)

10 mmol of 12,12',12'',12'''-(pyrene-4,5,9,10-tetrayltetrakis(oxy))tetrakis(dodecane-1-thiol) (Compound 141) obtained from Compound Preparation Example 14A was charged with 7.5 bar of $NH_3$, and refluxed for 12 hours with 0.01 mmol of RuHCl(a-iPr-PNP)(CO) in an argon atmosphere using toluene as a solvent to obtain 12,12',12'',12'''-(pyrene-4,5,9,10-tetrayltetrakis(oxy)tetrakis(dodecane-1-amine) (Compound 142) (Yield: 73%).

Compound Preparation Example 14C: 11,11'-(pyrene-4,5-diylbis(oxy))di(dodecane-1-amine)

The procedure of Preparation Example 14A was conducted except that 20 mmol of 12,12'-(Anthracene-2,3-diylbis(oxy))bis(dodecan-1-ol) (Compound 72-5) was used instead of 10 mmol of 12,12',12'',12'''-(pyrene-4,5,9,10-tetrayltetrakis(oxy)tetrakis(dodecan-1-ol) (compound 61-5) to obtain 11,11'-(pyrene-4,5-diylbis(oxy))di(dodecane-1-thiol).

The procedure of Preparation Example 14B was conducted except that 20 mmol of 11,11'-(pyrene-4,5-diylbis(oxy))di(dodecane-1-thiol) obtained above was used instead of 10 mmol of 12,12',12'',12'''-(pyrene-4,5,9,10-tetrayltetrakis(oxy))tetrakis(dodecane-1-thiol) (Compound 141) to obtain 11,11'-(pyrene-4,5-diylbis(oxy))di(dodecane-1-amine) (Compound 143) (Yield: 57%).

Compound Preparation Example 14D: 11,11',11'',11'''-(pyrene-4,5,9,10-tetrayltetrakis(oxy))tetrakis(undecan-1-amine)

The procedure of Preparation Example 1A was conducted except that 1,2-bromododecan-1-ol was used instead of bromododecyl in Step 1A-2 of Preparation Example 1A to obtain 11,11',11'',11'''-(pyrene-4,5,9,10-tetrayltetrakis(oxy)tetrakis (undecan-ol).

The procedure of Preparation Example 14A was conducted except that 11,11',11'',11'''-(pyrene-4,5,9,10-tetrayltetrakis(oxy)tetrakis(undecan-ol) was used instead of 12,12',12'',12'''-(pyrene-4,5,9,10-tetrayltetrakis(oxy)tetrakis(dodecan-1-ol) (compound 61-5) to obtain 11,11',11'',11'''-(pyrene-4,5,9,10-tetrayltetrakis(oxy) tetrakis(undecane-1-thiol).

The procedure of Preparation Example 14B was conducted except that 11,11',11'',11'''-(pyrene-4,5,9,10-tetrayltetrakis(oxy)tetrakis(undecane-1-thiol) obtained above was used instead of 12,12',12'',12'''-(pyrene-4,5,9,10-tetrayltetrakis(oxy))tetrakis(dodecane-1-thiol) (Compound 141) to obtain 11,11',11'',11'''-(pyrene-4,5,9,10-tetrayltetrakis(oxy))tetrakis(undecan-1-amine) (Compound 144) (Yield 70%).

TABLE 14

| Prep. Ex. # | Comp. # | Compound Structure | Compound Name | Reagent | Yield (%) |
|---|---|---|---|---|---|
| 14A | 141 | 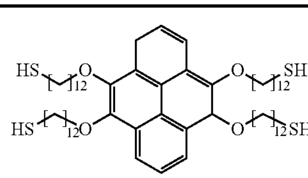 | 12,12',12'',12'''-(pyrene-4,5,9,10-tetrayltetrakis(oxy))tetrakis(dodecane-1-thiol) | compound 61-5 | 47 |

TABLE 14-continued

| Prep. Ex. # | Comp. # | Compound Structure | Compound Name | Reagent | Yield (%) |
|---|---|---|---|---|---|
| 14A | 141-1 | | 12,12',12'',12'''-((tetrahydroanthracene-2,3,6,7-tetrayl)tetrakis(oxy))tetrakis(dodecane-1-thiol) | compound 71-5 | 43 |
| 14A | 141-2 | | 12,12',12'',12'''-(coronene-1,2,7,8-tetrayltetrakis(oxy))tetrakis(dodecane-1-thiol) | compound 81-5 | 77 |
| 14A | 141-3 | | 12,12',12'',12'''-(cyclopenta[fg]acenaphthylene-1,2,5,6-tetrayltetrakis(oxy))tetrakis(dodecane-1-thiol) | compound 91-5 | 59 |
| 14B | 142 | | 12,12',12'',12'''-(pyrene-4,5,9,10-tetrayltetrakis(oxy)tetrakis(dodecane-1-amine) | compound 141 | 73 |
| 14B | 142-1 | | 12,12',12'',12'''-((tetrahydroanthracene-2,3,6,7-tetrayl)tetrakis(oxy))tetrakis(dodecane-1-amine) | compound 141-1 | 45 |
| 14B | 142-2 | | 12,12',12'',12'''-(coronene-1,2,7,8-tetrayltetrakis(oxy))tetrakis(dodecane-1-amine) | compound 141-2 | 35 |
| 14B | 142-3 | | 12,12',12'',12'''-(cyclopenta[fg]acenaphthylene-1,2,5,6-tetrayltetrakis(oxy))tetrakis(dodecane-1-amine) | compound 141-3 | 50 |
| 14C | 143 | 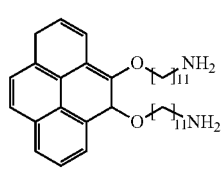 | 11,11'-(pyrene-4,5-diylbis(oxy))di(dodecane-1-amine) | | 57 |
| 14D | 144 | 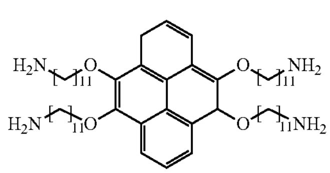 | 11,11',11'',11'''-(pyrene-4,5,9,10-tetrayltetrakis(oxy))tetrakis(undecan-1-amine) | | 70 |

Compound Preparation Example 15A: Compound 151

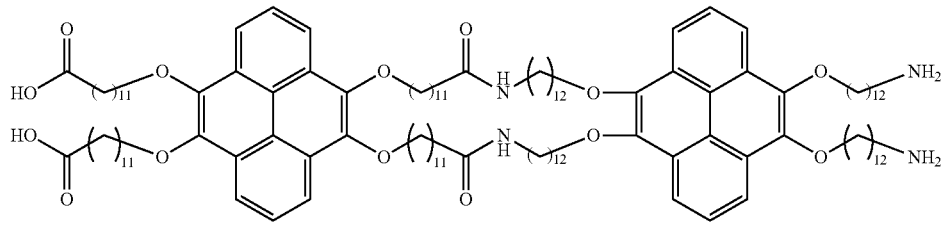

[Compound 151]

12,12',12'',12'''-(Pyrene-4,5,9,10-tetrayltetrakis(oxy))tetradodecanoic acid (compound 61-6) (10 mmol) and 12,12', 12'',12'''-(pyrene-4,5,9,10-tetrayltetrakis (oxy))tetrakis(dodecan-1-amine) (compound 142) (10 mmol) were dissolved in distilled water (70 ml) and tetrahydrofuran (THF), and refluxed at 65° C. for 5 hours to obtain the final product, Compound 151.

FIG. 23 is a $^1$H-NMR spectrum of Compound 151 according to Preparation Example 15A measured in a $CDCl_3$ solvent.

Compound Preparation Example 15B: Compound 152

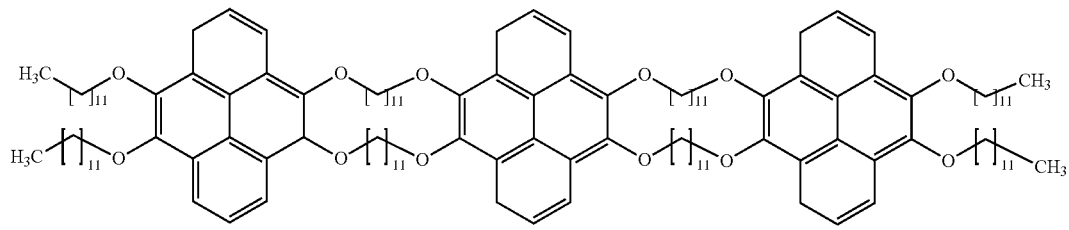

[Compound 152]

4,5-bis(dodecyloxy)-pyrene-9,10-dione (compound 15, 20 mmol) obtained from Preparation Example 1E and pyrene-4,5,9,10-tetraone (10 mmol) were dissolved in distilled water (70 ml) and tetrahydrofuran (THF) together with bromotetrabutylammonium ($Bu_4NBr$) (26 mmol) and sodium hydrosulfite ($Na_2S_2O_4$) (230 mmol), and refluxed at 65° C. for 5 minutes. After being refluxed, the solution was added to a aqueous solution of bromododecyl (60 mmol) and KOH (306 mmol) in distilled water (50 ml), and the mixture was refluxed at 65° C. for 16 hours to obtain Compound 152.

FIG. 24 is a $^1$H-NMR spectrum of Compound 152 according to Preparation Example 15B measured in a $CDCl_3$ solvent.

Compound Preparation Example 15C: Compound 153

[Compound 153]

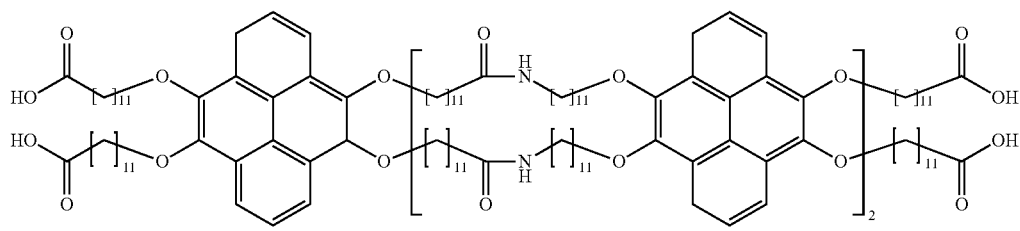

12,12′,12″,12‴-(Pyrene-4,5,9,10-tetrayltetrakis(oxy))tetradodecanoic acid (compound 61-6) (20 mmol) and 11,11′,11″,11‴-(pyrene-4,5,9,10-tetrayltetrakis(oxy))tetrakis(undecan-1-amine) (Compound 144) (10 mmol) were dissolved in distilled water (70 ml) and tetrahydrofuran (THF), and refluxed at 65° C. for 5 hours to obtain Compound 153.

FIG. 25 is a $^1$H-NMR spectrum of Compound 153 according to Preparation Example 15C measured in a $CDCl_3$ solvent.

FIGS. 26A and 26B are optical photographs of 4,5,9,10-tetrakis(dodecyloxy)-pyrene (compound 11) crystals according to a preparation example of the compound.

Referring to FIGS. 26A and 26B, it can be seen that organic crystals exhibit a rod shape having a width of several micrometers and a length of several tens to several hundreds of micrometers.

3-Dimensional Structure Evaluation Example 1: Confirmation of Structure of 3-Dimensional Structure by X-Ray Diffraction Analysis X-ray diffraction was performed using Cu-Kα (λ=0.15418 nm) radiation at 40 kV and 100 mA using D8 advance (Brucker) and D/MAX RINT 2000 (Rikaku), and measured from 1° to 45°. The crystal structure was confirmed using the program EXPO2013 [Altomare A, et al. EXPO2013: a kit of tools for phasing crystal structures from powder data. Journal of Applied Crystallography, 2013 46, 1231-1235].

The results of X-ray diffraction spectroscopy of compounds obtained in the Compound Preparation Examples using the measurement method are as follows.

FIG. 27 shows the X-ray spectrum of the three-dimensional structure crystal by 4,5,9,10-tetrakis(dodecyloxy)-pyrene (compound 11) according to the preparation example of the compound.

Referring to FIG. 27, it can be seen that, in the case of 4,5,9,10-tetrakis(dodecyloxy)-pyrene, the crystal of a=37.523 Å, b=34.476 Å and c=9.340 Å (residuals: Rp=8.532, Rwp=11.747) with an orthorhombic unit lattice was formed.

FIG. 28 shows the X-ray spectrum of a three-dimensional structure crystal formed by 2,3,6,7-tetrakis(dodecyloxy)anthracene (Compound 21) according to the preparation example of the compound.

FIG. 29 shows the X-ray spectrum of a three-dimensional structure crystal by 1,2,7,8-tetrakis(dodecyloxy)coronene (Compound 31) according to the preparation example of the compound.

FIG. 30 shows the X-ray spectrum of a three-dimensional structure crystal by 1,2,5,6-tetrakis(dodecyloxy)cyclopenta[f,g]acenaphthalene (Compound 41) according to the preparation example of the compound.

FIG. 31 shows the X-ray spectrum of a three-dimensional structure crystal by 2,3,6,7,10,11-hexakis(dodecyloxy)triphenylene (Compound 51) according to the preparation example of the compound.

FIGS. 32A and 32B are a perspective view and a top view, respectively, of the crystal structure of 4,5,9,10-tetrakis(dodecyloxy)-pyrene deduced from the X-ray spectrum of FIG. 27.

Referring to FIG. 32A, four oxy groups (A) in the unit organic molecule (UM) of 4,5,9,10-tetrakis(dodecyloxy)-pyrene forming the three-dimensional organic structure can induce the electron-rich region (δ−) and the electron-deficient region (δ+), i.e., the localization of the electron density in the aromatic ring, i.e., the pyrene (Ar).

In addition, the dodecyl groups (Y), two strains, adjacent to each other in the unit organic molecule of 4,5,9,10-tetrakis(dodecyloxy)-pyrene are stabilized by Van Der Waals interaction (PIa), thereby reducing flexibility and improving rigidity thereof compared to one strain of the dodecyl groups.

Also, the terminal portions (X) of the dodecyl groups between the unit organic molecules adjacent to each other in each layer can also be bonded by a physical interaction (PIb). At this time, the terminal portions of adjacent dodecyl groups may interdigitate with each other.

Meanwhile, the unit organic molecules in the Z direction are laminated by pi-pi interactions (PIc). In this case, attractive force (Pic) between the electron-rich region (δ−) and the electron-deficient region (δ+) of the adjacent pyrenes (Ar) in the Y direction can be induced due to the localized electron-rich region (δ−) and electron-deficient region (δ+) in each pyrene (Ar). Because of this, relative to the direction (X) in which the compound of the first layer ($F_1$) extends, the direction in which the compound of the second layer ($F_2$) extends may be shifted by 90 degrees to become the Y direction, and the direction in which the compound of the third layer ($F_3$) extends can be also rotated by 90 degrees relative to the direction in which the compound of the second layer ($F_2$) extends to become the X direction.

Referring to FIG. 32B, it can be seen that a large number of pores V are formed in the three-dimensional organic structure.

3-Dimensional Structure Evaluation Example 2: Identification of Porous Structure by Nitrogen Adsorption Experiment Nitrogen adsorption experiments were carried out using an Autosorb-iQ2ST/MP analyzer (Quantachrome Instruments). 4,5,9,10-tetrakis(dodecyloxy)-pyrene crystals, 4,5,9,10-tetrakis(tetradecyloxy)-pyrene crystal, and 4,5,9,10-tetrakis (octadecyloxy)-pyrene crystal were respectively degassed at room temperature for 16 hours, and Nitrogen adsorption experiments thereon were carried out using nitrogen at 77 K.

FIG. 33 is a nitrogen isotherm adsorption-desorption graph of 4,5,9,10-tetrakis(dodecyloxy)-pyrene crystal, 4,5,9,10-tetrakis(tetradecyloxy)-pyrene crystal, and 4,5,9,10-tetrakis(octadecyloxy)-pyrene crystal.

Referring to FIG. 33, it can be seen that a hysteresis curve is generated in which the nitrogen isothermal adsorption process and the nitrogen isothermal desorption process do not coincide with each other. In addition, all of the organic crystals showed mesoporous (2-50 nm) isothermal adsorption characteristics of type 4 according to IUPAC classification. This can be seen only in crystals having a porous structure, and it can be confirmed that the organic crystals effectively and clearly form a porous structure.

Further, the amount of nitrogen adsorption increases in the order of 4,5,9,10-tetrakis(dodecyloxy)-pyrene crystal, 4,5,9,10-tetrakis(tetradecyloxy)-pyrene crystal, and 4,5,9,10-tetrakis(octadecyloxy)-pyrene crystal, which is presumed to be due to an increase in pore area due to the length of the substituent bonded to pyrene.

Separation Sieve Preparation Example 1

20 mg of 4,5,9,10-tetrakis(dodecyloxy)-pyrene (Compound 11) according to Compound Production Example 1A was placed in an IR pellet die and pressurized at a pressure of 7000 kgf/cm², thereby preparing a pellet-shaped separation sieve.

Separation Sieve Preparation Example 2

2 g of 4,5,9,10-tetrakis(dodecyloxy)-pyrene (Compound 11) according to Compound Production Example 1A was uniformly spread on a PVDF (polyvinylidene fluoride) plate having an area of 144 cm² and pressurized at a pressure of 7000 kgf/cm², thereby preparing a separation sieve film, and then the separation sieve film was separated from the PVDF plate.

Separation Sieve Preparation Example 3

500 mg of 4,5,9,10-tetrakis(dodecyloxy)-pyrene (Compound 11) according to Compound Preparation Example 1A was charged into a porous aluminum pipe having a diameter of 2 mm and a length of 5 cm to prepare a separation sieve package.

Separation Sieve Preparation Example 4

1 g of 4,5,9,10-tetrakis(dodecyloxy)-pyrene (compound 11) according to Compound Production Example 1A was charged in a porous aluminum basket having a bottom area of 2.25 cm² and a height of 0.5 cm to prepare a separation sieve package.

Separation Sieve Preparation Example 5

500 mg of 4,5,9,10-tetrakis(dodecyloxy)-pyrene (Compound 11) according to Compound Preparation Example 1A was packed in a cellulose pouch having an area of 3 cm² to prepare a separation sieve package.

Separation Sieve Preparation Example 6

4,5,9,10-tetrakis(dodecyloxy)-pyrene (Compound 11) according to Compound Preparation Example 1A was added to a mixed solvent of chloroform and ethyl acetate having a volume ratio of 1:1 to prepare a homogeneous solution having a concentration of 12.5 mM. The solution was spin-coated on a PVDF plate at a speed of 1750 rpm, and dried to form a separation sieve film, and then the separation sieve film was separated from the PVDF plate.

Separation Sieve Preparation Example 7

A separation sieve film was prepared in the same manner as in Preparation Example 6, except that a PDMS (polydimethylsiloxane) plate was used instead of the PVDF plate.

Separation Sieve Preparation Example 8

A separation sieve film was prepared in the same manner as in Preparation Example 6 except that a PTFE (polytetrafluoroethylene) plate was used in place of the PVDF plate.

Separation Sieve Preparation Example 9

PC (polycarbonate) was added to a mixed solvent of chloroform and ethyl acetate having a volume ratio of 1:1 to prepare a uniform solution having a concentration of 1 mM. Then, 4,5,9,10-tetrakis(dodecyloxy)-pyrene (Compound 11) was added thereto to prepare a homogeneous solution having a concentration of 12.5 mM. The solution was spin-coated on a PTFE plate at a speed of 1750 rpm, and dried to form a separation sieve film, and then the separation sieve film was separated from the PTFE plate.

Separation Sieve Preparation Example 10

A separation sieve film was prepared in the same manner as in Preparation Example 9 except that PMMA (polymethylmethacrylate) was used in place of PC (polycarbonate).

Separation Sieve Preparation Example 11

A separation sieve film was prepared in the same manner as in Preparation Example 4 except that 2,3,4,6,7,10,11-hexakis(dodecyloxy)triphenylene (Compound 51) according to Compound Preparation Example 5A was used instead of 4,5,9,10-tetrakis(dodecyloxy)-pyrene (compound 11) according to Compound Production Example 1A.

Separation Sieve Evaluation Example 1: X-Ray Diffraction Analysis

X-ray diffraction analysis was performed in the same manner as the X-ray diffraction analysis of the three-dimensional structure.

FIG. 34 shows an X-ray spectrum of a separation sieve obtained by pelletizing 4,5,9,10-tetrakis(dodecyloxy)-pyrene (compound 11) according to Separation sieve Preparation Example 1.

FIG. 35 shows an X-ray spectrum of a separation sieve obtained by packaging 4,5,9,10-tetrakis(dodecyloxy)-pyrene (compound 11) according to Separation sieve Preparation Example 4.

FIG. 36 shows an X-ray spectrum of a film type separation sieve formed by spin coating a homogeneous solution of 4,5,9,10-tetrakis(dodecyloxy)-pyrene (compound 11) according to Separation sieve Preparation Example 6.

FIG. 37 shows an X-ray spectrum of the film type separation sieve formed by spin-coating a homogeneous solution of 4,5,9,10-tetrakis(dodecyloxy)-pyrene (compound 11) and PMMA according to Separation sieve Preparation Example 10.

FIG. 38 shows an X-ray spectrum of a separation sieve obtained by packaging 2,3,6,7,10,11-hexakis(dodecyloxy)triphenylene (compound 51) according to Separation sieve Preparation Example 11.

Separation Sieve Evaluation Example 2: Thermogravimetric Analysis

The separation sieve formed according to Separation sieve Preparation Example 1 was immersed in water, acetone, ethanol, butanol, or 1,4-dioxane for one minute, and taken out for thermogravimetric analysis.

FIG. 39 is a graph showing a change in weight of a separation sieve formed according to Separation sieve Preparation Example 1 carrying different solvents according to temperature.

Referring to FIG. 39, when the separation sieve contains acetone, ethanol, butanol, or 1,4-dioxane, the first weight loss at 100° C. or lower, specifically about 83% for acetone, about 95% for ethanol, about 97% for butanol, and about 97% for 1,4-dioxane, indicating that these solvents were contained at such a weight ratio in the separation sieve. In the case of the separation sieve carrying water and the separated itself, the first weight loss appears at about 350° C., and in the case of the separation sieve carrying acetone, ethanol, butanol, or 1,4-dioxane, the second weight loss appears at about 350° C., which is the result of decomposition of the separation sieve itself. From the above results, it can be seen that the separation sieve absorbs or adsorbs a very large amount of acetone, ethanol, butanol, or 1,4-dioxane, whereas the separation sieve does not substantially adsorb or adsorb water. Thus, it can be seen that the separation sieve can sufficiently separate acetone, ethanol, butanol, or 1,4-dioxane from a mixture of water and acetone, ethanol, butanol, or 1,4-dioxane.

Separation Sieve Evaluation Example 3: Evaluation of Edge Wettability

The edge wettability evaluation was carried out by referring to the document "Techniques for characterizing the wetting, coating and spreading of adhesives on surfaces" provided by the National Institute of Physics (NPL). The separation sieve was charged into an aluminum cylinder having a bottom surface of 0.25 cm² and a length of 0.5 cm, the bottom surface with an opening was brought into contact with a predetermined amount of the liquid to be adsorbed. Here, the liquid was on a scale, and the amount and speed of the adsorbed liquid were checked through the weight of the liquid which decreased with time.

FIG. 40 is a graph showing edge wettability of the separation sieve formed according to Separation sieve Preparation Example 1 for different solvents.

Referring to FIG. 40, it can be seen that the separation sieve formed according to Separation sieve Preparation Example 1 exhibits no adsorption or absorption at all on water, while adsorbed or absorbed on polar solvents such as methanol, acetone, butanol, 1,4-dioxane. In addition, since the adsorption or absorption rate is accelerated in the order of ethanol, 1,4-dioxane, butanol, acetone, and methanol, separation of these polar solvents may be possible by this speed difference.

Separation Sieve Evaluation Example 4: Evaluation of Separation Properties by Gas Chromatography This evaluation was performed using a gas chromatograph (trade name: agilent 6890) equipped with an HP-5MS UI capillary column (60 m×0.25 mm) and a mass spectrometer (trade name: finnigan TSQ-7000). The gas chromatography oven was maintained at 150° C. for 2 minutes, then heated to 300° C. at a rate of 6° C. per minute, and finally held at 300° C. for 33 minutes. Initially, 3 µl of sample was injected for 2 minutes and carrier gas was injected at 20 ml per minute.

FIG. 41 is a graph showing the resolving power of the separation sieve formed according to Separation sieve Preparation Example 1 for a mixed solution of water and ethanol using gas chromatography.

Referring to FIG. 41, when a mixed solution of water and ethanol (100 ppm of ethanol) itself is separated by using gas chromatography, separated peaks of water and ethanol are shown, but when this mixed solution is filtered through a separation sieve, no ethanol peak appears and only a water peak appears.

FIG. 42 is a graph showing the resolving power of the separation sieve formed according to Separation sieve Preparation Example 1 for a mixed solution of water and acetone using gas chromatography.

Referring to FIG. 42, when a mixed solution of water and acetone (100 ppm of acetone) itself is separated by using gas chromatography, separated peaks of water and acetone are shown, but when this mixed solution is filtered through a separation sieve, no acetone peak appears and only a water peak appears.

FIG. 43 is a graph showing the resolving power of the separation sieve formed according to Separation sieve Preparation Example 1 for a mixed solution of water and butanol using gas chromatography.

Referring to FIG. 43, when a mixed solution of water and butanol (100 ppm of butanol) itself is separated by using gas chromatography, separated peaks of water and butanol are shown, but when this mixed solution is filtered through a separation sieve, no butanol peak appears and only a water peak appears.

FIG. 44 is a graph showing the resolving power of the separation sieve formed according to Separation sieve Preparation Example 1 for a mixed solution of water and 1,4-dioxane using gas chromatography.

Referring to FIG. 44, when a mixed solution of water and 1,4-dioxane (100 ppm of 1,4-dioxane) itself is separated by using gas chromatography, separated peaks of water and 1,4-dioxane are shown, but when this mixed solution is filtered through a separation sieve, no 1,4-dioxane peak appears and only a water peak appears.

The separation sieve according to this embodiment can selectively adsorb or adsorb ethanol, acetone, butanol, or 4-dioxane from an aqueous solution containing ethanol, acetone, butanol, or 1,4-dioxane. Considering that gas chromatography can detect the ppb level, it can be seen that in the aqueous solution filtered by the separation sieve, there is no, or if any, less than the ppb level of ethanol, acetone, butanol, or 1,4-dioxane.

Separation Sieve Evaluation Example 5: Hansen Solubility Parameter Review

The Hansen solubility parameters of the compounds according to the above Preparation Examples of the compounds are as shown in the following table. In the following table, $\delta_h$ is the hydrogen bonding parameter, $\delta_p$ is the polarity parameter, $\delta_{d1}$ is the dispersion parameter, $R_O$ is the interaction radius of the Hansen Solubility Sphere, and $\theta$ is the dihedral angle shown in FIG. 2.

TABLE 15

| Prep. Ex. # | Comp. # | Compound Structure | $\delta_p$ | $\delta_h$ | $\delta_d$ | $R_O$ | $\theta$ |
|---|---|---|---|---|---|---|---|
| 1A | 11 | 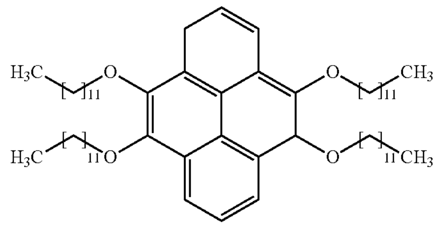 | 3.4 | 1.4 | 17.7 | 3.46 | 0.39 |

TABLE 15-continued
| Prep. Ex. # | Comp. # | Compound Structure | $\delta_p$ | $\delta_h$ | $\delta_d$ | $R_0$ | $\theta$ |
|---|---|---|---|---|---|---|---|
| 1B | 12 | 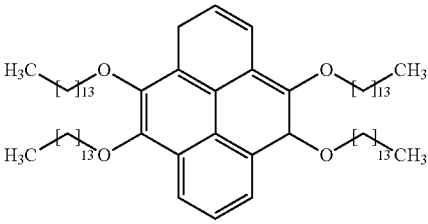 | 3.2 | 1.4 | 18.5 | 3.42 | 0.40 |
| 1C | 13 | 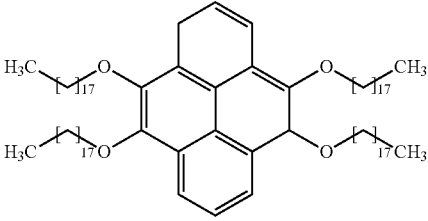 | 3.1 | 1.4 | 19.4 | 3.41 | 0.40 |
| 1D | 14 | 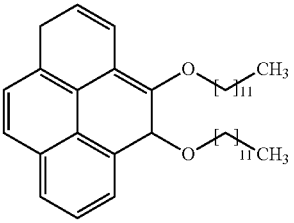 | 3.7 | 1.5 | 18.4 | 3.74 | 0.35 |
| 1E | 15 | 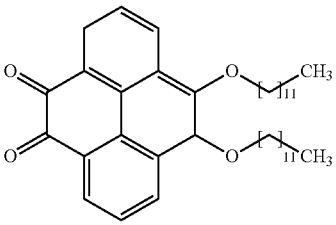 | 4.1 | 1.6 | 18.2 | 3.32 | 0.37 |
| 2A | 21 | 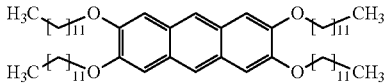 | 3.4 | 1.4 | 17.7 | 3.46 | 0.38 |
| 2B | 22 | 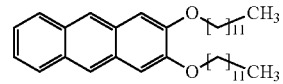 | 3.2 | 1.4 | 18.5 | 3.67 | 0.32 |
| 2C | 23 | 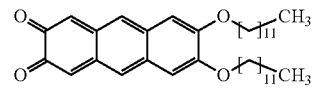 | 4.1 | 1.6 | 18.2 | 3.28 | 0.35 |
| 3A | 31 | 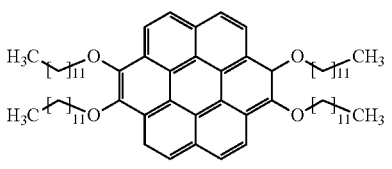 | 4.6 | 1.6 | 17.7 | 3.49 | 0.40 |

TABLE 15-continued

| Prep. Ex. # | Comp. # | Compound Structure | $\delta_p$ | $\delta_h$ | $\delta_d$ | $R_0$ | $\theta$ |
|---|---|---|---|---|---|---|---|
| 3B | 32 | 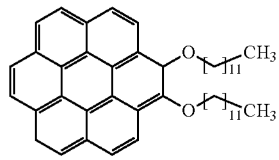 | 4.7 | 1.8 | 18.5 | 3.81 | 0.37 |
| 3C | 33 | 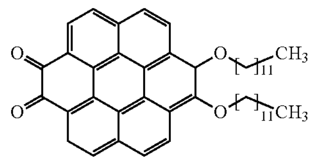 | 4.9 | 2.0 | 18.2 | 3.67 | 0.39 |
| 4A | 41 | 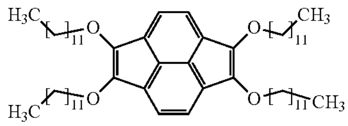 | 3.1 | 1.4 | 17.7 | 3.54 | 0.35 |

3-Dimensional Structure Evaluation Example 3: Verification of Optical Properties of Three-Dimensional Structure Crystals FIG. 45 is a photograph of the 4,5,9,10-tetrakis(dodecyloxy)-pyrene (compound 11) crystal according to Compound Preparation Example irradiated with light. Specifically, a BX-51 fluorescence polarization microscope (Olympus) and a direct irradiation light source having a U-RFL-T source were used, but light of 400 nm or less using an ultraviolet filter was irradiated to the crystal.

Referring to FIG. 45, it can be confirmed that the light inside the structure is prevented from diffusing into a specific part due to the characteristics of the photonic crystal material, and the light is strongly emitted only at the end of the structure.

Optical Amplification Layer Preparation Example 1

4,5,9,10-tetrakis(dodecyloxy)-pyrene (Compound 11) according to Compound Preparation Example 1A was added to a mixed solvent of chloroform and ethyl acetate having a volume ratio of 1:1 to prepare a homogeneous solution having a concentration of 12.5 mM, and the homogeneous solution was spin-coated on soda lime glass to form an optical amplification layer.

Light-Emitting Device Preparation Example 1 Having an Optical Amplification Layer 4,5,9,10-tetrakis(dodecyloxy)-pyrene (Compound 11) according to Compound Preparation Example 1A was put into a mixed solvent of chloroform and ethyl acetate having a volume ratio of 5:1 to obtain a homogeneous solution of 27.5 mM concentration, and an optical amplification layer was formed on the light emitting device by using a dip coating method in which a red LED bulb, a blue LED bulb, a green LED bulb, or a white LED bulb was immersed in the homogeneous solution and then dried.

Light-Emitting Device Preparation Example 2 Having an Optical Amplification Layer 4,5,9,10-tetrakis(dodecyloxy)-pyrene (Compound 11) according to Compound Preparation Example 1A was put into a mixed solvent of chloroform and ethyl acetate having a volume ratio of 1:1 to obtain a homogeneous solution of 12.5 mM concentration, and an optical amplification layer was formed on the light emitting device by using a spin coating method in which the homogeneous solution was spin-coated on a red LED array panel, a blue LED array panel, a green LED array panel, a white LED array panel, a red LED module, a blue LED module, a green LED module, or a white LED module and then dried.

Organic Light Emitting Device Preparation Example 1 Having an Optical Amplification Layer 4,5,9,10-tetrakis(dodecyloxy)-pyrene (Compound 11) according to Compound Preparation Example 1A was put into a mixed solvent of chloroform and ethyl acetate having a volume ratio of 5:1 to obtain a homogeneous solution of 27.5 mM concentration, and an optical amplification layer was formed on the organic light emitting device by using a dip coating method in which a red OLED bulb, a blue OLED bulb, a green OLED bulb, or a white OLED bulb was immersed in the homogeneous solution and then dried.

Organic Light Emitting Device Preparation Example 2 Having an Optical Amplification Layer 4,5,9,10-tetrakis(dodecyloxy)-pyrene (Compound 11) according to Compound Preparation Example 1A was put into a mixed solvent of chloroform and ethyl acetate having a volume ratio of 1:1 to obtain a homogeneous solution of 12.5 mM concentration, and an optical amplification layer was formed on the organic light emitting device by using a spin coating method in which the homogeneous solution was spin-coated on a red OLED array panel, a blue OLED array panel, a green OLED array panel, a white OLED array panel, a red OLED module, a blue OLED module, a green OLED module, or a white OLED module and then dried.

Fluorescent Lamp Preparation Example Having an Optical Amplification Layer 4,5,9,10-tetrakis(dodecyloxy)-pyrene (Compound 11) according to Compound Preparation Example 1A was put into a mixed solvent of chloroform and ethyl acetate having a volume ratio of 5:1 to obtain a homogeneous solution of 27.5 mM concentration, and an optical amplification layer was formed on the fluorescent lamp by using a dip coating method in which the fluorescent lamp was immersed in the homogeneous solution and then dried.

Incandescent Bulb Preparation Example Having an Optical Amplification Layer 4,5,9,10-tetrakis(dodecyloxy)-pyrene (Compound 11) according to Compound Preparation Example 1A was put into a mixed solvent of chloroform and ethyl acetate having a volume ratio of 5:1 to obtain a homogeneous solution of 27.5 mM concentration, and an optical amplification layer was formed on the incandescent bulb by using a dip coating method in which the incandescent bulb was immersed in the homogeneous solution and then dried.

Optical Amplification Layer Evaluation Example 1: X-Ray Diffraction Analysis

The X-ray diffraction analysis was performed on the optical amplification layer of the light emitting device or the organic light emitting device having the optical amplification layer formed therein as the same manner in the X-ray diffraction analysis of the three-dimensional structure.

FIG. 46 shows the X-ray spectrum of the optical amplification layer obtained in the light-emitting device preparation example 1 having the optical amplification layer.

Referring to FIG. 46, the X-ray spectrum of the optical amplification layer formed on the light-emitting device is similar to the X-ray spectrum of the three-dimensional structure crystal of 4,5,9,10-tetrakis (dodecyloxy)-pyrene (Compound 11, FIG. 27). It can be seen that the optical amplification layer keeps the three-dimensional structure crystal.

Also, X-ray spectrum substantially the same as in FIG. 46 was obtained in each case of the optical amplification layers from Light-emitting Device Preparation Example 2, Organic Light Emitting Device Preparation Examples 1 and 2, Fluorescent Lamp Preparation Example, and Incandescent Bulb Preparation Example.

Optical Amplification Layer Evaluation Example 2: Confirmation of Refractive Index and Permittivity The refractive index and the dielectric constant were measured by irradiating the optical amplification layer according to the optical amplification layer preparation example with light of 200 to 1800 nm.

FIG. 47A is a graph showing a refractive index and permittivity at an ordinary axis of an optical amplification layer according to an embodiment of the present invention, and FIG. 47B is a graph showing a refractive index and permittivity at an extra-ordinary axis of an optical amplification layer according to an embodiment of the present invention.

Referring to FIGS. 47A and 47B, it can be seen that a permittivity and a refractive index of less than or equal to 1, specifically, a permittivity and a refractive index close to 0 are exhibited in both the ordinary axis and the extra-ordinary axis in a wavelength range of about 300 nm or less.

Optical Amplification Layer Evaluation Example 3: Confirmation of Optical Amplification Through Ultraviolet/Visible Light Spectrometer Light transmittance was measured by irradiating light from 200 to 800 nm with an ultraviolet/visible light spectrophotometer (Jasco 500) to the optical amplification layer according to the optical amplification layer preparation example.

FIG. 48 is a graph showing light transmittance of an optical amplification layer according to an embodiment of the present invention.

Referring to FIG. 48, it can be seen that the transmittance between 200 to about 300 nm is about 2750%. Considering that the transmittance of a general material is maximally 100%, it can be seen that the optical amplification layer exhibits optical amplification due to physical properties having a dielectric constant (permittivity) close to 0, which is induced by periodic and regular characteristics.

Optical Amplification Layer Evaluation Example 4: Confirmation of the Relationship Between the Normalized Fermi Level and the Normalized Plasmon Frequency FIG. 49 is a graph showing the relationship between the normalized Fermi level and the normalized plasmon frequency of the optical amplification layer according to the optical amplification layer preparation example.

Referring to FIG. 49, it is well known that, when the normalized Fermi level is denoted by Ef0 and the normalized plasmon frequency is denoted by Ef, $\Delta Ef/\Delta Ef0$ represents a value of 1 when electrons have an effective mass, and $(\Delta Ef/\Delta Ef0)^{1/2}$ represents a value less than 1, specifically, $\frac{1}{2}$ when the effective mass of electrons is smaller than 1 [Nature Nanotechnology 7, 330-334 (2012)]. It can be seen that fitting data points obtained from the optical amplification layer, the resultant completely overlaps the graph representing $(\Delta Ef/\Delta Ef0)^{1/2}$ indicating $\frac{1}{2}$. Thus, it can be seen that electrons in the optical amplification layer can have an effective mass of zero. This means that the optical amplification layer according to this embodiment is a topological insulator having a Dirac band structure.

Optical Amplification Layer Evaluation Example 5: Confirmation of Optical Amplification Through Ultraviolet/Visible Light Photoluminescence Spectrometer Photoluminescence intensity was measured at every 5 nm with irradiating light from 200 to 800 nm at every 25 nm using a Varian cary eclipse fluorescence spectrometer to the optical amplification layer according to the optical amplification layer preparation example.

FIG. 50 is a graph showing the photoluminescence intensity of the optical amplification layer according to an embodiment of the present invention.

Referring to FIG. 50, when the optical amplification layer is excited by irradiating light of 300 nm on the optical amplification layer, luminescence was observed at 300 nm (A1), 600 nm (A2) which is twice the excitation wavelength, and 900 nm (A3) which is three times the excitation wavelength. Similar phenomena were observed at other wavelengths (B1, C1, D1, E1, F1, G1, H1, I1, J1, and K1).

Meanwhile, the light emission intensity at the same wavelength as the excitation wavelength was found to be 1000 au, and this can mean that optical amplification occurred in the optical amplification layer. This optical amplification may be a phenomenon due to the local surface plasmon resonance of Dirac plasmon caused by the characteristic as a topological insulator and the characteristic as a meta material of the optical amplification layer having a periodic and regular structure and having a dielectric constant near zero.

This shows that the optical layer according to this embodiment can also be used as a tunable amplifier. In addition, luminescent light having a wavelength corresponding to an integral multiple of the excitation wavelength was detected, which may be caused by the anisotropy of the molecules themselves and the quadrupole characteristic.

Optical Amplification Layer Evaluation Example 6: Confirmation of Degree of Optical Amplification According to the Energy of Incident Light According to the optical amplification layer preparation example, optical amplification layers were formed on soda lime glass at a thickness of 120 nm, 135 nm, or 150 nm, and 266 nm laser was irradiated on the optical amplification layers having different thicknesses and a bare soda lime glass having no optical amplification layer.

FIG. 51 is a graph showing the degree of amplification according to the incident energy of the laser.

Referring to FIG. 51, the optical amplification performance according to the amount of incident light can be confirmed.

Solar Cell Preparation Example 1 Having an Optical Amplification Layer 4,5,9,10-tetrakis(dodecyloxy)-pyrene (Compound 11) according to Compound Preparation Example 1A was added to a mixed solvent of chloroform and ethyl acetate having a volume ratio of 2:1 to prepare a homogeneous solution having a concentration of 27.5 mM, and the homogeneous solution was spin-coated on a silicon solar cell to form an optical amplification layer.

Solar Cell Preparation Example 2 Having an Optical Amplification Layer 4,5,9,10-tetrakis(dodecyloxy)-pyrene (Compound 11) according to Compound Preparation Example 1A was added to a solution in which 1 wt. % of PMMA was dissolved in chloroform to form a mixed solution having a concentration of 25 mM. Then, 0.1 wt. % of catechol relative to PMMA was mixed to form a mixture, and this mixture was spin-coated on a silicon solar cell to form an optical amplification layer.

Solar Cell Preparation Example 3 Having an Optical Amplification Layer

An optical amplification layer was formed in the same manner as in the solar cell preparation example 1 except that a cadmium telluride alloy solar cell was used instead of the silicon solar cell.

Solar Cell Preparation Example 4 Having an Optical Amplification Layer

An optical amplification layer was formed in the same manner as in the solar cell preparation example 1 except that a Copper Indium Gallium Selenium Alloy Solar Cell was used instead of the silicon solar cell.

Solar Cell Preparation Example 5 Having an Optical Amplification Layer

An optical amplification layer was formed in the same manner as in the solar cell preparation example 1 except that an Organic Solar Cell was used instead of the silicon solar cell.

Solar Cell Preparation Example 6 Having an Optical Amplification Layer

An optical amplification layer was formed in the same manner as in the solar cell preparation example 1 except that an Organic/inorganic hybrid solar cell was used instead of the silicon solar cell.

Solar Cell Preparation Example 7 Having an Optical Amplification Layer

An optical amplification layer was formed in the same manner as in the solar cell preparation example 1 except that a Dye-sensitized solar cell was used instead of the silicon solar cell.

Solar Cell Preparation Example 8 Having an Optical Amplification Layer

An optical amplification layer was formed in the same manner as in the solar cell preparation example 1 except that a Gallium arsenide solar cell was used instead of the silicon solar cell.

Solar Cell Preparation Example 9 Having an Optical Amplification Layer

An optical amplification layer was formed in the same manner as in the solar cell preparation example 1 except that a transparent solar cell was used instead of the silicon solar cell.

Evaluation Example of Solar Cell Having an Optical Amplification Layer

The open circuit voltage (Voc), the short circuit current (Jsc), and the fill factor (FF) of the solar cells each having the optical amplification layer obtained in the solar cell preparation examples 1 to 9 were measured. The results are summarized in Table 16 below. Meanwhile, the ratio of the power conversion efficiency (PCE) of each solar cell having the optical amplification layer according to the preparation examples to the power conversion efficiency of the same solar cell but having no optical amplification layer (comparative examples) is expressed as a relative efficiency.

TABLE 16

| | Voc (V) | Isc (A) | fill factor (FF) | relative efficiency (%) |
|---|---|---|---|---|
| preparation example 1 | 0.5994 | 0.963 | 57.3 | 186 |
| comparative example 1 | 0.5979 | 0.666 | 44.69 | 100 |
| preparation example 2 | 0.577 | 0.839 | 55.94 | 152 |
| comparative example 2 | 0.5984 | 0.666 | 44.67 | 100 |
| preparation example 3 | 0.5994 | 0.963 | 57.3 | 186 |
| comparative example 3 | 0.5979 | 0.666 | 44.69 | 100 |
| preparation example 4 | 0.577 | 0.839 | 55.94 | 152 |
| comparative example 4 | 0.5984 | 0.666 | 44.67 | 100 |
| preparation example 5 | 0.5994 | 0.963 | 57.3 | 186 |
| comparative example 5 | 0.5979 | 0.666 | 44.69 | 100 |

TABLE 16-continued

| | Voc (V) | Isc (A) | fill factor (FF) | relative efficiency (%) |
|---|---|---|---|---|
| preparation example 6 | 0.577 | 0.839 | 55.94 | 152 |
| comparative example 6 | 0.5984 | 0.666 | 44.67 | 100 |
| preparation example 7 | 0.5994 | 0.963 | 57.3 | 186 |
| comparative example 7 | 0.5979 | 0.666 | 44.69 | 100 |
| preparation example 8 | 0.577 | 0.839 | 55.94 | 152 |
| comparative example 8 | 0.5984 | 0.666 | 44.67 | 100 |
| preparation example 9 | 0.5994 | 0.963 | 57.3 | 186 |
| comparative example 9 | 0.5979 | 0.666 | 44.69 | 100 |

Referring to the above table, the optical amplification layer-introduce solar cells showed a greatly improved power conversion efficiency, indicating a relative efficiency of 152% or 186% as compared with the same solar cells but having no optical amplification layer.

It will be understood by those of ordinary skill in the art that various changes in form and details may be made therein without departing from the spirit and scope of the present invention as defined by the following claims. It is therefore to be understood that the above-described embodiments are illustrative in all aspects and not restrictive.

The scope of the present invention is defined by the appended claims, and all changes or modifications derived from the meaning and scope of the claims and their equivalents should be construed as being included within the scope of the present invention.

The invention claimed is:

1. A three-dimensional organic structure comprising a plurality of unit organic molecules which are self-assembled to form the three-dimensional organic structure,
wherein each of the unit organic molecules has at least one aromatic ring, a first pair of substituents being connected to immediately adjacent positions of substitutable positions of the aromatic ring, and a second pair of substituents being connected to immediately adjacent positions of substitutable positions of the aromatic ring,
wherein the substituents have terminal groups, respective of which is independently selected from the group consisting of $-CR_cR_dR_e$, $-OH$, $-COOH$, $-CHO$, $-SH$, $-COCR_cR_dR_e$, $-COOCR_cR_dR_e$, $-CR_c=CR_dR_e$, $-CN$, $-N=C=O$, $-C=N=N-CR_cR_dR_e$, $-C\equiv CR_a$, $-NHCR_cR_dR_e$, and $-NH_2$, wherein $R_c$, $R_d$, and $R_e$ are, independently of each other, H, F, Cl, Br, or I,
wherein the unit organic molecules contained in one layer of the three-dimensional structure are self-assembled by physical interaction between the terminal groups of the first pair of the substituents included in one unit organic molecule and the terminal groups of the second pair of the substituent groups included in another unit organic molecule among the unit organic molecules,
wherein the unit organic molecules contained in one layer and the unit organic molecules contained in another adjacent layer of the three-dimensional structure are self-assembled by pi-pi interactions between the aromatic rings,
wherein the three-dimensional organic structure is an organic crystal,
wherein the unit organic molecules has an organic compound of the following Chemical Formula 1:

[Chemical Formula 1]

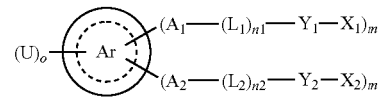

in Chemical-Formula 1,
$-A_1-(L_1)_{n1}-Y_1-X_1$ and $-A_2-(L_2)_{n2}-Y_2-X_2$ form one of the pairs of substituents being connected immediately adjacent positions among substitution positions of Ar,
$X_1$ and $X_2$ are the terminal groups,
$A_1$ and $A_2$ are, independently of each other, $-O-$ or $-S-$,
$L_1$ and $L_2$ are, independently of each other, -E-,

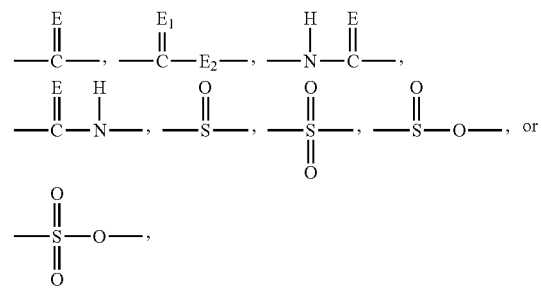

E, $E_1$, and $E_2$ are, independently of each other, O or S, $n_1$ and $n_2$ are, independently of each other, 0 or 1,
$Y_1$ and $Y_2$ are, independently of each other,

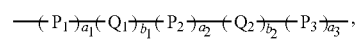

$a_1$, $a_2$, $a_3$, $b_1$, and $b_2$ are, independently of each other, integers of 0 to 30, and $a_1+a_2+a_3+b_1+b_2$ is an integer of 3 to 30,
$P_1$, $P_2$, and $P_3$ are, independently of each other, $-CR_aR_b-$ or $-(CR_aR_b)_rO-$, r is an integer of 1 to 3,
$Q_1$ and $Q_2$ are, independently of each other, $q_1-(p_1)_{c1}-q_2-(p_2)_{c2}-q_3$, $q_1$ and $q_3$ are, independently of each other, $-O-$ or $-S-$, $q_2$ is $-CH=CH-$, $-C\equiv C-$, $-N=N-$,

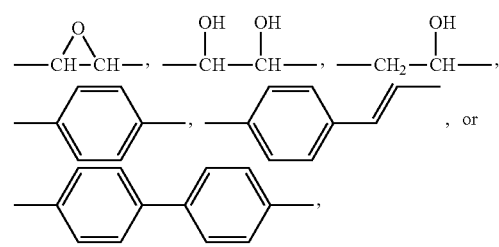

in which the hydrogen group bonded to the carbon is substituted with F, Cl, Br, or I, or unsubstituted, $p_1$ and $p_2$ are, independently of each other, —$CR_aR_b$—, $c_1$ and $c_2$ are, independently of each other, an integer of 0 to 2, $R_a$ and $R_b$ are, independently of each other, H, F, Cl, Br, or I, $R_c$, $R_d$, and $R_e$ are, independently of each other, H, F, Cl, Br, or I, U is one selected from the group consisting of a hydroxyl group, fluorine, chlorine, iodine, a substituted or unsubstituted alkyl group having 1 to 15 carbon atoms, a substituted or unsubstituted alkoxy group having 1 to 15 carbon atoms, a substituted or unsubstituted cycloalkyl group having 3 to 15 carbon atoms, a substituted or unsubstituted alkenyl group having 2 to 15 carbon atoms, and a substituted or unsubstituted alkynyl group having 2 to 15 carbon atoms, o is an integer between 0 and 16, m is an integer of 2 to 8, and the aromatic ring (Ar) is selected from the group consisting of an aromatic ring of the following Structural Formula 3, an aromatic ring of the following Structural Formula 6, an aromatic ring of the following Structural Formula 8, an aromatic ring of the following Structural Formula 10 and an aromatic ring of the following Structural Formula 12:

[Structural Formula 3]

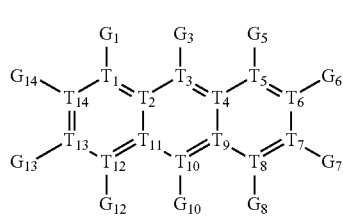

in Structural Formula 3, $T_1$ to $T_{14}$ are all C; or some of $T_1$ to $T_{14}$ are N, P, B or Si independently of each other and remainders are C, $G_1$, $G_3$, $G_5$, $G_6$, $G_7$, $G_8$, $G_{10}$, $G_{12}$, $G_{13}$, and $G_{14}$ represent substitution positions of the aromatic ring, a first pair of -$A_1$-$(L_1)_{n1}$-$Y_1$—$X_1$ and -$A_2$-$(L_2)_{n2}$-$Y_2$—$X_2$ are bonded to $G_6$ and $G_7$ positions, a second pair of -$A_1$-$(L_1)_{n1}$-$Y_1$—$X_1$ and -$A_2$-$(L_2)_{n2}$-$Y_2$—$X_2$ are bonded to $G_{13}$ and $G_{14}$ positions, U is bonded to any one of remaining $G_1$, $G_3$, $G_5$, $G_8$, $G_{10}$, and $G_{12}$ positions or not, and o is an integer of 0 to 6;

[Structural Formula 6]

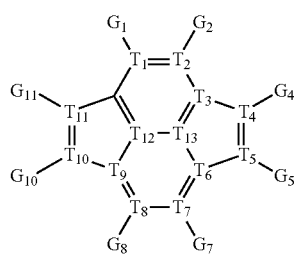

in Structural Formula 6, $T_1$ to $T_{13}$ are all C; or some of $T_1$ to $T_{13}$ are N, P, B or Si independently of each other and remainders are C, $G_1$, $G_2$, $G_4$, $G_5$, $G_7$, $G_8$, $G_{10}$, and $G_{11}$ represent substitution positions of the aromatic ring, a first pair of -$A_1$-$(L_1)_{n1}$-$Y_1$—$X_1$ and -$A_2$-$(L_2)_{n2}$-$Y_2$—$X_2$ are bonded to $G_4$ and $G_5$ positions, a second pair of -$A_1$-$(L_1)_{n1}$-$Y_1$—$X_1$ and -$A_2$-$(L_2)_{n2}$-$Y_2$—$X_2$ are bonded to $G_{10}$ and $G_{11}$ positions, U is bonded to any one of remaining $G_1$, $G_2$, $G_7$, and $G_8$ positions or not, and o is an integer of 0 to 4;

[Structural Formula 8]

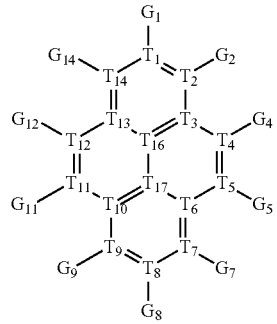

in Structural Formula 8, $T_1$ to $T_{14}$, $T_{16}$ and $T_{17}$ are all C; or some of $T_1$ to $T_{14}$, $T_{16}$ and $T_{17}$ are N, P, B or Si independently of each other and remainders are C, $G_1$, $G_2$, $G_4$, $G_5$, $G_7$, $G_8$, $G_9$, $G_{11}$, $G_{12}$, and $G_{14}$ represent substitution positions of the aromatic ring, a first pair of -$A_1$-$(L_1)_{n1}$-$Y_1$—$X_1$ and -$A_2$-$(L_2)_{n2}$-$Y_2$—$X_2$ are bonded to $G_4$ and $G_5$ positions, a second pair of -$A_1$-$(L_1)_{n1}$-$Y_1$—$X_1$ and -$A_2$-$(L_2)_{n2}$-$Y_2$—$X_2$ are bonded to $G_{11}$ and $G_{12}$ positions, U is bonded to any one of remaining $G_1$, $G_2$, $G_7$, $G_8$, $G_9$, and $G_{14}$ positions or not, and o is an integer of 0 to 6;

[Structural Formula 10]

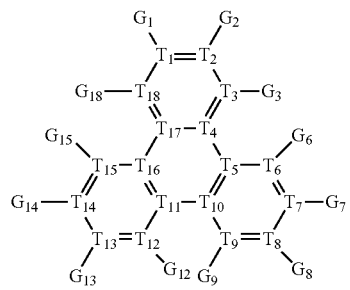

in Structural Formula 10, $T_1$ to $T_{18}$ are all C; or some of $T_1$ to $T_{18}$ are N, P, B or Si independently of each other and remainders are C, $G_1$, $G_2$, $G_3$, $G_6$, $G_7$, $G_8$, $G_9$, $G_{12}$, $G_{13}$, $G_{14}$, $G_{15}$, and $G_{18}$ represent substitution positions of the aromatic ring, a first pair of -$A_1$-$(L_1)_{n1}$-$Y_1$—$X_1$ and -$A_2$-$(L_2)_{n2}$-$Y_2$—$X_2$ are bonded to $G_1$ and $G_2$ positions, a second pair of -$A_1$-$(L_1)_{n1}$-$Y_1$—$X_1$ and -$A_2$-$(L_2)_{n2}$-$Y_2$—$X_2$ are bonded to $G_7$ and $G_8$ positions, a third pair of -$A_1$-$(L_1)_{n1}$-$Y_1$—$X_1$ and -$A_2$-$(L_2)_{n2}$-$Y_2$—$X_2$ are bonded to $G_{13}$ and $G_{14}$ positions, U is bonded to any one of remaining $G_3$, $G_6$, $G_9$, $G_{12}$, $G_{15}$, and $G_{18}$ positions or not, and o is an integer of 0 to 6;

[Structural Formula 12]

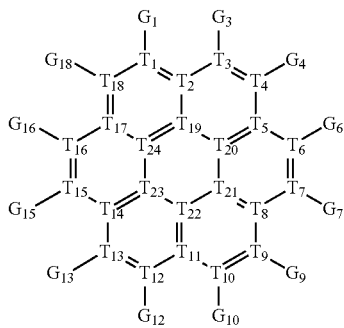

in Structural Formula 12, $T_1$ to $T_{24}$ are all C; or some of $T_1$ to $T_{24}$ are N, P, B or Si independently of each other and remainders are C, $G_1$, $G_3$, $G_4$, $G_6$, $G_7$, $G_9$, $G_{10}$, $G_{12}$, $G_{13}$, $G_{15}$, $G_{16}$, and $G_{18}$ represent substitution positions of the aromatic ring, a first pair of -A1-$(L_1)_{n1}$-$Y_1$—$X_1$ and -$A_2$-$(L_2)_{n2}$-$Y_2$—$X_2$ are bonded to $G_6$ and $G_7$ positions, a second pair of -$A_1$-$(L_1)_{n1}$-$Y_1$—$X_1$ and -$A_2$-$(L_2)_{n2}$-$Y_2$—$X_2$ are bonded to $G_{15}$ and $G_{16}$ positions, U is bonded to any one of remaining $G_1$, $G_3$, $G_4$, $G_9$, $G_{10}$, $G_{12}$, $G_{13}$, and $G_{18}$ positions or not, and o is an integer of 0 to 8.

2. The three-dimensional organic structure of claim 1, wherein the three-dimensional organic structure has a basic lattice of triclinic, monoclinic, orthorhombic, tetragonal, hexagonal, or cubic structure.

3. The three-dimensional organic structure of claim 1, wherein $P_1$, $P_2$, and $P_3$ independently represent —$(CH_2)$—, —$(CF_2)$—, —$(CH_2O)$—, —$(CH_2CH_2O)$—, or —$(CH_2CH_2CH_2O)$—.

4. The three-dimensional organic structure of claim 1, wherein $Q_1$ and $Q_2$ are, regardless of each other, —O—CH=CH—O—, —O—C≡C—O—, —O—N=N—O—,

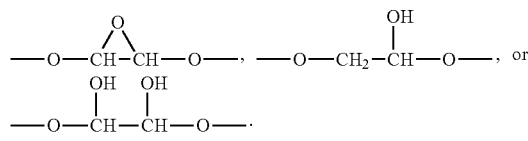

5. The three-dimensional organic structure of claim 1, wherein $Y_1$ and $Y_2$ are, independently from each other, —$(CH_2)_{a1}$—, wherein $a_1$ is an integer from 6 to 30, or —$(CH_2CH_2O)_{a1}$—, wherein $a_1$ is an integer of 3 to 10.

6. The three-dimensional organic structure of claim 1, wherein $Y_1$ and $Y_2$ are, independently from each other,

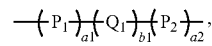

$P_1$ is —$(CH_2)$—, $a_1$ is an integer from 3 to 15, $Q_1$ is —O—CH=CH—O—, —O—C≡C—O—, —O—N=N—O—,

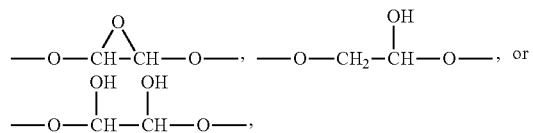

$b_1$ is 1, $P_2$ is —$(CH_2)$—, and $a_2$ is an integer of 1 to 3.

7. A separation sieve comprising the three-dimensional organic structure of claim 1.

8. The separation sieve of claim 7, wherein the separation sieve absorbs or adsorbs a first liquid or a second liquid from a mixed liquid in which the first liquid and the second liquid are mixed, wherein a Hansen solubility sphere of the separation sieve, point A of the first liquid, and point B of the second liquid are defined in a Hansen space which is a coordinate system in which a hydrogen bonding parameter is represented by a X axis, a polarity parameter is represented by a Y axis, and a value corresponding to twice a dispersion parameter value is represented by the Z axis, and wherein point A and point B are disposed outside the Hansen solubility sphere and are respectively disposed in two regions separated by a reference plane passing a center point of the sphere, wherein the reference plane has a dihedral angle of 0.1 to $0.45\pi$ with respect to an XY plane consisting of the X-axis and the Y-axis.

9. The separation sieve of claim 8, wherein the mixed liquid is an azeotropic mixture.

10. The separation sieve of claim 8, wherein the first liquid is water.

11. An optical layer comprising the three-dimensional organic structure of claim 1.

12. An optical device comprising the optical layer of claim 11 on an optical path thereof.

* * * * *